United States Patent
Kim et al.

(10) Patent No.: US 11,944,006 B2
(45) Date of Patent: Mar. 26, 2024

(54) DIAMINE COMPOUND AND ORGANIC LIGHT-EMITTING DEVICE INCLUDING THE SAME

(71) Applicant: Samsung Display Co., Ltd., Yongin-si (KR)

(72) Inventors: Jongwoo Kim, Yongin-si (KR); Dongjun Kim, Yongin-si (KR); Jangyeol Baek, Yongin-si (KR); Eunjae Jeong, Yongin-si (KR); Sanghyun Han, Yongin-si (KR); Youngkook Kim, Yongin-si (KR); Seokhwan Hwang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 809 days.

(21) Appl. No.: 16/277,289

(22) Filed: Feb. 15, 2019

(65) Prior Publication Data
US 2019/0334096 A1  Oct. 31, 2019

(30) Foreign Application Priority Data
Apr. 27, 2018 (KR) .................. 10-2018-0049403

(51) Int. Cl.
*H10K 85/60* (2023.01)
*C07D 209/88* (2006.01)
(Continued)

(52) U.S. Cl.
CPC ....... *H10K 85/6572* (2023.02); *C07D 209/88* (2013.01); *C07D 405/12* (2013.01);
(Continued)

(58) Field of Classification Search
CPC ............... H01L 51/0072; H01L 51/006; H01L 51/0061; H01L 51/0073; H01L 51/5088;
(Continued)

(56) References Cited

U.S. PATENT DOCUMENTS 8,026,514 B2   9/2011   Jang et al.
8,288,014 B2   10/2012  Hwang et al.
(Continued)

FOREIGN PATENT DOCUMENTS

CN   101508670 A   8/2009
EP   2093271 A1    8/2009
(Continued)

OTHER PUBLICATIONS

EPO Extended Search Report dated Sep. 27, 2019, for corresponding European Patent Application No. 19170211.7, (7 pages).

*Primary Examiner* — Michael Y Sun
(74) *Attorney, Agent, or Firm* — Lewis Roca Rothgerber Christie LLP

(57) ABSTRACT

A diamine compound includes a naphthyl-phenyl linker and a 2-carbazolyl group. An organic light-emitting device includes: a first electrode; a second electrode; and an organic layer between the first electrode and the second electrode
(Continued)

and including an emission layer, wherein the organic layer includes the diamine compound including the naphthyl-phenyl linker and the 2-carbazolyl group.

19 Claims, 2 Drawing Sheets

(51) Int. Cl.
*C07D 405/12* (2006.01)
*H10K 50/17* (2023.01)
*H10K 50/155* (2023.01)

(52) U.S. Cl.
CPC ........... *H10K 50/17* (2023.02); *H10K 85/633* (2023.02); *H10K 85/636* (2023.02); *H10K 85/6574* (2023.02); *H10K 50/155* (2023.02)

(58) Field of Classification Search
CPC ............... H01L 51/506; H01L 51/0081; H01L 51/5056; H01L 51/0035; C07D 209/88; C07D 405/12; C07D 209/82; C07D 307/91; H10K 85/6572; H10K 50/17; H10K 85/633; H10K 85/636; H10K 85/6574; H10K 50/155; H10K 50/15; H10K 85/324; H10K 85/111; H10K 50/11; H10K 85/657

See application file for complete search history.

(56) References Cited

U.S. PATENT DOCUMENTS

| | | | |
|---|---|---|---|
| 8,298,684 B2 | 10/2012 | Kwang et al. | |
| 8,394,511 B2 | 3/2013 | Hwang et al. | |
| 2010/0032656 A1* | 2/2010 | Kwang | ................ C07D 209/88 257/40 |
| 2010/0314648 A1* | 12/2010 | Fehrer | ................... H01L 51/504 257/98 |
| 2012/0319091 A1 | 12/2012 | Kato | |

FOREIGN PATENT DOCUMENTS

| | | | |
|---|---|---|---|
| KR | 10-2008-0096440 A | | 10/2008 |
| KR | 10-2009-0086756 A | | 8/2009 |
| KR | 10-2009-0120699 A | | 11/2009 |
| KR | 10-2010-0006072 A | | 1/2010 |
| KR | 10-2010-0008947 A | | 1/2010 |
| KR | 1020100006072 | * | 1/2010 |
| KR | 10-2010-0087120 A | | 8/2010 |
| KR | 10-2012-0096097 A | | 8/2012 |
| KR | 20130024521 A | * | 3/2013 |

* cited by examiner

DIAMINE COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2018-0049403, filed on Apr. 27, 2018, in the Korean Intellectual Property Office, the entire content of which is incorporated herein by reference.

BACKGROUND

1. Field

One or more embodiments of the present disclosure relate to a diamine compound and an organic light-emitting device including the same.

2. Description of the Related Art

Organic light-emitting devices are self-emission devices, have wide viewing angles, high contrast ratios, short response times, as well as excellent characteristics in terms of brightness, driving voltage, and response speed, and produce full-color images.

An example of such organic light-emitting devices may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transit (e.g., transition or relax) from an excited state to a ground state, thereby generating light.

SUMMARY

Aspects of embodiments of the present disclosure provide a diamine compound and an organic light-emitting device including the same.

Additional aspects of embodiments will be set forth in part in the description which follows and, in part, will be apparent from the description, or may be learned by practice of the presented embodiments.

An aspect of an embodiment provides an organic light-emitting device including: a first electrode; a second electrode; an organic layer between the first electrode and the second electrode and including an emission layer, wherein the organic layer includes a diamine compound including a naphthyl-phenyl linker and a 2-carbazolyl group.

In one embodiment, the first electrode is an anode, the second electrode is a cathode, the organic layer further includes a hole transport region between the first electrode and the emission layer, and the hole transport region includes the diamine compound.

In one embodiment, the hole transport region may include at least one of a hole injection layer and a hole transport layer, and at least one of the hole injection layer and the hole transport layer may include the diamine compound.

In one embodiment, the hole transport region may include a p-dopant, and
the p-dopant may have a lowest unoccupied molecular orbital (LUMO) energy level of about −3.5 eV or less.

Another aspect of an embodiment provides a diamine compound represented by Formula 1:

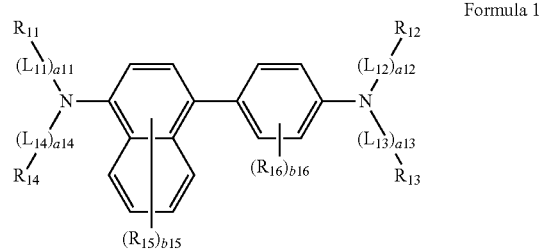

Formula 1

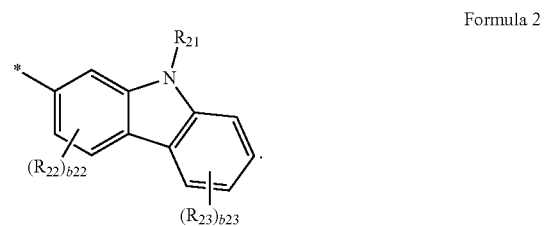

Formula 2

In Formula 1,
$L_{11}$ to $L_{14}$ may each independently be selected from a single bond, a substituted or unsubstituted $C_5$-$C_{60}$ carbocyclic group, and a substituted or unsubstituted $C_1$-$C_{60}$ heterocyclic group,
a11 to a14 may each independently be selected from 0, 1, 2, and 3,
$R_{11}$ to $R_{14}$ may each independently be selected from a group represented by Formula 2, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one of $R_{11}$ to $R_{14}$ is not a group represented by Formula 2,
$R_{15}$, $R_{16}$, and $R_{21}$ to $R_{23}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)($Q_1$), —P(=O)($Q_1$)($Q_2$), and —P(=S)($Q_1$)($Q_2$), b15 may be selected from 1, 2, 3, 4, 5, and 6, b16 and b23 may each independently be selected from 1, 2, 3, and 4, b22 may be selected from 1, 2, and 3, $Q_1$ to $Q_3$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a $C_1$-$C_{60}$ alkyl group substituted with at least one selected from deuterium, —F, and a cyano group, a $C_6$-$C_{60}$ aryl group substituted with at least one selected from deuterium, —F, and a cyano group, a biphenyl group, and a terphenyl group, and indicates a binding site to a neighboring atom.

BRIEF DESCRIPTION OF THE DRAWINGS

These and/or other aspects of embodiments of the present disclosure will become apparent and more readily appreciated from the following description of the embodiments, taken in conjunction with the accompanying drawings in which.

DETAILED DESCRIPTION

Figure 1:
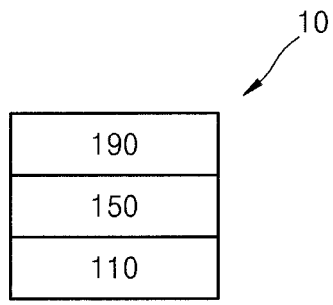
FIG. 1 is a schematic cross-sectional view of an organic light-emitting device according to an embodiment.

The subject matter of the present disclosure will now be described more fully with reference to exemplary embodiments. The subject matter of the disclosure may, however, be embodied in many different forms and should not be construed as being limited to the embodiments set forth herein; rather, these embodiments are provided so that this disclosure will be thorough and complete, and will fully convey the subject matter of the disclosure to those skilled in the art. Features of embodiments of the present disclosure, and how to achieve them, will become apparent by reference to the embodiments that will be described herein in more detail, together with the accompanying drawings. The subject matter of the present disclosure may, however, be embodied in many different forms and should not be limited to the exemplary embodiments.

Hereinafter, embodiments are described in more detail by referring to the attached drawings, and in the drawings, like reference numerals denote like elements, and a redundant explanation thereof will not be provided herein.

As used herein, the singular forms "a," "an" and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

It will be understood that when a layer, region, or component is referred to as being "on" or "onto" another layer, region, or component, it may be directly or indirectly formed on the other layer, region, or component. For example, intervening layers, regions, or components may be present.

Sizes of components in the drawings may be exaggerated for convenience of explanation. In other words, since sizes and thicknesses of components in the drawings may be arbitrarily illustrated for convenience of explanation, the following embodiments of the present disclosure are not limited thereto.

An organic light-emitting device according to an embodiment may include: a first electrode; a second electrode; an organic layer between the first electrode and the second electrode and including an emission layer, wherein the organic layer may include a diamine compound including a naphthyl-phenyl linker and a 2-carbazolyl group.

As used herein, the term "diamine compound" refers to a compound including two amino groups. For example, the diamine compound essentially includes a first amino group and a second amino group.

As used herein, the term "naphthyl-phenyl linker" refers to a divalent group having a structure in which a set or arbitrary carbon atom in a naphthalene group is linked to a set or arbitrary carbon atom in a benzene group. For example, the naphthyl-phenyl linker may be represented by Formula 1A, but embodiments of the present disclosure are not limited thereto. The naphthyl-phenyl linker may include other constitutional isomers of Formula 1A:

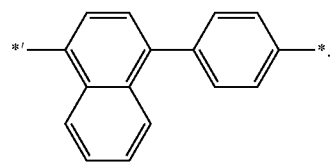

Formula 1A

In Formula 1A, indicates a binding site to a nitrogen atom of the first amino group, and *' indicates a binding site to a nitrogen atom of the second amino group; or indicates a binding site to a nitrogen atom of the second amino group, and *' indicates a binding site to a nitrogen atom of the first amino group, and any hydrogen or an arbitrary hydrogen in Formula 1A may be substituted with a substituent.

As used herein, the term "2-carbazolyl group" refers to a monovalent group in which the second carbon of the carbazole is directly linked to the nitrogen atom of the first amino group or the second amino group of the diamine compound, or linked thereto via an arbitrary divalent group. For example, the 2-carbazolyl group may be represented by Formula 2A:

Formula 2A

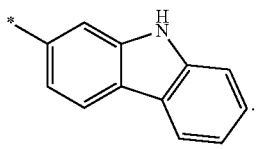

In Formula 2A, indicates a binding site to a nitrogen atom of the diamine compound, and any hydrogen or an arbitrary hydrogen in Formula 2A may be further substituted with a substituent.

For example, the diamine compound may include a naphthyl-phenyl linker between two amino groups, and at least one substituent of the two amino groups may be a 2-carbazolyl group. For example, the diamine compound may include a naphthyl-phenyl linker between the first amino group and the second amino group, and at least one substituent of the first amino group and the second amino group may be a 2-carbazolyl group.

For example, the first electrode may be an anode, the second electrode may be a cathode, the organic layer may further include a hole transport region between the first electrode and the emission layer, and the hole transport region may include the diamine compound, but embodiments of the present disclosure are not limited thereto.

For example, the hole transport region may include at least one of a hole injection layer and a hole transport layer, and at least one of the hole injection layer and hole transport layer may include the diamine compound, but embodiments of the present disclosure are not limited thereto.

In one embodiment, the hole transport region may include a p-dopant, and the p-dopant may have a lowest unoccupied molecular orbital (LUMO) energy level of about −3.5 eV or less, but embodiments of the present disclosure are not limited thereto.

In one embodiment, the diamine compound may be represented by Formula 1.

In one or more embodiments, the diamine compound may be represented by Formula 1, and at least one of $R_{11}$ to $R_{14}$ may be a group represented by Formula 2:

Formula 1

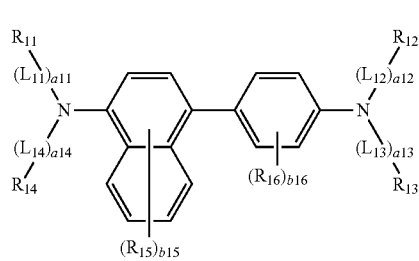

Formula 2

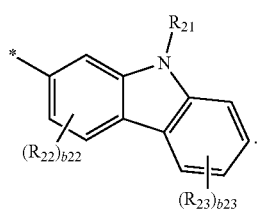

For example, in Formula 1, $R_{11}$ may be a group represented by Formula 2;

$R_{12}$ may be a group represented by Formula 2;

$R_{11}$ and $R_{12}$ may each be a group represented by Formula 2;

$R_{11}$ and $R_{14}$ may each be a group represented by Formula 2;

$R_{11}$, $R_{12}$, and $R_{14}$ may each be a group represented by Formula 2;

$R_{11}$, $R_{12}$, and $R_{13}$ may each be a group represented by Formula 2; or $R_{11}$, $R_{12}$, $R_{13}$, and $R_{14}$ may each be a group represented by Formula 2, but embodiments of the present disclosure are not limited thereto.

In more detail, in Formula 1, $R_{11}$ may be a group represented by Formula 2; or $R_{12}$ may be a group represented by Formula 2, but embodiments of the present disclosure are not limited thereto.

In Formula 1, $L_{11}$ to $L_{14}$ may each independently be selected from a single bond, a substituted or unsubstituted $C_5$-$C_{60}$ carbocyclic group, and a substituted or unsubstituted $C_1$-$C_{60}$ heterocyclic group.

For example, in Formula 1, $L_{11}$ to $L_{14}$ may each independently be selected from:

a single bond, a benzene group, a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a perylene group, a thiophene group, a furan group, a silole group, a carbazole group, an indole group, an isoindole group, a benzofuran group, a benzothiophene group, a benzosilole group, a dibenzofuran group, a dibenzothiophene group, a benzocarbazole group, a dibenzocarbazole group, and a dibenzosilole group; and a benzene group, a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a perylene group, a thiophene group, a furan group, a silole group, a carbazole group, an indole group, an isoindole group, a benzofuran group, a benzothiophene group, a benzosilole group, a dibenzofuran group, a dibenzothiophene group, a benzocarbazole group, a dibenzocarbazole group, and a dibenzosilole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a thiophenyl group, a furanyl group, a silolyl group, a carbazolyl group, an indolyl group, an isoindolyl group, a benzofuranyl group, a benzothiophenyl group, a benzosilolyl group, a dibenzofuranyl group, a dibenzothiophenyl group, a benzocarbazolyl group, a dibenzocarbazolyl group, a dibenzosilolyl group, —Si($Q_{31}$)($Q_{32}$)($Q_{33}$), —N($Q_{31}$)($Q_{32}$), and —B($Q_{31}$)($Q_{32}$), and $Q_{31}$ to $Q_{33}$ may each independently be selected from a $C_1$-$C_{60}$ alkyl group, a phenyl group, a biphenyl group, and a terphenyl group, but embodiments of the present disclosure are not limited thereto.
In one embodiment, in Formula 1, $L_{11}$ to $L_{14}$ may each independently be selected from a single bond and groups represented by Formulae 3-1 to 3-41, but embodiments of the present disclosure are not limited thereto:
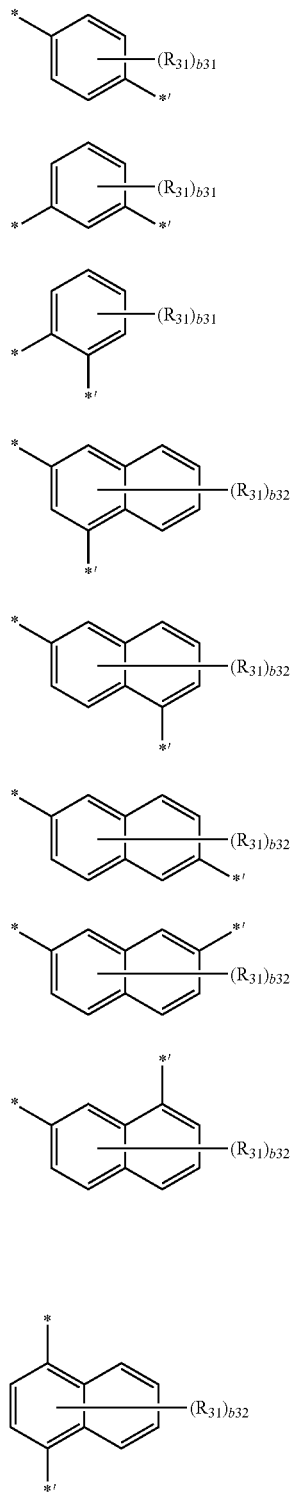
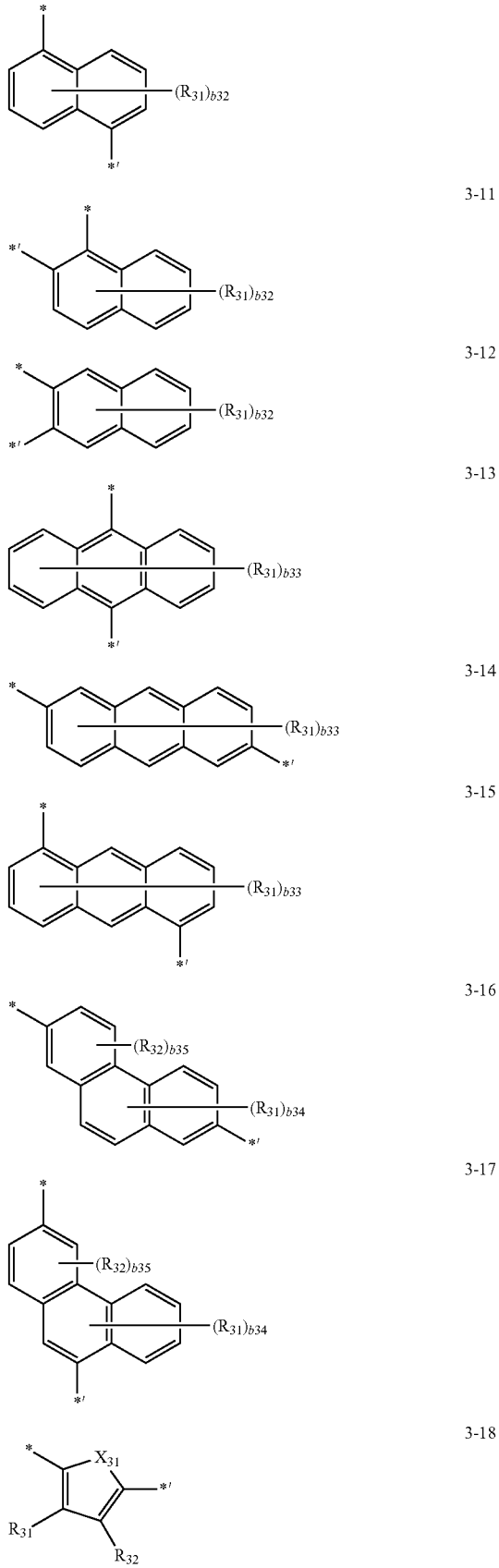

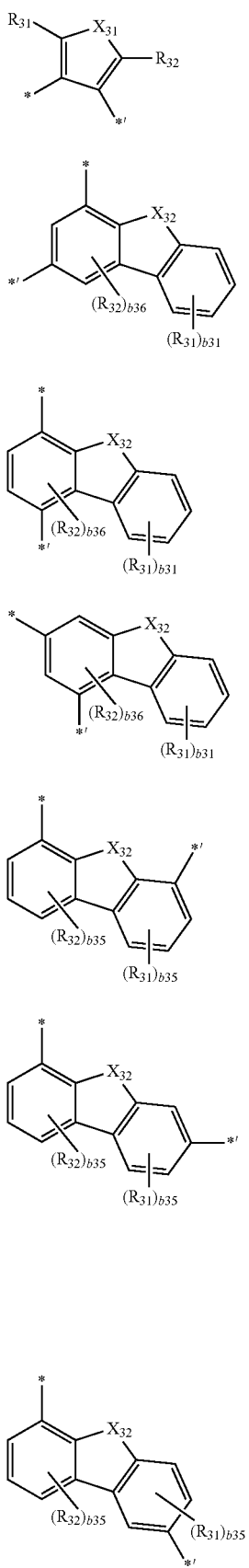
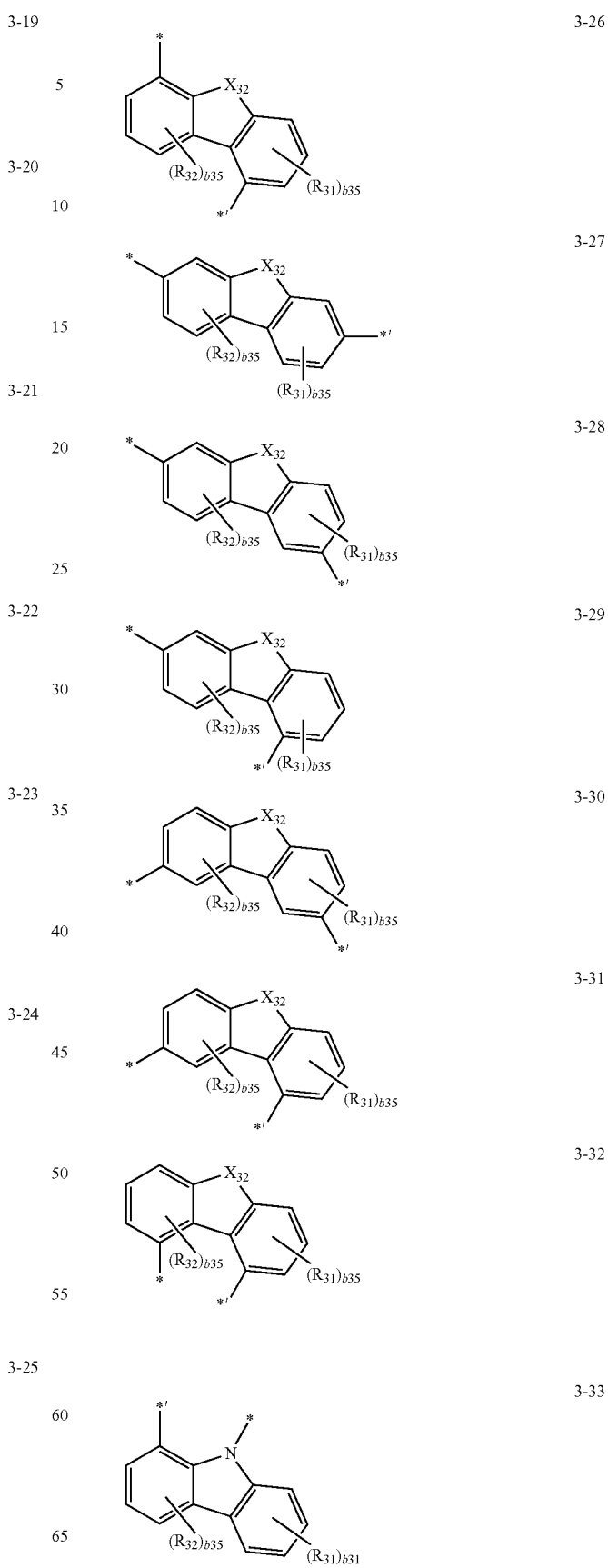

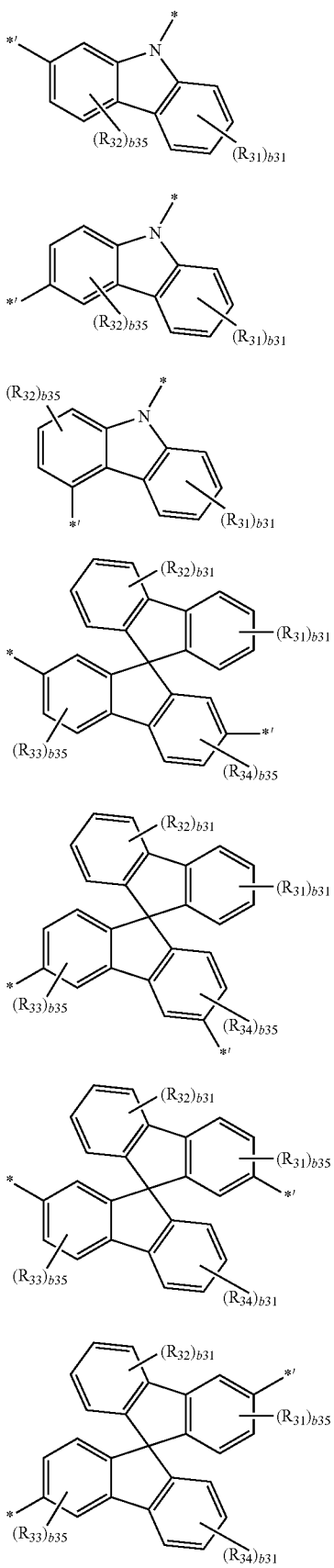

In Formulae 3-1 to 3-41, $X_{31}$ may be selected from O and S, $X_{32}$ may be selected from O, S, $N(R_{33})$, and $C(R_{33})(R_{34})$, $R_{31}$ to $R_{34}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a thiophenyl group, a furanyl group, a silolyl group, a carbazolyl group, an indolyl group, an isoindolyl group, a benzofuranyl group, a benzothiophenyl group, a benzosilolyl group, a dibenzofuranyl group, a dibenzothiophenyl group, a benzocarbazolyl group, a dibenzocarbazolyl group, a dibenzosilolyl group, —Si($Q_{31}$)($Q_{32}$)($Q_{33}$), —N($Q_{31}$)($Q_{32}$), and —B($Q_{31}$)($Q_{32}$), $Q_{31}$ to $Q_{33}$ may each independently be selected from a $C_1$-$C_{60}$ alkyl group, a phenyl group, a biphenyl group, and a terphenyl group, b31 may be selected from 1, 2, 3, and 4, b32 may be selected from 1, 2, 3, 4, 5, and 6, b33 may be selected from 1, 2, 3, 4, 5, 6, 7, and 8, b34 may be selected from 1, 2, 3, 4, and 5, b35 may be selected from 1, 2, and 3, b36 may be selected from 1 and 2, and and *' each indicate a binding site to a neighboring atom.

In Formula 1, a11 indicates the repeating number of $L_{11}$, and may be selected from 0, 1, 2, and 3. Likewise, in Formula 1, a12 to a14 indicate the repeating number of $L_{12}$ to $L_{14}$, respectively, and a12 to a14 may each independently be selected from 0, 1, 2, and 3.

For example, in Formula 1, a11 to a14 may each independently be selected from 0 and 1, but embodiments of the present disclosure are not limited thereto.

In Formula 1, $R_{11}$ to $R_{14}$ may each independently be selected from a group represented by Formula 2, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from $R_{11}$ to $R_{14}$ may be a group represented by Formula 2.-

For example, in Formula 1, $R_{11}$ to $R_{14}$ may each independently be selected from:

a group represented by Formula 2, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzolhiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group; and a cyclopentyl group, a cyclohexyl group, a cydoheptyl group, a cydopentenyl group, a cydohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group, each substituted with at least one selected from deuterium, —F, —Cl, —Br, —I, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group, wherein at least one selected from $R_{11}$ to $R_{14}$ may be a group represented by Formula 2, but embodiments of the present disclosure are not limited thereto.

In one embodiment, in Formula 1, $R_{11}$ to $R_{14}$ may each independently be selected from a group represented by Formula 2 and groups represented by Formulae 5-1 to 5-138, but embodiments of the present disclosure are not limited thereto:

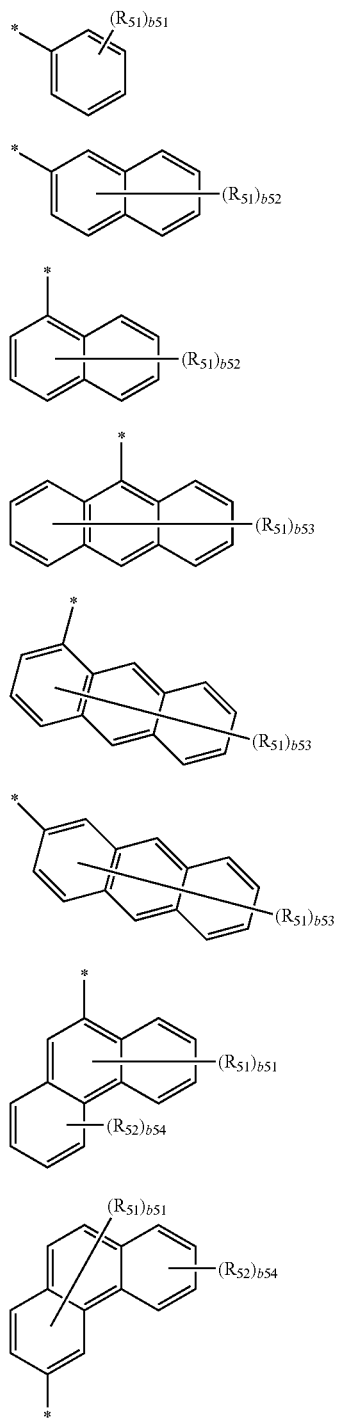

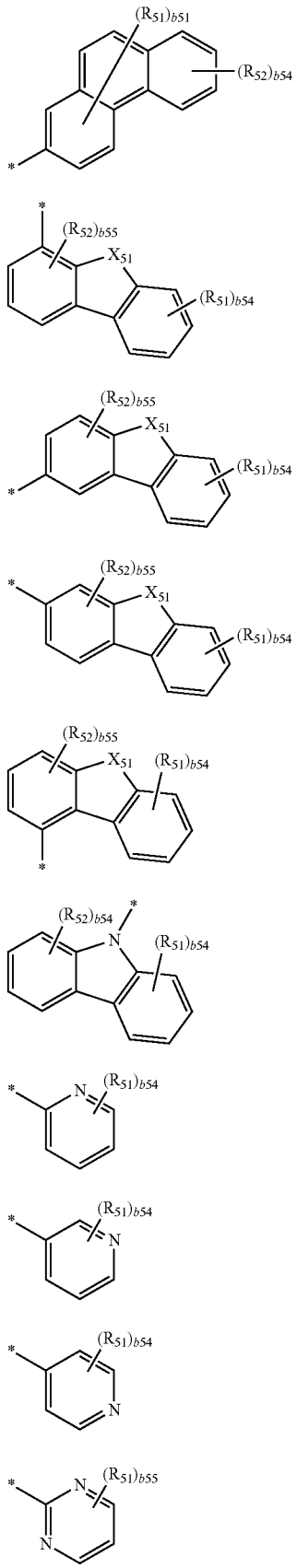

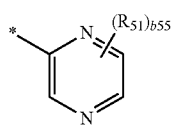
5-19
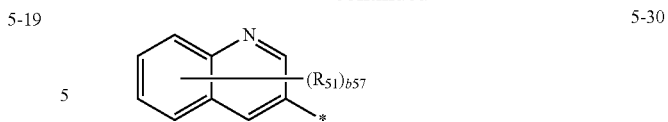
5-30
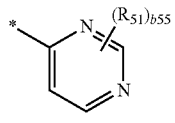
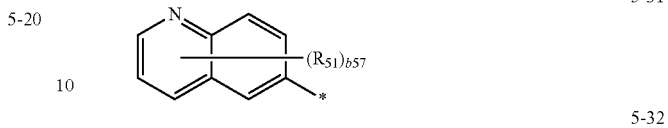
5-31

5-20
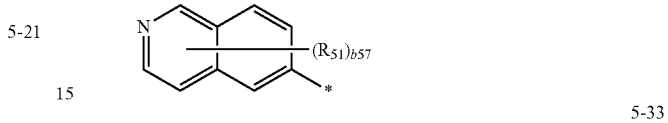
5-32
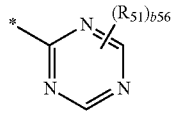
5-21
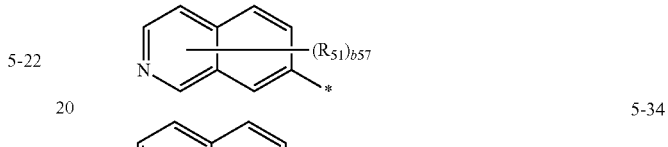
5-33
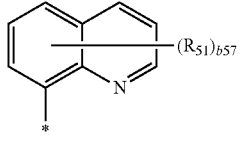
5-22
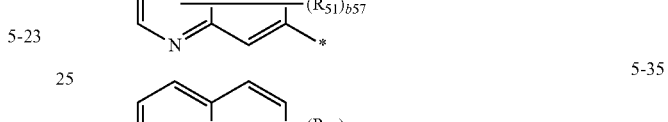
5-34
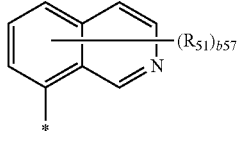
5-23
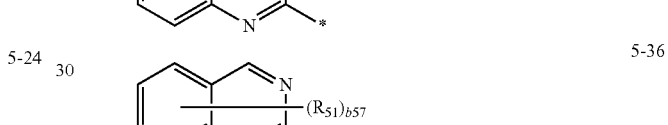
5-35
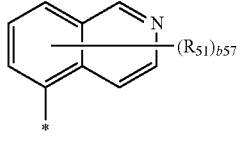
5-24
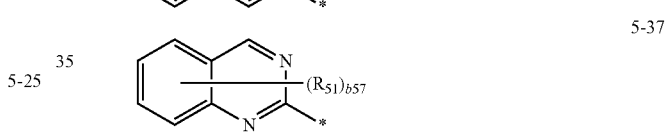
5-36
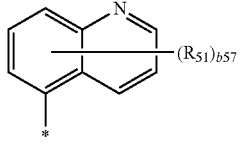
5-25
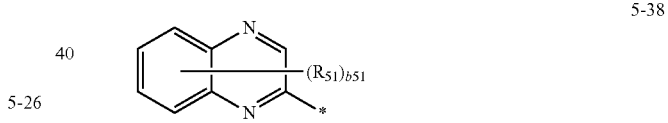
5-37
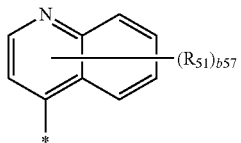
5-26
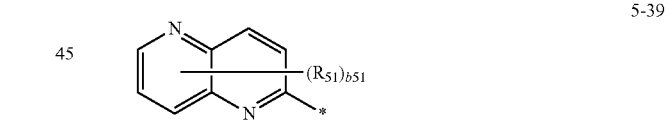
5-38
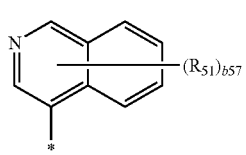
5-27
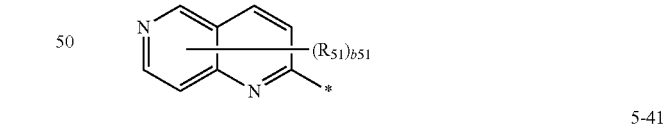
5-39
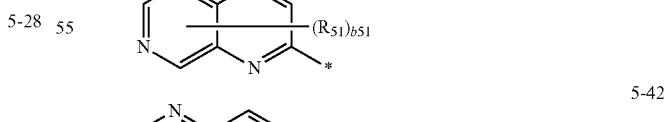
5-40
5-28
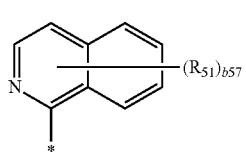
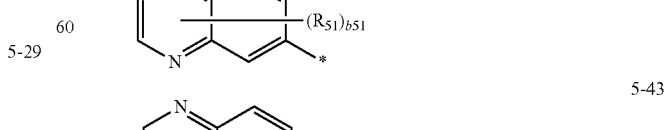
5-41
5-29
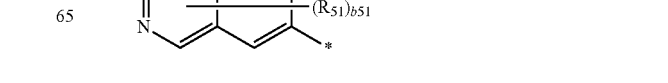
5-42
5-43

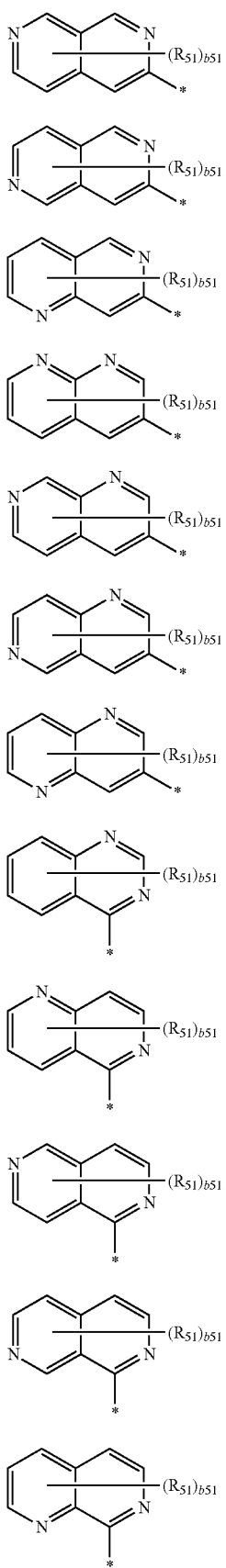
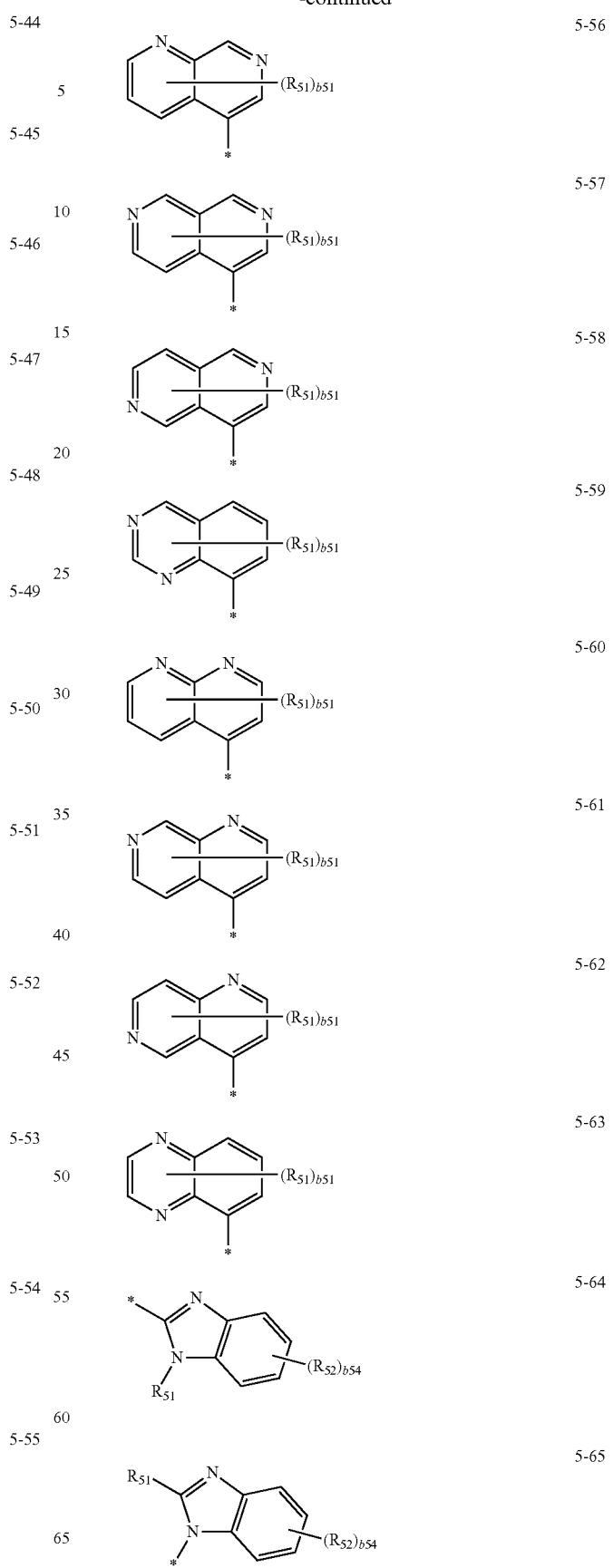

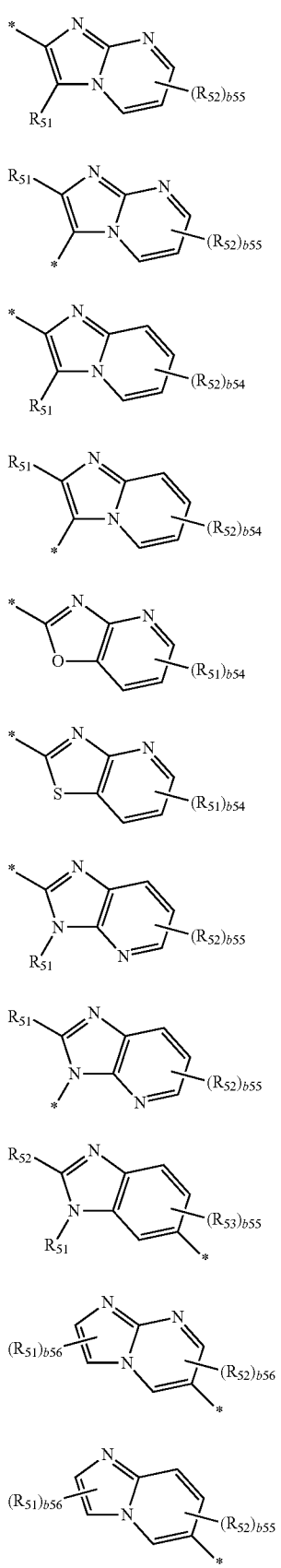
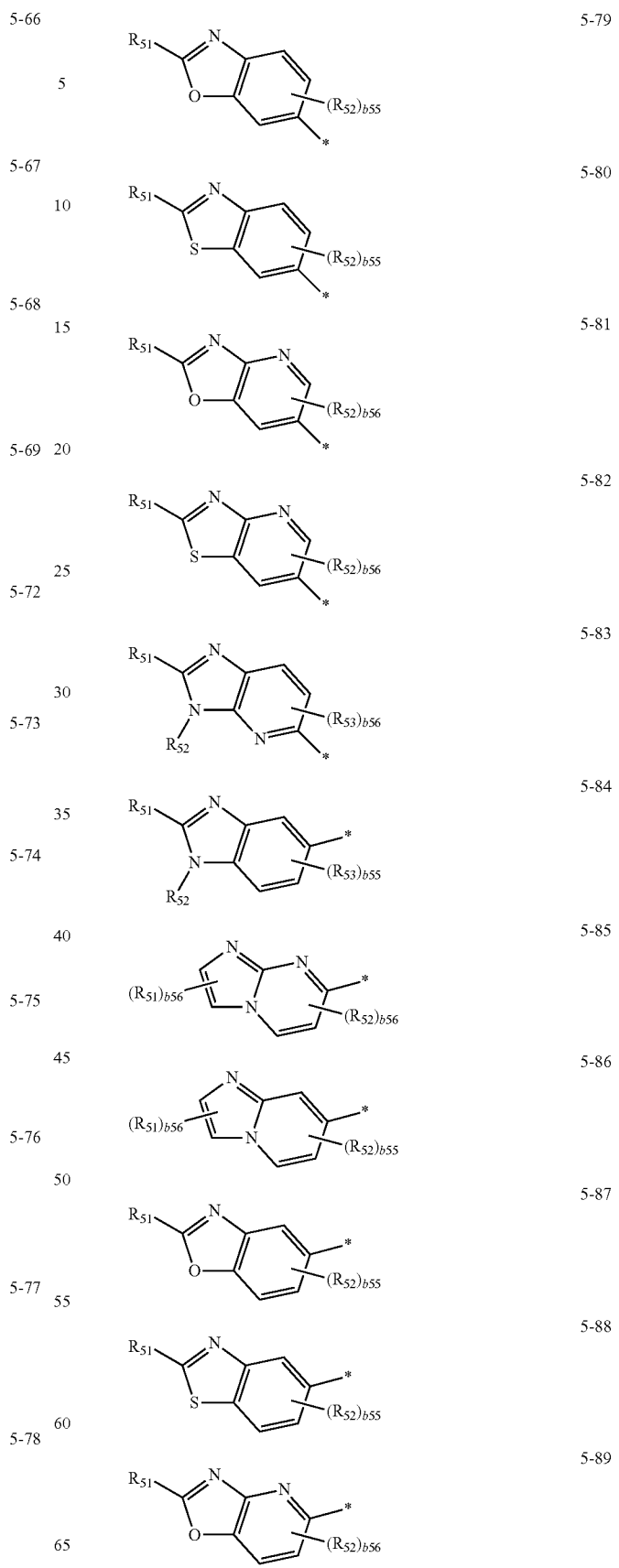

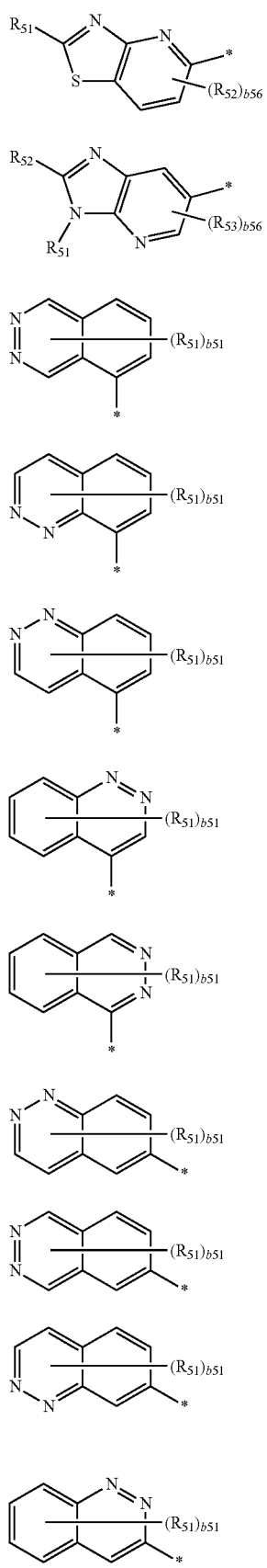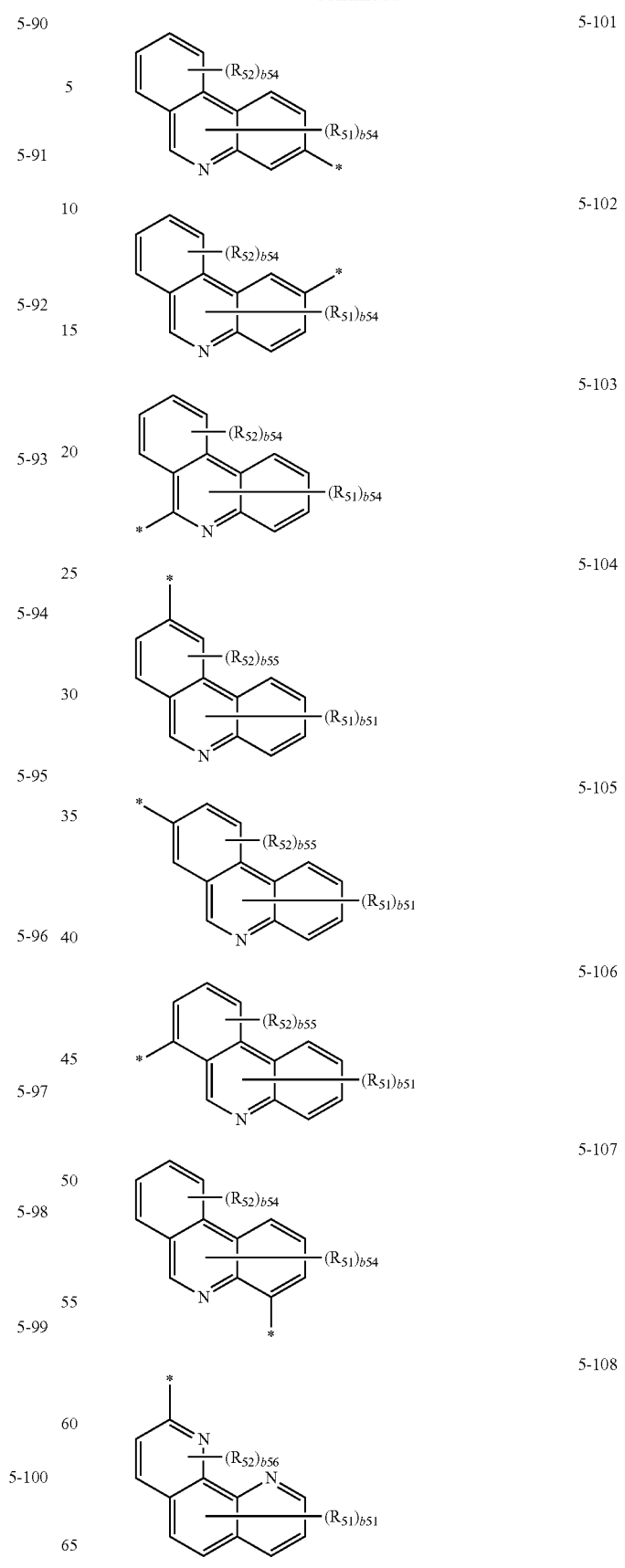

5-109 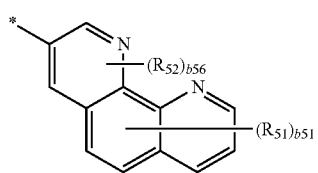
5-110 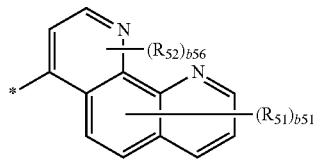
5-111 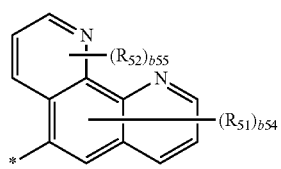
5-112 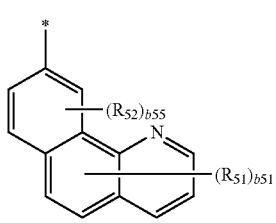
5-113 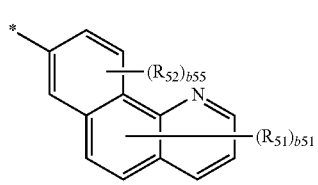
5-114 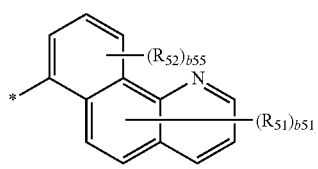
5-115 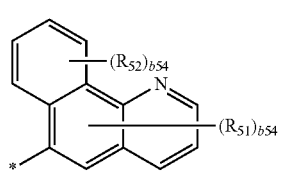
5-116 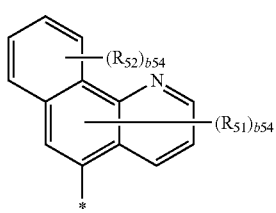
5-117 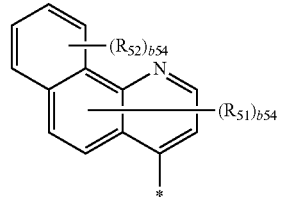
5-118 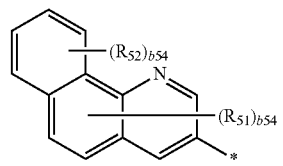
5-119 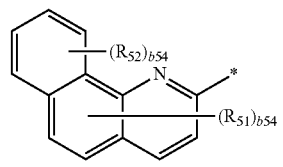
5-120 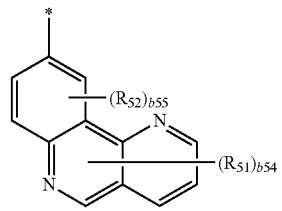
5-121 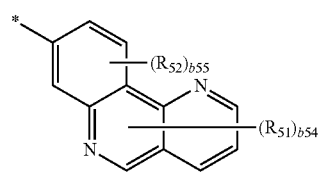
5-122 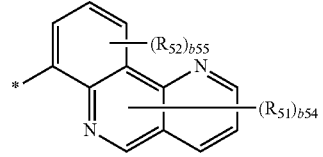
5-123 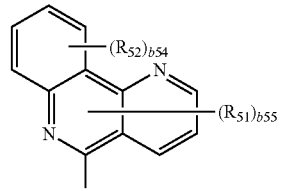
5-124 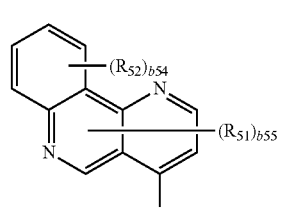

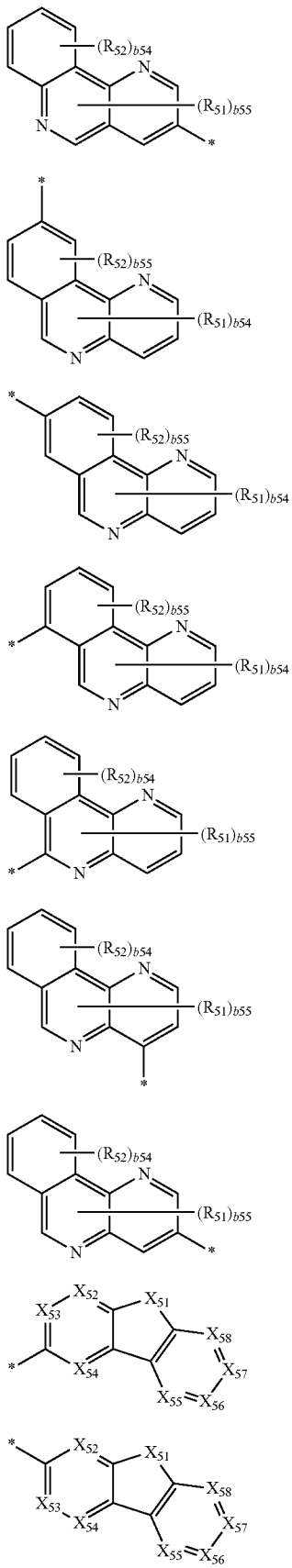

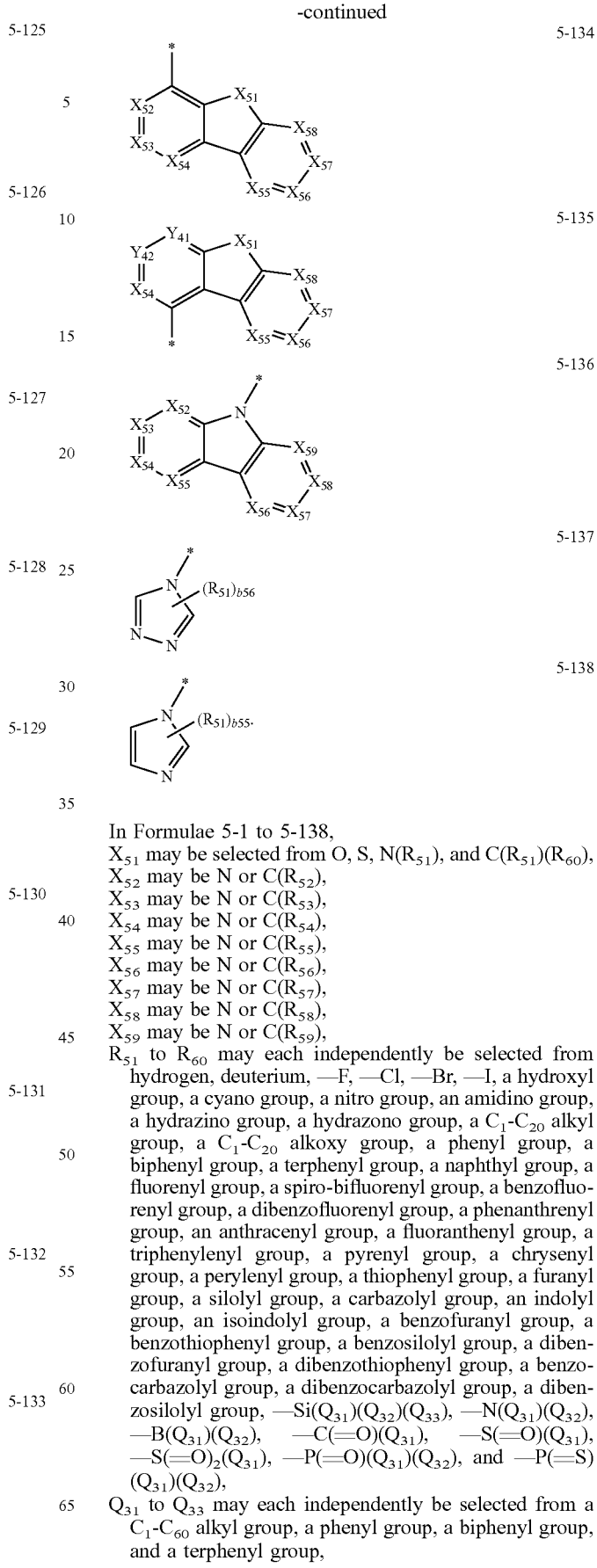

In Formulae 5-1 to 5-138,
X$_{51}$ may be selected from O, S, N(R$_{51}$), and C(R$_{51}$)(R$_{60}$),
X$_{52}$ may be N or C(R$_{52}$),
X$_{53}$ may be N or C(R$_{53}$),
X$_{54}$ may be N or C(R$_{54}$),
X$_{55}$ may be N or C(R$_{55}$),
X$_{56}$ may be N or C(R$_{56}$),
X$_{57}$ may be N or C(R$_{57}$),
X$_{58}$ may be N or C(R$_{58}$),
X$_{59}$ may be N or C(R$_{59}$),
R$_{51}$ to R$_{60}$ may each independently be selected from hydrogen, deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a thiophenyl group, a furanyl group, a silolyl group, a carbazolyl group, an indolyl group, an isoindolyl group, a benzofuranyl group, a benzothiophenyl group, a benzosilolyl group, a dibenzofuranyl group, a dibenzothiophenyl group, a benzocarbazolyl group, a dibenzocarbazolyl group, a dibenzosilolyl group, —Si(Q$_{31}$)(Q$_{32}$)(Q$_{33}$), —N(Q$_{31}$)(Q$_{32}$), —B(Q$_{31}$)(Q$_{32}$), —C(=O)(Q$_{31}$), —S(=O)(Q$_{31}$), —S(=O)$_2$(Q$_{31}$), —P(=O)(Q$_{31}$)(Q$_{32}$), and —P(=S)(Q$_{31}$)(Q$_{32}$),
Q$_{31}$ to Q$_{33}$ may each independently be selected from a C$_1$-C$_{60}$ alkyl group, a phenyl group, a biphenyl group, and a terphenyl group, b51 may be selected from 1, 2, 3, 4, and 5,
b52 may be selected from 1, 2, 3, 4, 5, 6, and 7,
b53 may be selected from 1, 2, 3, 4, 5, 6, 7, 8, and 9,
b54 may be selected from 1, 2, 3, and 4,
b55 may be selected from 1, 2, and 3,
b56 may be selected from 1 and 2,
b57 may be selected from 1, 2, 3, 4, 5, and 6, and
indicates a binding site to a neighboring atom.

In one embodiment, in Formula 1, $R_{11}$ to $R_{14}$ may each independently be selected from a group represented by Formula 2 and groups represented by Formulae 6-1 to 6-257, but embodiments of the present disclosure are not limited thereto:

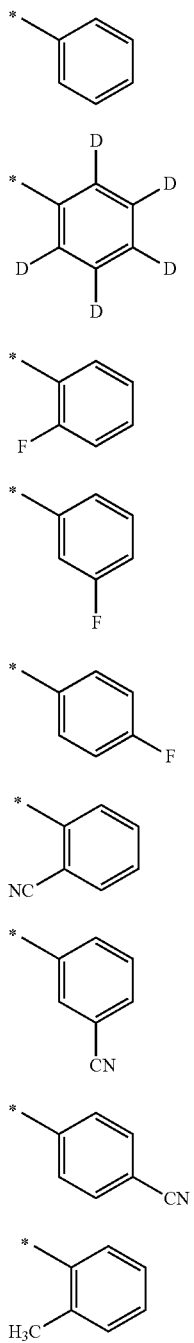

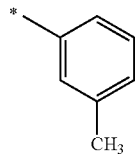

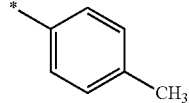

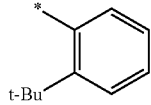

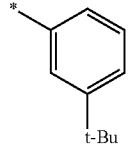

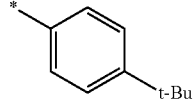

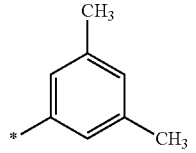

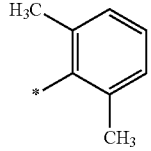

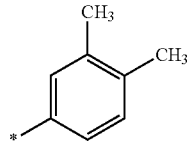

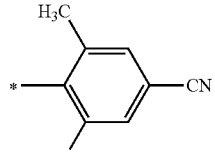

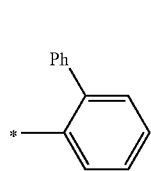

-continued
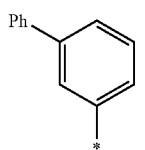
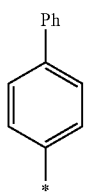
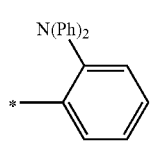
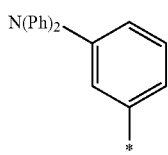
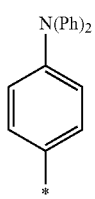
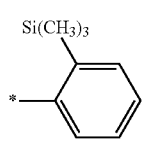
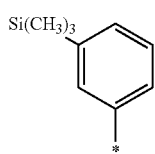
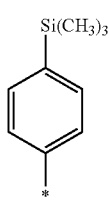
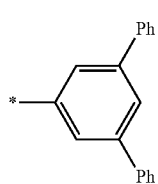
-continued
6-20
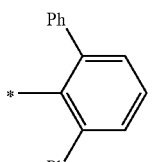
6-21
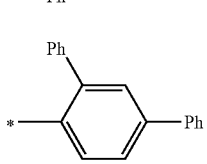
6-22
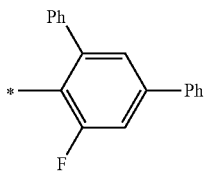
6-23
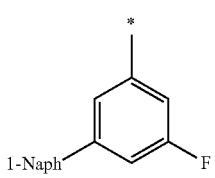
6-24
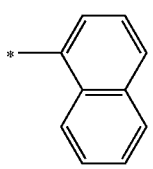
6-25
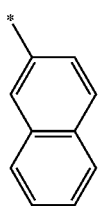
6-26
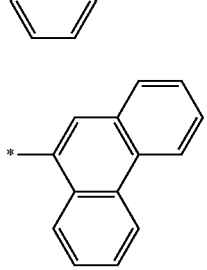
6-27
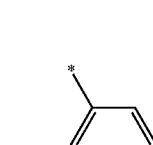
6-28
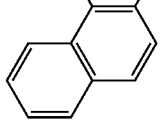
6-29
6-30
6-31
6-32
6-33
6-34
6-35
6-36

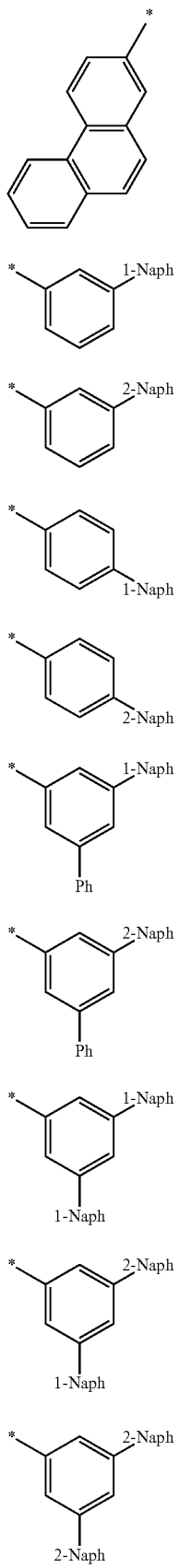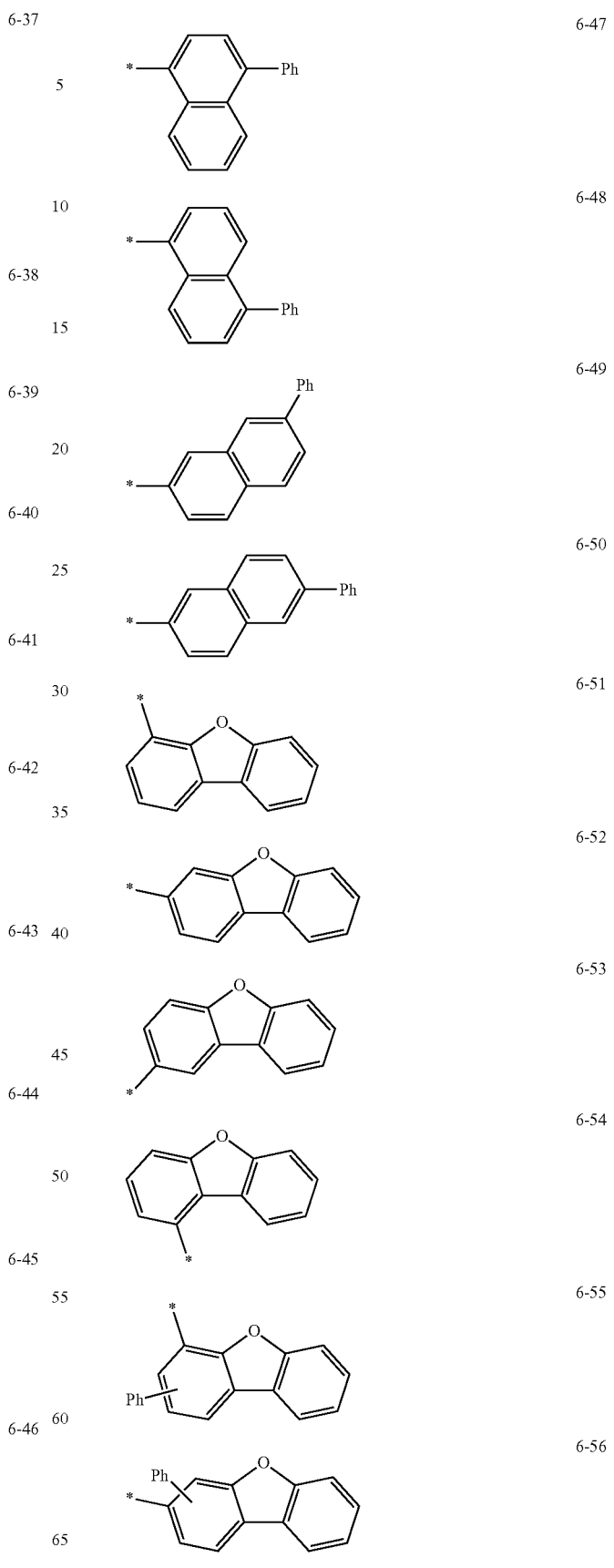

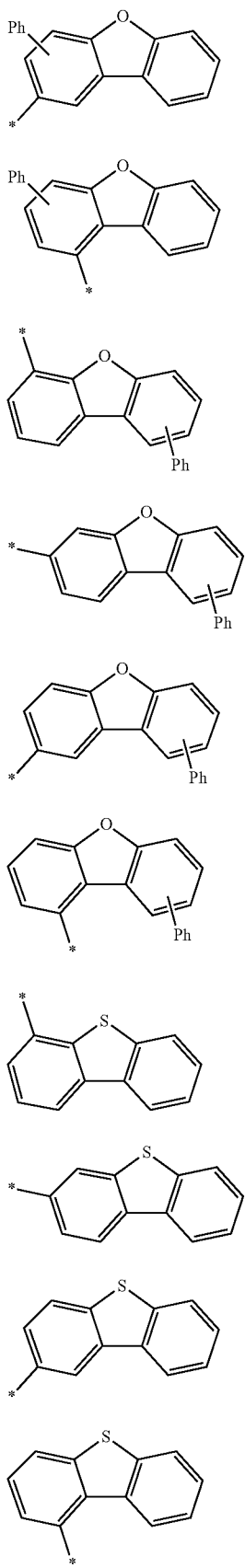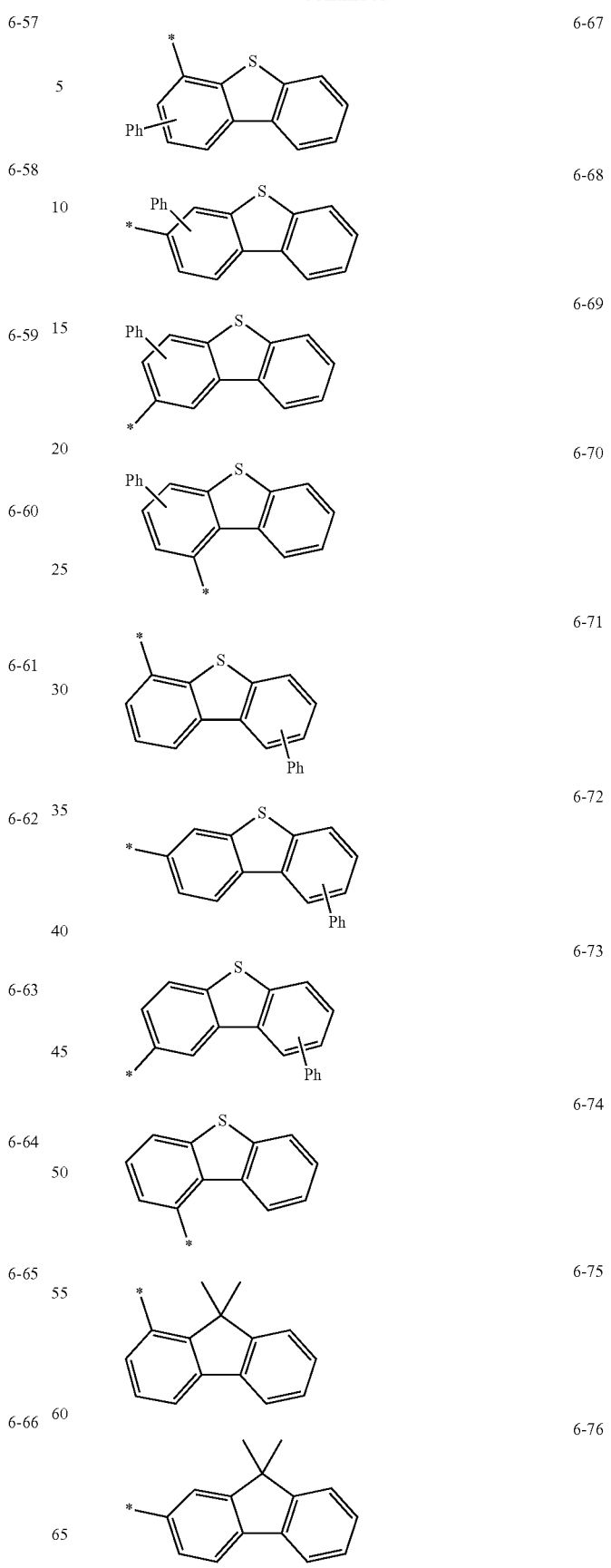

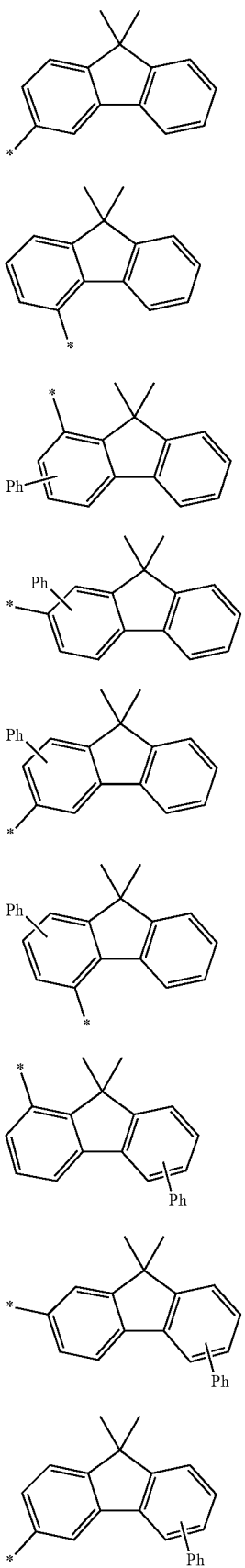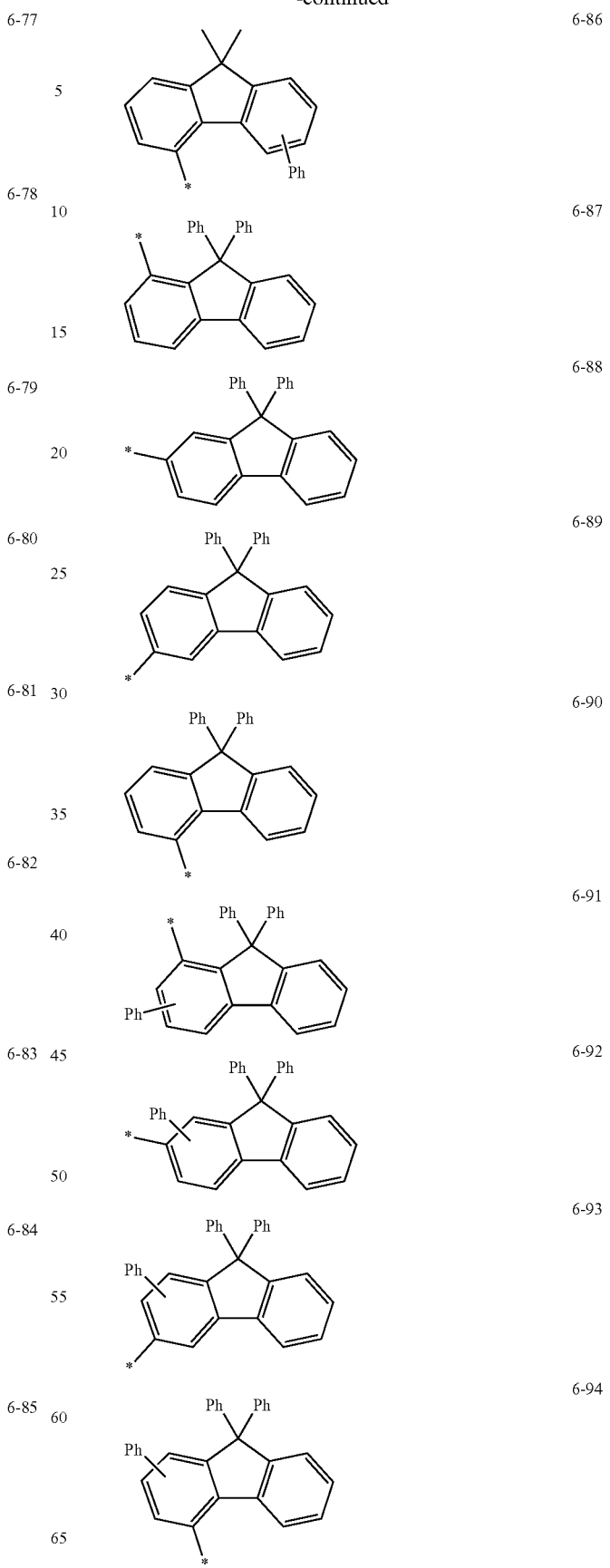

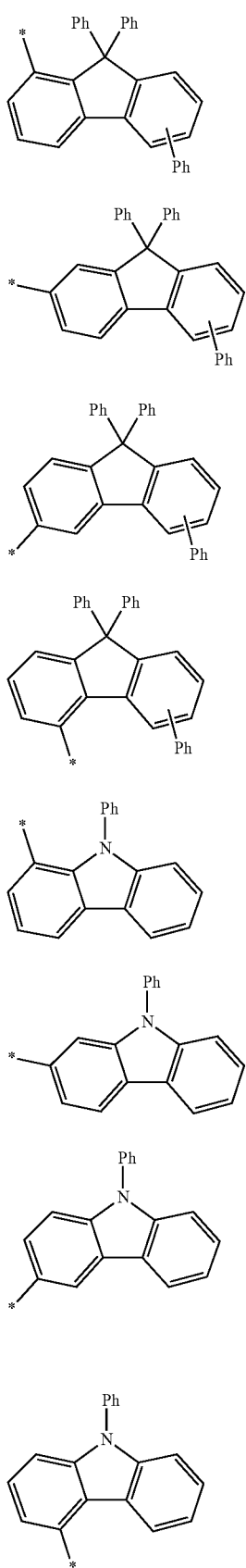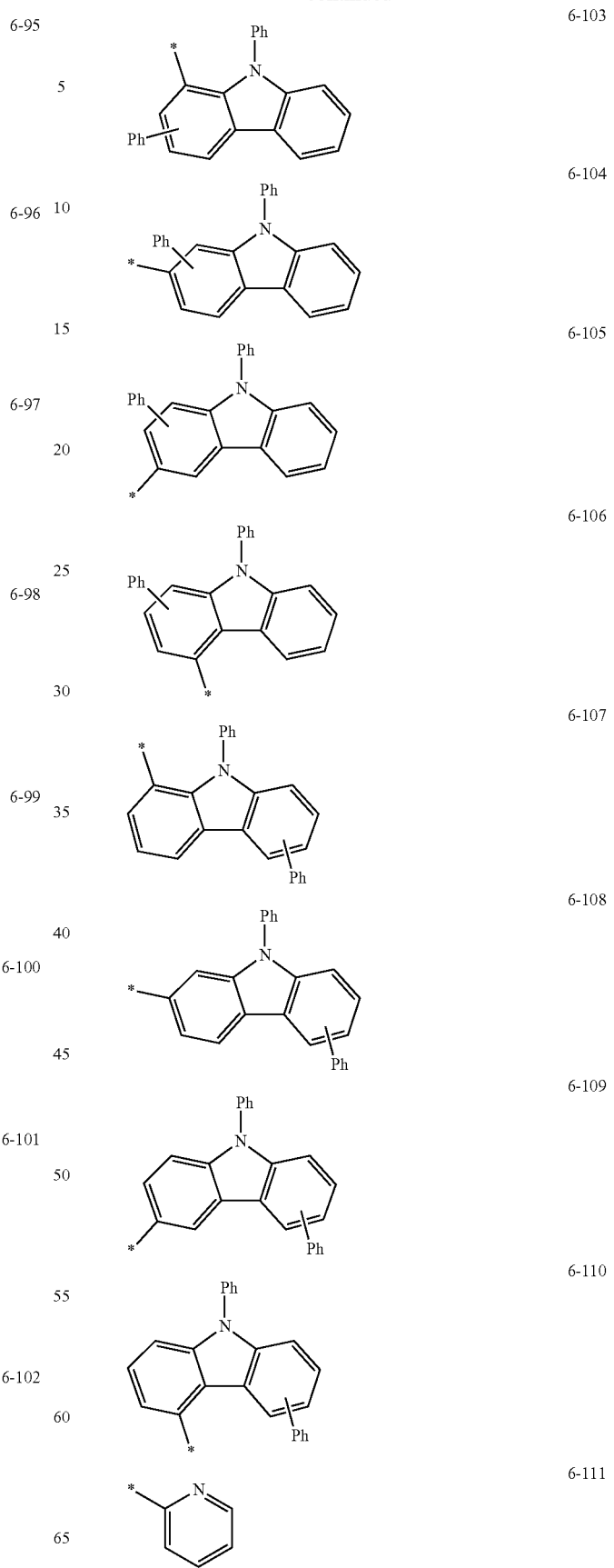

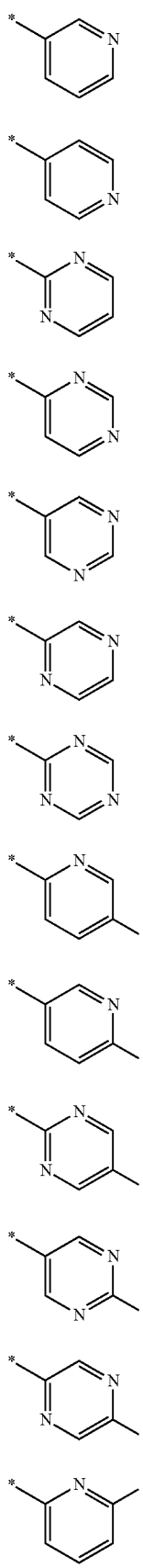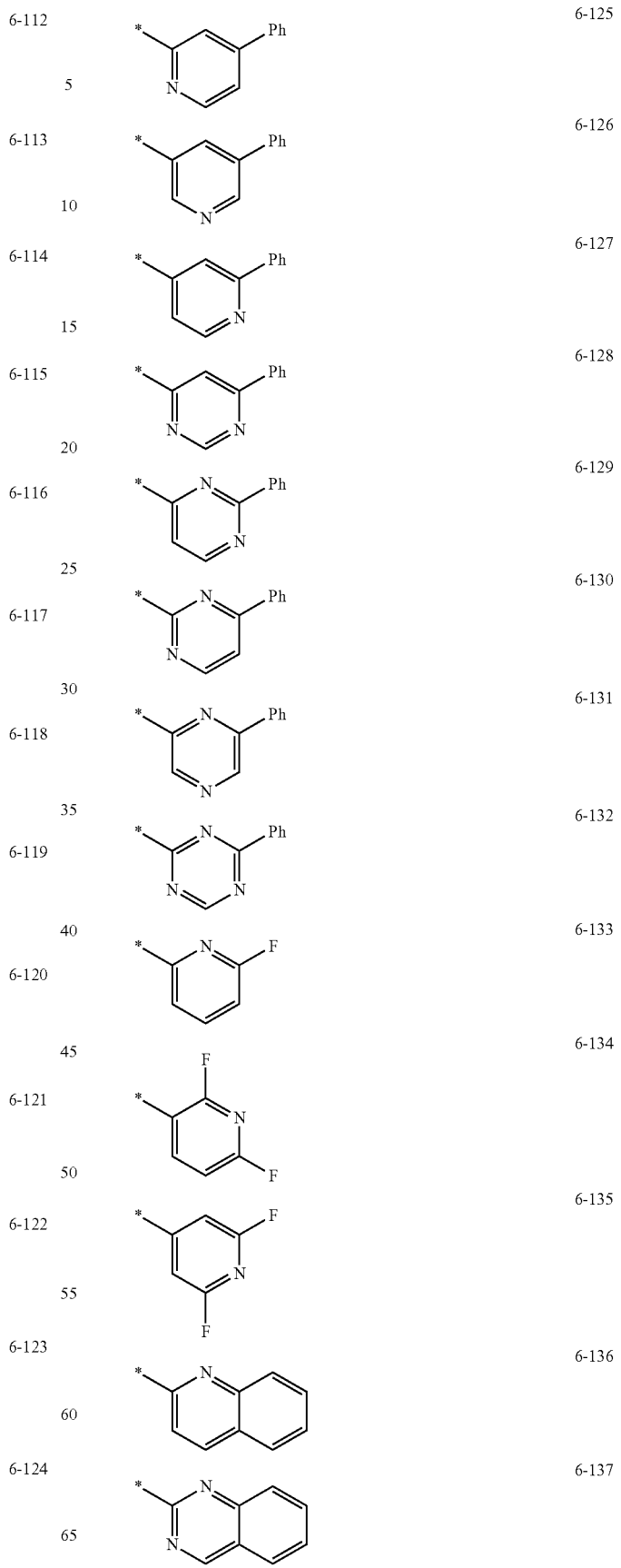

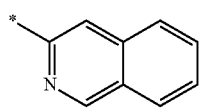
6-138
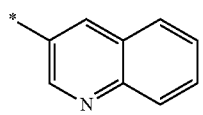
6-139
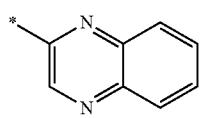
6-140
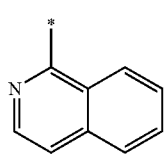
6-141
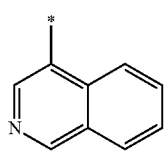
6-142
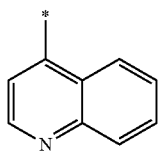
6-143
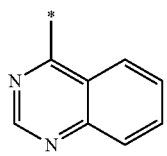
6-144
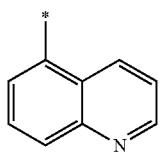
6-145
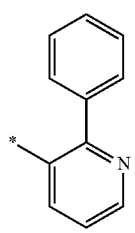
6-146
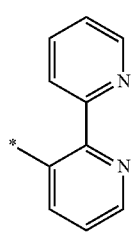
6-147
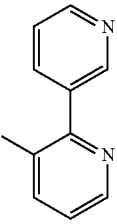
6-148
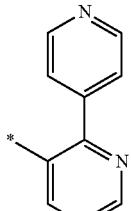
6-149
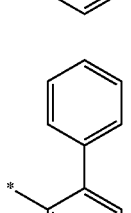
6-150
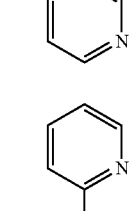
6-151
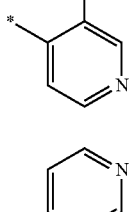
6-152
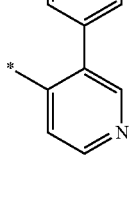
6-153
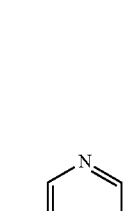

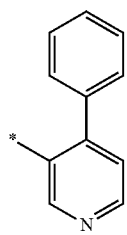
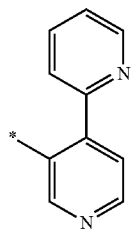
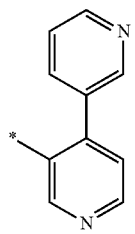
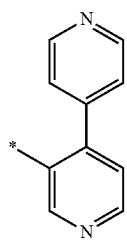
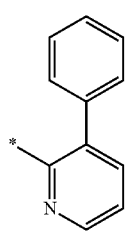
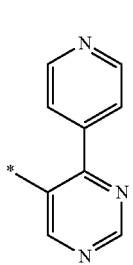
6-154 
6-155 
6-156 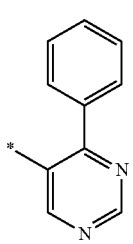
6-157 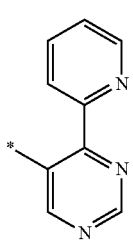
6-158 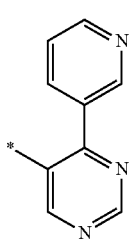
6-159
6-160
6-161
6-162
6-163
6-164
6-165

6-166
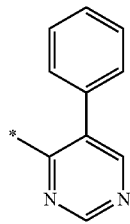
6-167
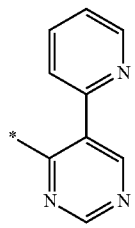
6-168
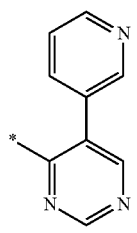
6-169
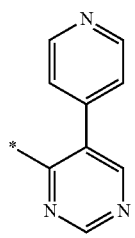
6-170
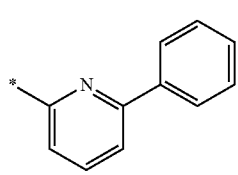
6-171
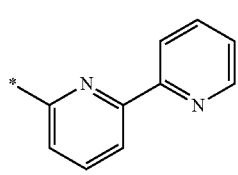
6-172
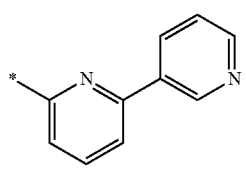
6-173
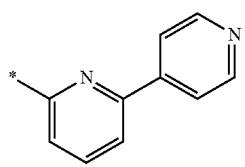
6-174
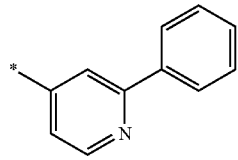
6-175
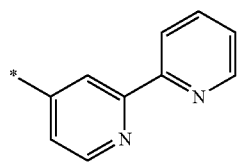
6-176
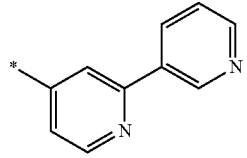
6-177
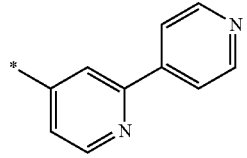
6-178

6-179
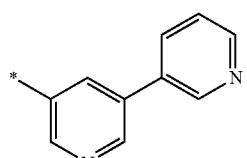
6-180
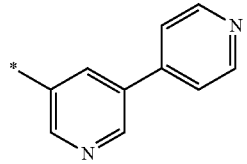
6-181
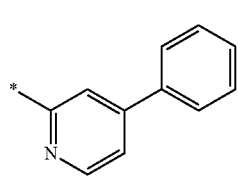
6-182

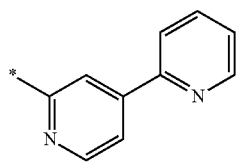
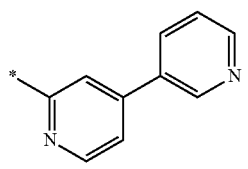
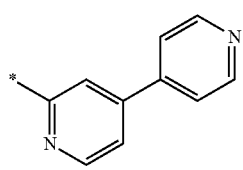
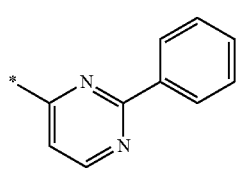
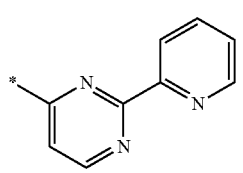

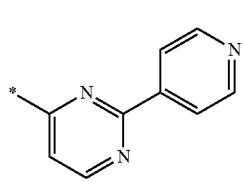

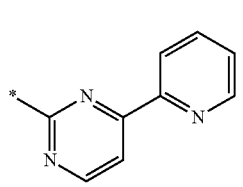
6-183
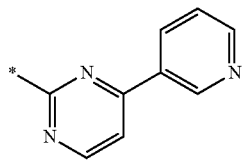
6-184
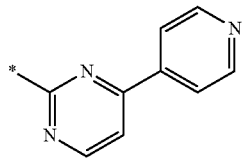
6-185
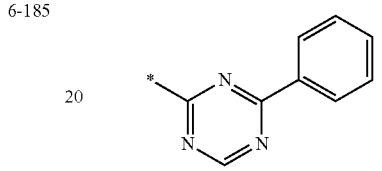
6-186
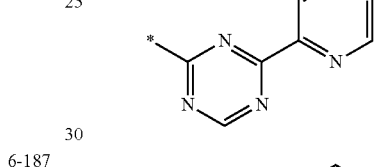
6-187
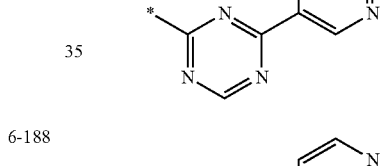
6-188
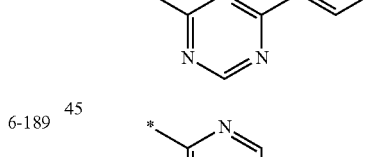
6-189
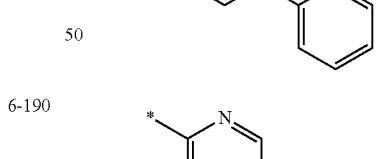
6-190
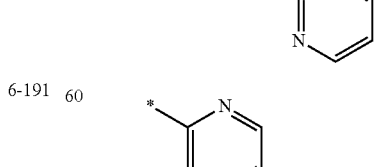
6-191
6-192
6-193
6-194
6-195
6-196
6-197
6-198
6-199
6-200

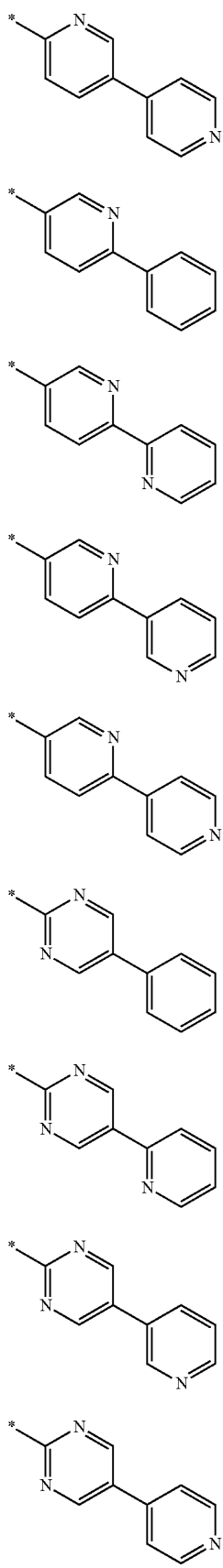
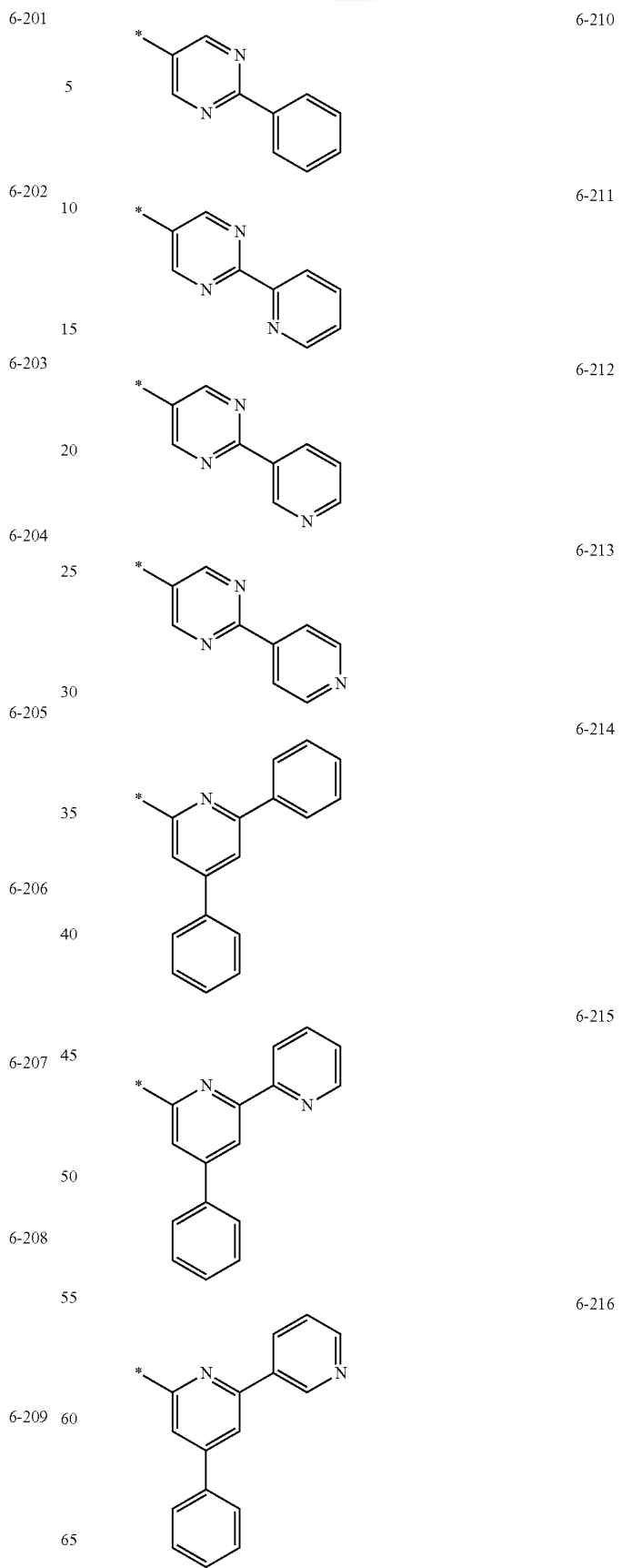

6-217 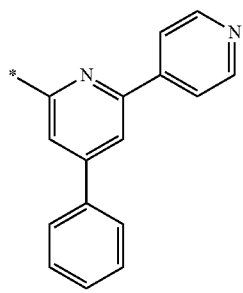
6-218 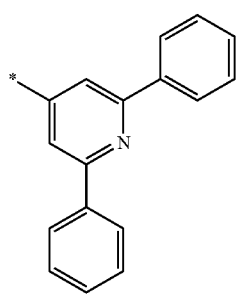
6-219 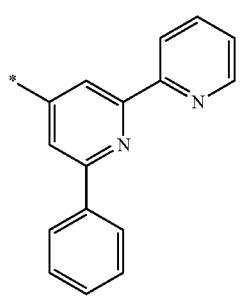
6-220 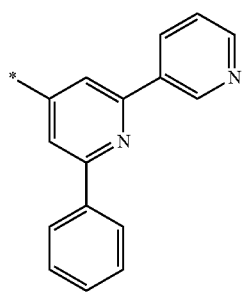
6-221 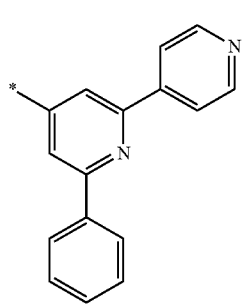
6-222 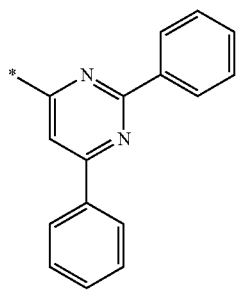
6-223 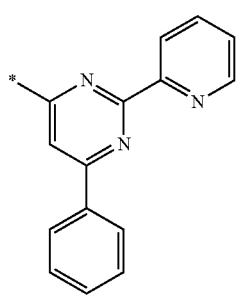
6-224 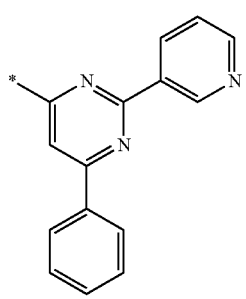
6-225 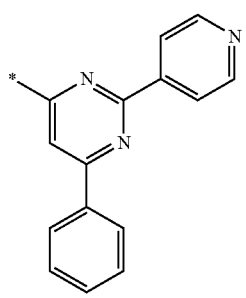
6-226 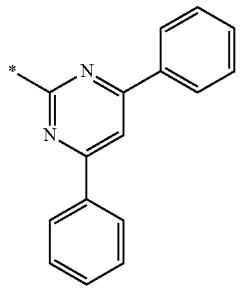

6-227 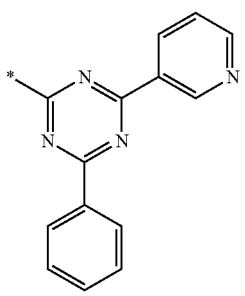
6-228
6-229 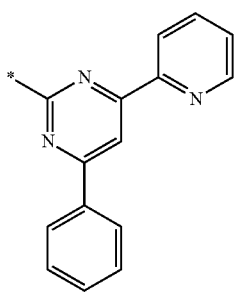
6-230
6-231 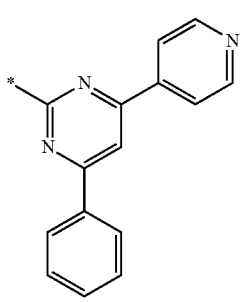
6-232
6-233
6-234 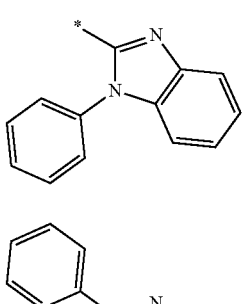
6-235
6-236
6-237
6-238 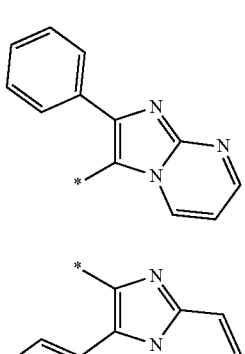

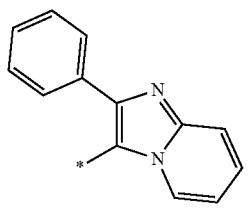
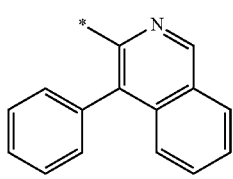
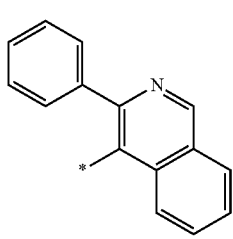
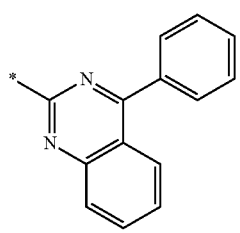

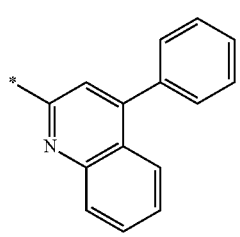
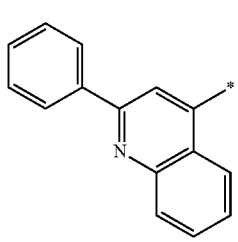
6-239
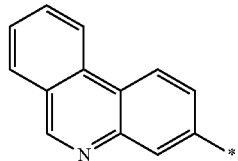
6-240
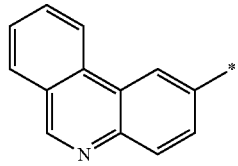
6-241
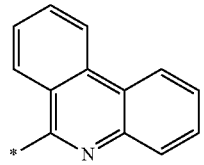
6-242
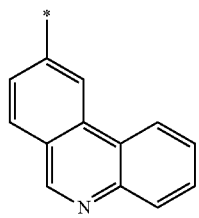
6-243
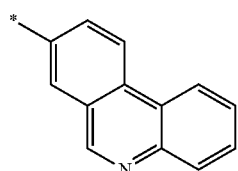
6-244
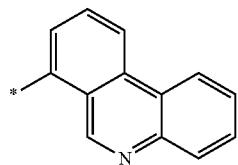
6-245
6-246
6-247
6-248
6-249
6-250
6-251
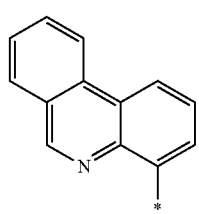
6-252
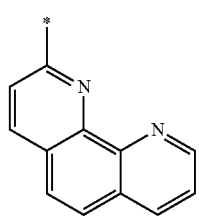
6-253

-continued

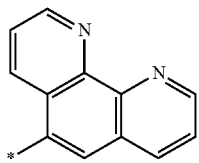
6-254

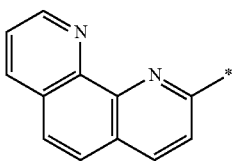
6-255

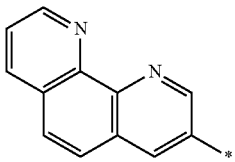
6-256

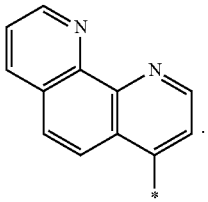
6-257

In Formulae 6-1 to 6-257,
"t-Bu" indicates a tert-butyl group,
"Ph" indicates a phenyl group,
"1-Naph" indicates a 1-naphthyl group,
"2-Naph" indicates a 2-naphthyl group, and
* indicates a binding site to a neighboring atom.

In one embodiment, in Formula 1, $R_{11}$ to $R_{14}$ may each independently be selected from a group represented by Formula 2 and groups represented by Formulae 6-1 to 6-110, but embodiments of the present disclosure are not limited thereto.

In Formulae 1 and 2, $R_{15}$, $R_{16}$, and $R_{21}$ to $R_{23}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), and $Q_1$ to $Q_3$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a $C_1$-$C_{60}$ alkyl group substituted with at least one selected from deuterium, —F, and a cyano group, a $C_6$-$C_{60}$ aryl group substituted with at least one selected from deuterium, —F, and a cyano group, a biphenyl group, and a terphenyl group.

For example, in Formulae 1 and 2, $R_{15}$, $R_{16}$, and $R_{21}$ to $R_{23}$ may each independently be selected from:
hydrogen, deuterium, —F, —Cl, —Br, —I, a cyano group, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one selected from deuterium, —F, —Cl, —Br, —I, a cyano group, a phenyl group, and a biphenyl group;
a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group, each substituted with at least one selected from deuterium, —F, —Cl, —Br, —I, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, an indolocarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)($Q_{31}$), —S(=O)$_2$($Q_{31}$), —P(=O)($Q_{31}$)($Q_{32}$), and —P(=S)($Q_{31}$)($Q_{32}$); and —Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), and $Q_1$ to $Q_3$ and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, but embodiments of the present disclosure are not limited thereto.

In one embodiment, in Formulae 1 and 2, $R_{15}$, $R_{16}$, and $R_{21}$ to $R_{23}$ may each independently be selected from:
hydrogen, deuterium, —F, —Cl, —Br, —I, a cyano group, and a $C_1$-$C_{20}$ alkyl group;
a $C_1$-$C_{20}$ alkyl group substituted with at least one selected from deuterium, —F, —Cl, —Br, —I, and a cyano group;
groups represented by Formulae 5-1 to 5-138; and
—Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), but embodiments of the present disclosure are not limited thereto.

In one embodiment, in Formulae 1 and 2, $R_{15}$, $R_{16}$, and $R_{21}$ to $R_{23}$ may each independently be selected from:
hydrogen, deuterium, —F, —Cl, —Br, —I, a cyano group, a methyl group, an ethyl group, an n-propyl group, an isopropyl group, an n-butyl group, an isobutyl group, a sec-butyl group, and a tert-butyl group;

a methyl group, an ethyl group, an n-propyl group, an isopropyl group, an n-butyl group, an isobutyl group, a sec-butyl group, and a tert-butyl group, each substituted with at least one selected from deuterium, —F, —Cl, —Br, —I, and a cyano group; and groups represented by Formulae 6-1 to 6-257, but embodiments of the present disclosure are not limited thereto.

In one embodiment, in Formulae 1 and 2, $R_{15}$, $R_{16}$, $R_{22}$, and $R_{23}$ may each independently be selected from:

hydrogen, deuterium, —F, —Cl, —Br, —I, a cyano group, a methyl group, an ethyl group, an n-propyl group, an isopropyl group, an n-butyl group, an isobutyl group, a sec-butyl group, and a tert-butyl group; and a methyl group, an ethyl group, an n-propyl group, an isopropyl group, an n-butyl group, an isobutyl group, a sec-butyl group, and a tert-butyl group, each substituted with at least one selected from deuterium, —F, —Cl, —Br, —I and a cyano group, but embodiments of the present disclosure are not limited thereto.

In Formula 1, b15 indicates the number of substituent(s) for $R_{15}$, and may be selected from 1, 2, 3, 4, 5, and 6.

In Formula 1, b16 indicates the number of substituent(s) for $R_{16}$, and may be selected from 1, 2, 3, and 4.

In Formula 2, b22 indicates the number of substituent(s) for $R_{22}$, and may be selected from 1, 2, and 3.

In Formula 2, b23 indicates the number of substituent(s) for $R_{23}$, and may be selected from 1, 2, 3, and 4.

In one embodiment, the diamine compound represented by Formula 1 may be represented by one selected from Formulae 1-1 and 1-2, but embodiments of the present disclosure are not limited thereto:

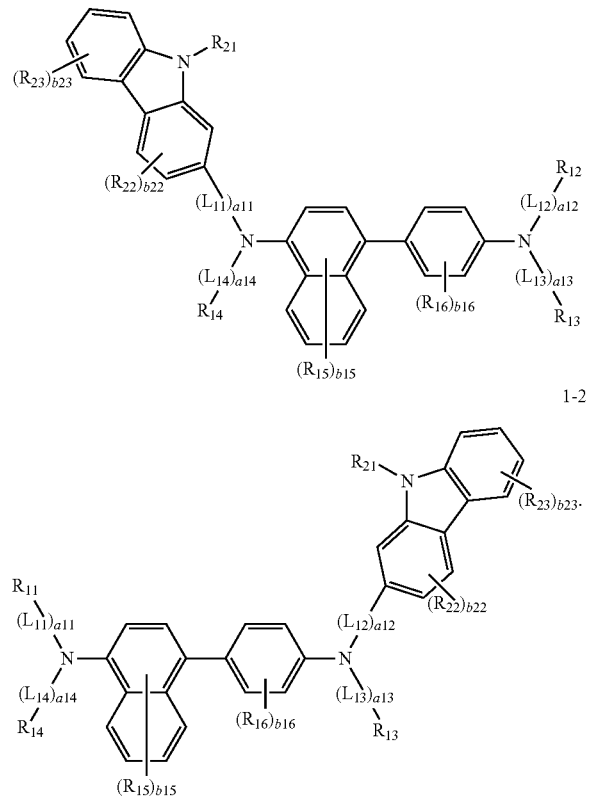

In Formulae 1-1 and 1-2, $L_{11}$ to $L_{14}$, a11 to a14, $R_{15}$, $R_{16}$, b15, and b16 may respectively be the same as described in Formula 1, $R_{21}$ to $R_{23}$, b22, and b23 may respectively be the same as described in Formula 2, and $R_{11}$ to $R_{14}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In one or more embodiments, the diamine compound represented by Formula 1 may be represented by one selected from Formulae 1-11 and 1-12, but embodiments of the present disclosure are not limited thereto:

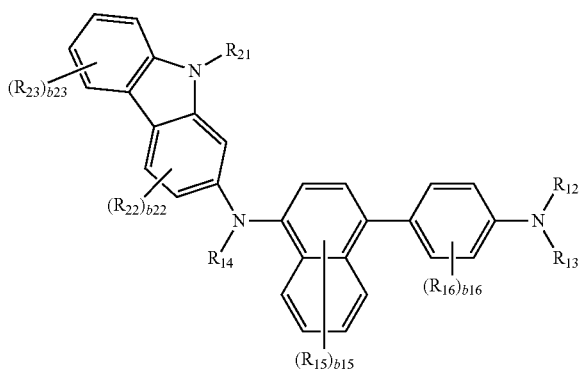

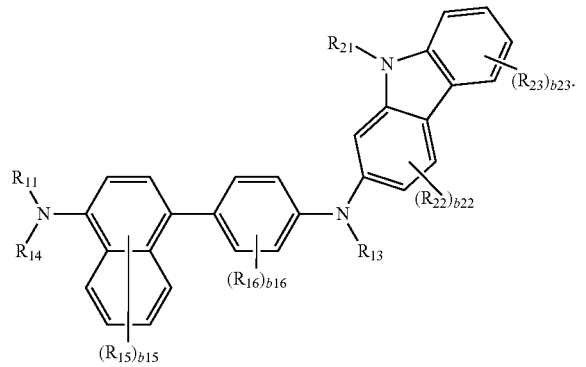

In Formulae 1-11 and 1-12, $R_{15}$, $R_{16}$, b15, and b16 may respectively be the same as described in Formula 1, $R_{21}$ to $R_{23}$, b22, and b23 may respectively be the same as described in Formula 2, and $R_{11}$ to $R_{14}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formulae 1-11 and 1-12, $R_{15}$, $R_{16}$, $R_{22}$, and $R_{23}$ may each independently be selected from:

hydrogen, deuterium, —F, —Cl, —Br, —I, a cyano group, a methyl group, an ethyl group, an n-propyl group, an isopropyl group, an n-butyl group, an isobutyl group, a sec-butyl group, and a tert-butyl group; and a methyl group, an ethyl group, an n-propyl group, an isopropyl group, an n-butyl group, an isobutyl group, a sec-butyl group, and a tert-butyl group, each substituted with at least one selected from deuterium, —F, —Cl, —Br, —I and a cyano group, but embodiments of the present disclosure are not limited thereto.

In more detail, the diamine compound represented by Formula 1 may be selected from Compounds 145 to 176, but embodiments of the present disclosure are not limited thereto:

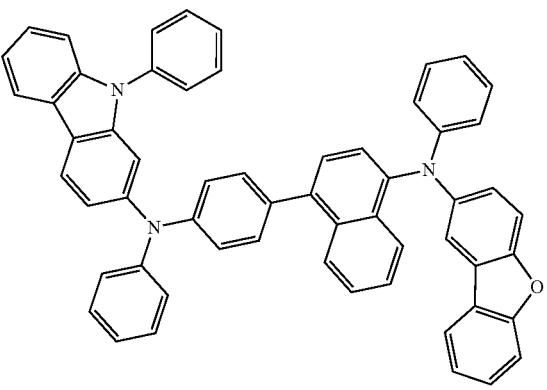

147

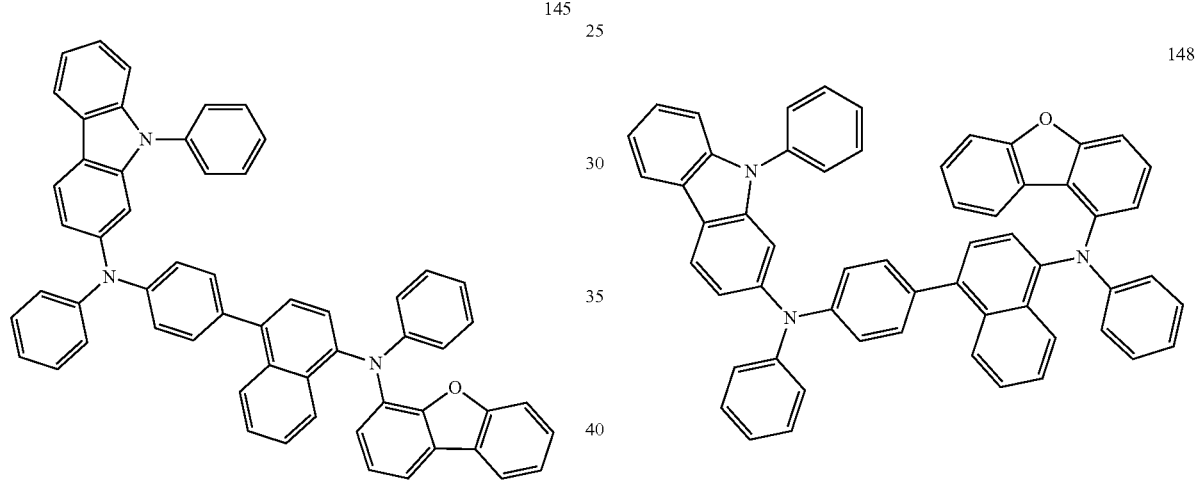

145

148

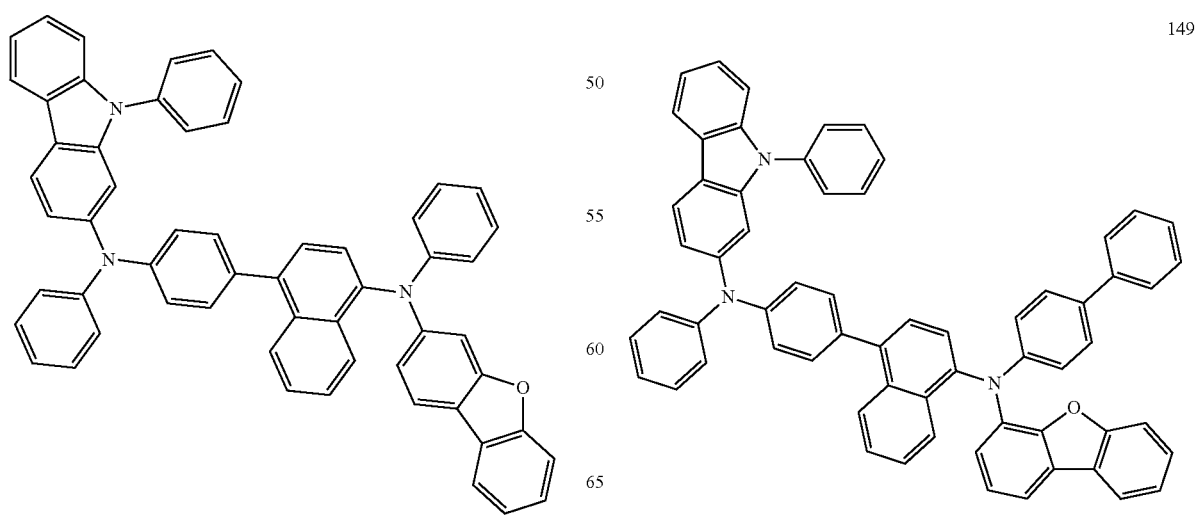

146

149

150
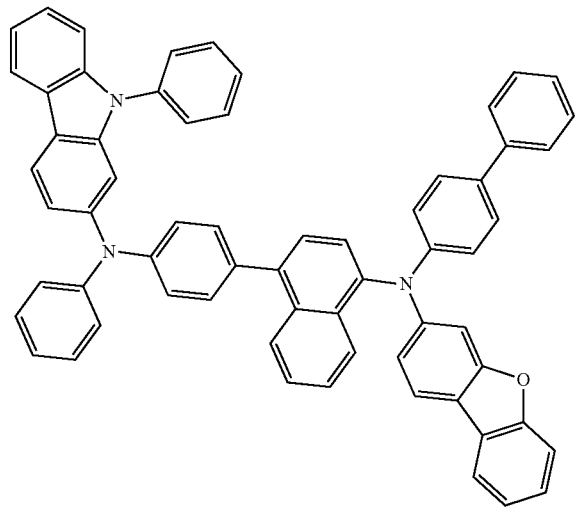
151
153
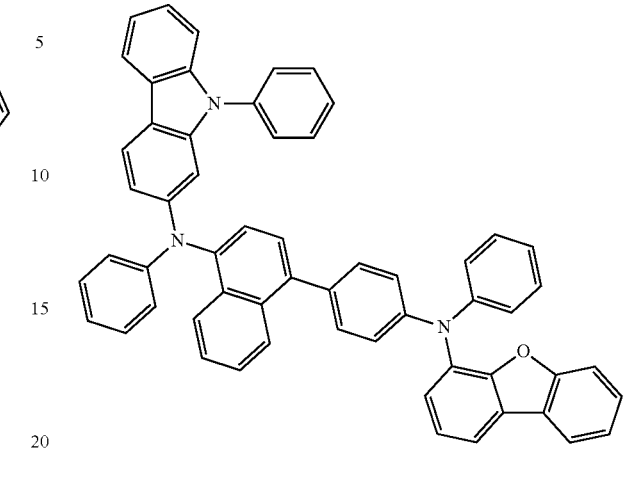
154
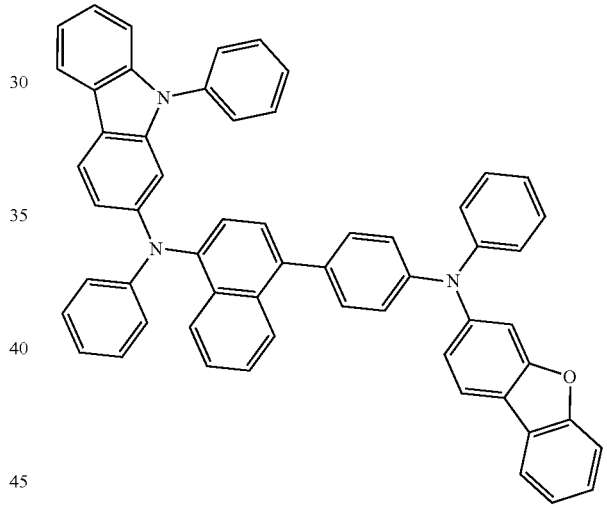
152
155
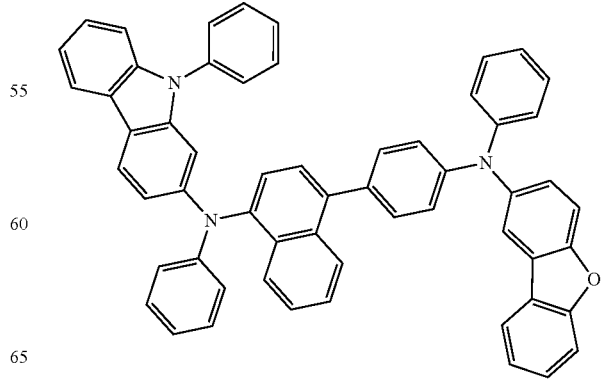

156
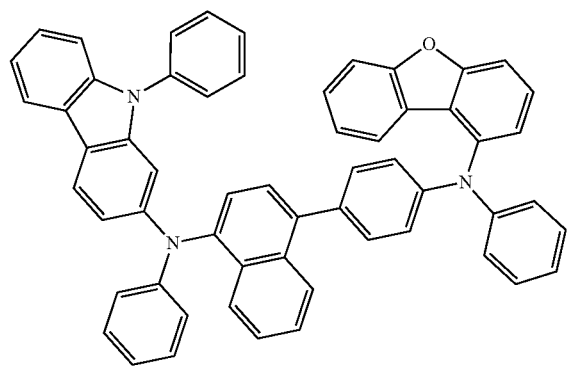
157
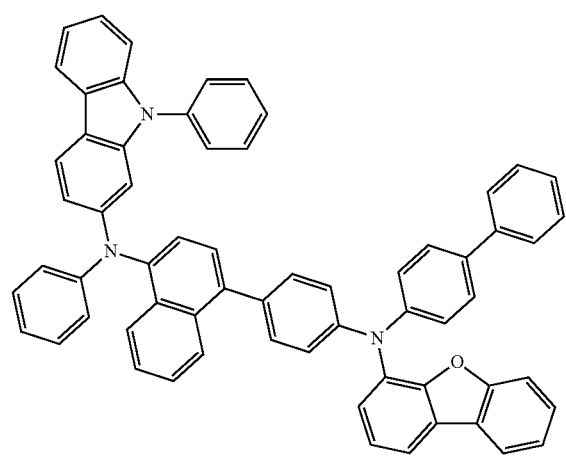
158
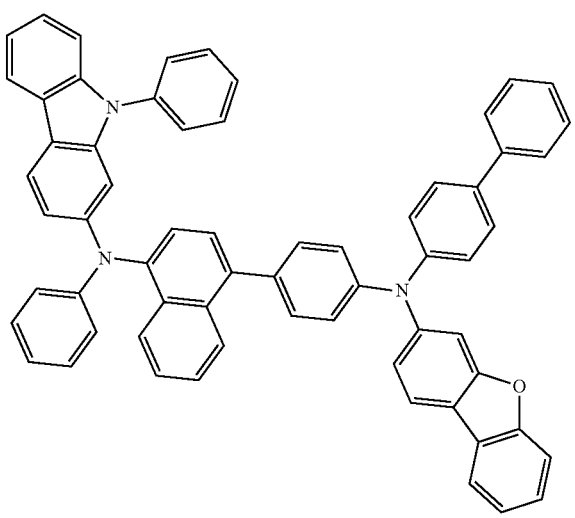
159
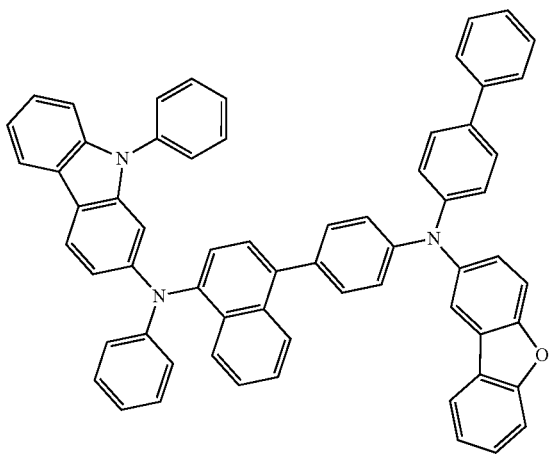
160
161
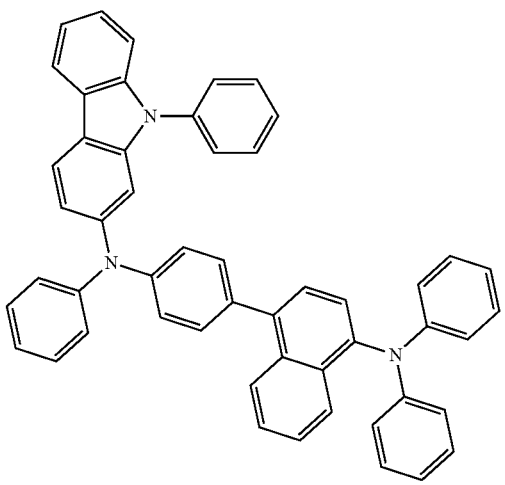

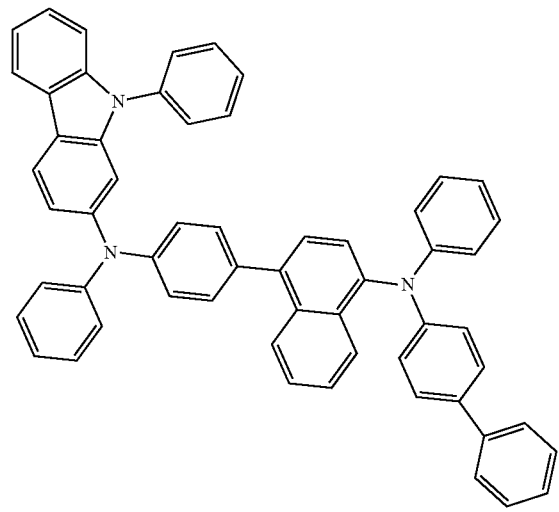
162
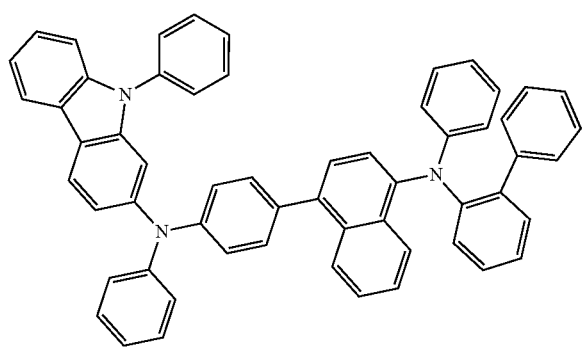
163
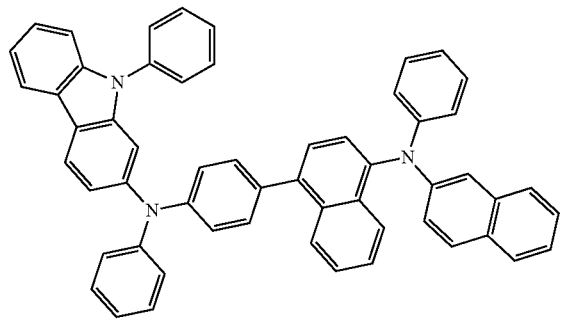
164
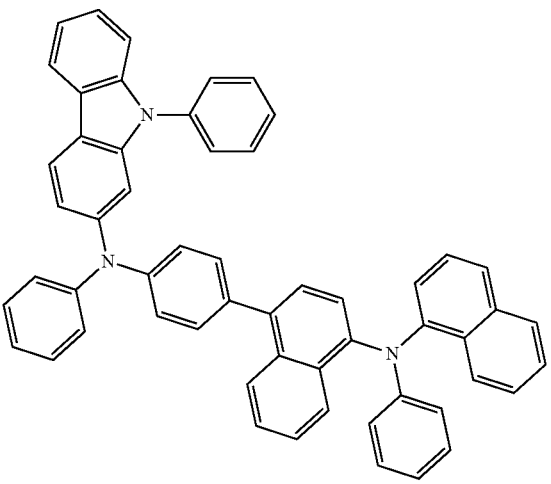
165
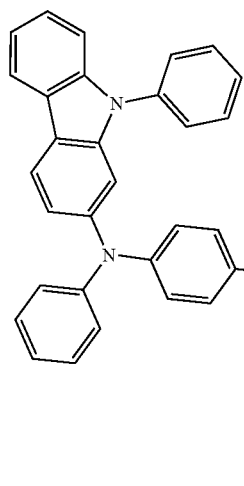
166
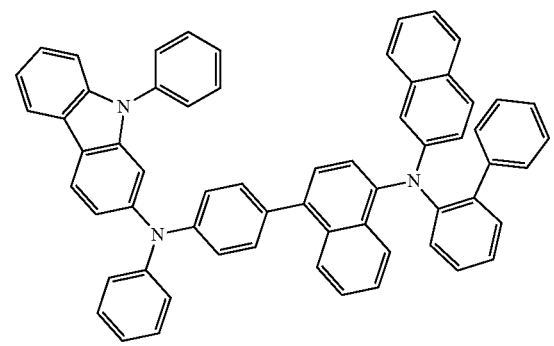
167

168
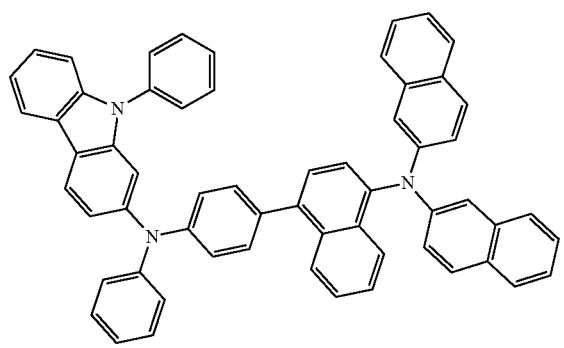
169
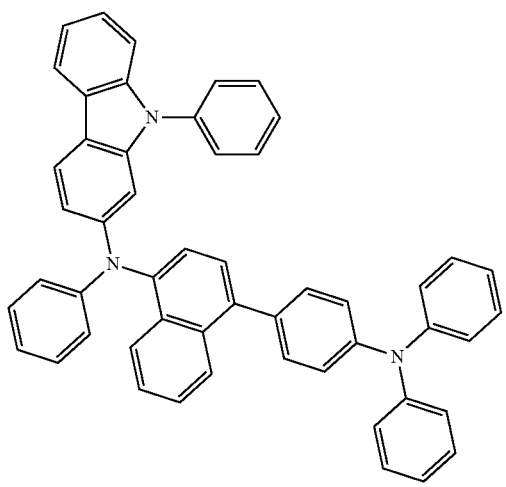
170
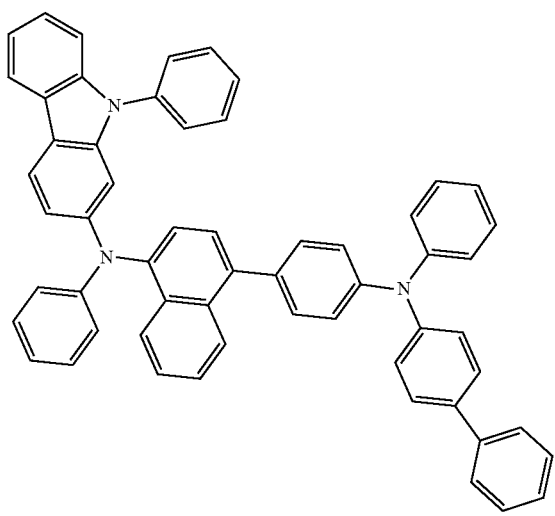
171
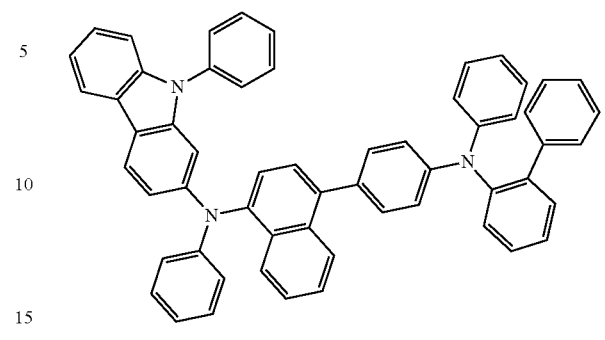
172
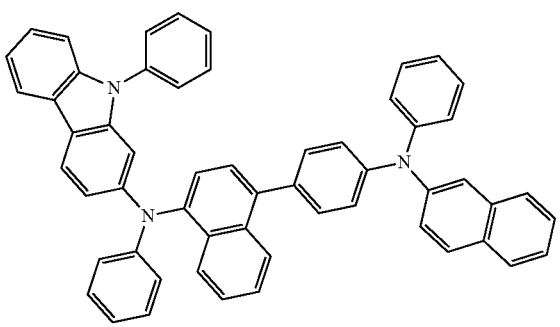
173
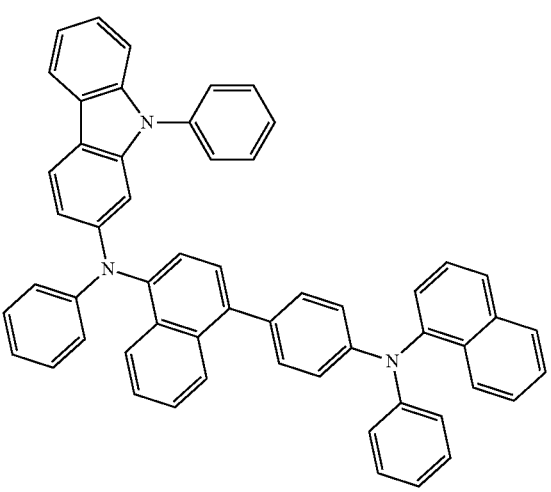

-continued

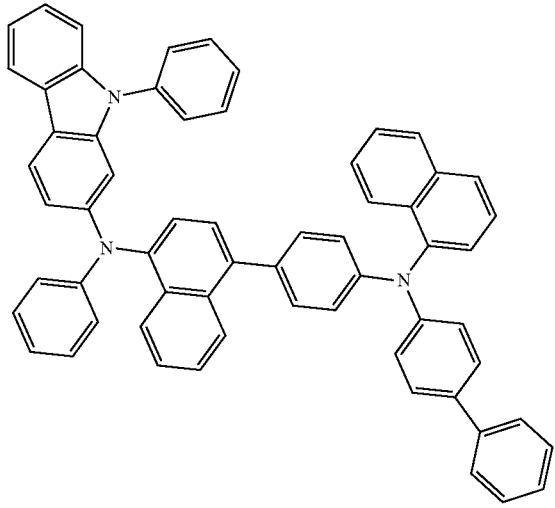

174

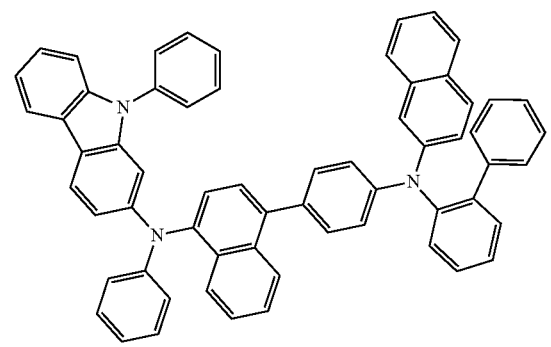

175

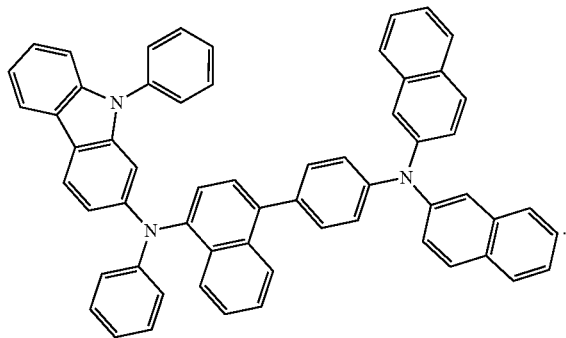

176

While the present disclosure is not limited by any particular mechanism or theory, it is believed that since the diamine compound represented by Formula 1 essentially includes the 2-carbazolyl group, the glass transition temperature and/or the melting point of the diamine compound may be improved. Therefore, an organic light-emitting device including the diamine compound represented by Formula 1 may exhibit long lifespan characteristics, improved storage stability, and/or improved reliability.

In addition, it is believed that since the diamine compound represented by Formula 1 essentially includes the 2-carbazolyl group, the hole injection and/or the mobility of the diamine compound are improved. Therefore, the light-emitting region of the organic light-emitting device including the diamine compound may be widened, thereby delaying or reducing the deterioration of the organic light-emitting device.

Additionally, it is believed that since the diamine compound represented by Formula 1 includes the naphthyl-phenyl linker, a plane including two amino groups as a substrate may have a tilted structure. Therefore, when the diamine compound is deposited, the diamine compound tends to be densely stacked, thereby improving charge mobility. Therefore, the organic light-emitting device including the diamine compound represented by Formula 1 may have low driving voltage and high efficiency characteristics.

The diamine compound represented by Formula 1 may be synthesized by using any suitable organic synthesis method available in the art. Methods of synthesizing the diamine compound may be readily recognized by those of skill in the art by referring to Examples provided below.

The diamine compound represented by Formula 1 may be used between a pair of electrodes of an organic light-emitting device.

The expression "(an organic layer) includes at least one diamine compound," as used herein, may include a case in which "(an organic layer) includes identical diamine compound represented by Formula 1" and a case in which "(an organic layer) includes two or more different diamine compounds represented by Formula 1".

For example, the organic layer may include, as the diamine compound, Compound 1 only. In this regard, Compound 1 may exist in a hole transport layer of the organic light-emitting device. In one or more embodiments, the organic layer may include, as the diamine compound, Compound 1 and Compound 2. In one or more embodiments, Compound 1 and Compound 2 may both exist in an identical layer (for example, Compound 1 and Compound 2 may both exist in a hole transport layer), or may exist in different layers (for example, Compound 1 may exist in a hole transport layer and Compound 2 may exist in a hole injection layer).

The organic layer includes i) a hole transport region that is disposed between the first electrode (anode) and the emission layer and includes at least one of a hole injection layer, a hole transport layer, a buffer layer, and an electron blocking layer, and ii) an electron transport region that is disposed between the emission layer and the second electrode (cathode) and includes at least one selected from a hole blocking layer, an electron transport layer, and an electron injection layer. For example, the hole transport region of the organic light-emitting device may include at least one of the diamine compound represented by Formula 1.

The term "organic layer," as used herein, refers to a single layer and/or a plurality of layers disposed between the first electrode and the second electrode of the organic light-emitting device. A material included in the "organic layer" is not limited to an organic material. For example, the organic layer may include an inorganic material in addition to an organic material.

Description of FIG. 1

FIG. 1 is a schematic view of an organic light-emitting device 10 according to an embodiment. The organic light-emitting device 10 includes a first electrode 110, an organic layer 150, and a second electrode 190.

Hereinafter, the structure of the organic light-emitting device 10 according to an embodiment and a method of manufacturing the organic light-emitting device 10 will be described in connection with FIG. 1.

First Electrode 110

In FIG. 1, a substrate may be additionally disposed under the first electrode 110 or above the second electrode 190. The substrate may be a glass substrate or a plastic substrate, each having excellent mechanical strength, thermal stability, transparency, surface smoothness, ease of handling, and water resistance.

The first electrode 110 may be formed by depositing or sputtering a material for forming the first electrode 110 on the substrate. When the first electrode 110 is an anode, the material for a first electrode may be selected from materials having a high work function to facilitate hole injection.

The first electrode 110 may be a reflective electrode, a semi-transmissive electrode, or a transmissive electrode. When the first electrode 110 is a transmissive electrode, a material for forming a first electrode may be selected from indium tin oxide (ITO), indium zinc oxide (IZO), tin oxide ($SnO_2$), zinc oxide (ZnO), and any combinations thereof, but embodiments of the present disclosure are not limited thereto. In one or more embodiments, when the first electrode 110 is a semi-transmissive electrode or a reflectable electrode, a material for forming a first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments of the present disclosure are not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

Organic Layer 150

The organic layer 150 is disposed on the first electrode 110. The organic layer 150 may include an emission layer.

The organic layer 150 may further include a hole transport region between the first electrode 110 and the emission layer, and an electron transport region between the emission layer and the second electrode 190.

Hole Transport Region in Organic Layer 150

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer, a hole transport layer, an emission auxiliary layer, and an electron blocking layer.

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein for each structure, constituting layers are sequentially stacked from the first electrode 110 in this stated order, but the structure of the hole transport region is not limited thereto.

The electron transport region may further include the diamine compound.

The hole transport region may further include, in addition to the diamine compound, at least one selected from TDATA, 2-TNATA, NPB(NPD), 13-NPB, TPD, Spiro-TPD, Spiro-NPB, methylated-NPB, TAPC, HMTPD, 4,4',4"-tris (N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201, and a compound represented by Formula 202:

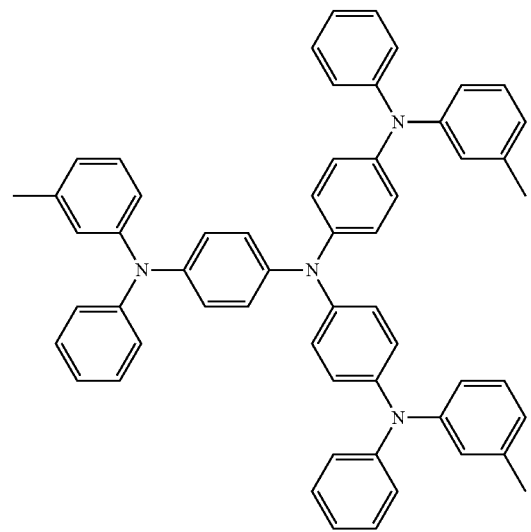

m-MTDATA

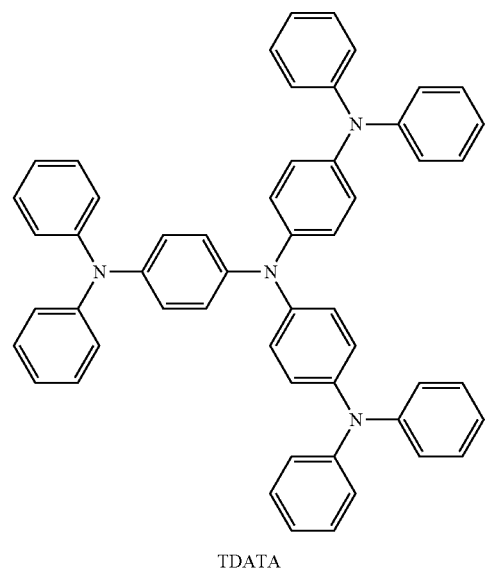

TDATA

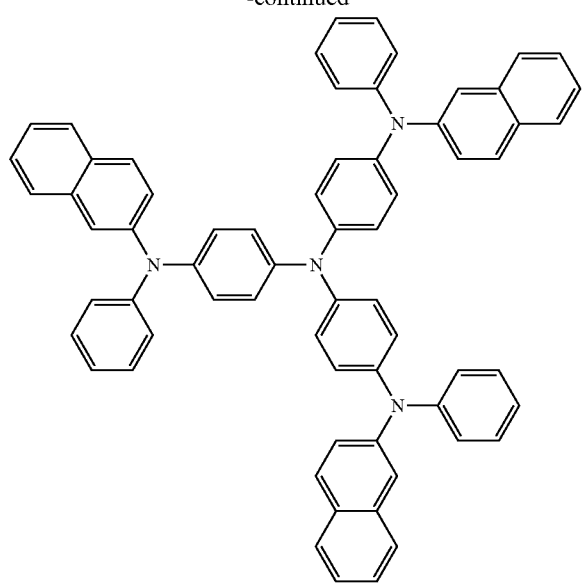
2-TNATA
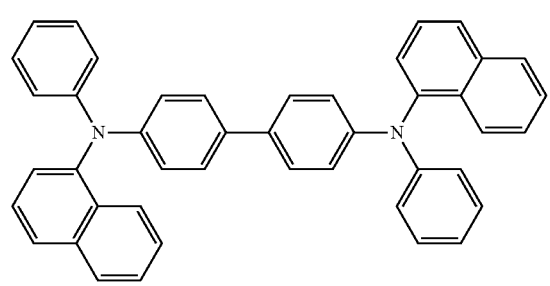
NPB
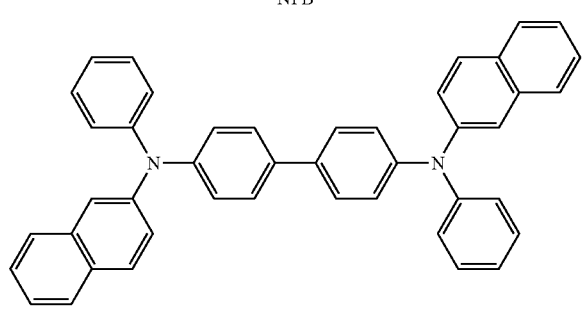
β-NPB
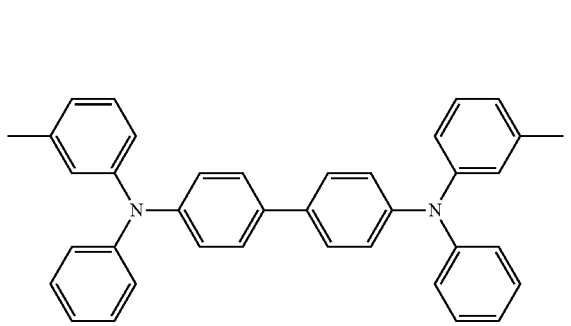
TPD
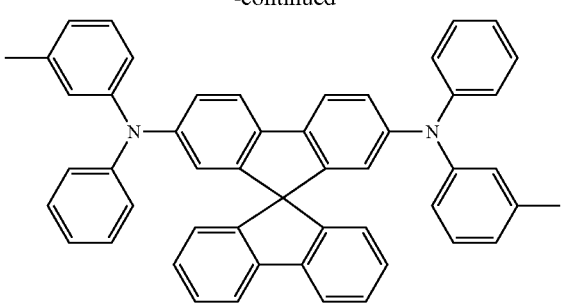
Spiro-TPD
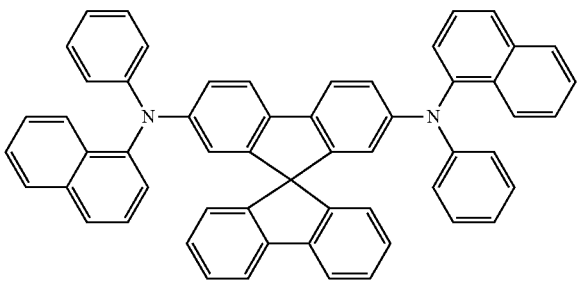
Spiro-NPB
methylated NPB
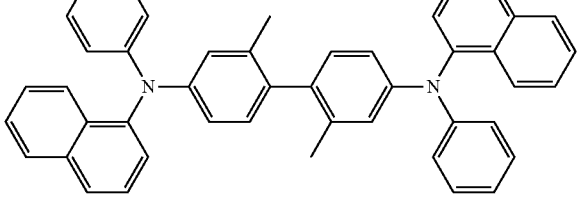
TAPC
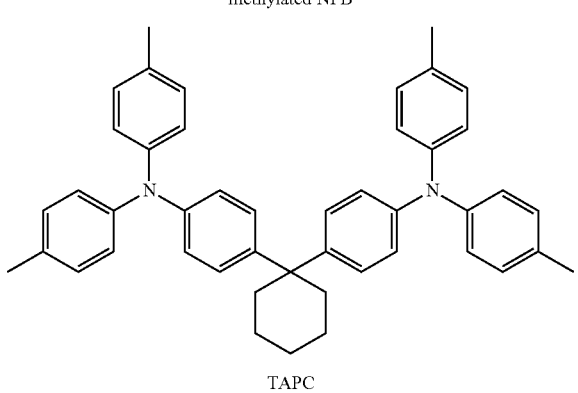
HMTPD

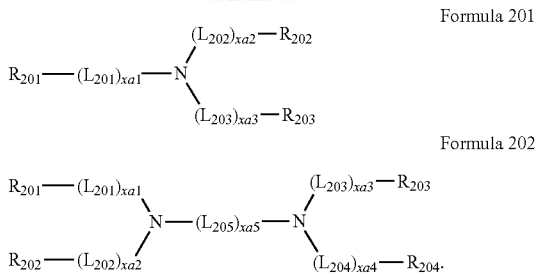

Formula 201

Formula 202

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

$L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer of 0 to 3, xa5 may be an integer of 1 to 10, and $R_{201}$ to $R_{204}$ and $Q_{201}$ may each independently a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In one embodiment, in Formula 202, $R_{201}$ and $R_{202}$ may optionally be linked via a single bond, a dimethyl-methylene group, or a diphenyl-methylene group, and $R_{203}$ and $R_{204}$ may optionally be linked via a single bond, a dimethyl-methylene group, or a diphenyl-methylene group.

In one embodiment, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may respectively be the same as described above.

In one or more embodiments, in Formula 201, at least one selected from $R_{201}$ to $R_{203}$ may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

In one or more embodiments, in Formula 202, i) $R_{201}$ and $R_{202}$ may be linked each other via a single bond, and/or ii) $R_{203}$ and $R_{204}$ may be linked each other via a single bond.

In one or more embodiments, in Formula 202, at least one selected from $R_{201}$ to $R_{204}$ may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

The compound represented by Formula 201 may be represented by Formula 201A:

Formula 201A

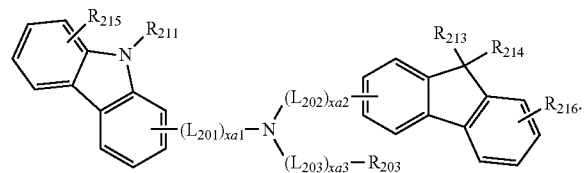

In one embodiment, the compound represented by Formula 201 may be represented by Formula 201A(1) below, but embodiments of the present disclosure are not limited thereto:

Formula 201A(1)

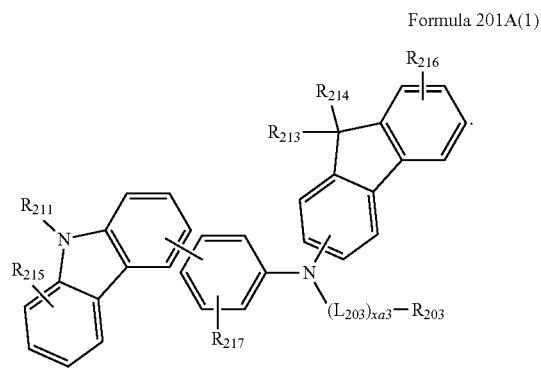

In one embodiment, the compound represented by Formula 201 may be represented by Formula 201A-1 below, but embodiments of the present disclosure are not limited thereto:

Formula 201A-1

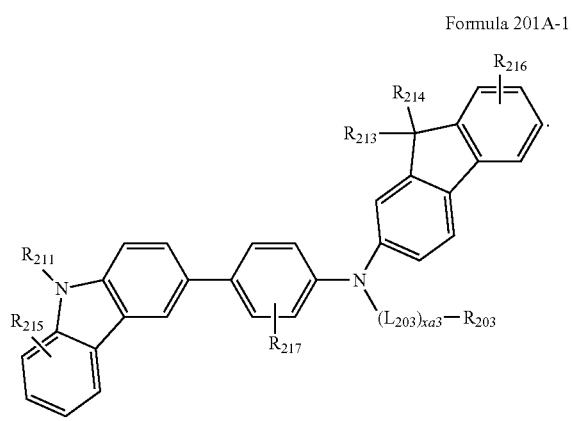

In one embodiment, the compound represented by Formula 202 may be represented by Formula 202A:

Formula 202A

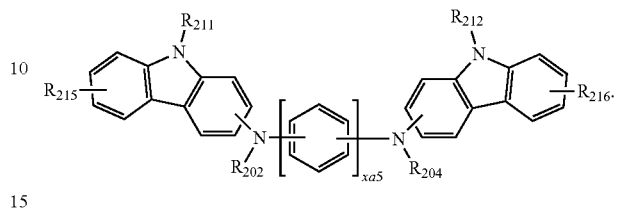

In one or more embodiments, the compound represented by Formula 202 may be represented by Formula 202A-1:

Formula 202A-1

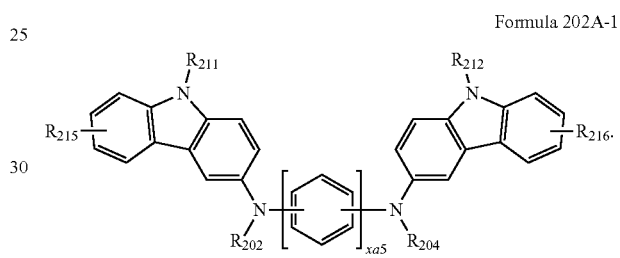

In Formulae 201A, 201A(1), 201A-1, 202A, and 202A-1, $L_{201}$ to $L_{203}$, xa1 to xa3, xa5, and $R_{202}$ to $R_{204}$ may respectively be the same as described above, $R_{211}$ and $R_{212}$ may respectively be the same as described in connection with $R_{203}$, and $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.
The hole transport region may include at least one compound selected from Compounds HT1 to HT39, but embodiments of the present disclosure are not limited thereto:
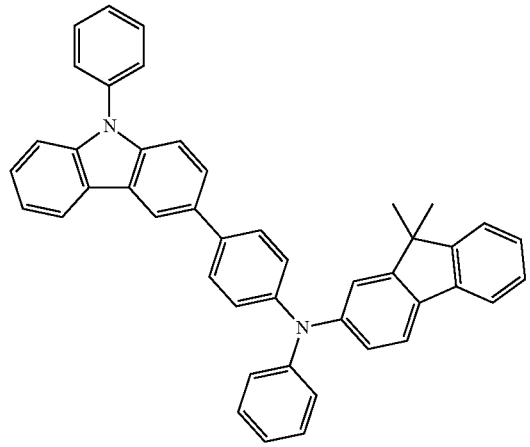
HT1
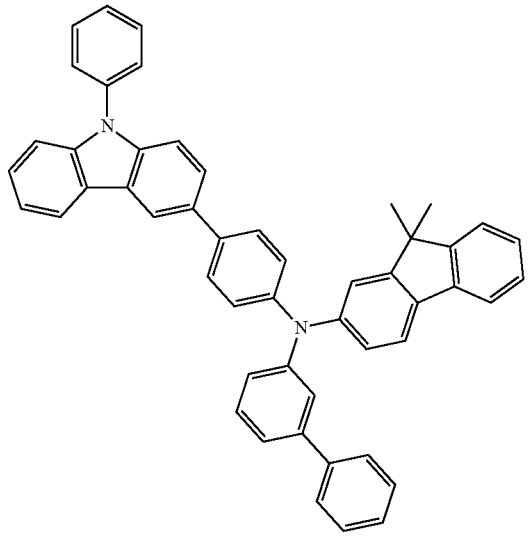
HT2
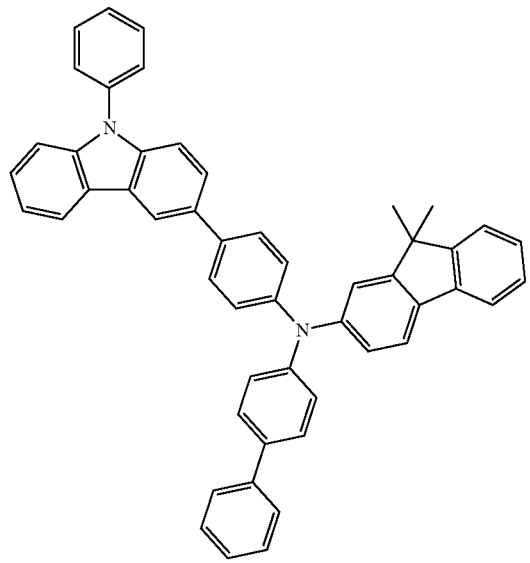
HT3
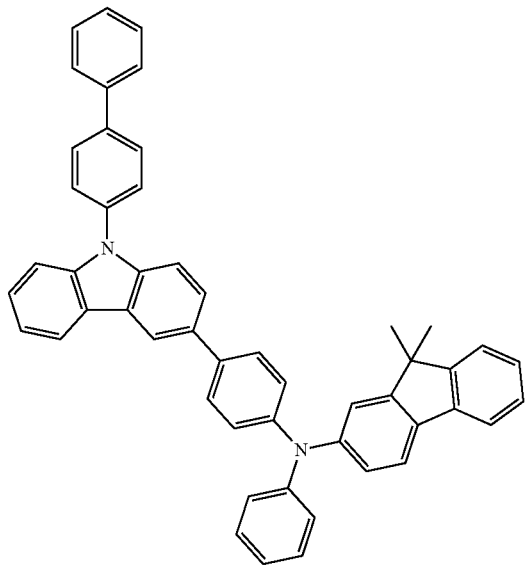
HT4

-continued
HT5
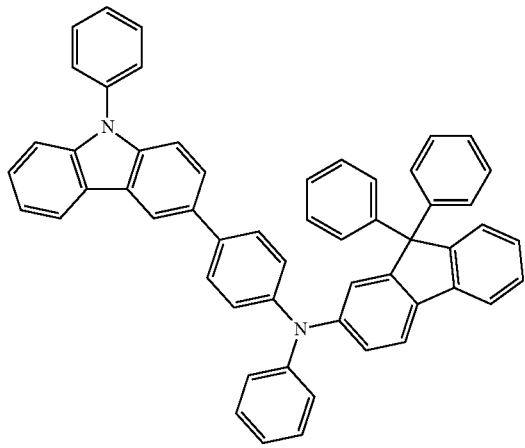
HT6
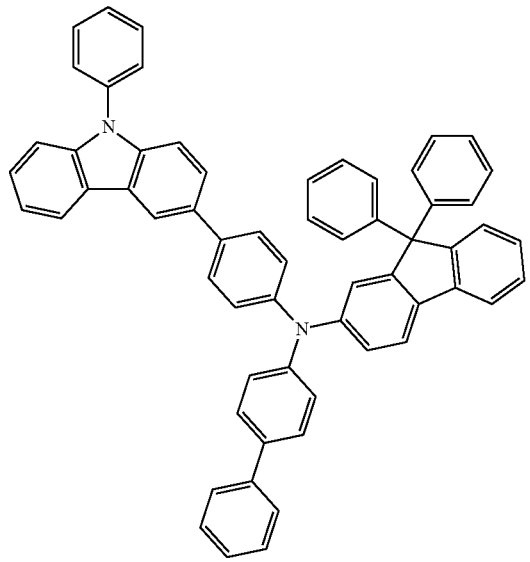
HT7
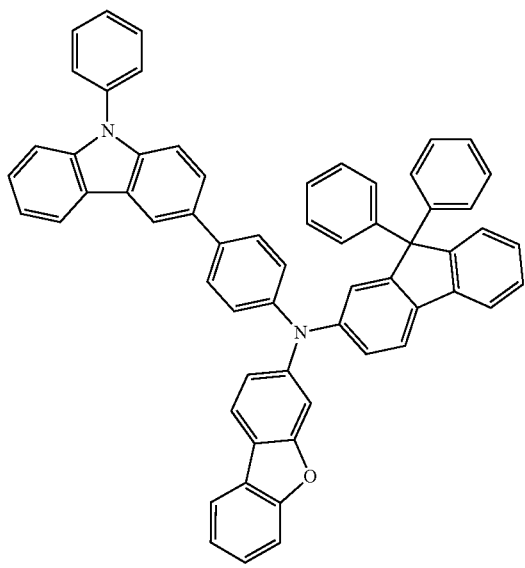
HT8
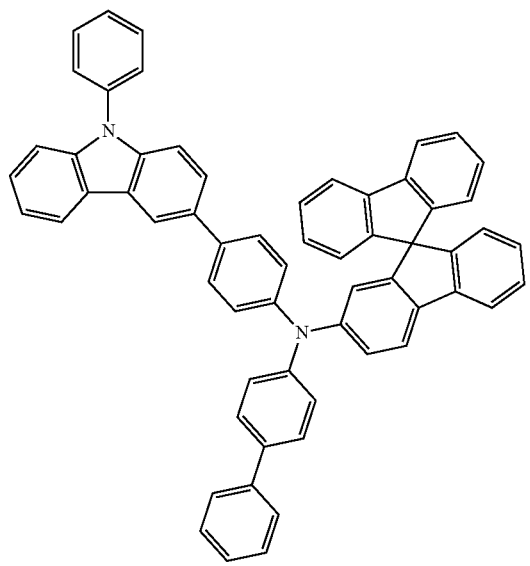

-continued
HT9
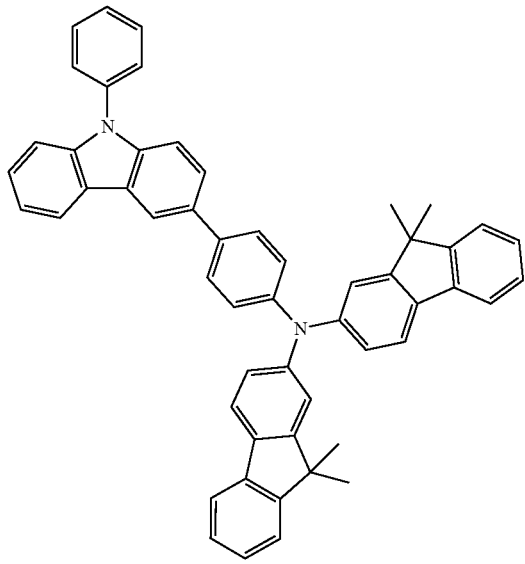
HT10
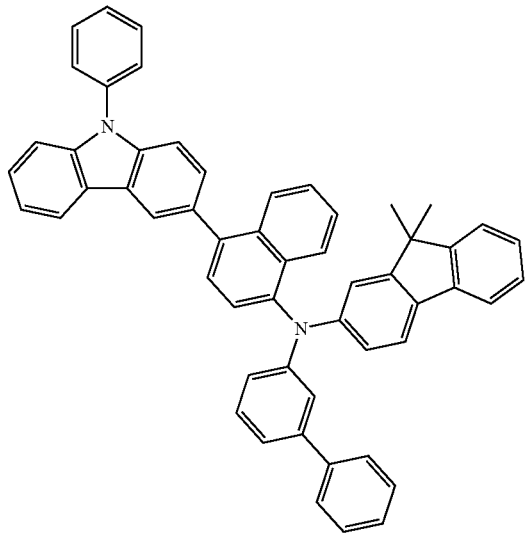
HT11
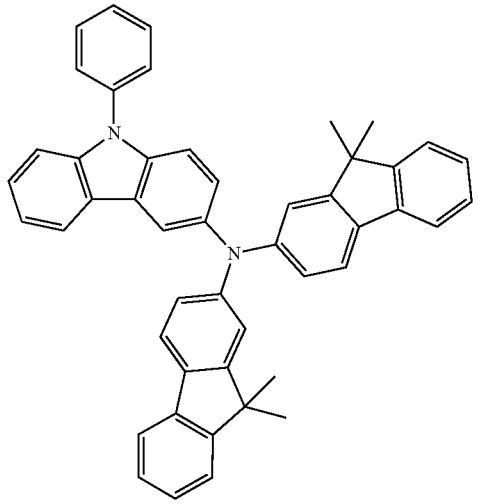
HT12
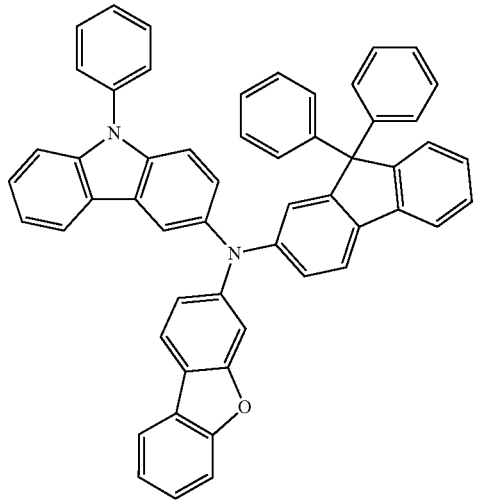
HT13
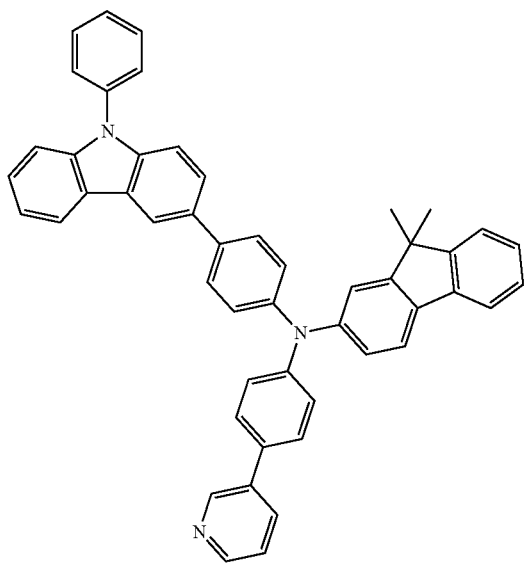
HT14
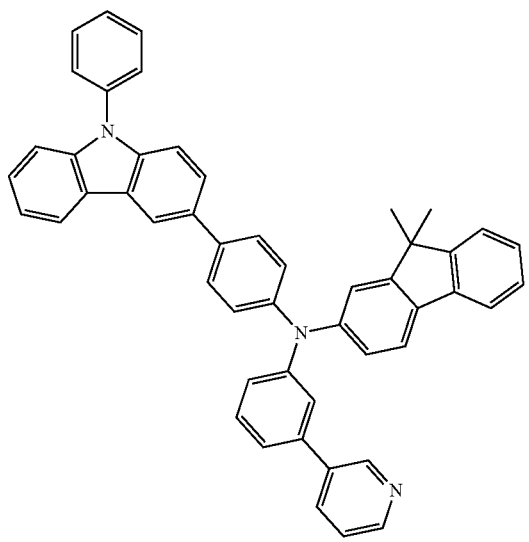

-continued
HT15
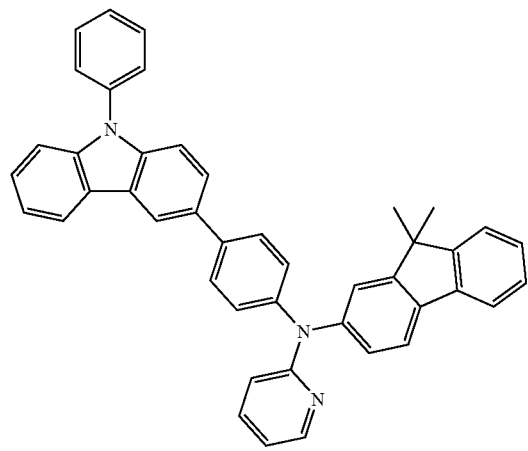
HT16
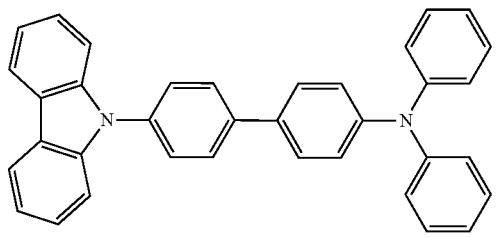
HT17
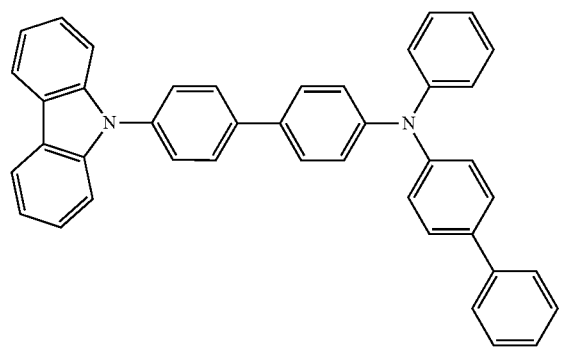
HT18
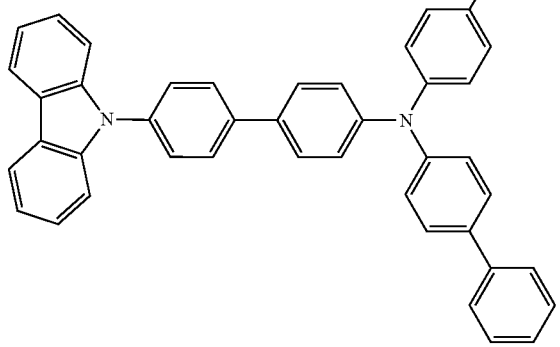
HT19
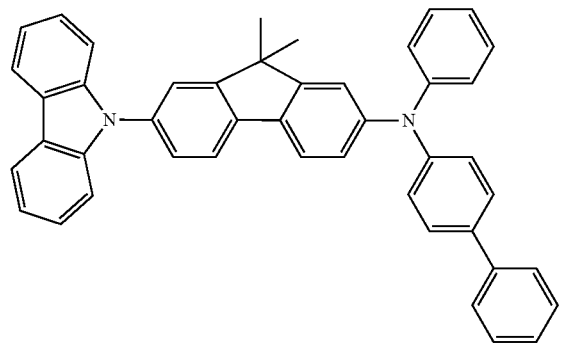
HT20
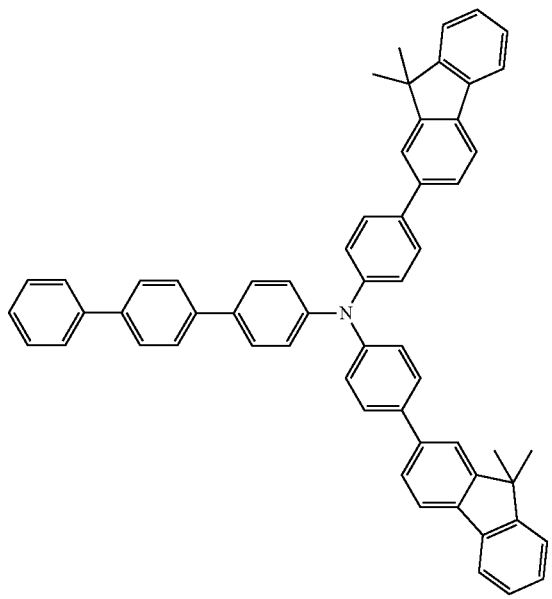

-continued
HT21
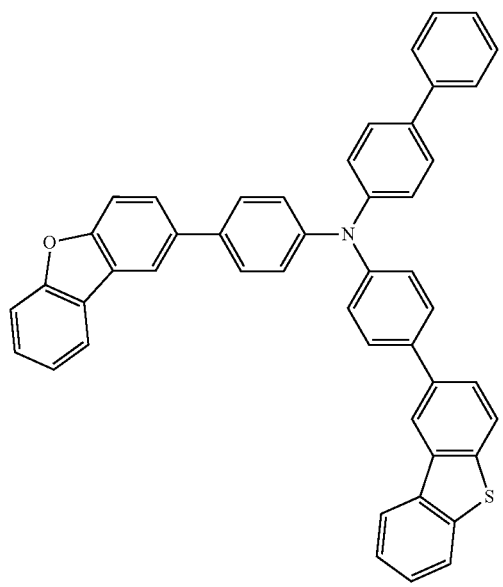
HT22
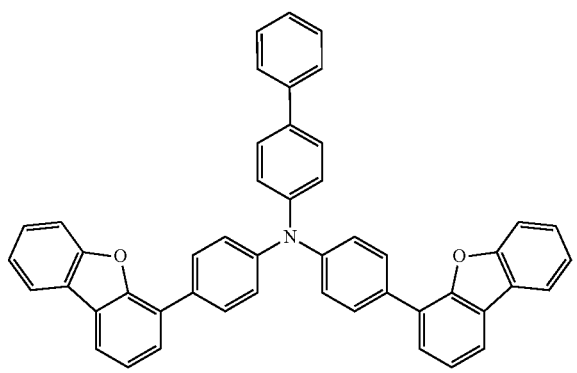
HT23
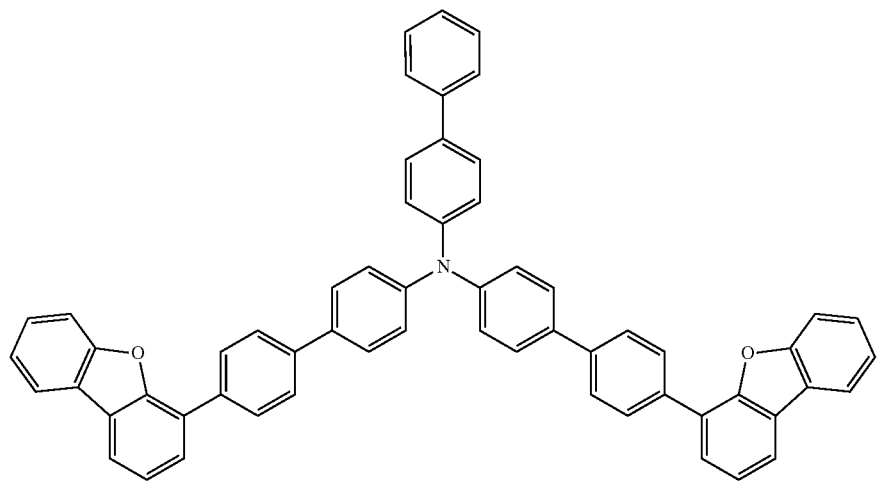
HT24
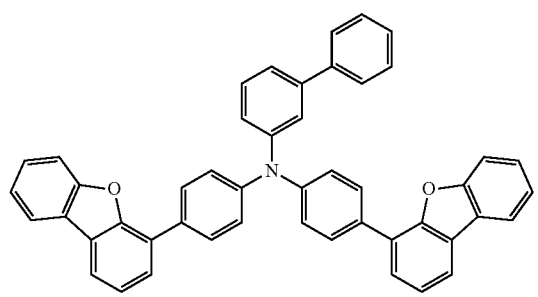
HT25
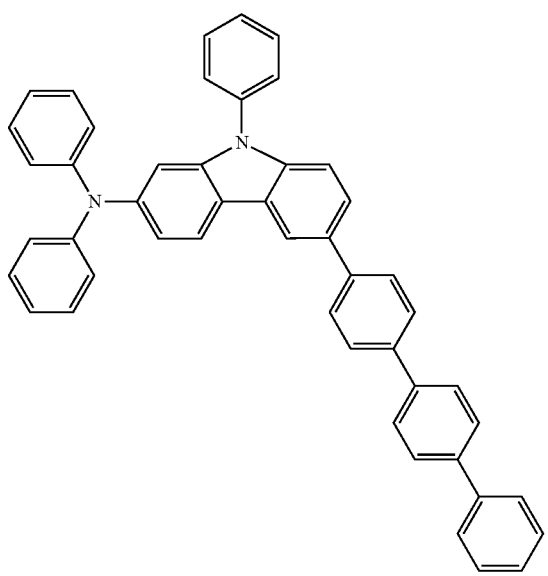

-continued
HT26
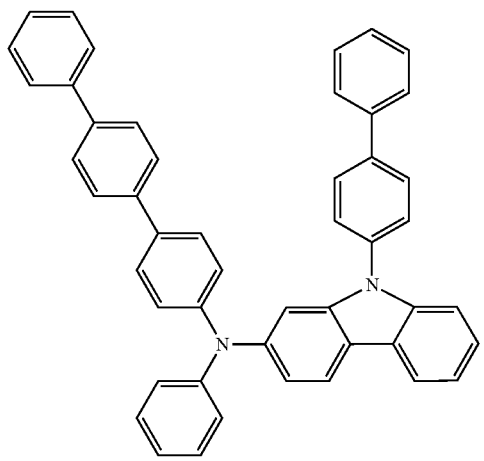
HT27
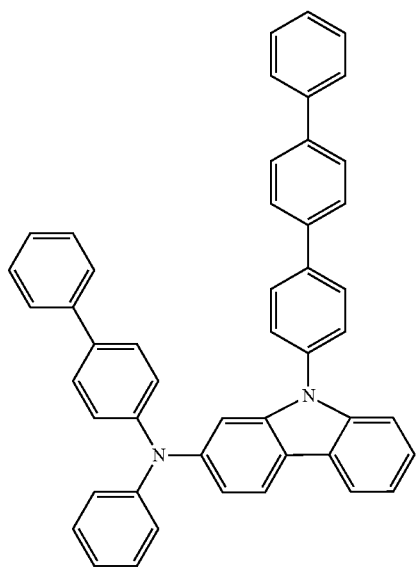
HT28
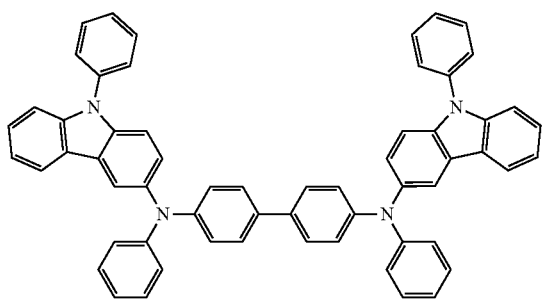
HT29
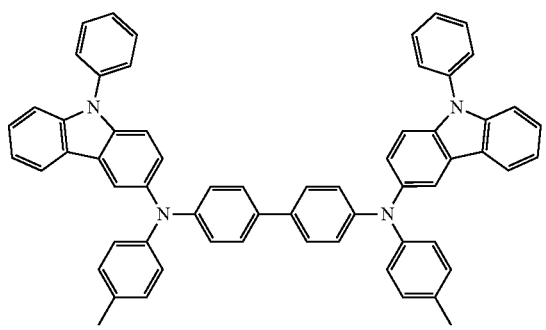
HT30
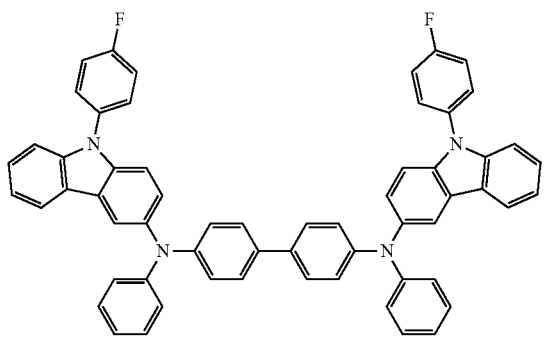
HT31
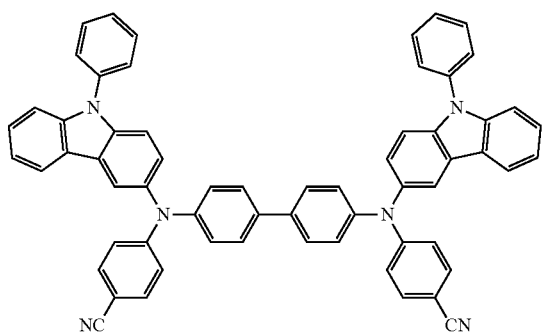

-continued
HT32
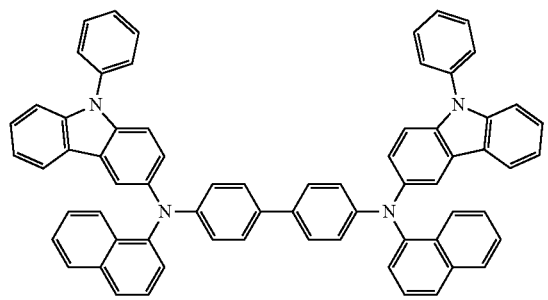
HT33
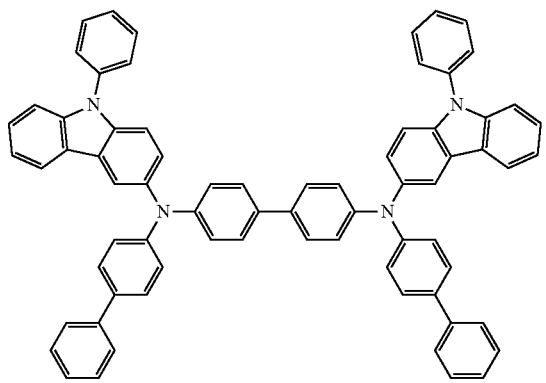
HT34
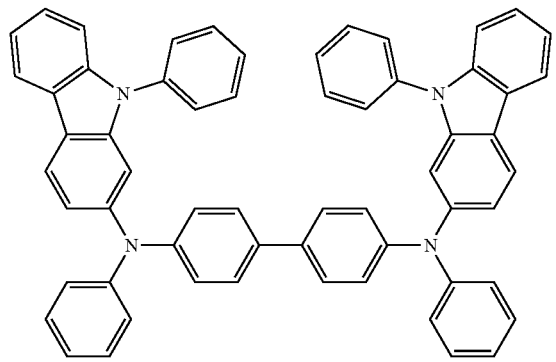
HT35
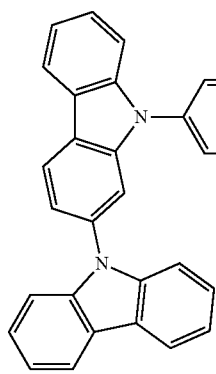
HT36
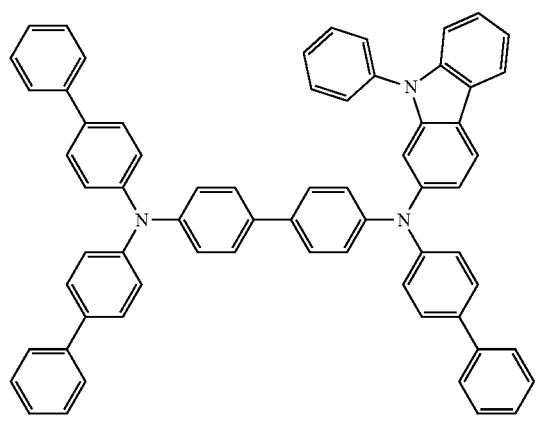
HT37
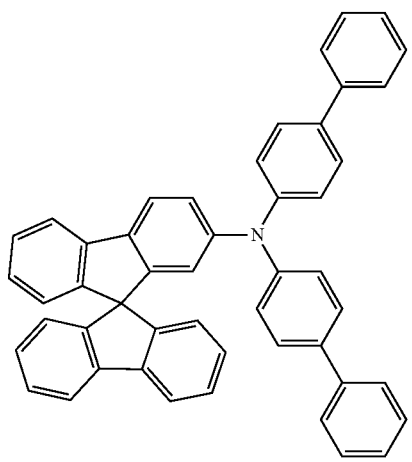

HT38

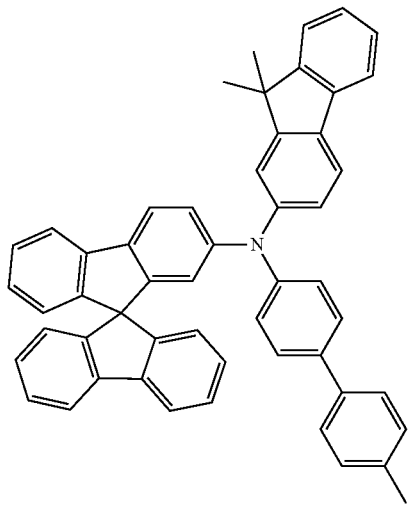

HT39

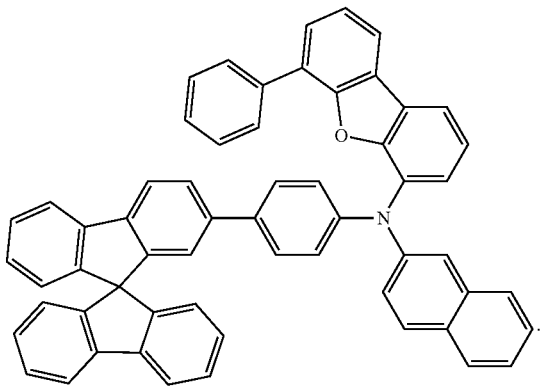

A thickness of the hole transport region may be in a range of about 100 Å to about 10,000 Å, for example, about 100 Å to about 1,000 Å. When the hole transport region includes at least one of a hole injection layer and a hole transport layer, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer, and the hole transport layer are within the foregoing ranges, suitable or satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may include the materials as described above.

p-Dopant

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In one embodiment, the p-dopant may have a lowest unoccupied molecular orbital (LUMO) energy level of about −3.5 eV or less.

The p-dopant may include at least one selected from a quinone derivative, a metal oxide, and a cyano group-containing compound, but embodiments of the present disclosure are not limited thereto.

For example, the p-dopant may include at least one selected from:
  a quinone derivative, such as tetracyanoquinodimethane (TCNQ) or 2,3,5,6-tetrafluoro-7,7,8,8-tetracyanoquinodimethane (F4-TCNQ);
  a metal oxide, such as tungsten oxide or molybdenum oxide;
  1,4,5,8,9,12-hexaazatriphenylene-hexacarbonitrile (HAT-CN); and
  a compound represented by Formula 221 below,
but embodiments of the present disclosure are not limited thereto:

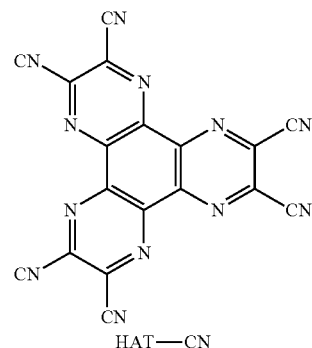

HAT—CN

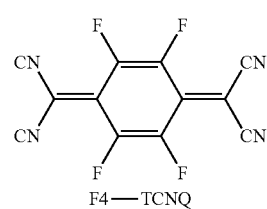

F4—TCNQ

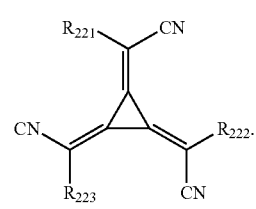

Formula 221

In Formula 221,

R$_{221}$ to R$_{223}$ may each independently be selected from a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_1$-C$_{60}$ heteroaryl group, a substituted or unsubstituted monovalent non-aromatic condensed polycyclic group, and a substituted or unsubstituted monovalent non-aromatic condensed heteropolycyclic group, wherein at least one selected from R$_{221}$ to R$_{223}$ may each independently be selected from a cyano group, —F, —Cl, —Br, —I, a C$_1$-C$_{20}$ alkyl group substituted with —F, a C$_1$-C$_{20}$ alkyl group substituted with —Cl, a C$_1$-C$_{20}$ alkyl group substituted with Br, and a C$_1$-C$_{20}$ alkyl group substituted with —I.

Emission Layer in Organic Layer 150

When the organic light-emitting device 10 is a full-color organic light-emitting device, the emission layer may be patterned into a red emission layer, a green emission layer, or a blue emission layer, according to a sub-pixel. In one or more embodiments, the emission layer may have a stacked structure of two or more layers selected from a red emission layer, a green emission layer, and a blue emission layer, in which the two or more layers contact each other or are separated from each other. In one or more embodiments, the emission layer may include two or more materials selected from a red light-emitting material, a green light-emitting material, and a blue light-emitting material, in which the two or more materials are mixed with each other in a single layer to emit white light.

The emission layer may include a host and a dopant. The dopant may include at least one selected from a phosphorescent dopant and a fluorescent dopant.

An amount of the dopant in the emission layer may be in a range of about 0.01 parts by weight to about 15 parts by weight based on 100 parts by weight of the host, but embodiments of the present disclosure are not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Host in Emission Layer

In one or more embodiments, the host may include a compound represented by Formula 301 below:

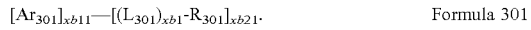

Formula 301

In Formula 301,

Ar$_{301}$ may be a substituted or unsubstituted C$_5$-C$_{60}$ carbocyclic group or a substituted or unsubstituted C$_1$-C$_{60}$ heterocyclic group, xb11 may be 1, 2, or 3, L$_{301}$ may be selected from a substituted or unsubstituted C$_3$-C$_{10}$ cycloalkylene group, a substituted or unsubstituted C$_1$-C$_{10}$ heterocycloalkylene group, a substituted or unsubstituted C$_3$-C$_{10}$ cycloalkenylene group, a substituted or unsubstituted C$_1$-C$_{10}$ heterocycloalkenylene group, a substituted or unsubstituted C$_6$-C$_{60}$ arylene group, a substituted or unsubstituted C$_1$-C$_{60}$ heteroarylene group, a substituted or unsubstituted divalent non-aromatic condensed polycyclic group, and a substituted or unsubstituted divalent non-aromatic condensed heteropolycyclic group, xb1 may be an integer of 0 to 5, R$_{301}$ may be selected from deuterium, —F, —Cl, —Br, —I, a hydroxyl group, a cyano group, a nitro group, an amidino group, a hydrazino group, a hydrazono group, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, —Si(Q$_{301}$)(Q$_{302}$)(Q$_{303}$), —N(Q$_{301}$)(Q$_{302}$), —B(Q$_{301}$)(Q$_{302}$), —C(=O)(Q$_{301}$), —S(=O)$_2$(Q$_{301}$), and —P(=O)(Q$_{301}$)(Q$_{302}$), xb21 may be an integer of 1 to 5, and Q$_{301}$ to Q$_{303}$ may each independently be selected from a C$_1$-C$_{10}$ alkyl group, a C$_1$-C$_{10}$ alkoxy group, a phenyl group, a biphenyl group, a terphenyl group, and a naphthyl group, but embodiments of the present disclosure are not limited thereto.

In one embodiment, in Formula 301, Ar$_{301}$ may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a biphenyl group, a terphenyl group, a naphthyl group, —Si(Q$_{31}$)(Q$_{32}$)(Q$_{33}$), —N(Q$_{31}$)(Q$_{32}$), —B(Q$_{31}$)(Q$_{32}$), —C(=O)(Q$_{31}$), —S(=O)$_2$(Q$_{31}$), and —P(=O)(Q$_{31}$)(Q$_{32}$), and Q$_{31}$ to Q$_{33}$ may each independently be selected from a C$_1$-C$_{10}$ alkyl group, a C$_1$-C$_{10}$ alkoxy group, a phenyl group, a biphenyl group, a terphenyl group, and a naphthyl group, but embodiments of the present disclosure are not limited thereto.

When xb11 in Formula 301 is two or more, two or more Ar301(s) may be linked via a single bond.

In one or more embodiments, the compound represented by Formula 301 may be represented by Formula 301-1 or 301-2:

Formula 301-1

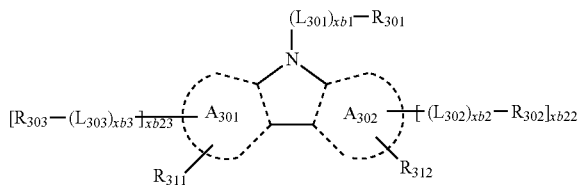

Formula 301-2

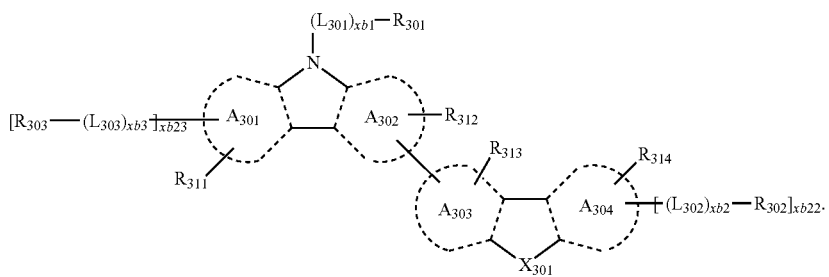

In Formulae 301-1 and 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or $N-[(L_{304})_{xb4}-R_{304}]$, $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(C_{31})(Q_{32})$, xb22 and xb23 may each independently be 0, 1, or 2, $L_{301}$, xb1, $R_{301}$, and $Q_{31}$ to $Q_{33}$ may respectively be same as described above, $L_{302}$ to $L_{304}$ may respectively be same as described in connection with $L_{301}$, xb2 to xb4 may respectively be same as described in connection with xb1, and $R_{302}$ to $R_{304}$ may respectively be same as described in connection with $R_{301}$.

For example, in Formulae 301, 301-1, and 301-2, $L_{301}$ to $L_{304}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may respectively be the same as described above.

In one embodiment, in Formulae 301, 301-1, and 301-2, $R_{301}$ to $R_{304}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si(Q$_{31}$)(Q$_{32}$)(Q$_{33}$), —N(Q$_{31}$)(Q$_{32}$), —B(Q$_{31}$)(Q$_{32}$), —C(=O)(Q$_{31}$), —S(=O)$_2$(Q$_{31}$), and —P(=O)(Q$_{31}$)(Q$_{32}$), and Q$_{31}$ to Q$_{33}$ may respectively be the same as described above.

In one embodiment, the host may include an alkaline earth metal complex. For example, the host may be selected from a Be complex (for example, Compound H55), a Mg complex, and a Zn complex.

The host may include at least one selected from 9,10-di (2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments of the present disclosure are not limited thereto:

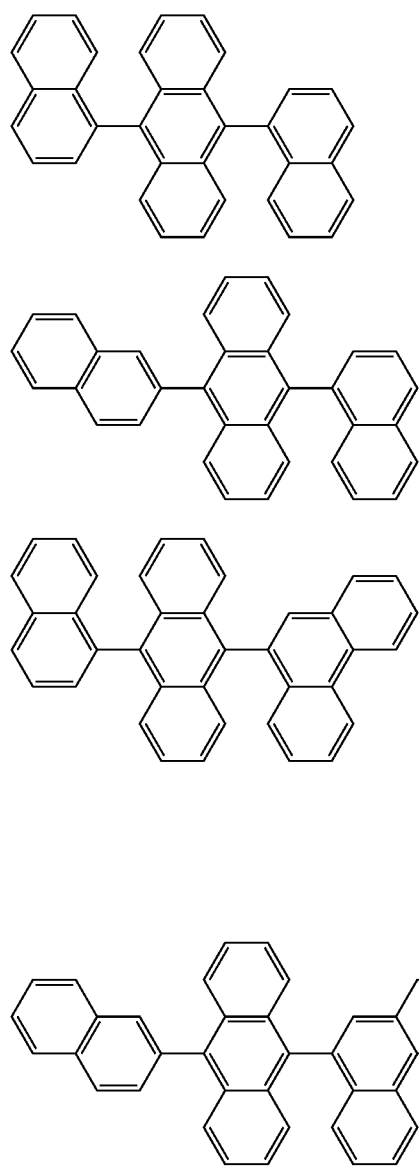

H1

H2

H3

H4

-continued

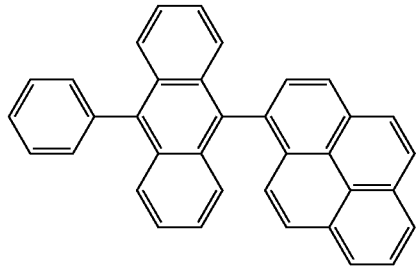

H5

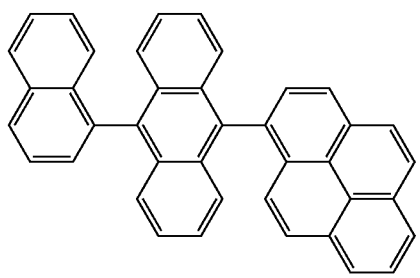

H6

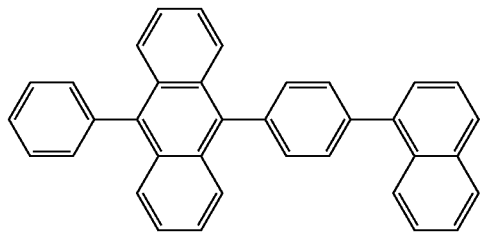

H7

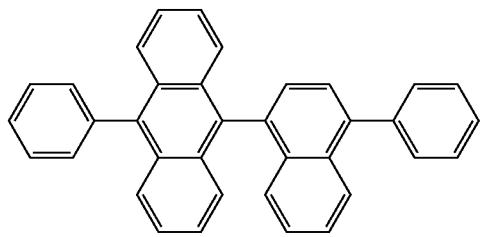

H8

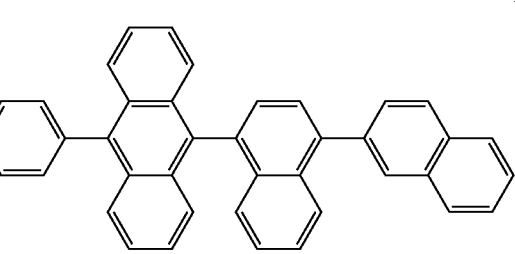

H9

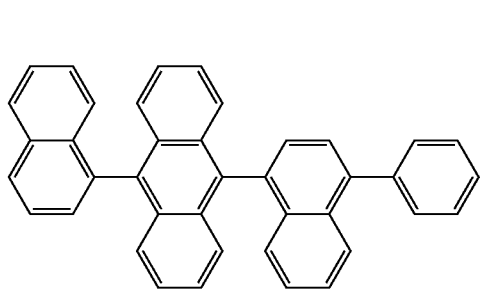

H10

111
-continued
H11
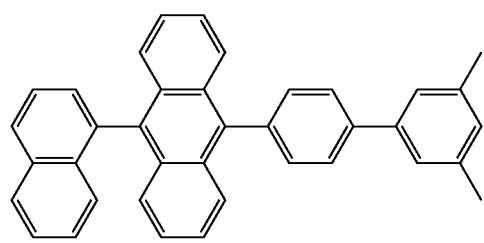
H12
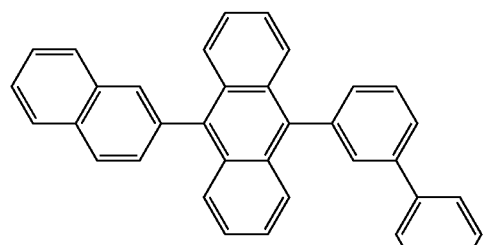
H13
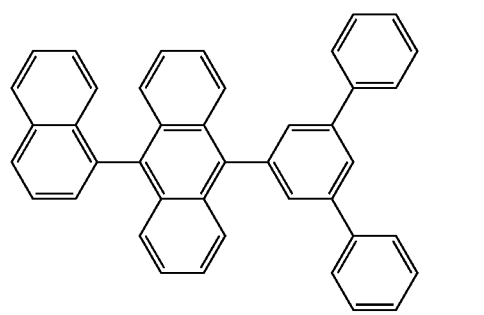
H14
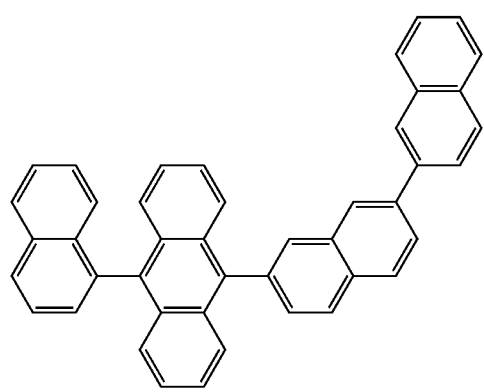
H15
112
-continued
H16
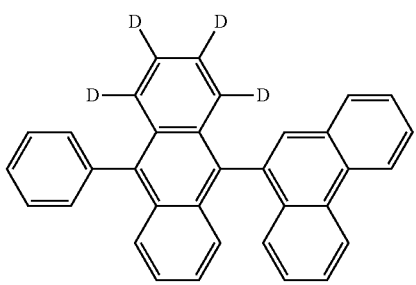
H17
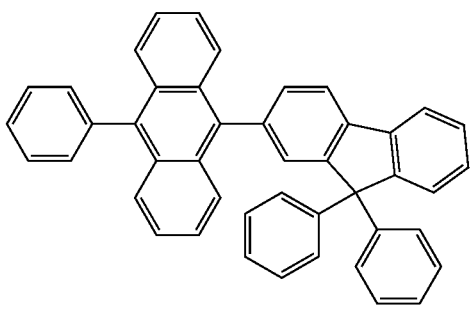
H18
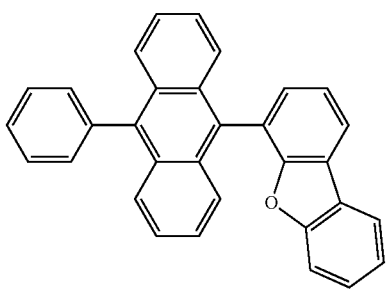
H19
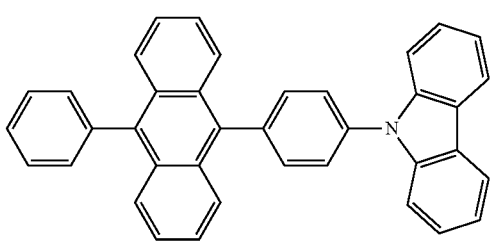
H20
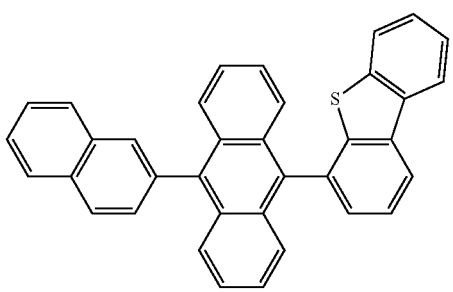

-continued
H21
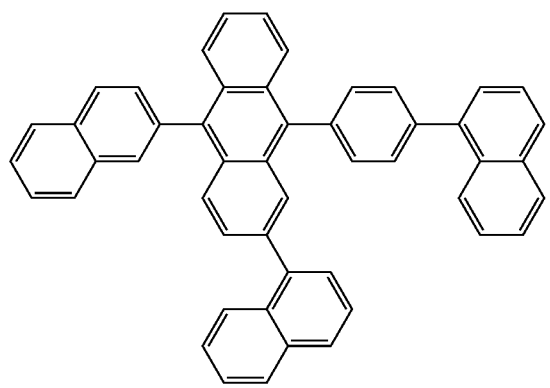
H22
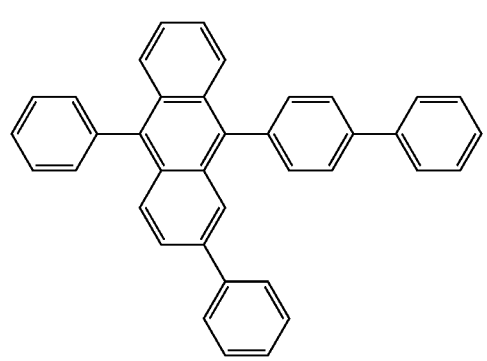
H23
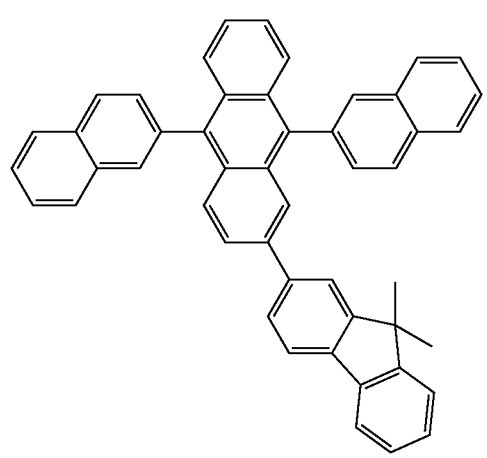
H24
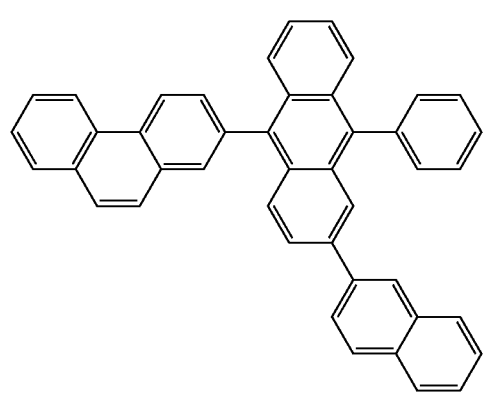
-continued
H25
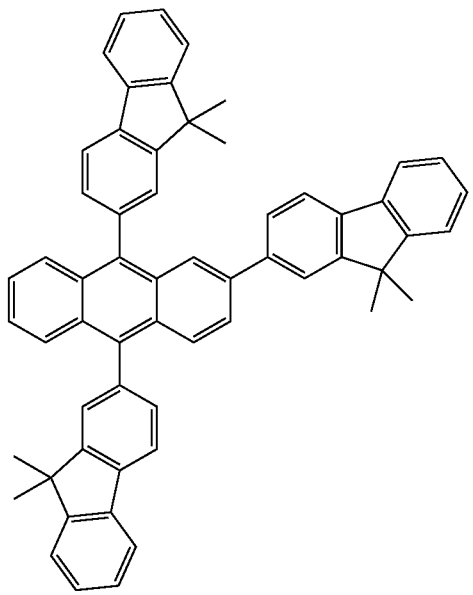
H26
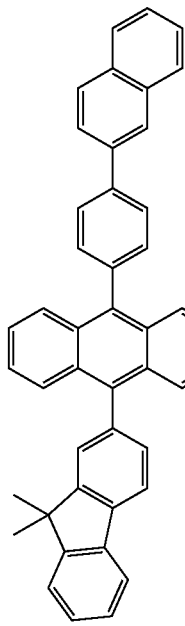
H27
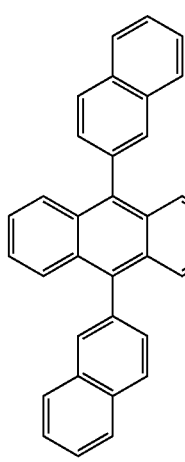

H28 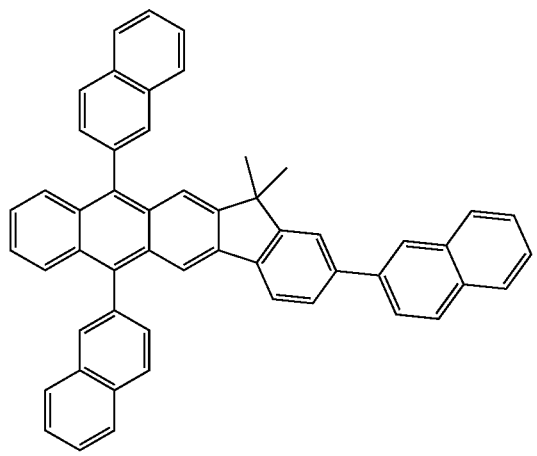
H29 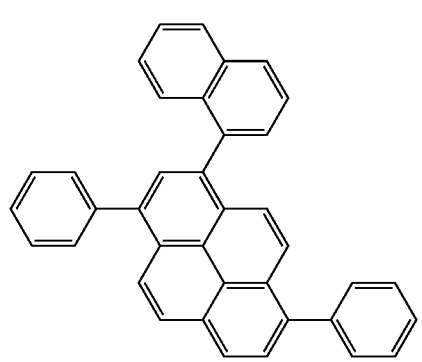
H30 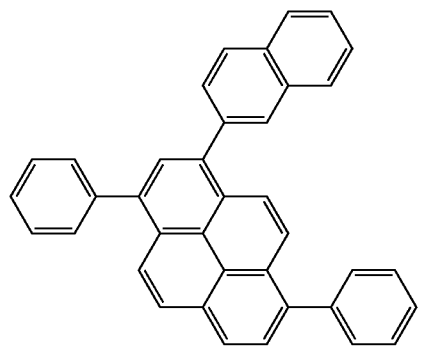
H31 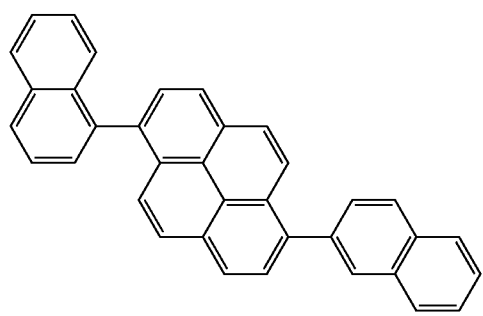
H32 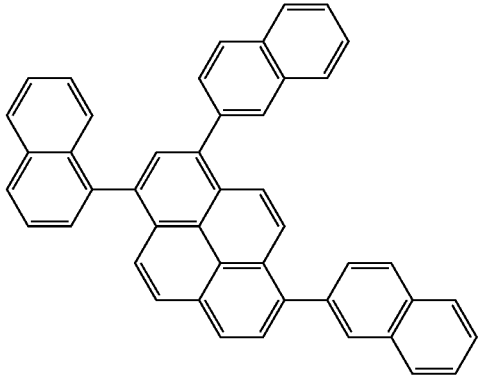
H33 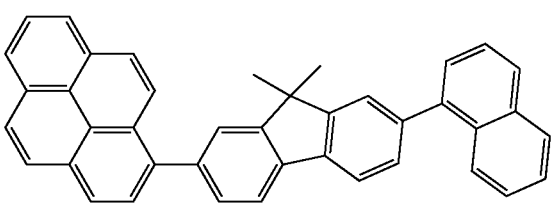
H34 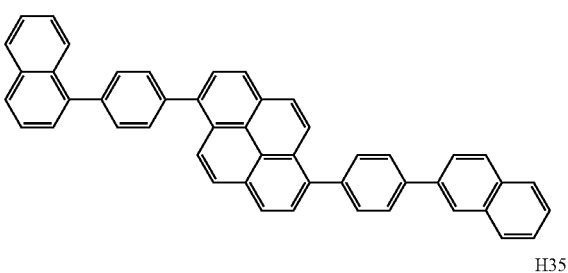
H35 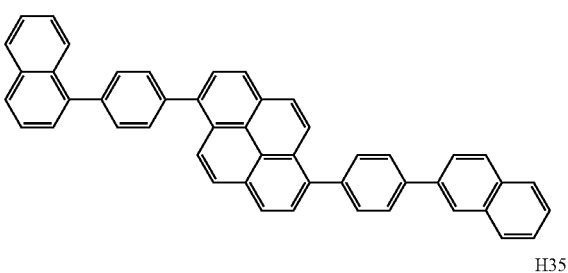
H36 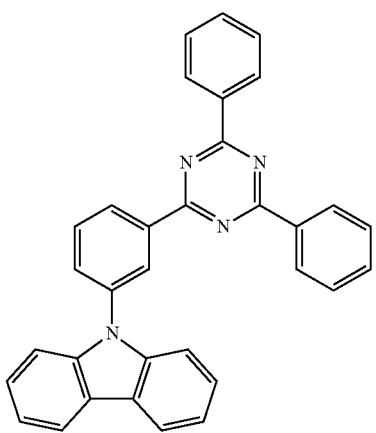

H37
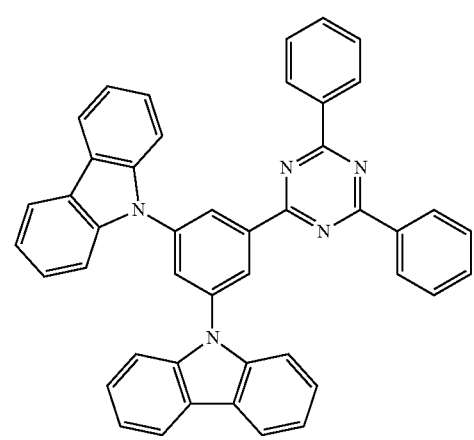
H38
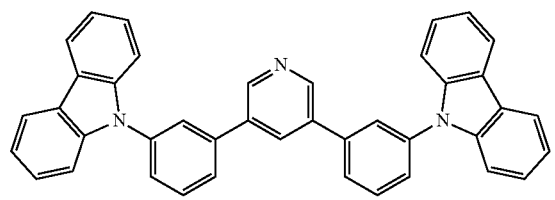
H39
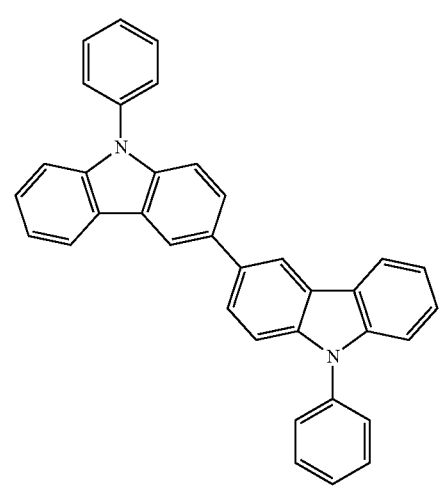
H40
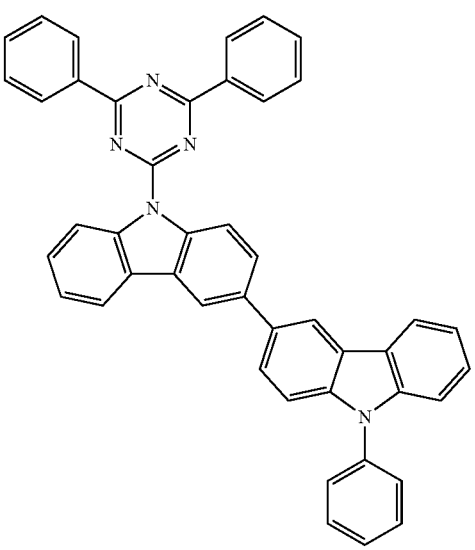
H41
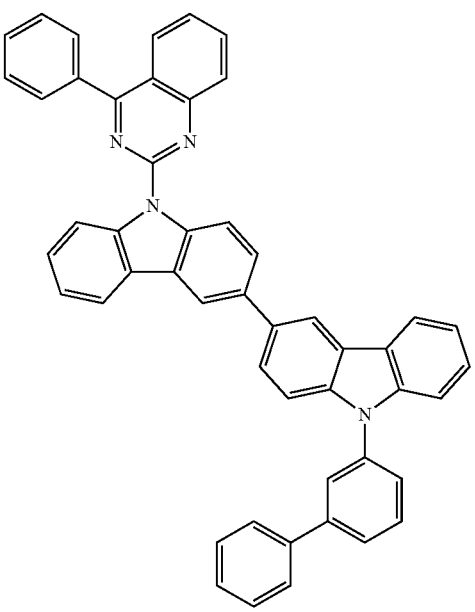
H42
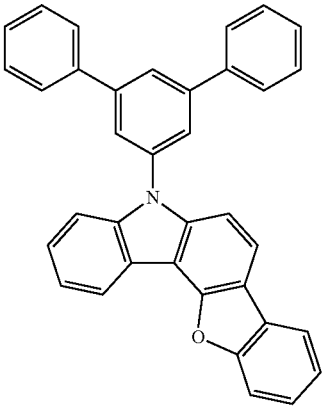

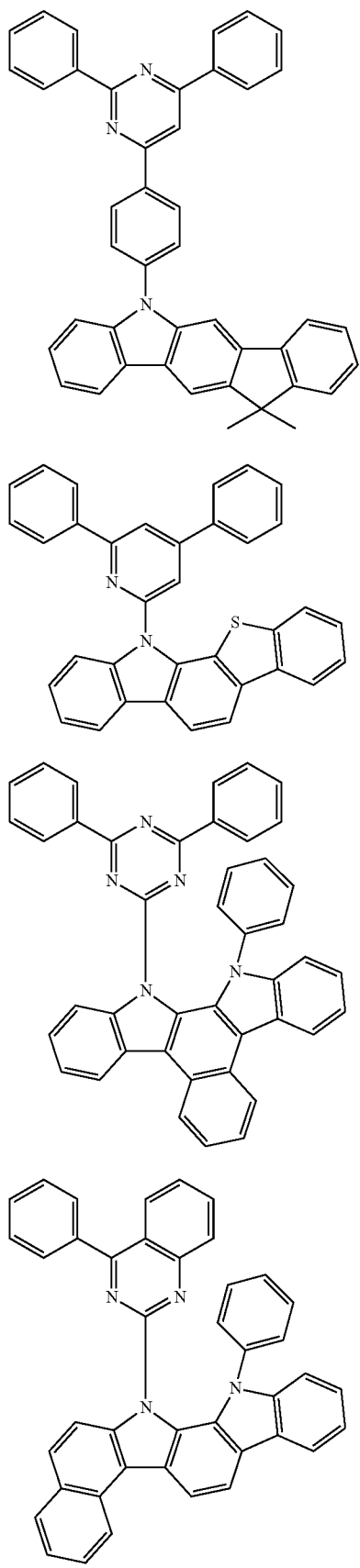
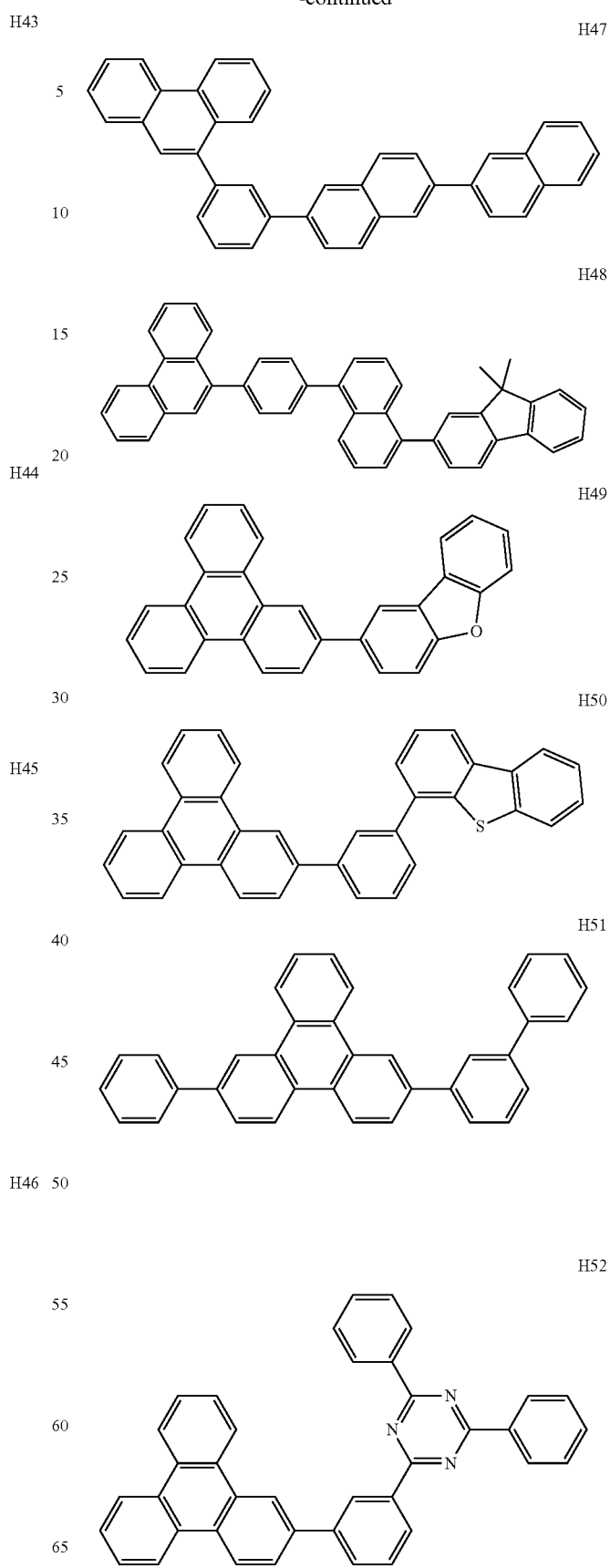

-continued

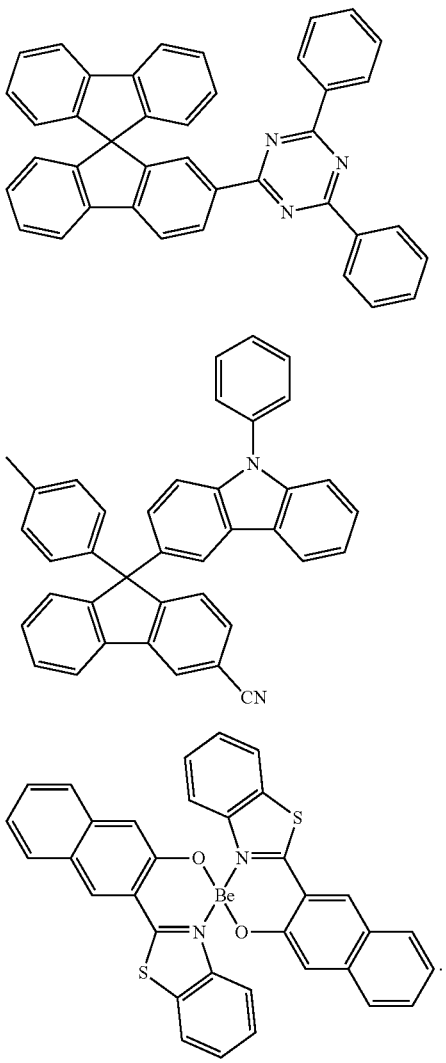

H53

H54

H55

Phosphorescent Dopant Included in Emission Layer in Organic Layer 150

The phosphorescent dopant may include an organometallic complex represented by Formula 401 below:

$$M(L_{401})_{xc1}(L_{402})_{xc2}$$ Formula 401

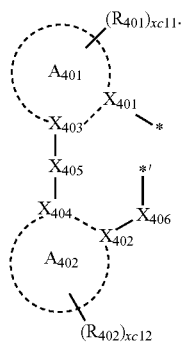

Formula 402

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, wherein, when xc1 is two or more, two or more $L_{401}$(s) may be identical to or different from each other, $L_{402}$ may be an organic ligand, and xc2 may be an integer of 0 to 4, wherein, when xc2 is two or more, two or more $L_{402}$(s) may be identical to or different from each other, $X_{401}$ to $X_{404}$ may each independently be nitrogen or carbon, $X_{401}$ and $X_{403}$ may be linked via a single bond or a double bond, and $X_{402}$ and $X_{404}$ may be linked via a single bond or a double bond, $A_{401}$ and $A_{402}$ may each independently be a $C_5$-$C_{60}$ carbocyclic group or a $C_1$-$C_{60}$ heterocyclic group, $X_{405}$ may be a single bond, *—O—*', *S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C($Q_{411}$)=', wherein $Q_{411}$ and $Q_{412}$ may be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer of 0 to 10, and and *' in Formula 402 each indicate a binding site to M in Formula 401.

In one embodiment, in Formula 402, $A_{401}$ and $A_{402}$ may each independently be selected from a benzene group, a naphthalene group, a fluorene group, a spiro-bifluorene group, an indene group, a pyrrole group, a thiophene group, a furan(furan) group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may each be nitrogen concurrently (e.g., at the same time).

In one or more embodiments, $R_{401}$ and $R_{402}$ in Formula 402 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group, and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), and $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but embodiments of the present disclosure are not limited thereto.

In one or more embodiments, in Formula 401, when xc1 is two or more, two $A_{401}$(S) among a plurality of $L_{401}$(S) may optionally be linked via a linking group, $X_{407}$, or two $A_{402}$(S) may optionally be linked via a linking group, $X_{408}$ (see Compounds PD1 to PD4 and PD7). $X_{407}$ and $X_{408}$ may each independently be a single bond, *—O—*', *—S—*', *—C(=O)—*', *—N($Q_{413}$)—*', *—C($Q_{413}$)($Q_{414}$)-*', or *—C($Q_{413}$)=C($Q_{414}$)-*' (wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group), but embodiments of the present disclosure are not limited thereto.

$L_{402}$ in Formula 401 may be a monovalent, divalent, or trivalent organic ligand. For example, $L_{402}$ may be selected from halogen, diketone (for example, acetylacetonate), carboxylic acid (for example, picolinate), —C(=O), isonitrile, —CN, and phosphorus (for example, phosphine, or phosphite), but embodiments of the present disclosure are not limited thereto.

In one or more embodiments, the phosphorescent dopant may be selected from, for example, Compounds PD1 to PD25, but embodiments of the present disclosure are not limited thereto:

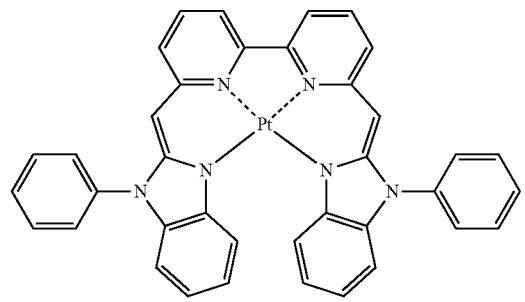

PD1

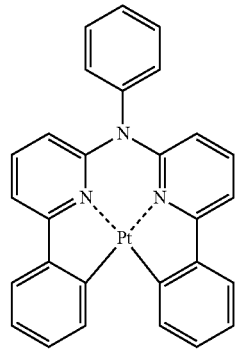

PD2

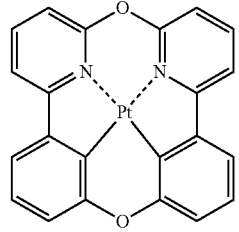

PD3

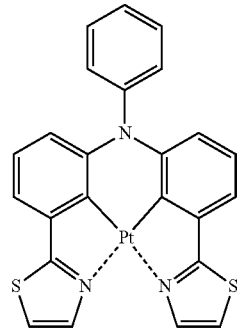

PD4

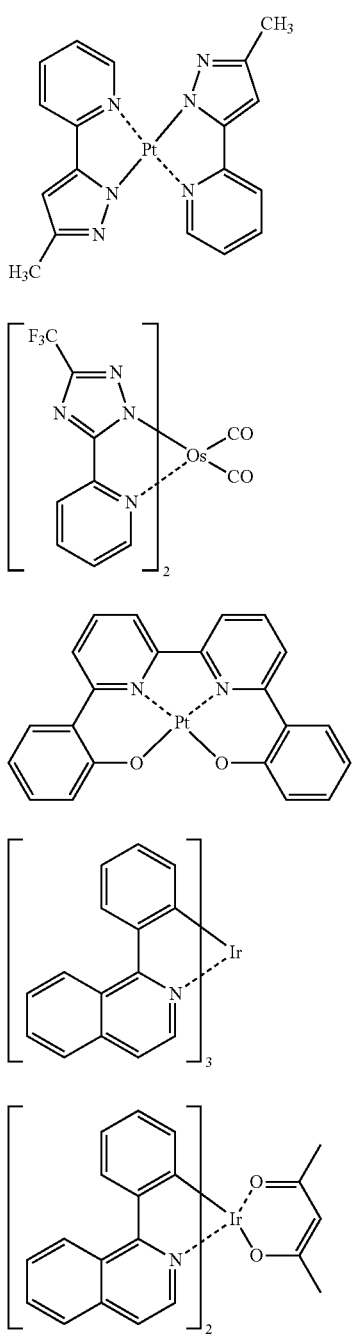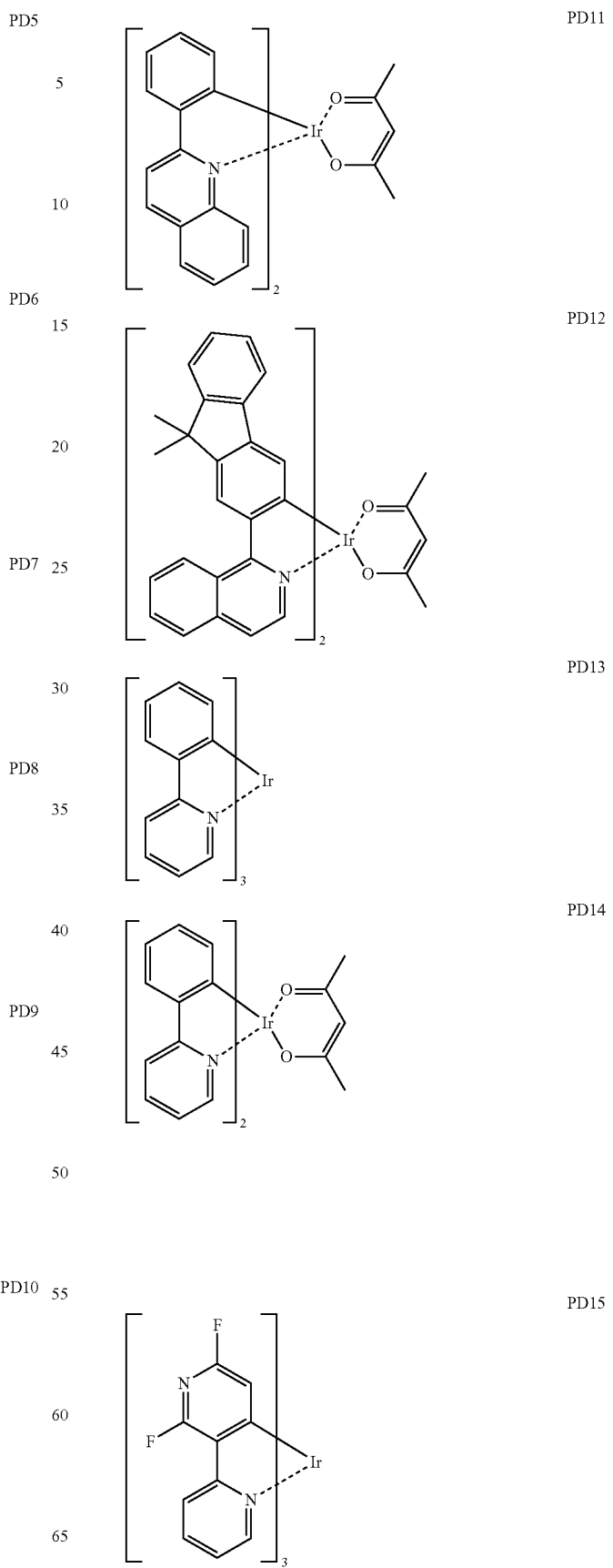

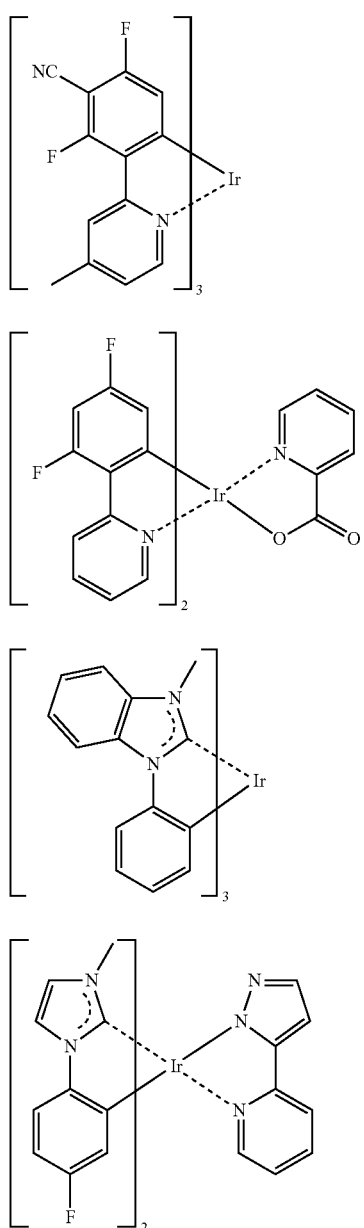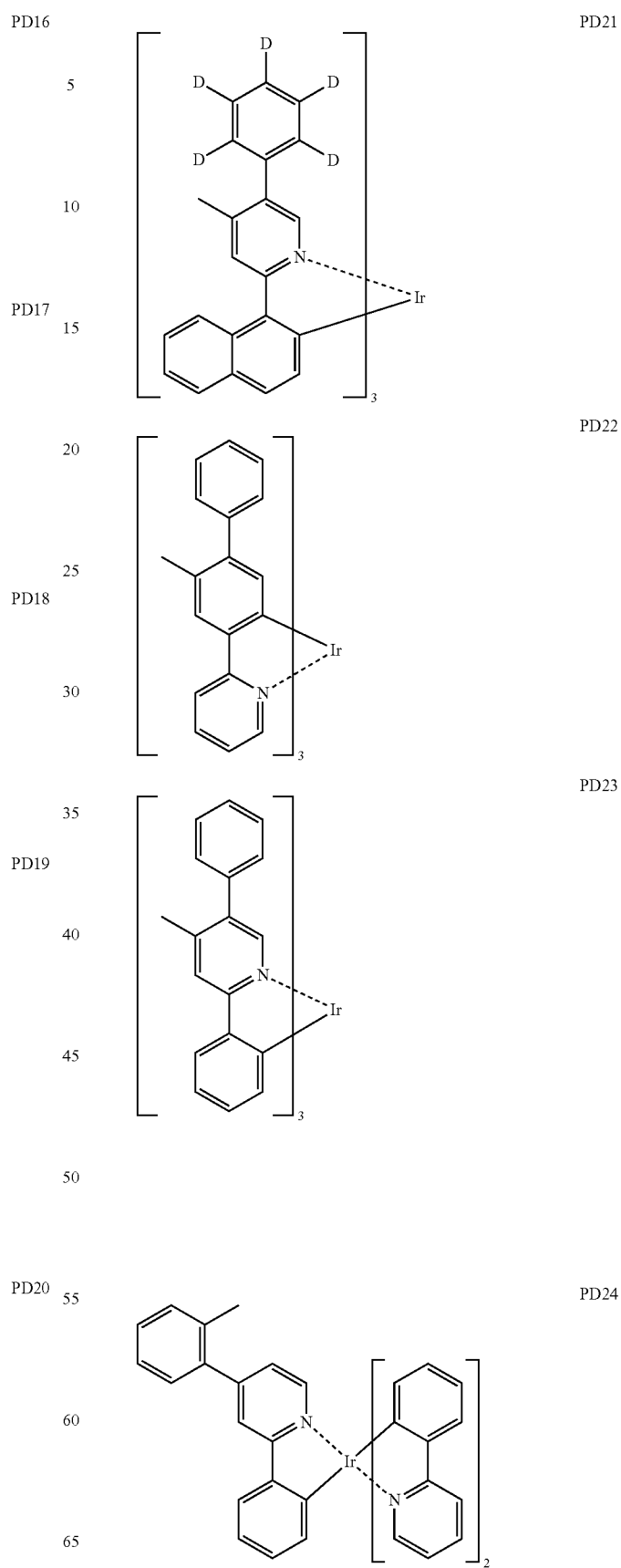

PD25

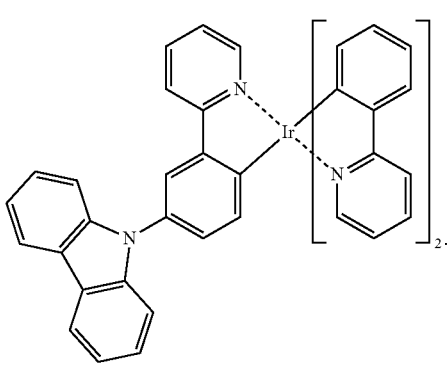

Fluorescent Dopant in Emission Layer

The fluorescent dopant may include an arylamine compound or a styrylamine compound.

The fluorescent dopant may include a compound represented by Formula 501 below.

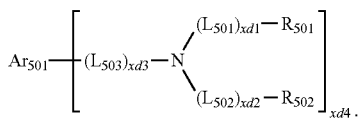

Formula 501

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer of 0 to 3, $R_{501}$ and $R_{502}$ may each independently be selected from a substituted or unsubstituted $C_3$-$C_{00}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer of 1 to 6.

In one embodiment, in Formula 501, $Ar_{501}$ may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, in Formula 501, $L_{501}$ to $L_{503}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, in Formula 501, $R_{501}$ and $R_{502}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, in Formula 501, xd4 may be two or more, but embodiments of the present disclosure are not limited thereto.

For example, the fluorescent dopant may be selected from Compounds FD1 to FD22:

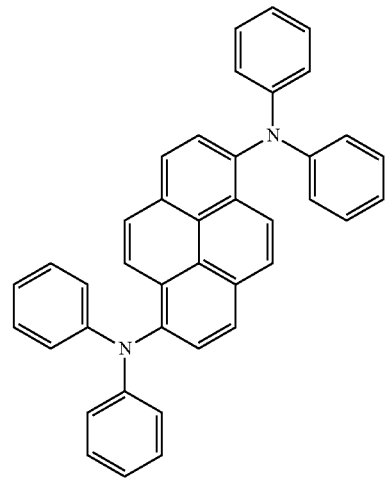

FD1

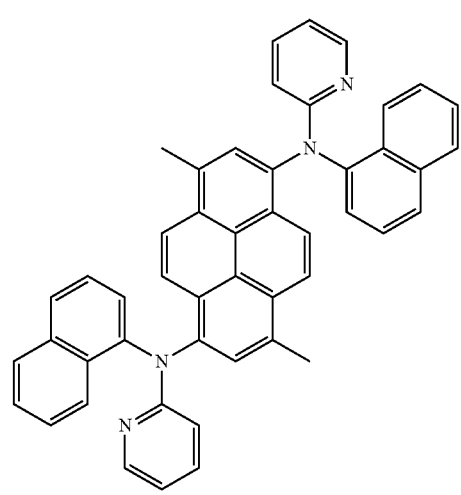

FD2

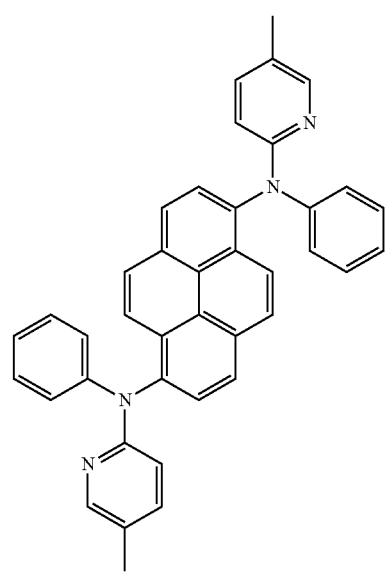

FD3

FD4 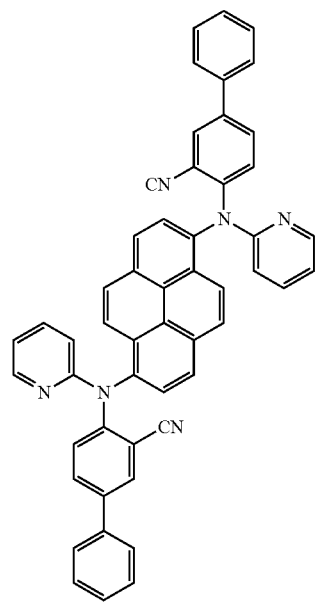
FD5 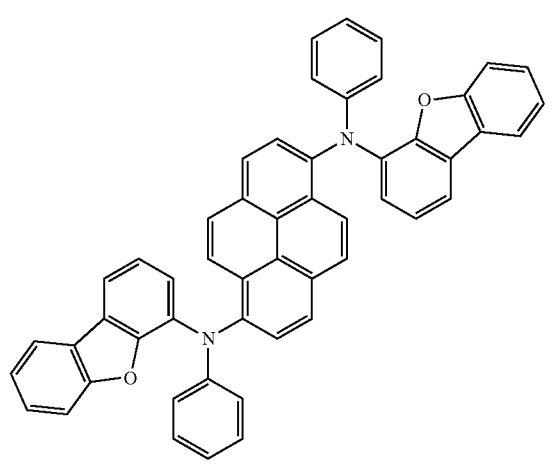
FD6 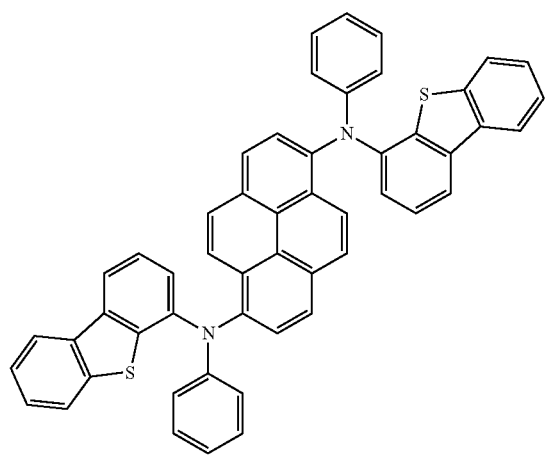
FD7 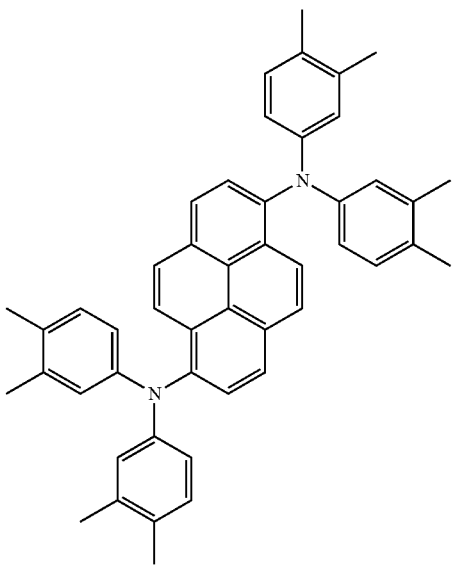
FD8 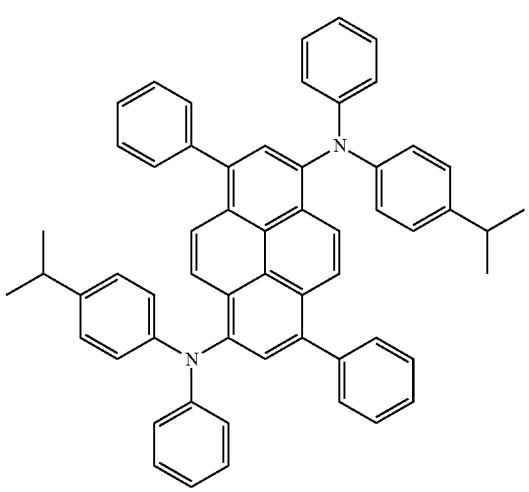
FD9 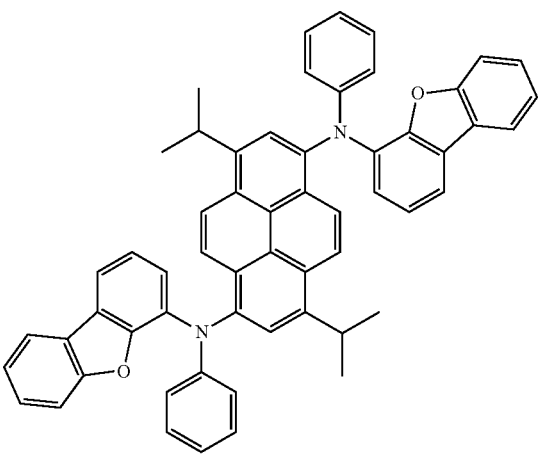

FD10
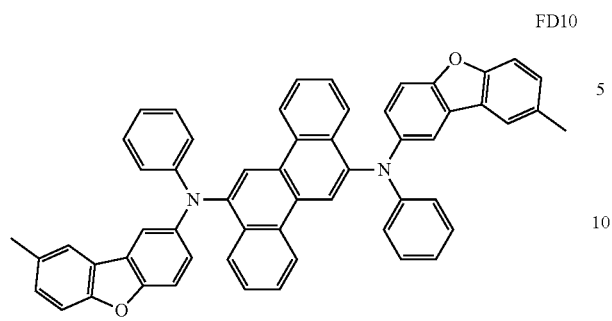
FD11
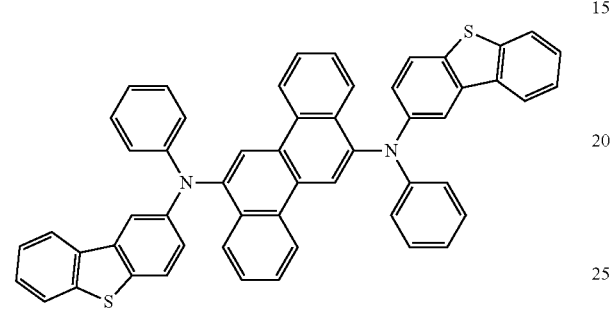
FD12
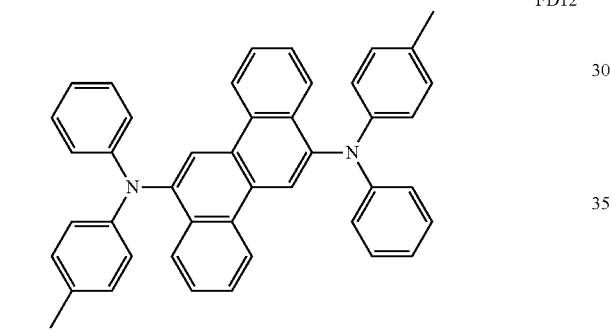
FD13
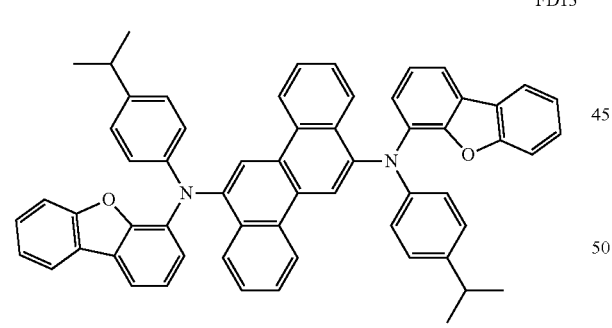
FD14
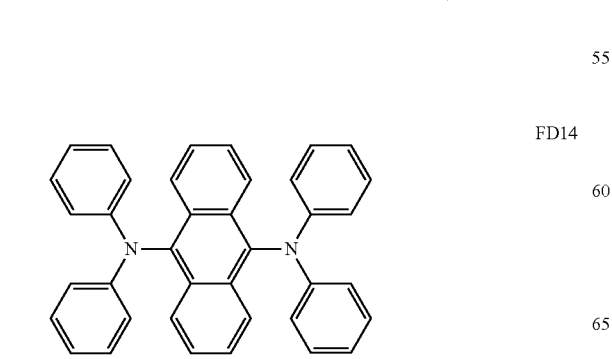
FD15
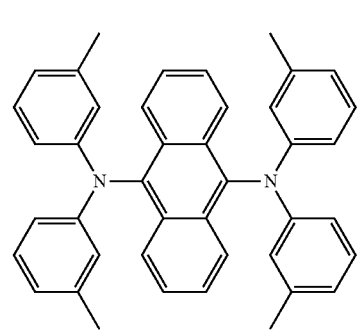
FD16
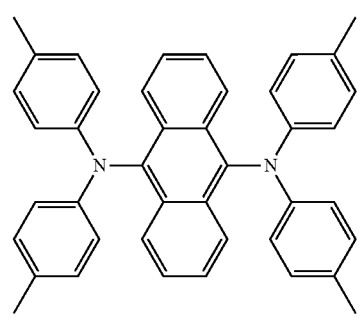
FD17
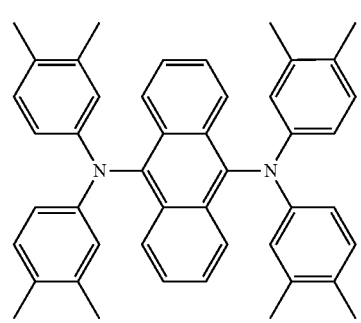
FD18
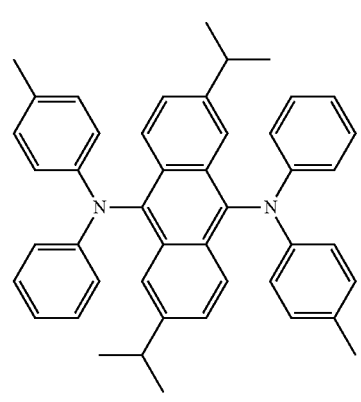

-continued
FD19
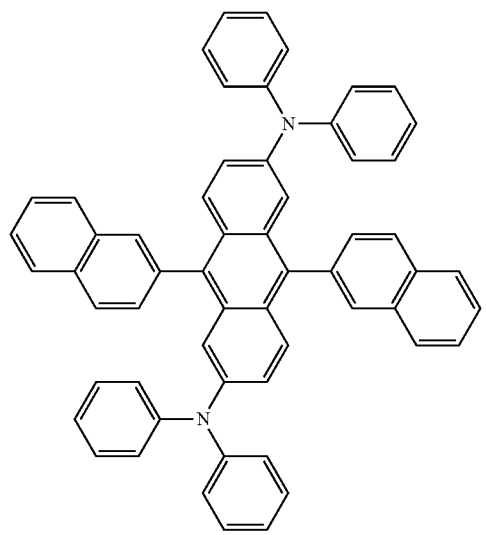
FD20
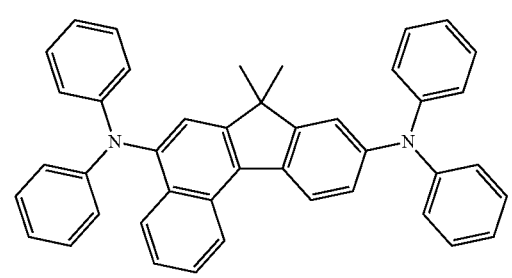
FD21
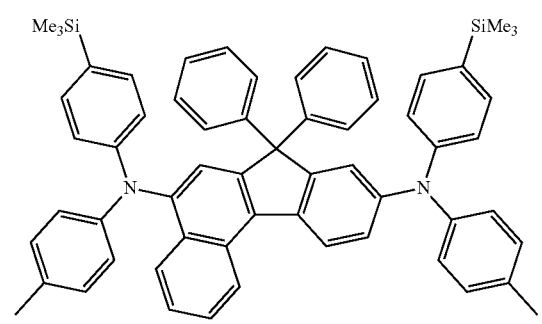
FD22
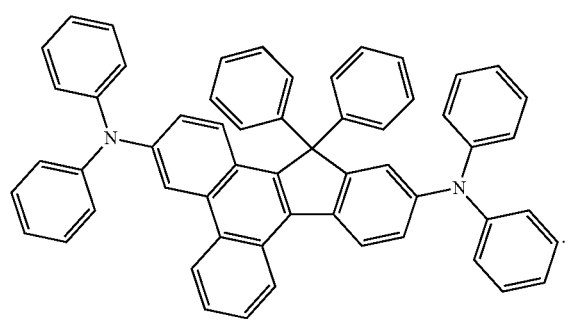
In one or more embodiments, the fluorescent dopant may be selected from the following compounds, but embodiments of the present disclosure are not limited thereto.
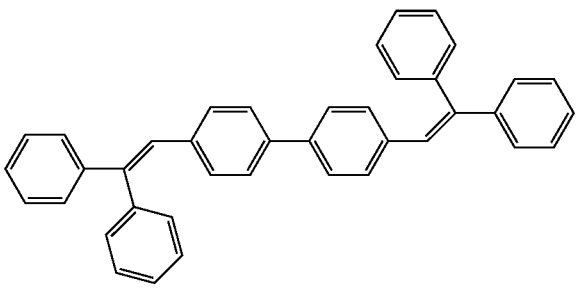
DPVBi
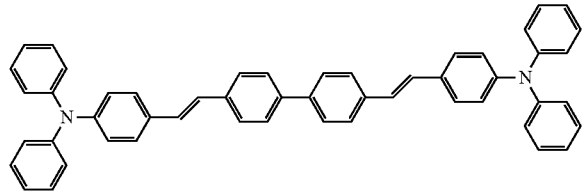
DPAVBi
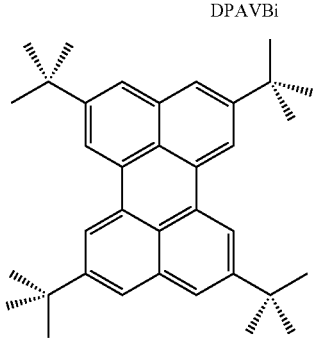
TBPe
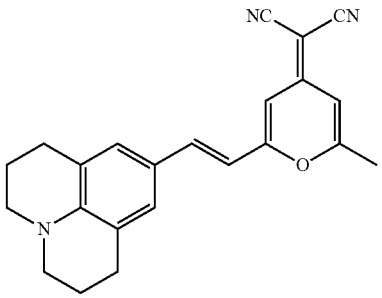
DCM
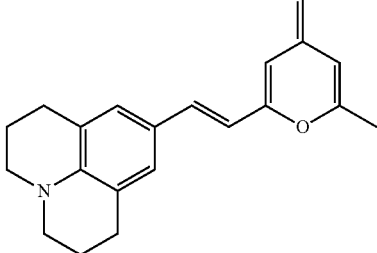
DCJTB

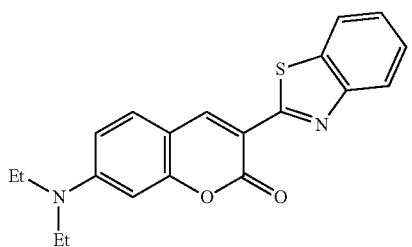

Coumarin 6

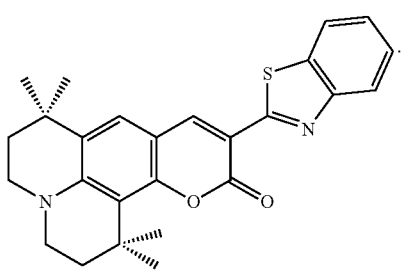

C545T

Electron Transport Region in Organic Layer 150

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer, but embodiments of the present disclosure are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from an emission layer. However, embodiments of the structure of the electron transport region are not limited thereto.

The electron transport region (for example, a buffer layer, a hole blocking layer, an electron control layer, or an electron transport layer in the electron transport region) may include a metal-free compound containing at least one π electron-depleted nitrogen-containing ring.

The term "π electron-depleted nitrogen-containing ring," as used herein, indicates a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups each having at least one *—N=*' moiety are condensed with each other (e.g., combined together), or iii) a heteropolycyclic group in which at least one of 5-membered to 7-membered heteromonocyclic groups, each having at least one *—N=*' moiety, is condensed with (e.g., combined together with) at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, thiadiazol, an imidazopyridine, an imidazopyrimidine, and an azacarbazole, but are not limited thereto.

For example, the electron transport region may include a compound represented by Formula 601:

$$[\text{Ar}_{601}]_{xe11}\text{-}[(\text{L}_{601})_{xe1}\text{-R}_{601}]_{xe21}. \qquad \text{Formula 601}$$

In Formula 601, $\text{Ar}_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $\text{L}_{601}$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer of 0 to 5, $\text{R}_{601}$ may be selected from a substituted or unsubstituted $C_3$-$C_{00}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer of 1 to 5.

In one embodiment, at least one of $\text{Ar}_{601}(\text{S})$ in the number of xe11 and $\text{R}_{601}(\text{s})$ in the number of xe21 may include the π electron-depleted nitrogen-containing ring.

In one embodiment, ring $\text{Ar}_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or more, two or more Ar601(s) may be linked via a single bond.

In one or more embodiments, Ar$_{601}$ in Formula 601 may be an anthracene group.

In one or more embodiments, a compound represented by Formula 601 may be represented by Formula 601-1:

Formula 601-1

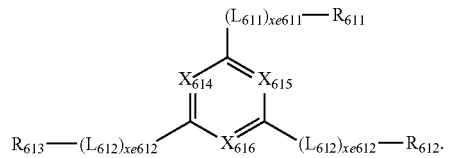

In Formula 601-1, $X_{614}$ may be N or C($R_{614}$), $X_{615}$ may be N or C($R_{615}$), $X_{616}$ may be N or C($R_{616}$), and at least one selected from $X_{614}$ to $X_{616}$ may be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, in Formulae 601 and 601-1, $L_{601}$ and $L_{611}$ to $L_{613}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments of the present disclosure are not limited thereto.

In one or more embodiment, in Formulae 601 and 601-1, xe1 and xe611 to xe613 may each independently be 0, 1, or 2.

In one or more embodiments, in Formulae 601 and 601-1, $R_{601}$ and $R_{611}$ to $R_{613}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), and Q$_{601}$ and Q$_{602}$ may respectively be the same as described above.
The electron transport region may include at least one compound selected from Compounds ET1 to ET36, but embodiments of the present disclosure are not limited thereto:
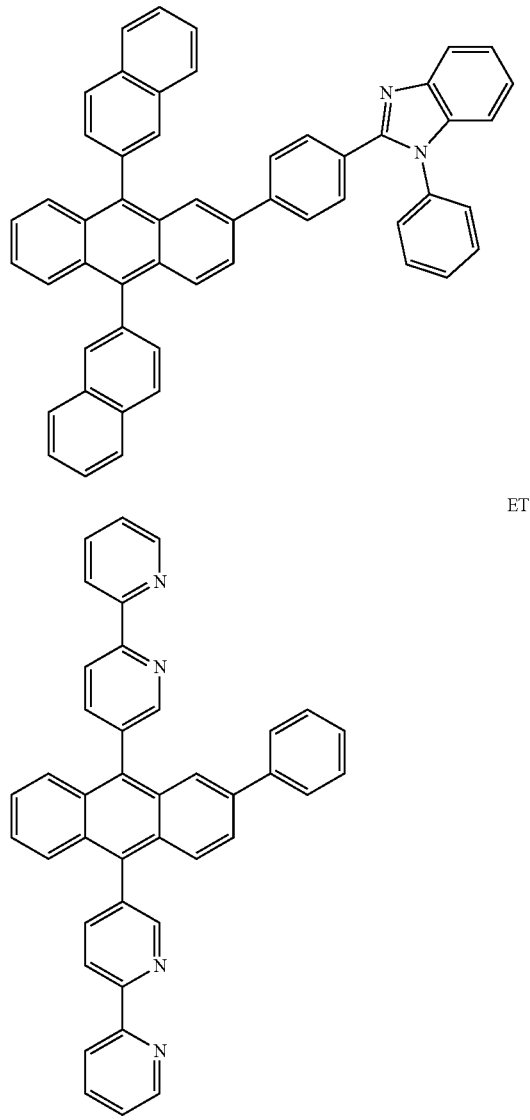
ET1
ET2
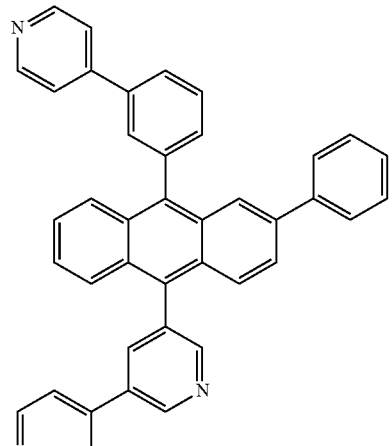
ET3
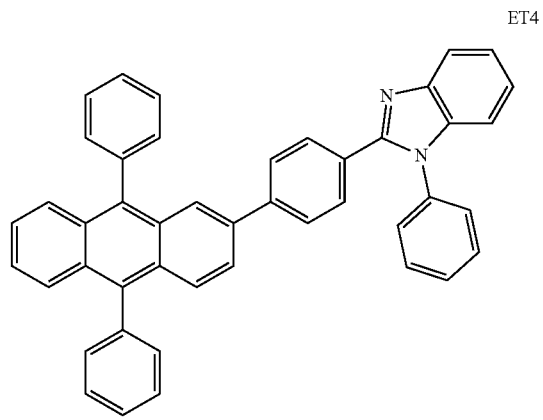
ET4
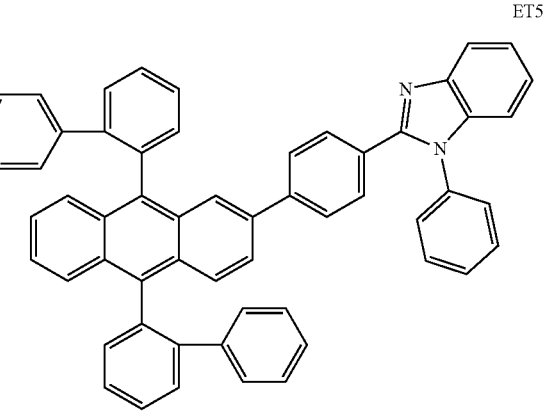
ET5

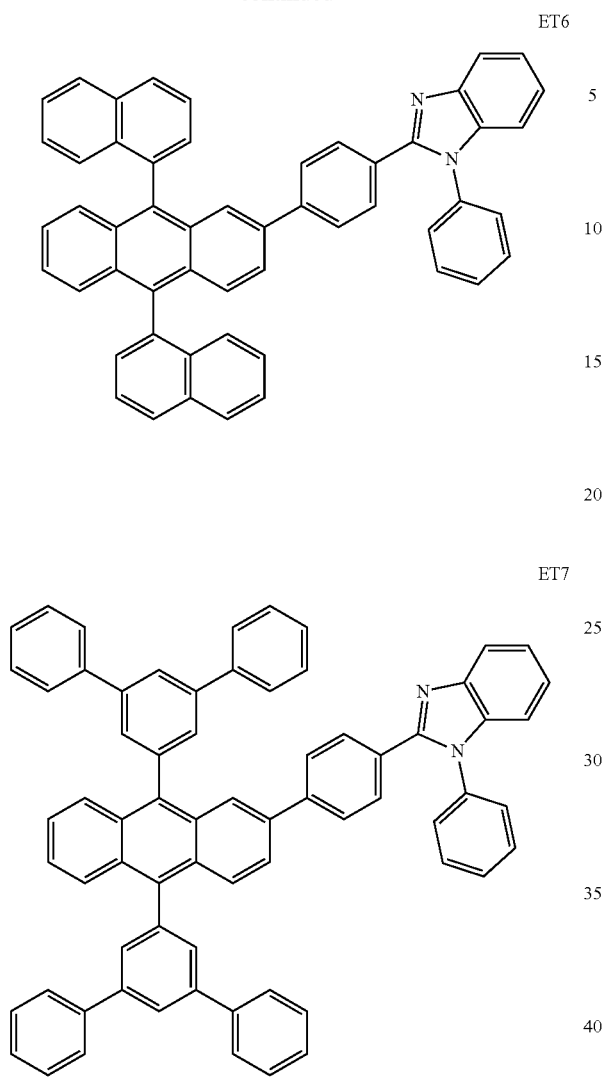
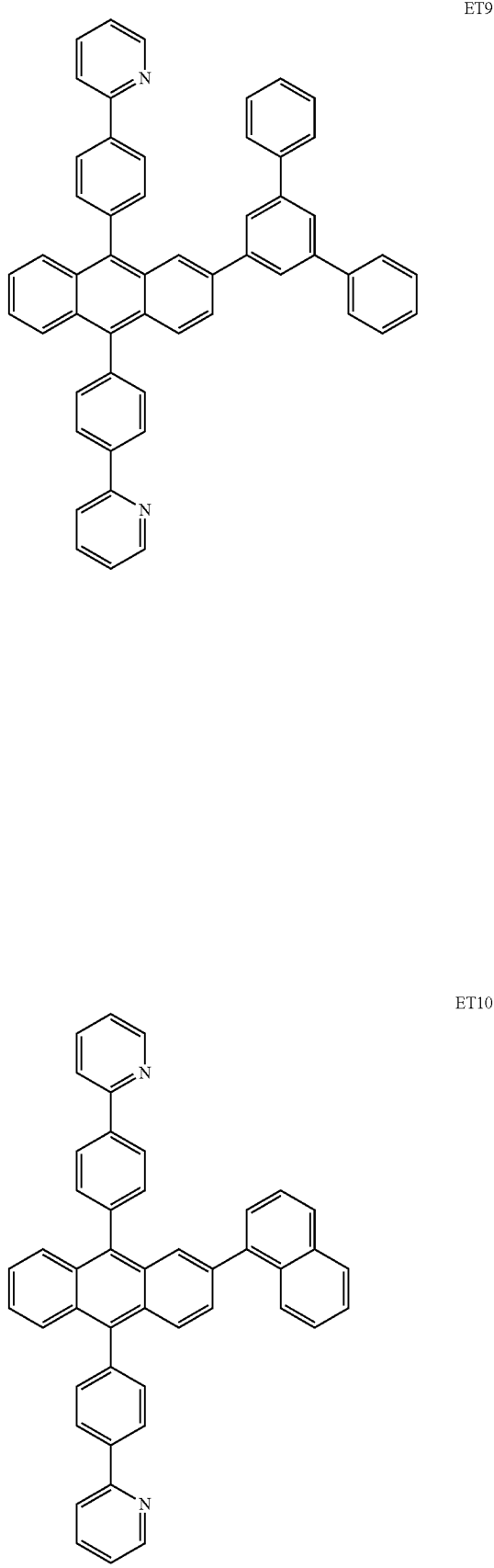

-continued
ET11
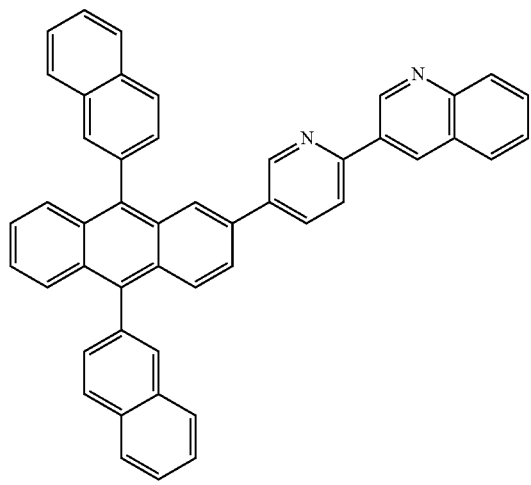
ET12
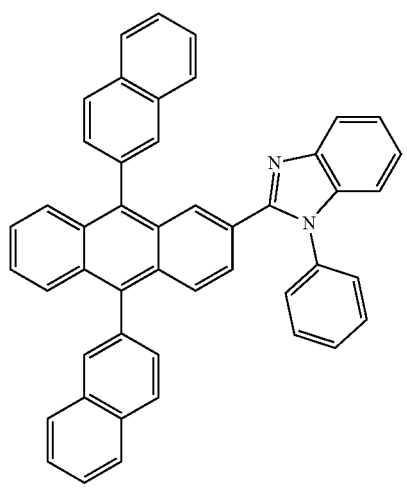
ET13
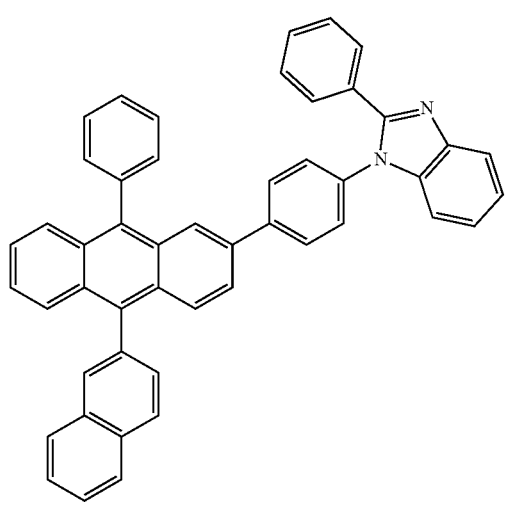
-continued
ET14
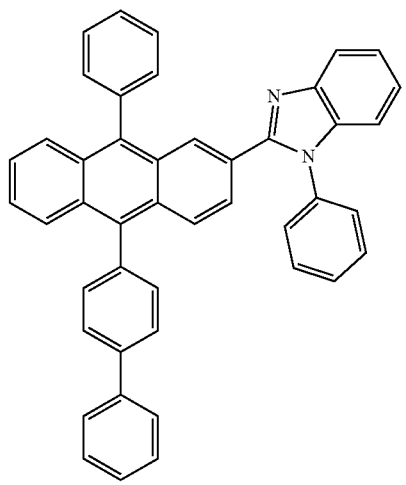
ET15
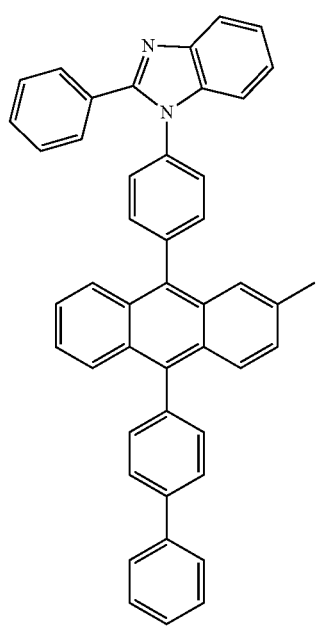
ET16
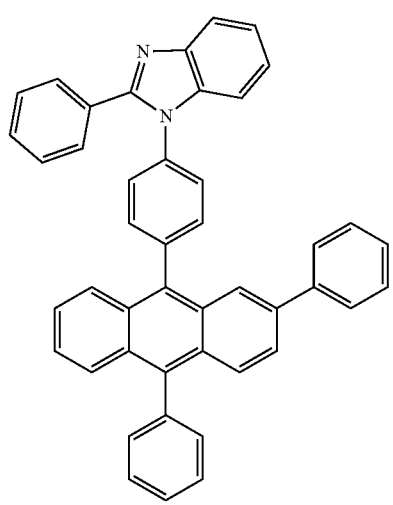

ET17
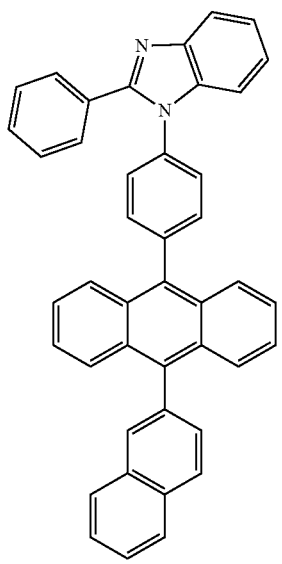
ET18
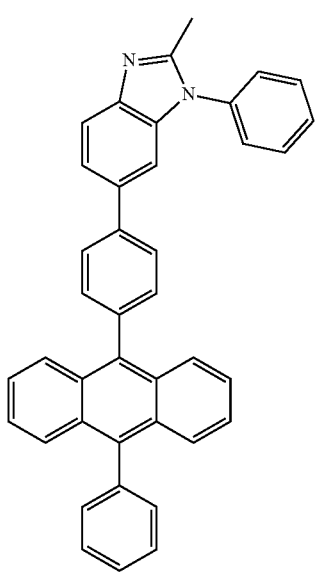
ET19
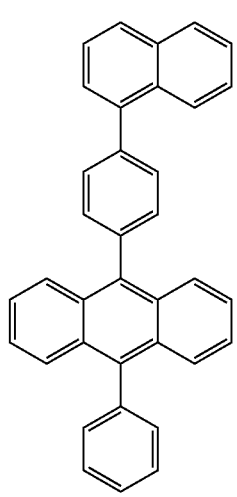
ET20
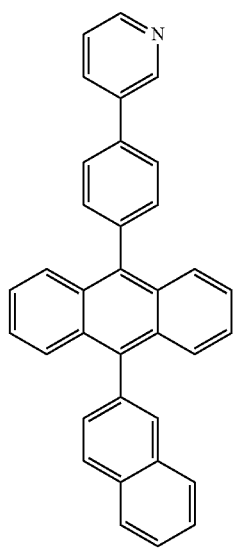
ET21
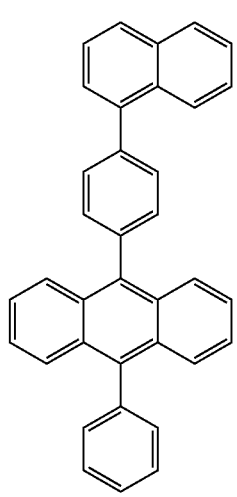
ET22
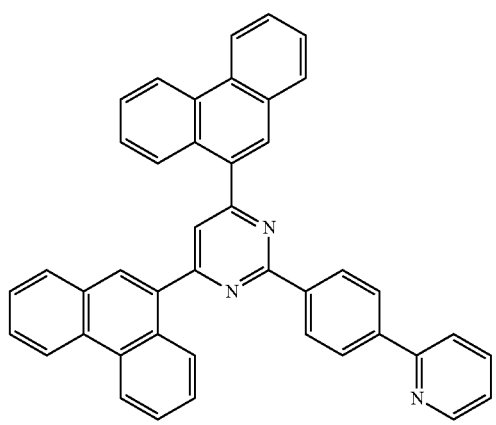

ET23
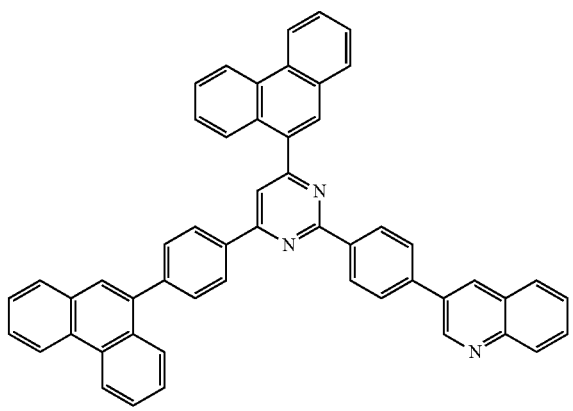
ET24
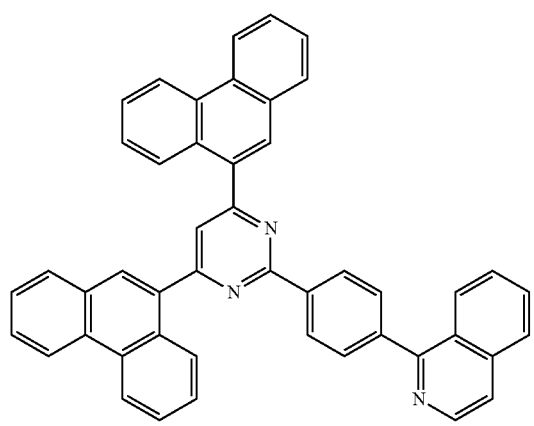
ET25
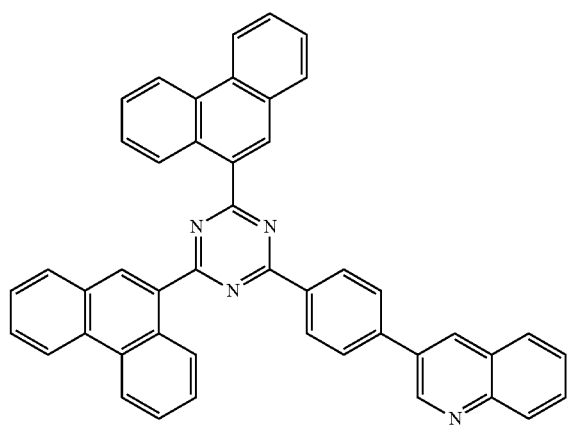
ET26
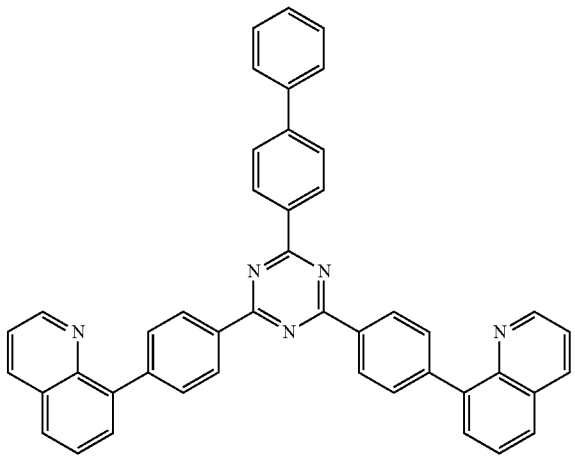
ET27
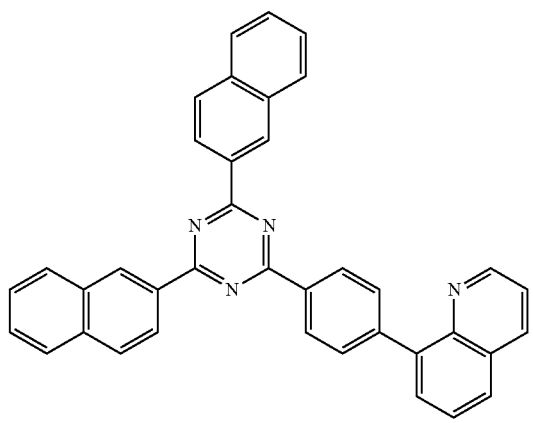
ET28
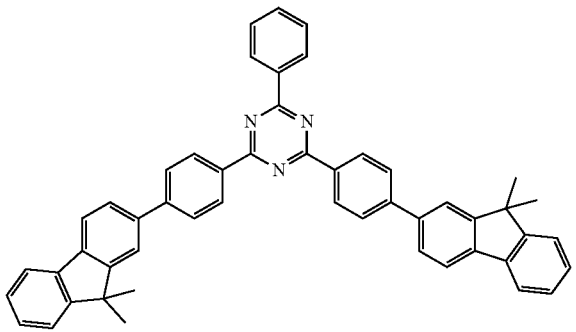

ET29
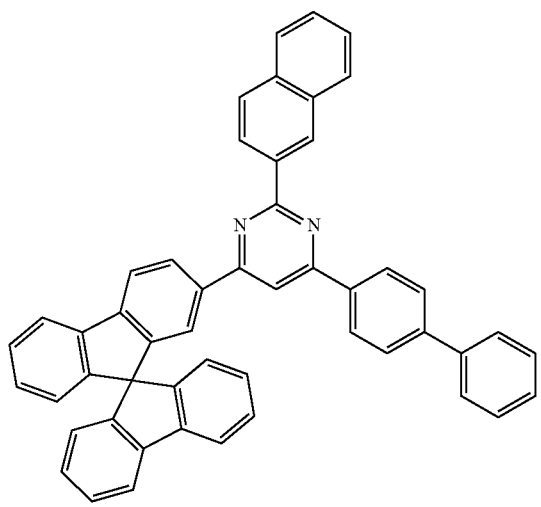
ET30
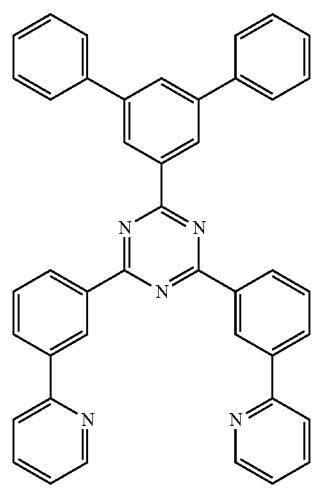
ET31
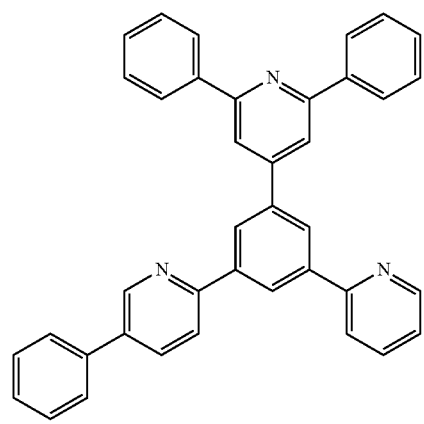
ET32
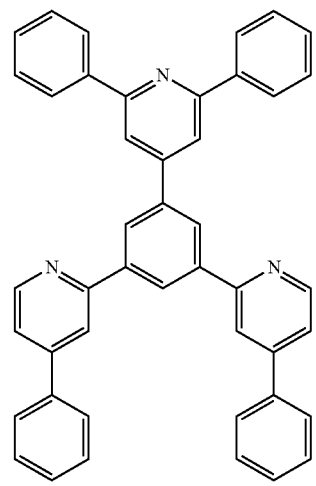
ET33
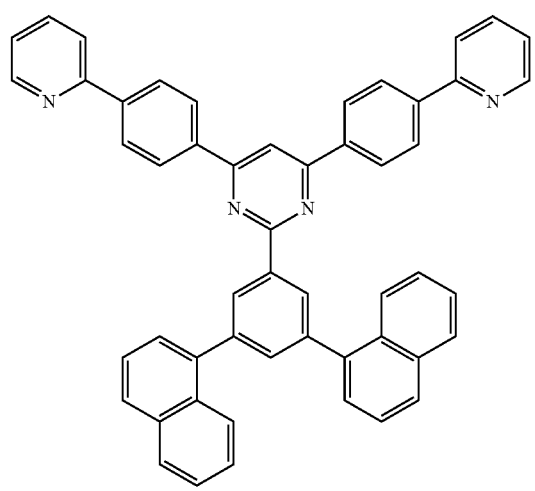
ET34
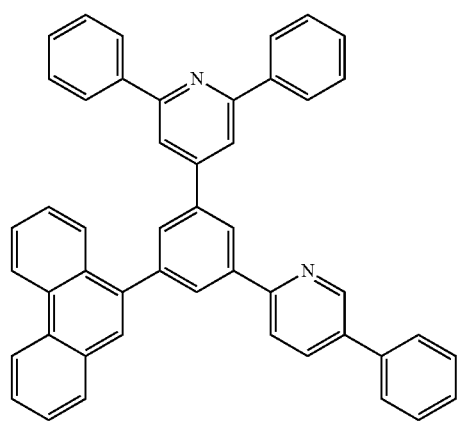

-continued

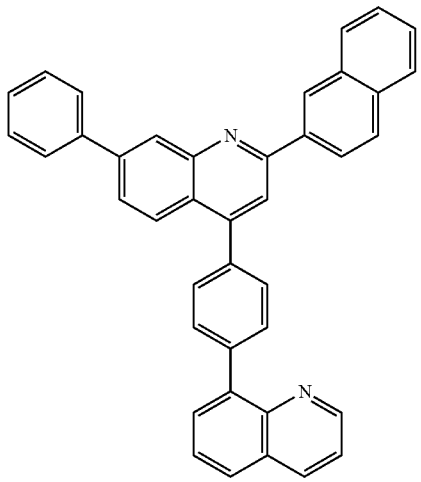
ET35

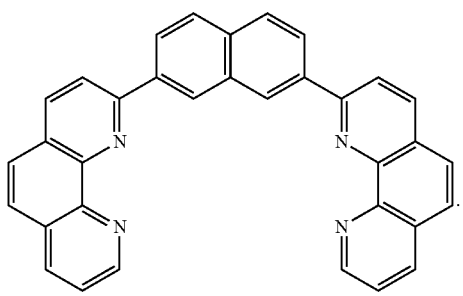
ET36

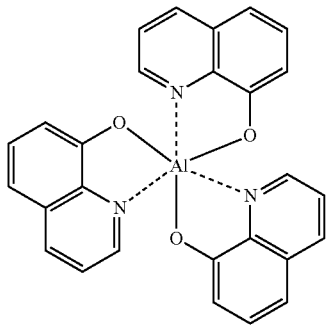
Alq₃

-continued

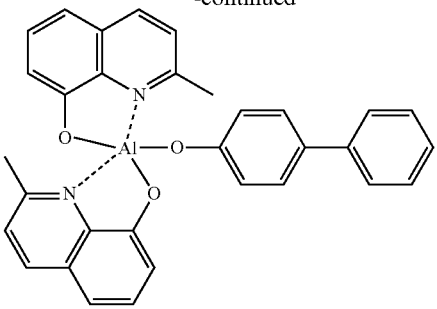

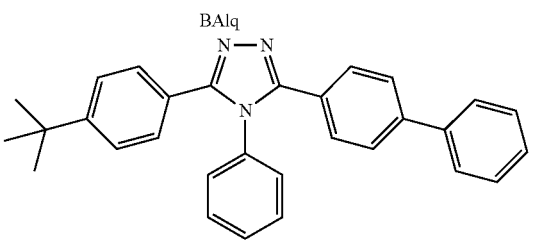
BAlq

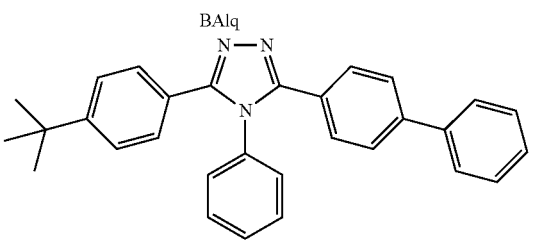
TAZ

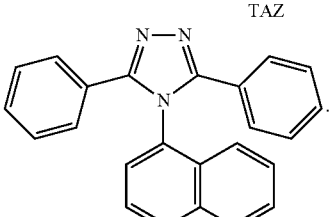

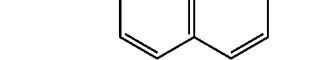
NTAZ

In one or more embodiments, the electron transport region may include at least one selected from 2,9-dimethyl-4,7-diphenyl-1,10-phenanthroline (BCP), 4,7-diphenyl-1,10-phenanthroline (Bphen), Alq₃, BAlq, 3-(biphenyl-4-yl)-5-(4-tert-butylphenyl)-4-phenyl-4H-1,2,4-triazole (TAZ), and NTAZ.

A thickness of the buffer layer, the hole blocking layer, or the electron control layer may be in a range of about 20 Å to about 1,000 Å, for example, about 30 Å to about 300 Å. When the thicknesses of the buffer layer, the hole blocking layer, and the electron control layer are within the foregoing ranges, the electron blocking layer may have excellent electron blocking characteristics or electron control characteristics without a substantial increase in driving voltage.

A thickness of the electron transport layer may be in a range of about 100 Å to about 1,000 Å, for example, about 150 Å to about 500 Å. When the thickness of the electron transport layer is within the range described above, the electron transport layer may have suitable or satisfactory electron transport characteristics without a substantial increase in driving voltage.

The electron transport region (for example, the electron transport layer in the electron transport region) may further include, in addition to the materials described above, a metal-containing material.

The metal-containing material may include at least one selected from alkali metal complex and alkaline earth-metal complex. The alkali metal complex may include a metal ion selected from a Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazol, a hydroxy phenylpyridine, a hydroxy phenylbenzimidazole, a hydroxy phenylbenzothiazole, a bipyridine, a phenanthroline, and a cyclopentadiene, but embodiments of the present disclosure are not limited thereto.

For example, the metal-containing material may include a Li complex. The Li complex may include, for example, Compound ET-D1 (lithium quinolate, LiQ) or ET-D2.

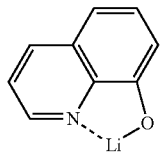

ET-D1

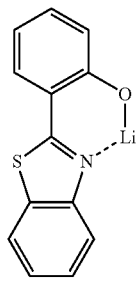

ET-D2

The electron transport region may include an electron injection layer that facilitates injection of electrons from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof.

The alkali metal may be selected from Li, Na, K, Rb, and Cs. In one embodiment, the alkali metal may be Li, Na, or Cs. In one or more embodiments, the alkali metal may be Li or Cs, but embodiments of the present disclosure are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth-metal compound, and the rare earth metal compound may be selected from oxides and halides (for example, fluorides, chlorides, bromides, or iodides) of the alkali metal, the alkaline earth-metal, and the rare earth metal.

The alkali metal compound may be selected from alkali metal oxides, such as $Li_2O$, $Cs_2O$, or $K_2O$, and alkali metal halides, such as LiF, NaF, CsF, KF, LiI, NaI, CsI, KI, or RbI. In one embodiment, the alkali metal compound may be selected from LiF, $Li_2O$, NaF, LiI, NaI, CsI, and KI, but embodiments of the present disclosure are not limited thereto.

The alkaline earth-metal compound may be selected from alkaline earth-metal oxides, such as BaO, SrO, CaO, $Ba_xSr_{1-x}O$ (0<x<1), $Ba_xCa_{1-x}O$ (0<x<1). In one embodiment, the alkaline earth-metal compound may be selected from BaO, SrO, and CaO, but embodiments of the present disclosure are not limited thereto.

The rare earth metal compound may be selected from $YbF_3$, $ScF_3$, $ScO_3$, $Y_2O_3$, $Ce_2O_3$, $GdF_3$, and $TbF_3$. In one embodiment, the rare earth metal compound may be selected from $YbF_3$, $ScF_3$, $TbF_3$, $YbI_3$, $ScI_3$, and $TbI_3$, but embodiments of the present disclosure are not limited thereto.

The alkali metal complex, the alkaline earth-metal complex, and the rare earth metal complex may include an ion of alkali metal, alkaline earth-metal, and rare earth metal as described above, and a ligand coordinated with a metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenyloxazole, hydroxy phenylthiazole, hydroxy diphenyloxadiazole, hydroxy diphenylthiadiazol, hydroxy phenylpyridine, hydroxy phenylbenzimidazole, hydroxy phenylbenzothiazole, bipyridine, phenanthroline, and cyclopentadiene, but embodiments of the present disclosure are not limited thereto.

The electron injection layer may consist of an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof, as described above. In one or more embodiments, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the range described above, the electron injection layer may have suitable or satisfactory electron injection characteristics without a substantial increase in driving voltage.

Second Electrode 190

The second electrode 190 may be disposed on the organic layer 150 having such a structure. The second electrode 190 may be a cathode which is an electron injection electrode, and in this regard, a material for forming the second electrode 190 may be selected from metal, an alloy, an electrically conductive compound, and a combination thereof, which have a relatively low work function.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode 190 may be a transmissive electrode, a semi-transmissive electrode, or a reflective electrode.

The second electrode 190 may have a single-layered structure, or a multi-layered structure including two or more layers.

Figure 2:
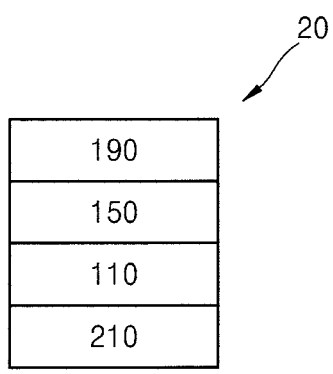
FIG. 2 is a schematic cross-sectional view of an organic light-emitting device according to an embodiment.
Figure 3:
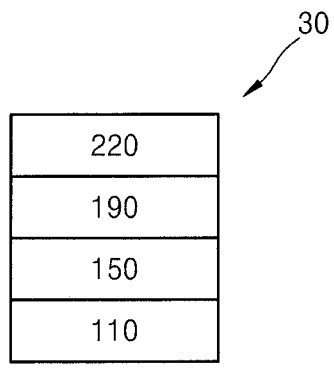
FIG. 3 is a schematic cross-sectional view of an organic light-emitting device according to an embodiment.
Figure 4:
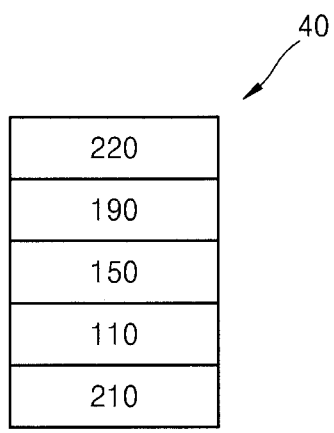
FIG. 4 is a schematic cross-sectional view of an organic light-emitting device according to an embodiment.

Description of FIGS. 2-4

An organic light-emitting device 20 of FIG. 2 includes a first capping layer 210, a first electrode 110, an organic layer 150, and a second electrode 190 which are sequentially stacked in this stated order, an organic light-emitting device 30 of FIG. 3 includes a first electrode 110, an organic layer 150, a second electrode 190, and a second capping layer 220 which are sequentially stacked in this stated order, and an organic light-emitting device 40 of FIG. 4 includes a first capping layer 210, a first electrode 110, an organic layer 150, a second electrode 190, and a second capping layer 220.

Regarding FIGS. 2-4, the first electrode 110, the organic layer 150, and the second electrode 190 may be understood by referring to the description presented in connection with FIG. 1.

In the organic layer 150 of each of the organic light-emitting devices 20 and 40, light generated in an emission layer may pass through the first electrode 110, which is a semi-transmissive electrode or a transmissive electrode, and the first capping layer 210 toward the outside, and in the organic layer 150 of each of the organic light-emitting devices 30 and 40, light generated in an emission layer may pass through the second electrode 190, which is a semi-transmissive electrode or a transmissive electrode, and the second capping layer 220 toward the outside.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may each independently include at least one material selected from carbocyclic compounds, heterocyclic compounds, amine-based compounds, porphyrine derivatives, phthalocyanine derivatives, a naphthalocyanine derivatives, alkali metal complexes, and alkaline earth-based complexes. The carbocyclic compound, the heterocyclic compound, and the amine-based compound may be optionally substituted with a substituent containing at least one element selected from O, N, S, Se, Si, F, Cl, Br, and I. In one embodiment, at least one selected from the first capping layer 210 and the second capping layer 220 may each independently include an amine-based compound.

In one embodiment, at least one selected from the first capping layer 210 and the second capping layer 220 may each independently include the compound represented by Formula 201 or the compound represented by Formula 202.

In one or more embodiments, at least one selected from the first capping layer 210 and the second capping layer 220 may each independently include a compound selected from Compounds HT28 to HT33 and Compounds CP1 to CP5, but embodiments of the present disclosure are not limited thereto.

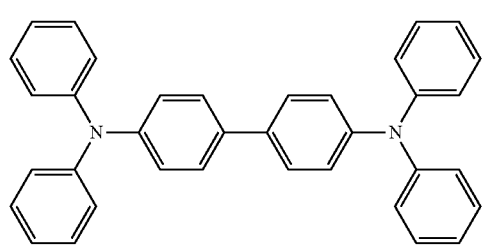

CP1

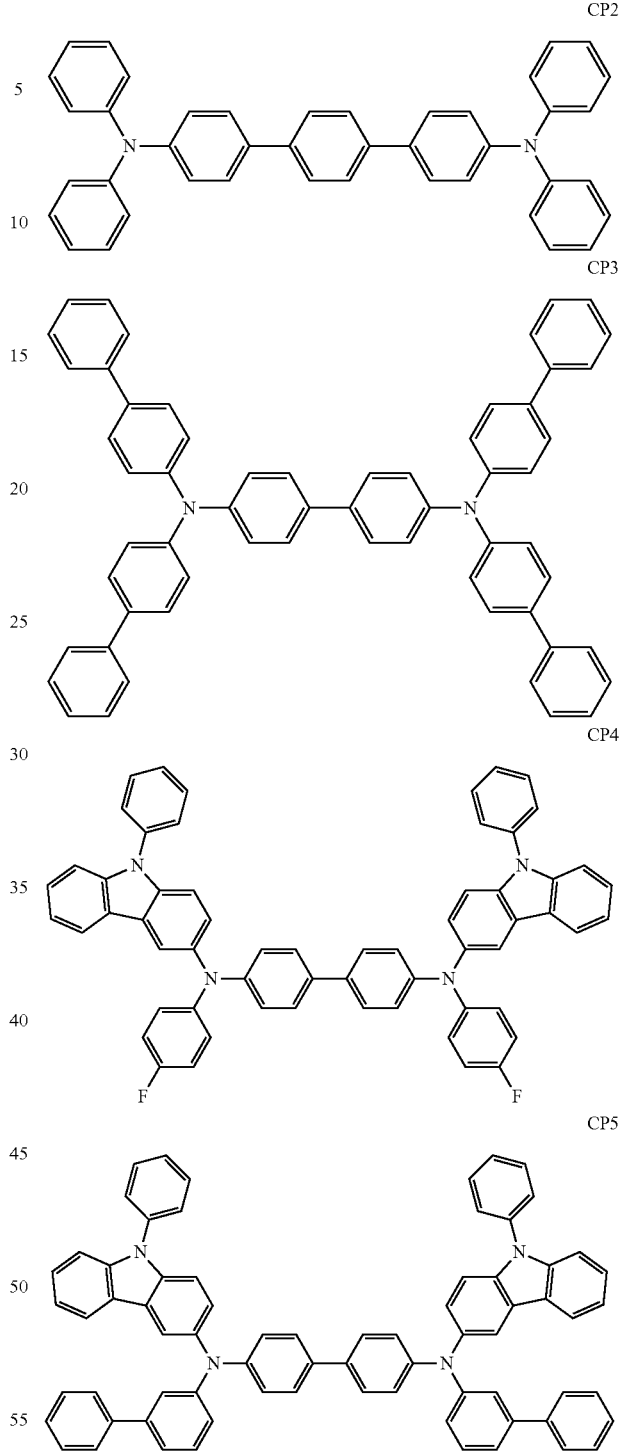

Hereinbefore, the organic light-emitting device according to an embodiment has been described in connection with FIGS. 1-4. However, embodiments of the present disclosure are not limited thereto.

Layers constituting the hole transport region, an emission layer, and layers constituting the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec by taking into account a material to be included in a layer to be formed, and the structure of a layer to be formed.

When layers constituting the hole transport region, an emission layer, and layers constituting the electron transport region are formed by spin coating, the spin coating may be performed at a coating speed of about 2,000 rpm to about 5,000 rpm and at a heat treatment temperature of about 80° C. to about 200° C. by taking into account a material to be included in a layer to be formed, and the structure of a layer to be formed.

General Definition of Some of the Substituents

The term "$C_1$-$C_{60}$ alkyl group," as used herein, refers to a linear or branched saturated aliphatic hydrocarbon monovalent group having 1 to 60 carbon atoms, and examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group," as used herein, refers to a divalent group having substantially the same structure as the $C_1$-$C_{60}$ alkyl group.

The term "$C_2$-$C_{60}$ alkenyl group," as used herein, refers to a hydrocarbon group having at least one carbon-carbon double bond at a main chain (e.g., in the middle) or at a terminus of the $C_2$-$C_{60}$ alkyl group, and examples thereof include an ethenyl group, a propenyl group, and a butenyl group. The term "$C_2$-$C_{60}$ alkenylene group," as used herein, refers to a divalent group having substantially the same structure as the $C_2$-$C_{60}$ alkenyl group.

The term "$C_2$-$C_{60}$ alkynyl group," as used herein, refers to a hydrocarbon group having at least one carbon-carbon triple bond at a main chain (e.g., in the middle) or at a terminus of the $C_2$-$C_{60}$ alkyl group, and examples thereof include an ethynyl group, and a propynyl group. The term "$C_2$-$C_{60}$ alkynylene group", as used herein, refers to a divalent group having substantially the same structure as the $C_2$-$C_{60}$ alkynyl group.

The term "$C_1$-$C_{60}$ alkoxy group," as used herein, refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group," as used herein, refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having substantially the same structure as the $C_3$-$C_{10}$ cycloalkyl group.

The term "$C_1$-$C_{10}$ heterocycloalkyl group," as used herein, refers to a monovalent monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group," as used herein, refers to a divalent group having substantially the same structure as the $C_1$-$C_{10}$ heterocycloalkyl group.

The term "$C_3$-$C_{10}$ cycloalkenyl group," as used herein, refers to a monovalent monocyclic group that has 3 to 10 carbon atoms and at least one carbon-carbon double bond in the ring thereof and no aromaticity (e.g., the entire ring, group, and/molecule is not aromatic), and examples thereof include a cyclopentenyl group, a cyclohexenyl group, and a cycloheptenyl group. The term "$C_3$-$C_{10}$ cycloalkenylene group," as used herein, refers to a divalent group having substantially the same structure as the $C_3$-$C_{10}$ cycloalkenyl group.

The term "$C_1$-$C_{10}$ heterocycloalkenyl group," as used herein, refers to a monovalent monocyclic group that has at least one heteroatom selected from N, O, Si, P, and S as a ring-forming atom, 1 to 10 carbon atoms, and at least one carbon-carbon double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group," as used herein, refers to a divalent group having substantially the same structure as the $C_1$-$C_{10}$ heterocycloalkenyl group.

The term "$C_6$-$C_{60}$ aryl group," as used herein, refers to a monovalent group having a carbocyclic aromatic system having 6 to 60 carbon atoms, and the term "$C_6$-$C_{60}$ arylene group," as used herein, refers to a divalent group having a carbocyclic aromatic system having 6 to 60 carbon atoms. Examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other (e.g., combined together).

The term "$C_1$-$C_{60}$ heteroaryl group," as used herein, refers to a monovalent group having a carbocyclic aromatic system that has at least one heteroatom selected from N, O, Si, P, and S as a ring-forming atom, in addition to 1 to 1 carbon atoms. The term "$C_1$-$C_{60}$ heteroarylene group," as used herein refers to a divalent group having a carbocyclic aromatic system that has at least one heteroatom selected from N, O, Si, P, and S as a ring-forming atom, in addition to 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other (e.g., combined together).

The term "$C_6$-$C_{60}$ aryloxy group," as used herein, indicates —$OA_{102}$ (wherein $A_{102}$ is the $C_6$-$C_{60}$ aryl group), and a $C_6$-$C_{60}$ arylthio group indicates —$SA_{103}$ (wherein $A_{103}$ is the $C_6$-$C_{60}$ aryl group).

The term "$C_1$-$C_{60}$ heteroaryloxy group," as used herein, indicates —$OA_{104}$ (wherein $A_{104}$ is the $C_1$-$C_{60}$ heteroaryl group), and the term "$C_6$-$C_{60}$ heteroarylthio group," as used herein, indicates —$SA105$ (wherein $A_{105}$ is the $C_1$-$C_{60}$ heteroaryl group).

The term "monovalent non-aromatic condensed polycyclic group," as used herein, refers to a monovalent group (for example, having 8 to 60 carbon atoms) having two or more rings condensed with each other (e.g., combined together), only carbon atoms as ring-forming atoms, and no aromaticity in its entire molecular structure (e.g., the entire group and/or molecule is not aromatic). An example of the monovalent non-aromatic condensed polycyclic group is a fluorenyl group. The term "divalent non-aromatic condensed polycyclic group," as used herein, refers to a divalent group having substantially the same structure as the monovalent non-aromatic condensed polycyclic group.

The term "monovalent non-aromatic condensed heteropolycyclic group," as used herein, refers to a monovalent group (for example, having 1 to 60 carbon atoms) having two or more rings condensed to each other (e.g., combined together), at least one heteroatom selected from N, O, Si, P, and S, other than carbon atoms, as a ring-forming atom, and no aromaticity in its entire molecular structure (e.g., the entire group and/or molecule is not aromatic). An example of the monovalent non-aromatic condensed heteropolycyclic group is a carbazolyl group. The term "divalent non-aromatic condensed heteropolycyclic group," as used herein, refers to a divalent group having substantially the same structure as the monovalent non-aromatic condensed heteropolycyclic group.

The term "$C_5$-$C_{60}$ carbocyclic group," as used herein, refers to a monocyclic or polycyclic group having 5 to 60 carbon atoms in which a ring-forming atom is a carbon atom only. The $C_5$-$C_{60}$ carbocyclic group may be an aromatic carbocyclic group or a non-aromatic carbocyclic group. The $C_5$-$C_{60}$ carbocyclic group may be a ring, such as benzene, a monovalent group, such as a phenyl group, or a divalent group, such as a phenylene group. In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group," as used herein, refers to a group having substantially the same structure as the $C_5$-$C_{60}$ carbocyclic group, except that as a ring-forming atom, at least one heteroatom selected from N, O, Si, P, and S is used in addition to carbon (the number of carbon atoms may be in a range of 1 to 60).

At least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted $C_1$-$C_{60}$ heteroaryloxy group, the substituted $C_1$-$C_{60}$ heteroarylthio group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_0$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a biphenyl group, and a terphenyl group.

The term "Ph," as used herein, represents a phenyl group, the term "Me," as used herein, represents a methyl group, the term "Et," as used herein, represents an ethyl group, and the term "ter-Bu" or "Bu$^t$," as used herein, represents a tert-butyl group.

The term "biphenyl group," as used herein, refers to "a phenyl group substituted with a phenyl group." In other words, the "biphenyl group" is a substituted phenyl group having a $C_6$-$C_{60}$ aryl group as a substituent.

The term "terphenyl group," as used herein, refers to "a phenyl group substituted with a biphenyl group." In other words, the "terphenyl group" is a phenyl group having, as a substituent, a $C_6$-$C_{60}$ aryl group substituted with a $C_6$-$C_{60}$ aryl group.

and *' used herein, unless defined otherwise, each refer to a binding site to a neighboring atom in a corresponding formula.

Hereinafter, a compound according to embodiments and an organic light-emitting device according to embodiments will be described in more detail with reference to Synthesis Examples and Examples. The wording "B was used instead of A" used in describing Synthesis Examples refers to that an identical (e.g., substantially identical) molar equivalent of B was used in place of A.

EXAMPLES

Synthesis Example 1: Synthesis of Compound 146

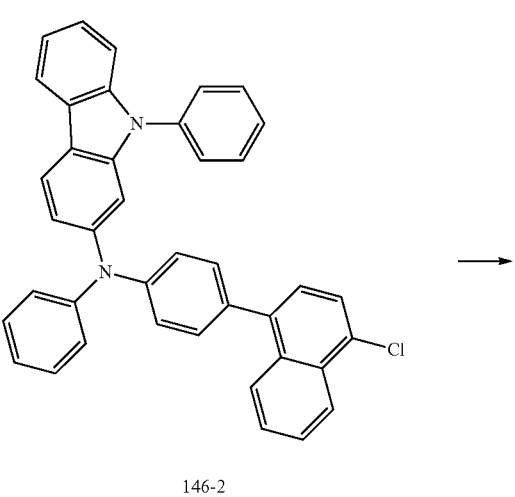

-continued

146

(1) Synthesis of Intermediate 146-1

4 g of (4-bromophenyl)boronic acid and 4.8 g of 1-bromo-4-chloronaphthalene were added to 80 ml of tetrahydrofuran (THF), 560 mg of Pd(PPh$_3$)$_4$ and 5.4 g of potassium carbonate diluted in 20 ml of water were added dropwise thereto, and the reaction mixture was stirred at a temperature of 60° C. for 4 hours. The reaction mixture was cooled to room temperature, and an organic layer was extracted three times by using ethyl acetate and separated therefrom. The organic layer was dried by anhydrous magnesium sulfate and filtered under reduced pressure. A residue obtained therefrom was separated and purified by column chromatography to obtain 5 g (yield of 81%) of Intermediate 146-1.

$C_{16}H_{10}BrCl$: M+ Calcd: 315.97 Found: 316.0.

(2) Synthesis of Intermediate 146-2

3.2 g of Intermediate 146-1, 3.4 g of N,9-diphenyl-9H-carbazole-2-amine, 0.34 g of Pd$_2$(dba)$_3$, 0.1 ml of PtBu$_3$, and 3.4 g of KOt-Bu were dissolved in 60 ml of toluene and stirred at a temperature of 85° C. for 1 hour. The mixture was cooled to room temperature, and the reaction was terminated with water. Then, an organic layer was extracted therefrom three times by using ethyl acetate. The extracted organic layer was dried by using anhydrous magnesium sulfate and distilled under reduced pressure. A residue obtained therefrom was separated and purified by column chromatography to obtain 4.9 g (yield of 87%) of Intermediate 146-2.

$C_{40}H_{27}ClN_2$: M+ Calcd: 570.19 Found: 571.2.

(3) Synthesis of Compound 146

3.2 g (yield of 77%) of Compound 146 was obtained in substantially the same manner as in Synthesis of Intermediate 146-2, except that 3 g of Intermediate 146-2 and 1.6 g of N-phenyldibenzo[b,d]furan-3-amine were used.

Synthesis Example 2: Synthesis of Compound 152

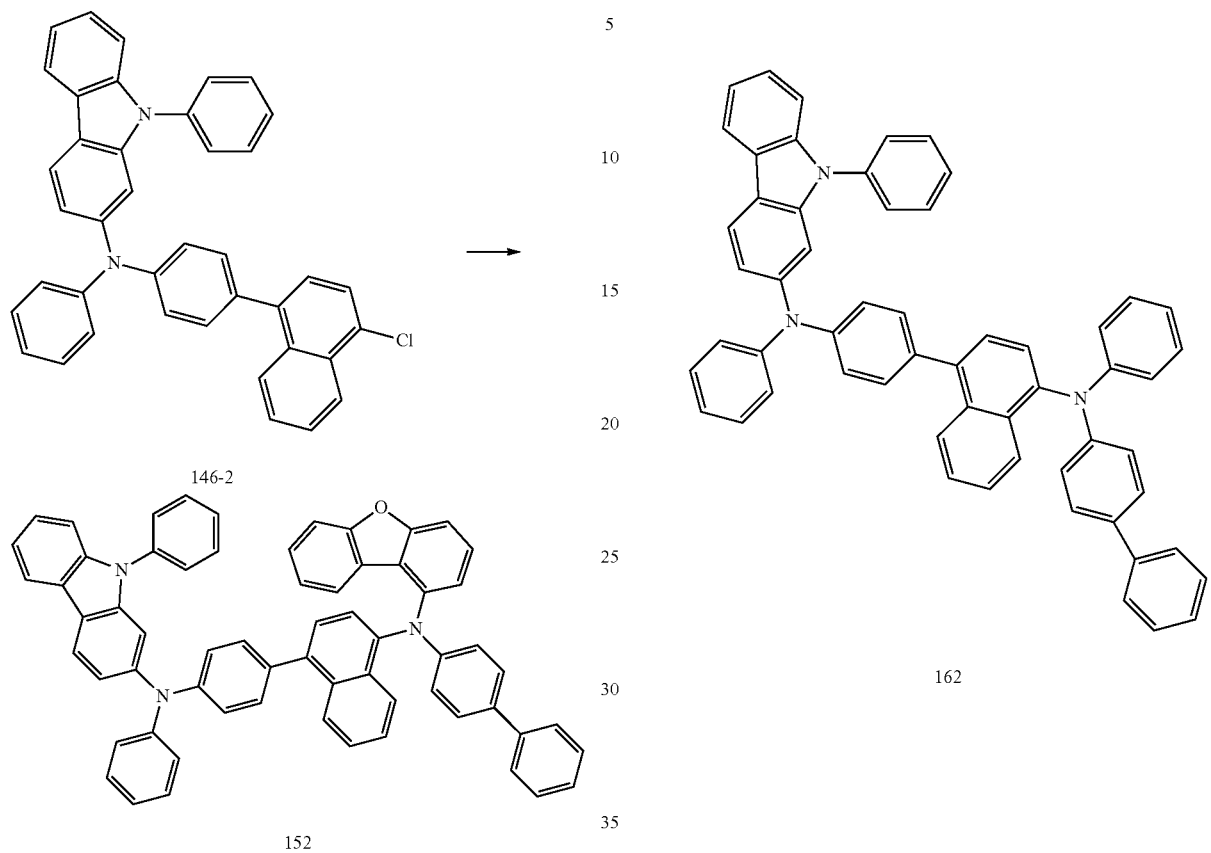

3.3 g (yield of 69%) of Compound 152 was obtained in substantially the same manner as in Synthesis of Compound 146, except that 2.1 g of N-([1,1'-biphenyl]-4-yl)dibenzo[b,d]furan-1-amine was used instead of 1.6 g of N-phenyldibenzo[b,d]furan-3-amine.

Synthesis Example 3: Synthesis of Compound 162

3 g (71%) of Compound 162 was obtained in substantially the same manner as in Synthesis of Compound 146, except that 1.5 g of N-phenyl-[1,1'-biphenyl]-4-amine was used instead of 1.6 g of N-phenyldibenzo[b,d]furan-3-amine.

Synthesis Example 4: Synthesis of Compound 163

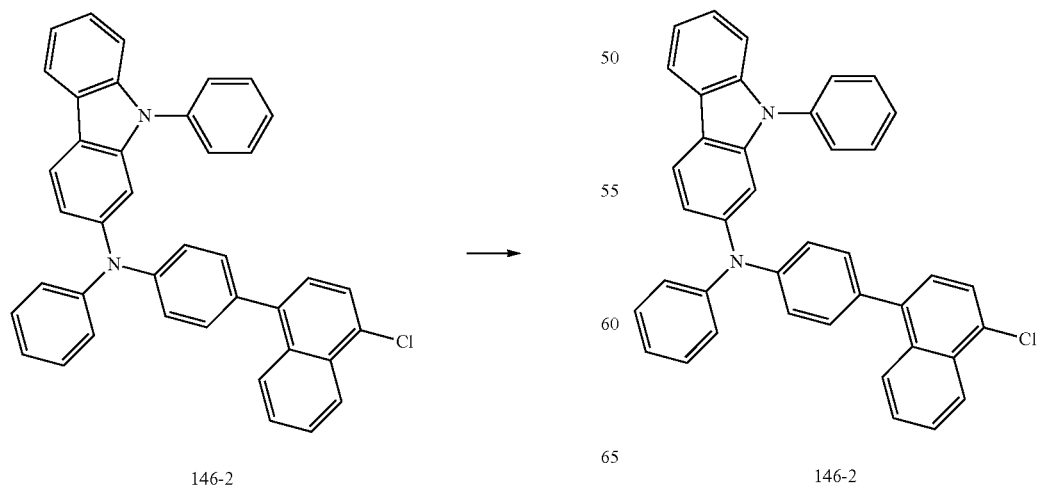

-continued

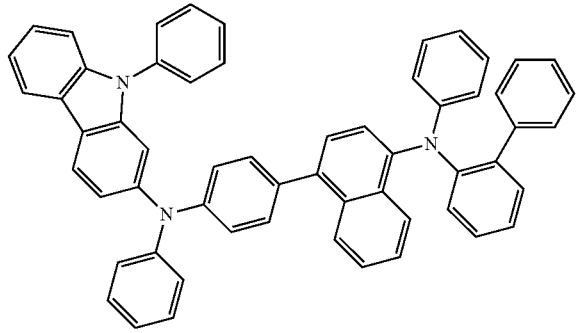

163

3.1 g (yield of 72%) of Compound 163 was obtained in substantially the same manner as in Synthesis of Compound 146, except that 1.5 g of N-phenyl-[1,1'-biphenyl]-2-amine was used instead of 1.6 g of N-phenyldibenzo[b,d]furan-3-amine.

Synthesis Example 5: Synthesis of Compound 166

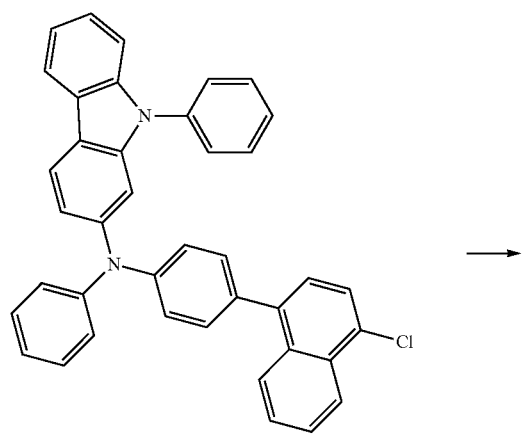

146-2

-continued

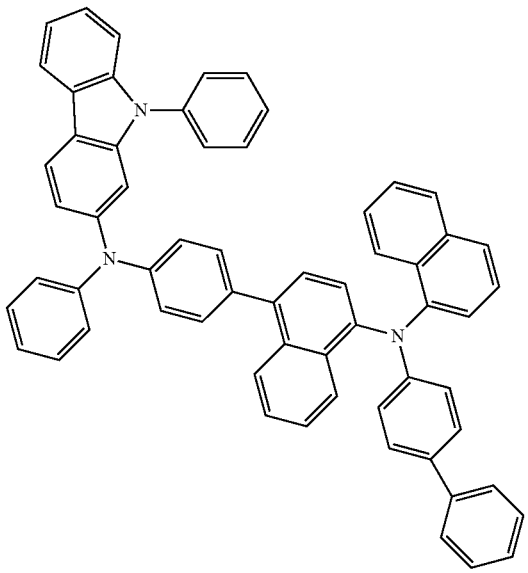

166

2.8 g (yield of 66%) of Compound 166 was obtained in substantially the same manner as in Synthesis of Compound 146, except that 1.8 g of N-([1,1'-biphenyl]-4-yl)naphthalene-1-amine was used instead of 1.6 g of N-phenyldibenzo[b,d]furan-3-amine.

Synthesis Example 6: Synthesis of Compound 170

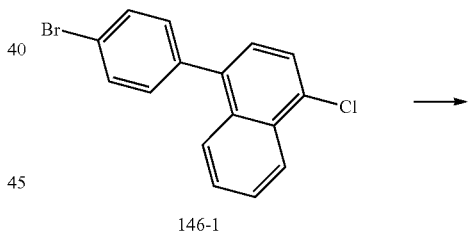

146-1

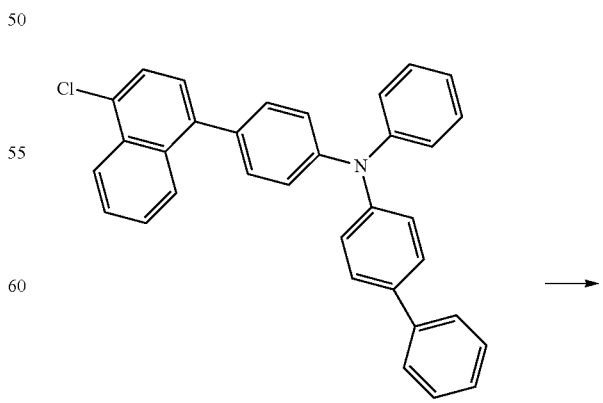

170-1

-continued

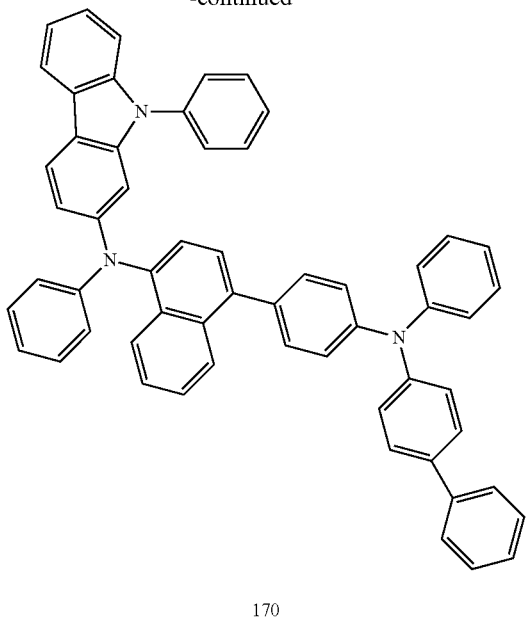

170

(1) Synthesis of Intermediate 170-1

4 g (yield of 84%) of Intermediate 170-1 was obtained in substantially the same manner as in Synthesis of Intermediate 146-2, except that 2.5 g of N-phenyl-[1,1'-biphenyl]-4-amine was used instead of 3.4 g of N,9-diphenyl-9H-carbazole-2-amine.

(2) Synthesis of Compound 170

5.1 g (yield of 79%) of Compound 170 was obtained in substantially the same manner as in Synthesis of Compound 146, except that 4 g of Intermediate 170-1 and 3.3 g of N,9-diphenyl-9H-carbazole-2-amine were respectively used instead of 3 g of Intermediate 146-2 and 1.6 g of N-phenyldibenzo[b,d]furan-3-amine.

$^1$H NMR and MS/FAB of Compounds synthesized in Synthesis Examples 1 to 6 were shown in Table 1 below.

Methods of synthesizing compounds other than the compound shown in Table 1 (where the term "Calcd" indicates that the values were calculated) should be readily recognizable by those of ordinary skill in the art by referring to the synthesis paths and source materials described above.

TABLE 1

| Compound | $^1$H NMR(CDCl$_3$, 400 MHz) | MS/FAB Found | MS/FAB Calcd |
|---|---|---|---|
| 146 | 8.17(m, 1H), 7.82(m, 1H), 7.75-7.65(m, 4H), 7.54-7.23(m, 15H), 7.08-7.02(m, 4H), 6.96-6.87(m, 5H), 6.80(dd, 1H), 6.66-6,.60(m, 2H), 6.53-6.50(m, 2H), 6.41-6.39(m, 2H), 6.26-6.22(m, 2H) | 793.32 | 793.31 |
| 152 | 8.17(m, 1H), 7.82-7.80(m, 2H), 7.72-7.70(m, 1H), 7.63-7.61(m, 2H). 7.54-7.23(m, 23H), 7.09-7.04(m, 2H). 6.95-6.87(4H), 6.82(dd, 1H). 6.66-6.59(m, 2H), 6.54-6.49(m, 4H). 6.42-6.39(m, 2H) | 869.35 | 869.34 |
| 162 | 8.17(m, 1H), 7.82-7.80(m, 1H), 7.66-7.62(m, 3H), 7.55-7.23(m, 18H), 7.16(d, 1H), 7.09-7.04(m, 4H), 6.95-6.79(m, 5H), 6.66-6.59(m, 2H), 6.54-6.49(m, 2H). 6.42-6.39(m, 2H)m 6.14-6.11(m, 2H) | 779.35 | 779.33 |
| 163 | 8.17(m, 1H). 7.82-7.80(m, 1H), 7.60-7.44(m, 13H), 7.40-7.22(m, 6H), 7.18-7.12(m, 2H), 7.08-6.83(m, 9H), 6.81(dd, 1H), 6.65-6.60(m, 2), 6.54-6.50(m, 2H), 6.41-6.38(m, 2H), 6.17-6.14(m, 2H) | 779.35 | 779.33 |
| 166 | 8.17-8.15(m, 1H). 8.04-8.01(m, 1H). 7.87(m, 1H). 7.80(m, 1H), 7.63-7.61(m, 2H). 7.55-7.21(m, 22H), 7.17(t, 1H). 7.09-7.04(m, 2H). 6.92-6.88(m, 2H), 6.81 (dd, 1H), 6.70-6.62(m, 3H). 6.54-6.50(m, 3H), 6.43-6.39(m, 2H). 6.27-6.23(m, 2H) | 829.38 | 829.35 |
| 170 | 8.18-8.15(m, 1H). 7.85-7.83(m, 1H). 7.71(dd, 1), 7.64-7.61(m, 2H), 7.55-7.23(m, 18H), 7.08-6.82(m, 11H), 6.67-6.61(m, 2H). 6.55(dd, 1H). 6.27-6.18(m, 4H) | 779.35 | 779.33 |

Example 1

As an anode, a 15 Ω/cm² (1200 Å) ITO glass substrate was cut to a size of 50 mm×50 mm×0.7 mm, sonicated with isopropyl alcohol and pure water each for 5 minutes, and then cleaned by exposure to ultraviolet rays and ozone for 30 minutes. Then, the ITO glass substrate was provided to a vacuum deposition apparatus.

2-TNATA was vacuum-deposited on the ITO glass substrate to form a hole injection layer having a thickness of 600 Å, Compound 146 was vacuum-deposited on the hole injection layer to form a hole transport layer having a thickness of 300 Å.

9,10-di-naphthalene-2-yl-anthracene (ADN) (blue fluorescent host) and DPAVBi (blue fluorescent dopant) were co-deposited on the hole transport layer at a weight ratio of 98:2 to form an emission layer having a thickness of 300 Å.

$Alq_3$ was deposited on the emission layer to form an electron transport layer having a thickness of 300 Å, LiF was deposited on the electron transport layer to form an electron injection layer having a thickness of 10 Å, and Al was deposited on the electron injection layer to form a cathode having a thickness of 3000 Å, thereby completing the manufacture of an organic light-emitting device.

Examples 2 to 6 and Comparative Examples 1 to 3

Organic light-emitting devices were manufactured in substantially the same manner as in Example 1, except that Compounds shown in Table 2 were each used instead of Compound 146 in forming a hole transport layer.

Evaluation Example

The driving voltage, luminance, efficiency, and lifespan of the organic light-emitting devices manufactured according to Examples 1 to 6 and Comparative Examples 1 to 3 were measured at a current density of 10 mA/cm² by using Keithley SMU 236 and a luminance meter PR650, and results thereof are shown in Table 2. The lifespan indicates an amount of time that lapses when luminance was 50% of initial luminance (100%) (at a current density of 100 mA/cm²) after driving an organic light-emitting device.

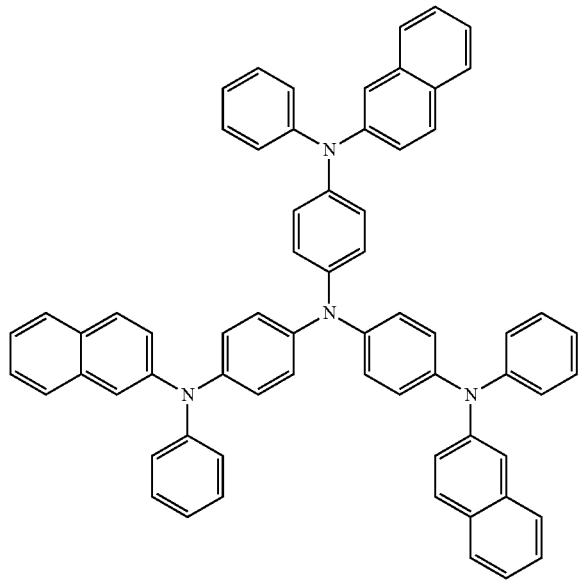

2-TNATA

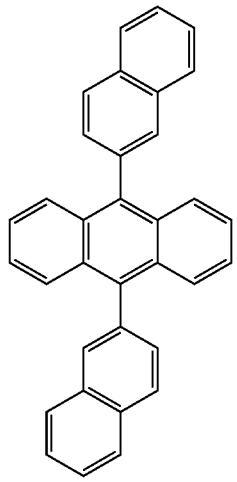

ADN

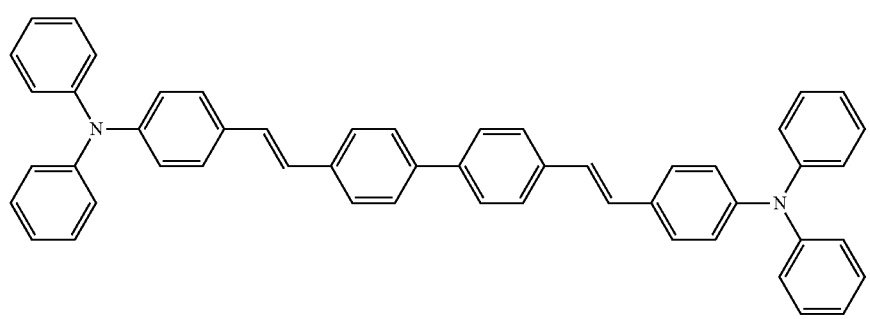

DPAVBi

TABLE 2

|  | Material for hole transport layer | Driving voltage (V) | Current density (mA/cm$^2$) | Luminance (cd/m$^2$) | Efficiency (cd/A) | Emission color | Lifespan (time) |
|---|---|---|---|---|---|---|---|
| Comparative Example 1 | NPB | 7.01 | 50 | 2645 | 5.29 | Blue | 258 |
| Comparative Example 2 | Compound A | 4.53 | 50 | 3300 | 6.6 | Blue | 291 |
| Comparative Example 3 | Compound B | 4.48 | 50 | 3215 | 6.43 | Blue | 293 |
| Example 1 | Compound 146 | 4.20 | 50 | 3750 | 7.50 | Blue | 320 |
| Example 2 | Compound 152 | 4.20 | 50 | 3750 | 7.50 | Blue | 324 |
| Example 3 | Compound 162 | 4.26 | 50 | 3730 | 7.46 | Blue | 371 |
| Example 4 | Compound 163 | 4.26 | 50 | 3670 | 7.34 | Blue | 332 |
| Example 5 | Compound 166 | 4.25 | 50 | 3675 | 7.35 | Blue | 392 |
| Example 6 | Compound 170 | 4.32 | 50 | 3585 | 7.17 | Blue | 414 |

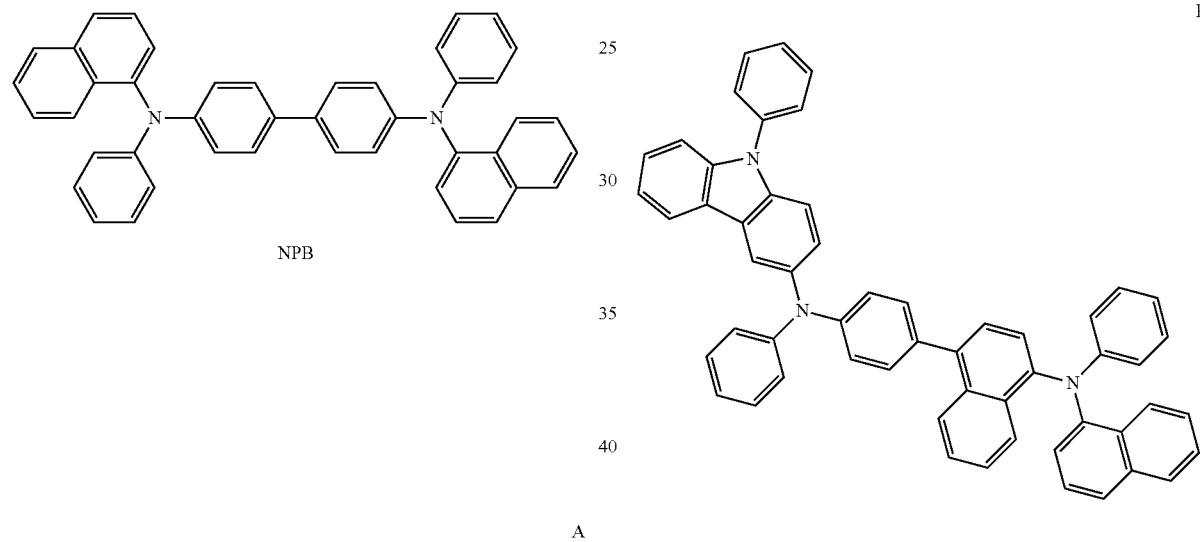

B

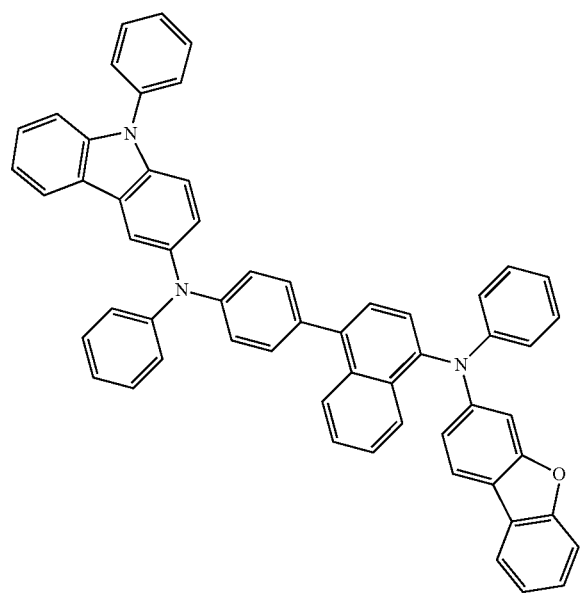

A

Referring to Table 1, it is confirmed that the driving voltage and the efficiency of the organic light-emitting devices of Examples 1 to 6 are improved as compared with the organic light-emitting devices of Comparative Examples 1 to 3. For example, it has been confirmed that the lifespan of the organic light-emitting devices of Examples 1 to 6 is remarkably improved as compared with the organic light-emitting devices of Comparative Examples 1 to 3.

The organic light-emitting device including the diamine compound may have a low driving voltage, high efficiency, high luminance, high color purity, and a long lifespan.

It should be understood that embodiments described herein should be considered in a descriptive sense only and not for purposes of limitation. Descriptions of features or aspects within each embodiment should typically be considered as available for other similar features or aspects in other embodiments.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

As used herein, the term "and/or" includes any and all combinations of one or more of the associated listed items. Expressions such as "at least one of," when preceding a list of elements, modify the entire list of elements and do not modify the individual elements of the list.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While one or more embodiments have been described with reference to the figures, it will be understood by those of ordinary skill in the art that various changes in form and details may be made therein without departing from the spirit and scope of the appended claims, and equivalents thereof.

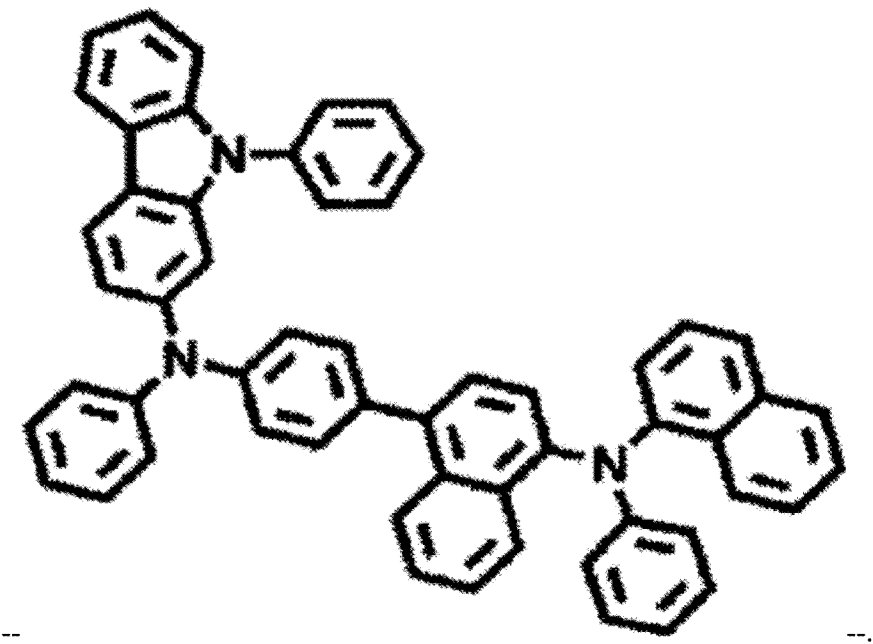

What is claimed is:
1. An organic light-emitting device comprising:
a first electrode;
a second electrode; and
an organic layer between the first electrode and the second electrode and comprising an emission layer,
wherein the organic layer comprises a diamine compound comprising a naphthyl-phenyl linker and a 2-carbazolyl group,
wherein the diamine compound is a diamine compound represented by Formula 1:

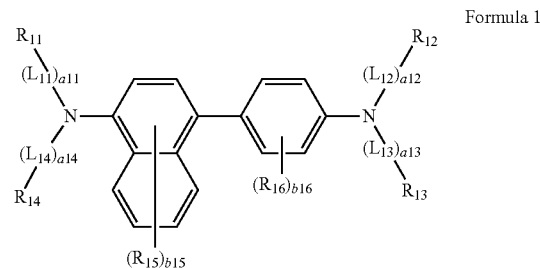

Formula 1

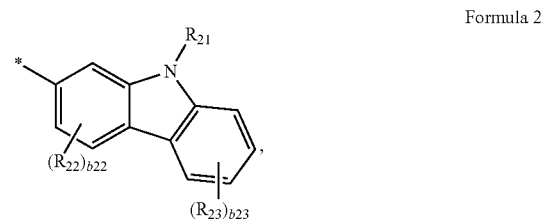

Formula 2 wherein, in Formula 1,
$L_{11}$ to $L_{14}$ are each independently selected from a single bond, a substituted or unsubstituted $C_5$-$C_{60}$ carbocyclic group, and a substituted or unsubstituted $C_1$-$C_{60}$ heterocyclic group,
a11 to a14 are each independently selected from 0, 1, 2, and 3,
$R_{11}$ to $R_{14}$ are each independently selected from a group represented by Formula 2, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group,
wherein at least one of $R_{11}$ to $R_{14}$ is a group represented by Formula 2, and one of $R_{11}$ to $R_{14}$ which is represented by Formula 2 is different from the remaining $R_{11}$ to $R_{14}$,
$R_{15}$, $R_{16}$, and $R_{21}$ to $R_{23}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), b15 is selected from 1, 2, 3, 4, 5, and 6, b16 and b23 are each independently selected from 1, 2, 3, and 4, b22 is selected from 1, 2, and 3, $Q_1$ to $Q_3$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a $C_1$-$C_{60}$ alkyl group substituted with at least one selected from deuterium, —F, and a cyano group, a $C_6$-$C_{60}$ aryl group substituted with at least one selected from deuterium, —F, and a cyano group, a biphenyl group, and a terphenyl group, and

* indicates a binding site to a neighboring atom.

2. The organic light-emitting device of claim 1, wherein:

the first electrode is an anode, the second electrode is a cathode, the organic layer further comprises a hole transport region between the first electrode and the emission layer, and the hole transport region comprises the diamine compound.

3. The organic light-emitting device of claim 2, wherein:

the hole transport region comprises at least one of a hole injection layer and a hole transport layer, and at least one of the hole injection layer and the hole transport layer comprises the diamine compound.

4. The organic light-emitting device of claim 2, wherein:

the hole transport region comprises a p-dopant, and the p-dopant has a lowest unoccupied molecular orbital (LUMO) energy level of about −3.5 eV or less.

5. A diamine compound represented by Formula 1:

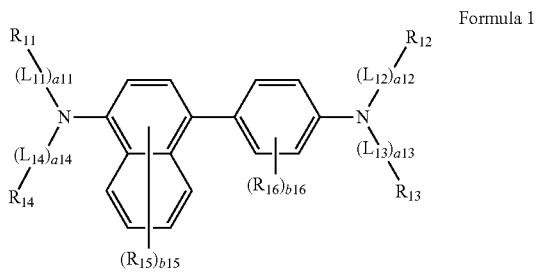

Formula 1

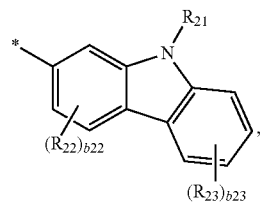

Formula 2 wherein, in Formula 1, $L_{11}$ to $L_{14}$ are each independently selected from a single bond, a substituted or unsubstituted $C_5$-$C_{60}$ carbocyclic group, and a substituted or unsubstituted $C_1$-$C_{60}$ heterocyclic group, a11 to a14 are each independently selected from 0, 1, 2, and 3, $R_{11}$ to $R_{14}$ are each independently selected from a group represented by Formula 2, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one of $R_{11}$ to $R_{14}$ is a group represented by Formula 2, $R_{15}$, $R_{16}$, and $R_{21}$ to $R_{23}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), b15 is selected from 1, 2, 3, 4, 5, and 6, b16 and b23 are each independently selected from 1, 2, 3, and 4, b22 is selected from 1, 2, and 3, $Q_1$ to $Q_3$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a $C_1$-$C_{60}$ alkyl group substituted with at least one selected from deuterium, —F, and a cyano group, a $C_6$-$C_{60}$ aryl group substituted with at least one selected from deuterium, —F, and a cyano group, a biphenyl group, and a terphenyl group, and indicates a binding site to a neighboring atom.

6. The diamine compound of claim 5, wherein:
$R_{11}$ is a group represented by Formula 2;
$R_{12}$ is a group represented by Formula 2;
$R_{11}$ and $R_{12}$ are each a group represented by Formula 2;
$R_{11}$ and $R_{14}$ are each a group represented by Formula 2;
$R_{11}$, $R_{12}$, and $R_{14}$ are each a group represented by Formula 2;
$R_{11}$, $R_{12}$, and $R_{13}$ are each a group represented by Formula 2; or
$R_{11}$, $R_{12}$, $R_{13}$, and $R_{14}$ are each a group represented by Formula 2.

7. The diamine compound of claim 5, wherein:
$R_{11}$ is a group represented by Formula 2; or
$R_{12}$ is a group represented by Formula 2.

8. The diamine compound of claim 5, wherein:
$L_{11}$ to $L_{14}$ are each independently selected from a single bond, a benzene group, a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a perylene group, a thiophene group, a furan group, a silole group, a carbazole group, an indole group, an isoindole group, a benzofuran group, a benzothiophene group, a benzosilole group, a dibenzofuran group, a dibenzothiophene group, a benzocarbazole group, a dibenzocarbazole group, and a dibenzosilole group; and
a benzene group, a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a perylene group, a thiophene group, a furan group, a silole group, a carbazole group, an indole group, an isoindole group, a benzofuran group, a benzothiophene group, a benzosilole group, a dibenzofuran group, a dibenzothiophene group, a benzocarbazole group, a dibenzocarbazole group and a dibenzosilole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a thiophenyl group, a furanyl group, a silolyl group, a carbazolyl group, an indolyl group, an isoindolyl group, a benzofuranyl group, a benzothiophenyl group, a benzosilolyl group, a dibenzofuranyl group, a dibenzothiophenyl group, a benzocarbazolyl group, a dibenzocarbazolyl group, a dibenzosilolyl group, —Si($Q_{31}$)($Q_{32}$)($Q_{33}$), —N($Q_{31}$)($Q_{32}$), and —B($Q_{31}$)($Q_{32}$), and $Q_{31}$ to $Q_{33}$ are each independently selected from a $C_1$-$C_{60}$ alkyl group, a phenyl group, a biphenyl group, and a terphenyl group.

9. The diamine compound of claim 5, wherein:
$L_{11}$ to $L_{14}$ are each independently selected from a single bond and groups represented by Formulae 3-1 to 3-41:

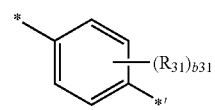

3-1

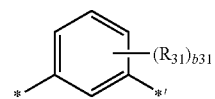

3-2

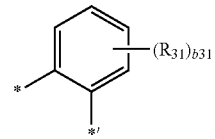

3-3

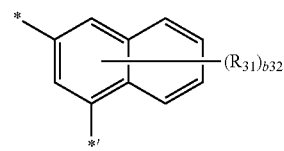

3-4

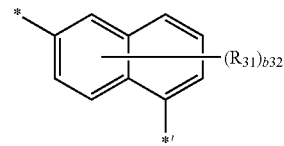

3-5

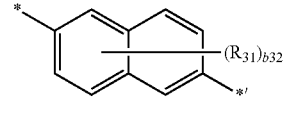

3-6

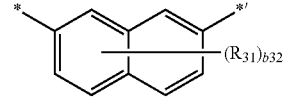

3-7

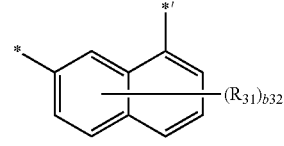

3-8

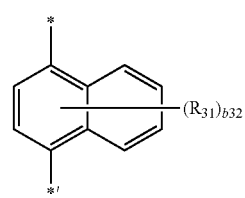

3-9

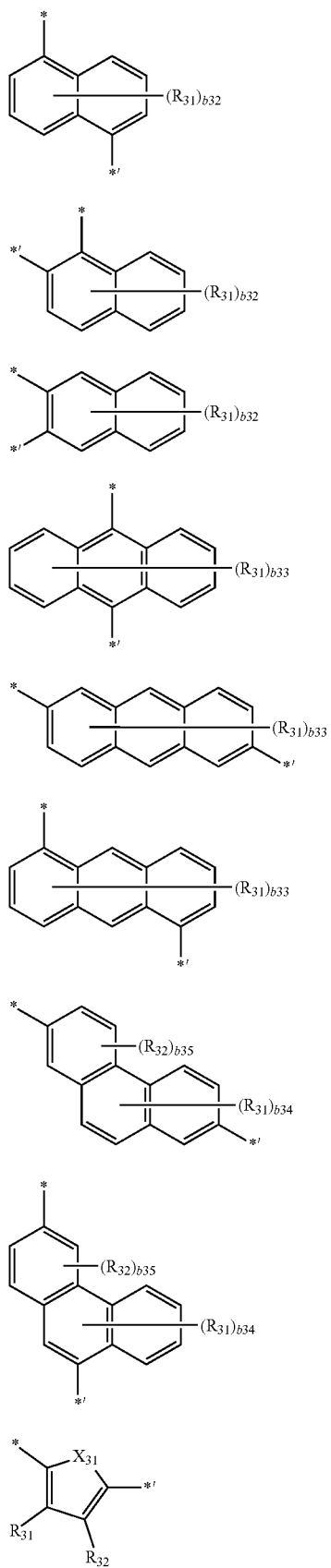
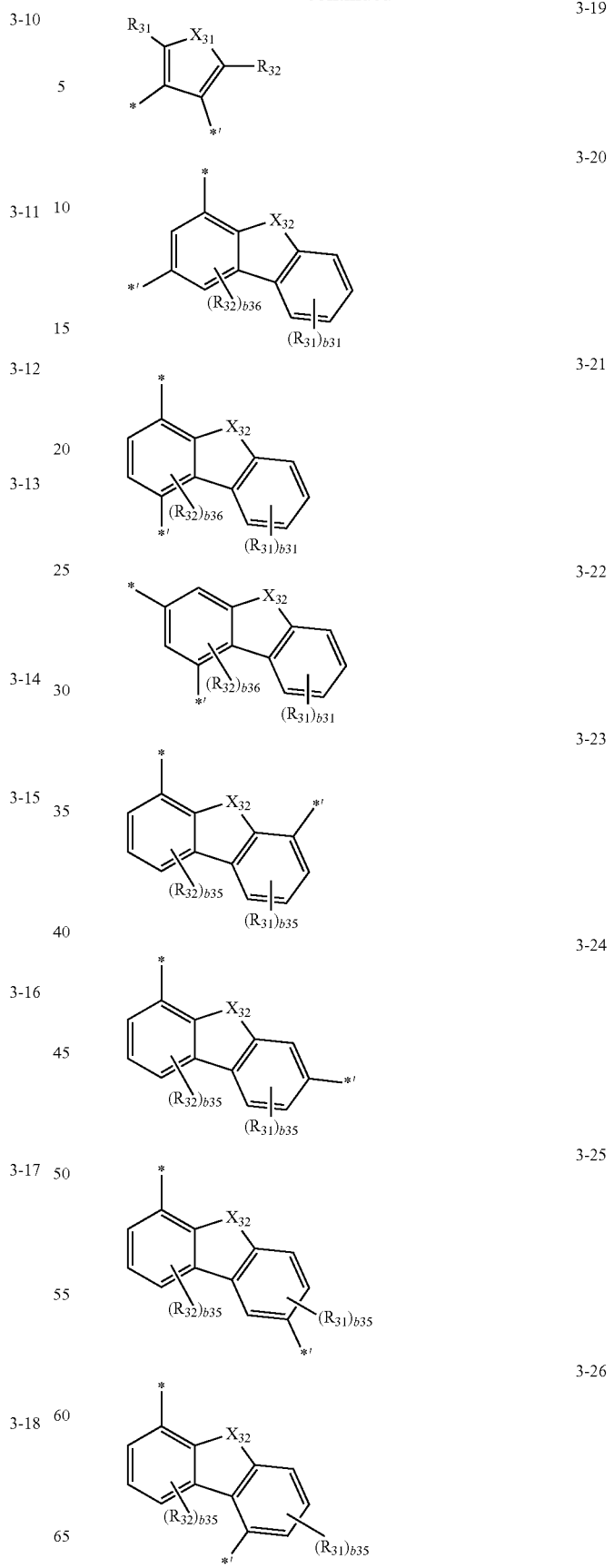

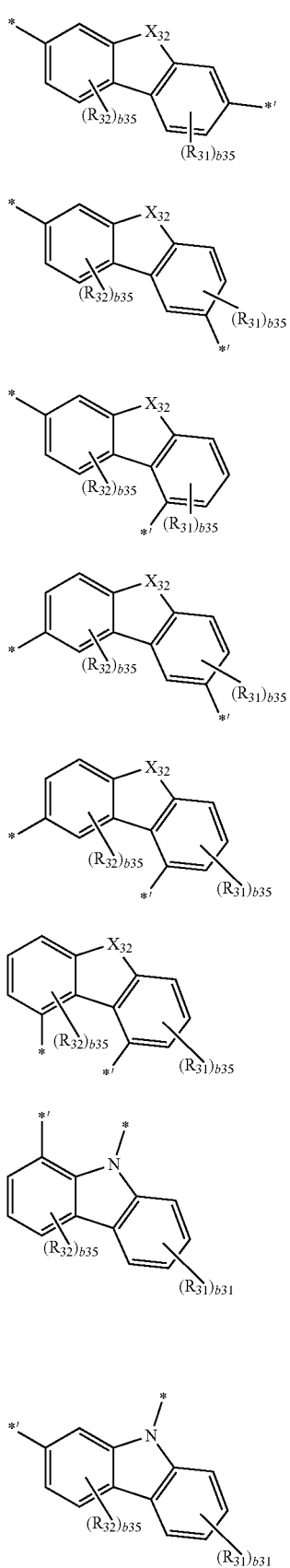
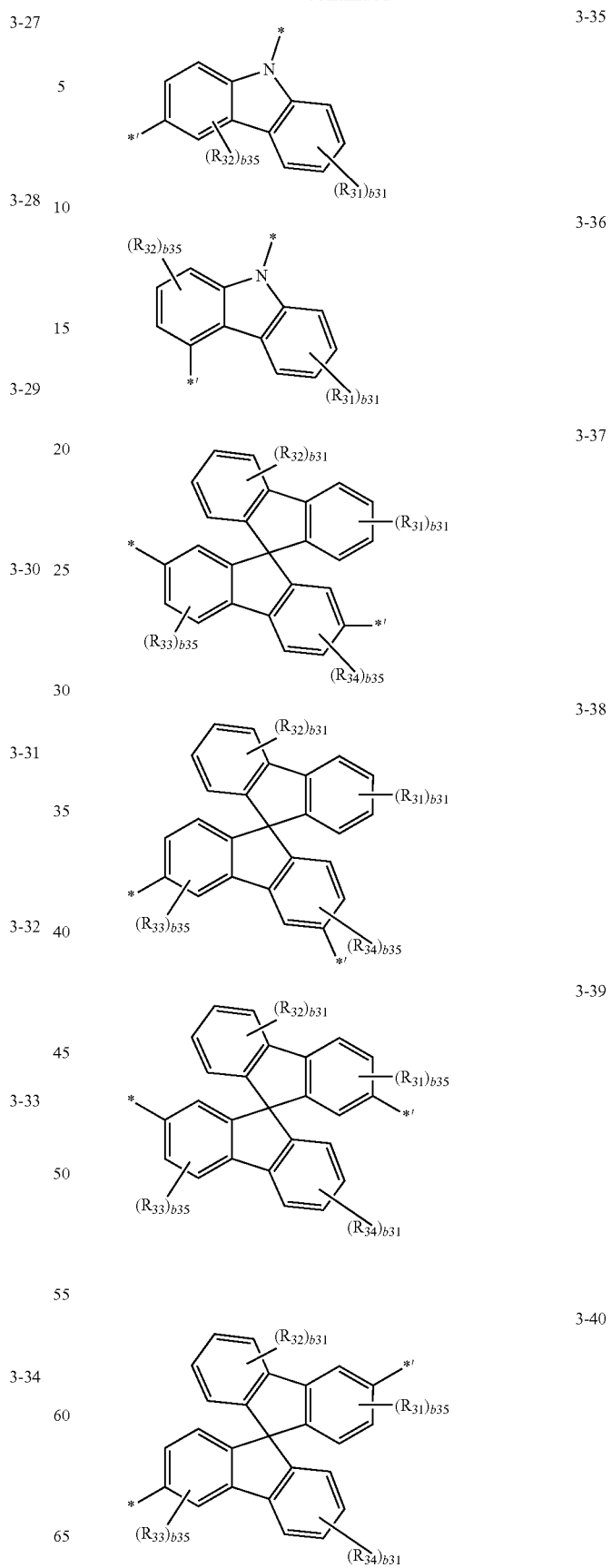

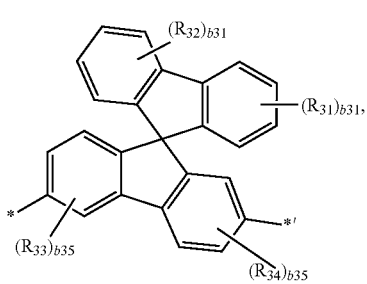

3-41 wherein, in Formulae 3-1 to 3-41,
$X_{31}$ is selected from O and S,
$X_{32}$ is selected from O, S, $N(R_{33})$, and $C(R_{33})(R_{34})$,
$R_{31}$ to $R_{34}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_1$-$C_{60}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a thiophenyl group, a furanyl group, a silolyl group, a carbazolyl group, an indolyl group, an isoindolyl group, a benzofuranyl group, a benzothiophenyl group, a benzosilolyl group, a dibenzofuranyl group, a dibenzothiophenyl group, a benzocarbazolyl group, a dibenzocarbazolyl group, a dibenzosilolyl group, —$Si(Q_{31})(Q_{32})(Q_{33})$, —$N(Q_{31})(Q_{32})$, and —$B(Q_{31})(Q_{32})$,
$Q_{31}$ to $Q_{33}$ are each independently selected from a $C_1$-$C_{60}$ alkyl group, a phenyl group, a biphenyl group, and a terphenyl group,
b31 is selected from 1, 2, 3, and 4,
b32 is selected from 1, 2, 3, 4, 5, and 6,
b33 is selected from 1, 2, 3, 4, 5, 6, 7, and 8,
b34 is selected from 1, 2, 3, 4, and 5,
b35 is selected from 1, 2, and 3,
b36 is selected from 1 and 2, and
* and *' each indicate a binding site to a neighboring atom.

10. The diamine compound of claim 5, wherein:
a11 to a14 are each independently selected from 0 and 1.

11. The diamine compound of claim 5, wherein:
$R_{11}$ to $R_{14}$ are each independently a group represented by Formula 2, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group, each substituted with at least one selected from deuterium, —F, —Cl, —Br, —I, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group, wherein at least one of $R_{11}$ to $R_{14}$ is a group represented by Formula 2.

12. The diamine compound of claim 5, wherein:
$R_{11}$ to $R_{14}$ are each independently selected from a group represented by Formula 2 and groups represented by Formulae 5-1 to 5-138:

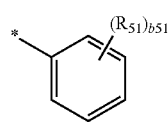

5-1

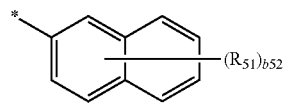

5-2

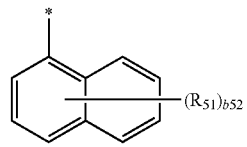

5-3

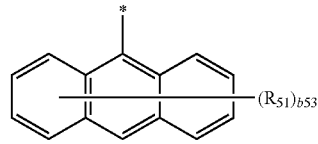

5-4

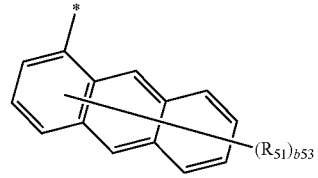

5-5

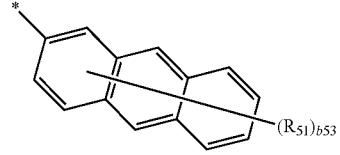

5-6

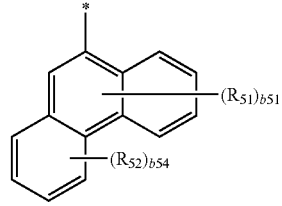

5-7

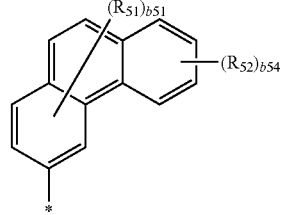

5-8

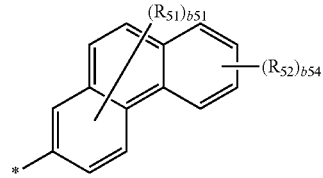

5-9

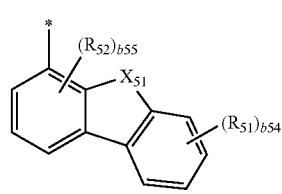

5-10

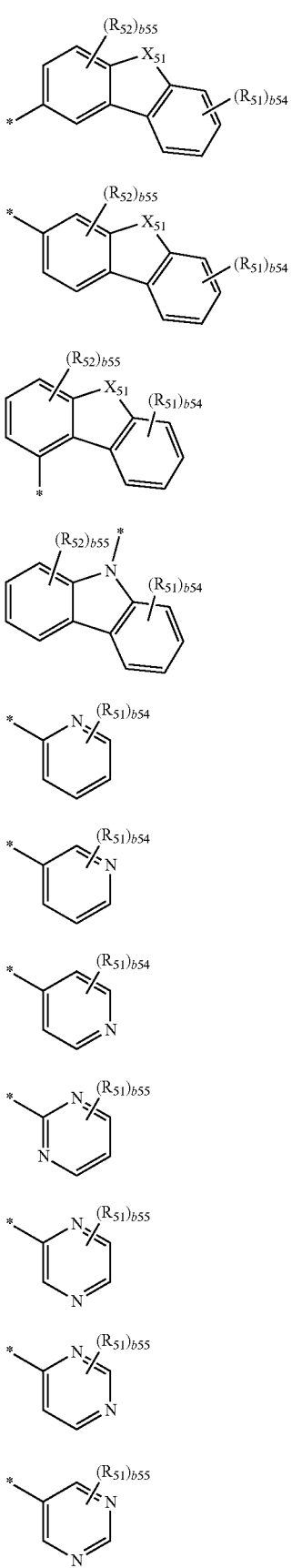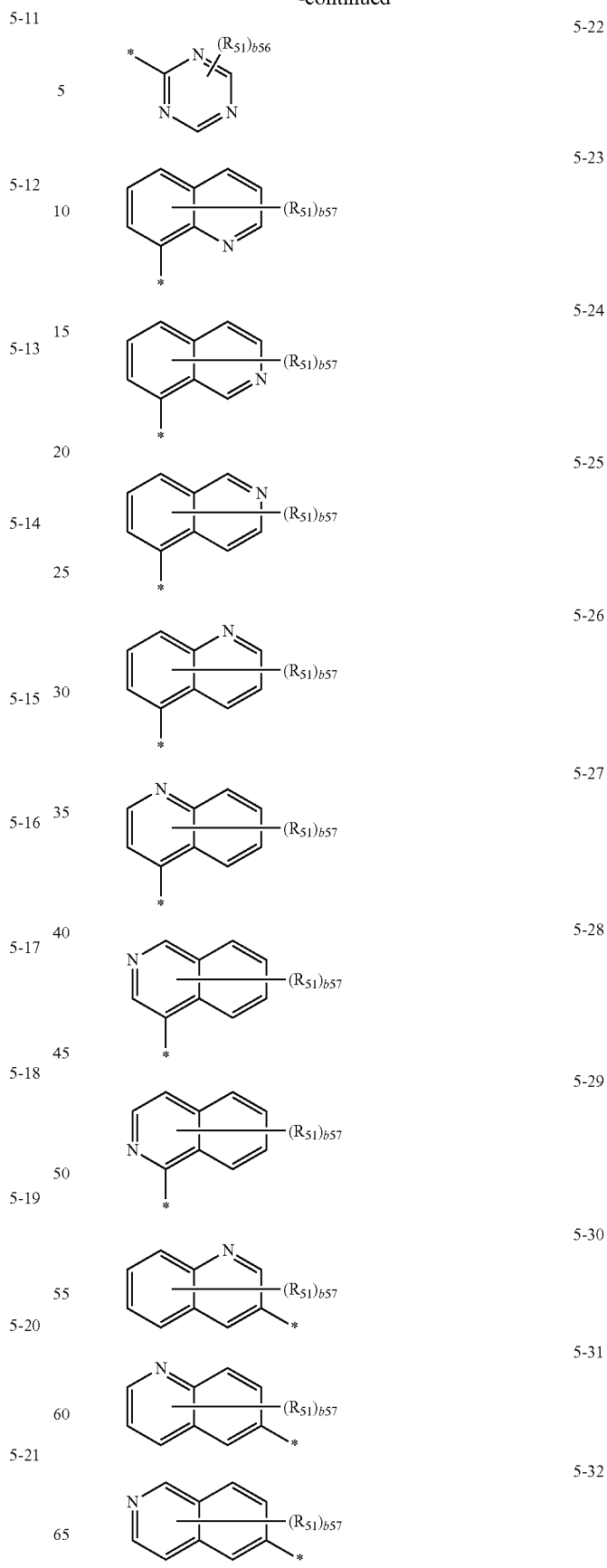

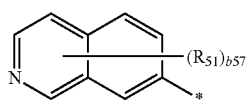
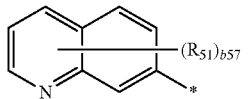
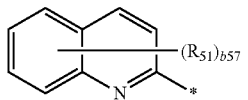
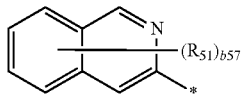
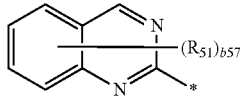
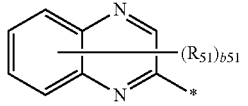
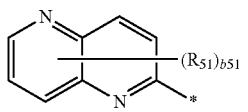
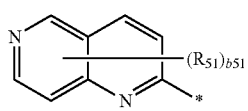
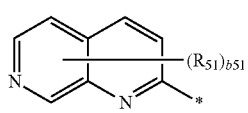
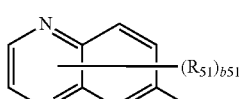
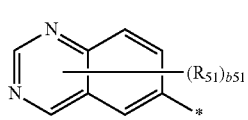
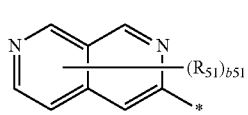
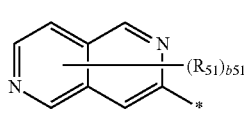
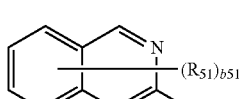
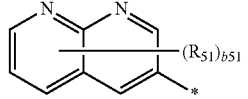
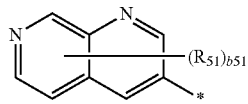
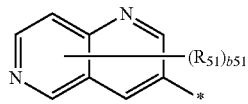
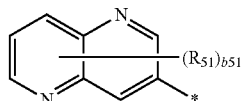
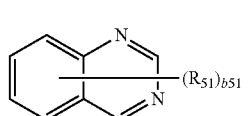
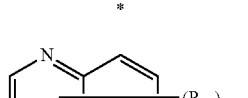
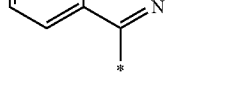
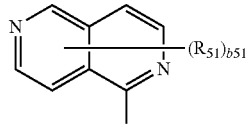
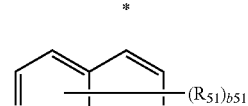
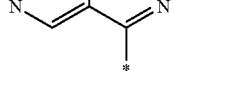
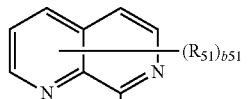
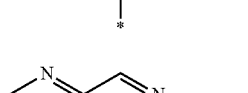
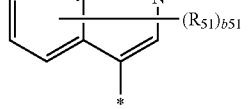
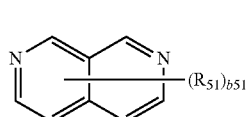

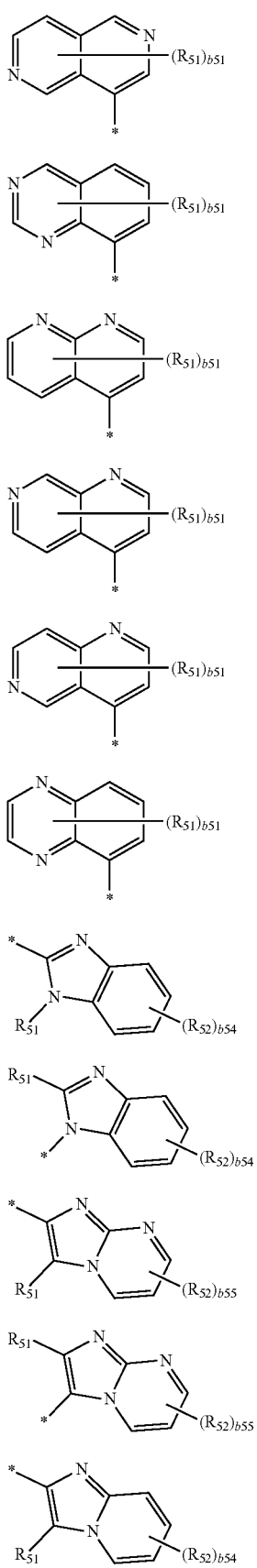
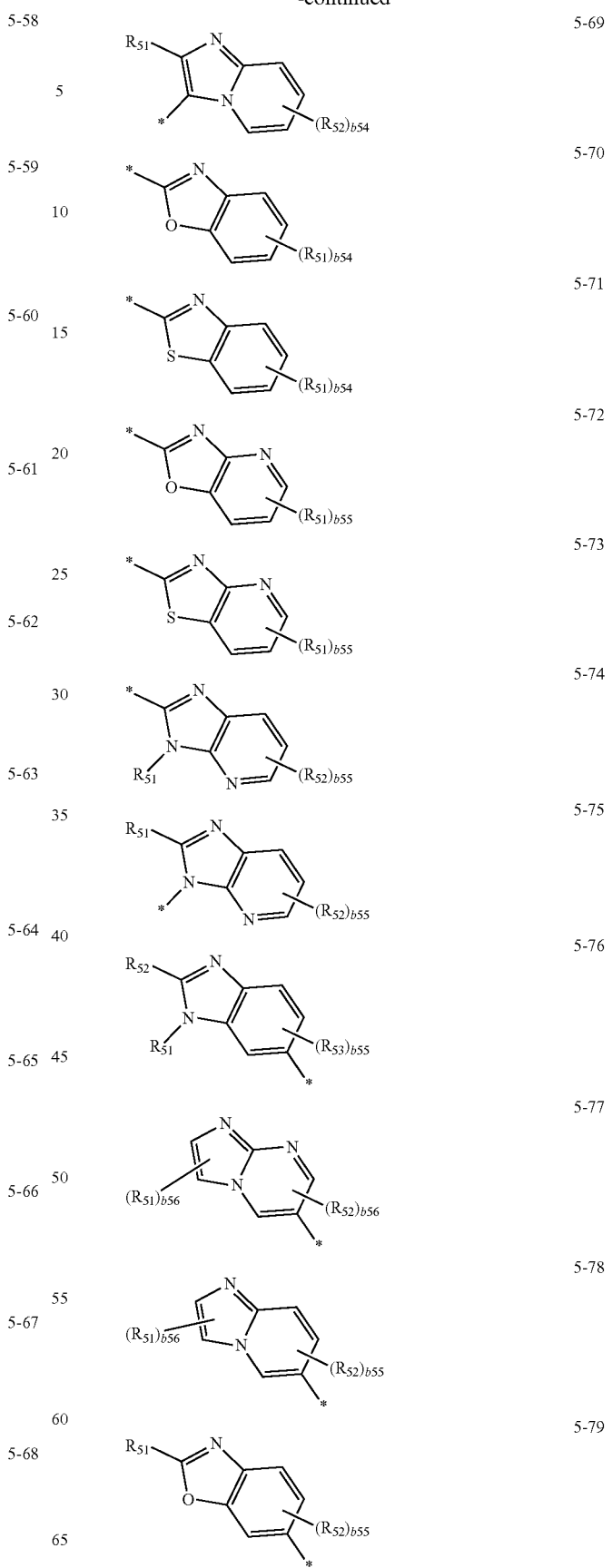

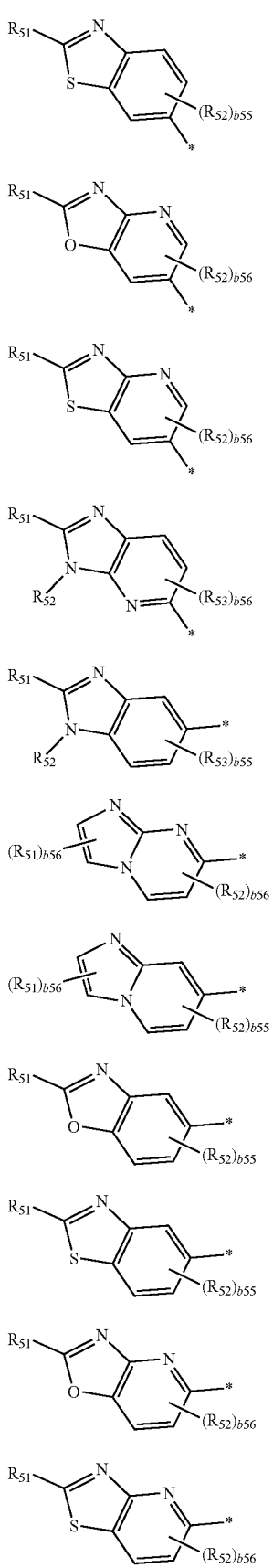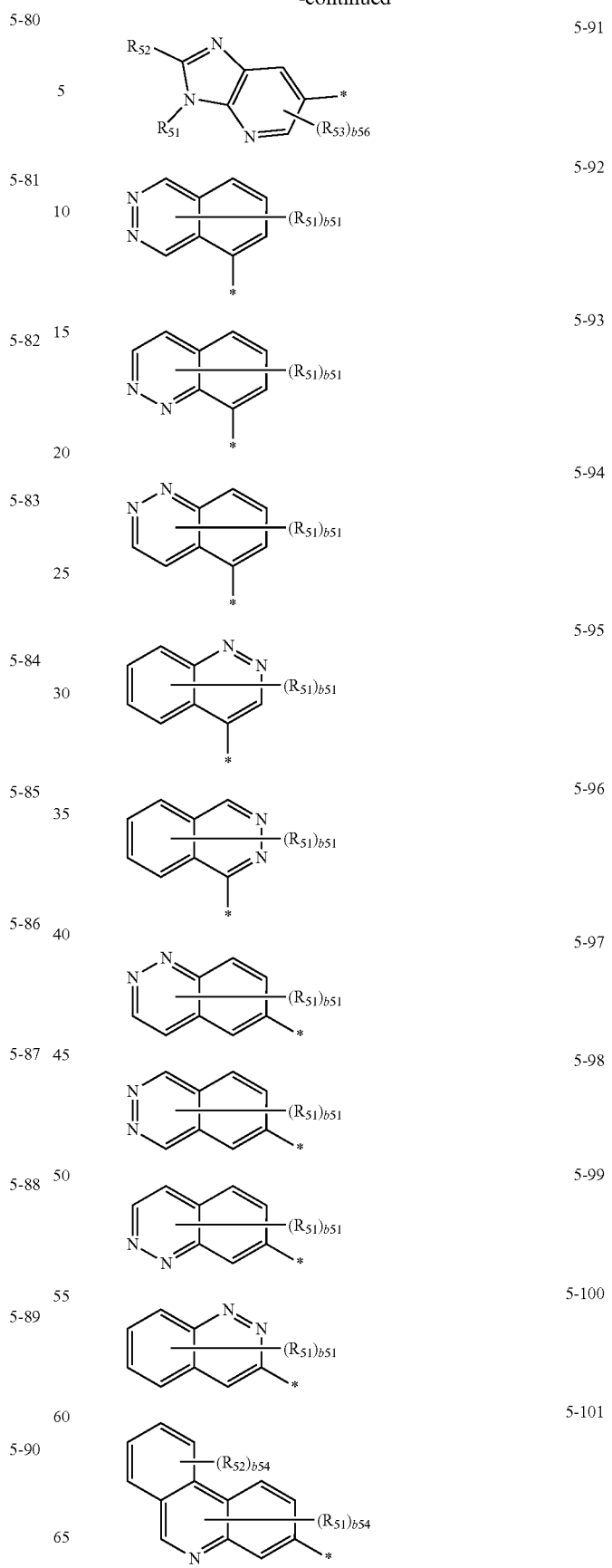

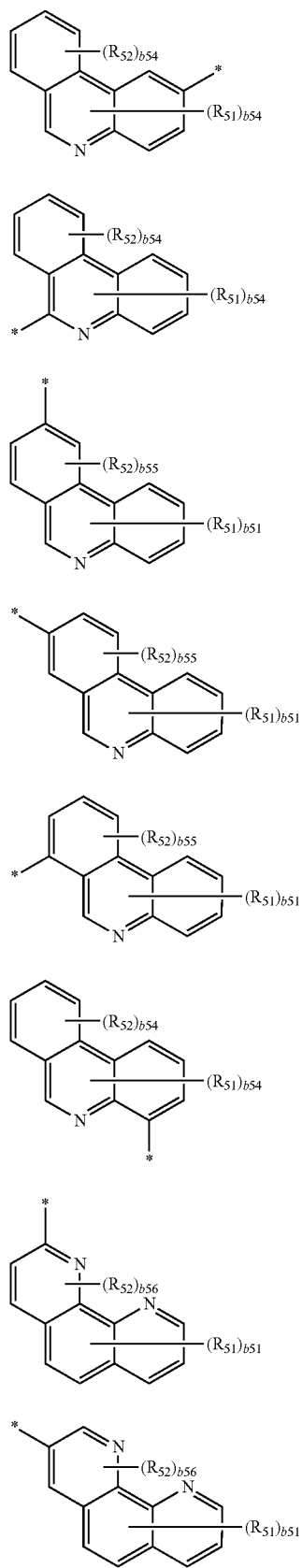
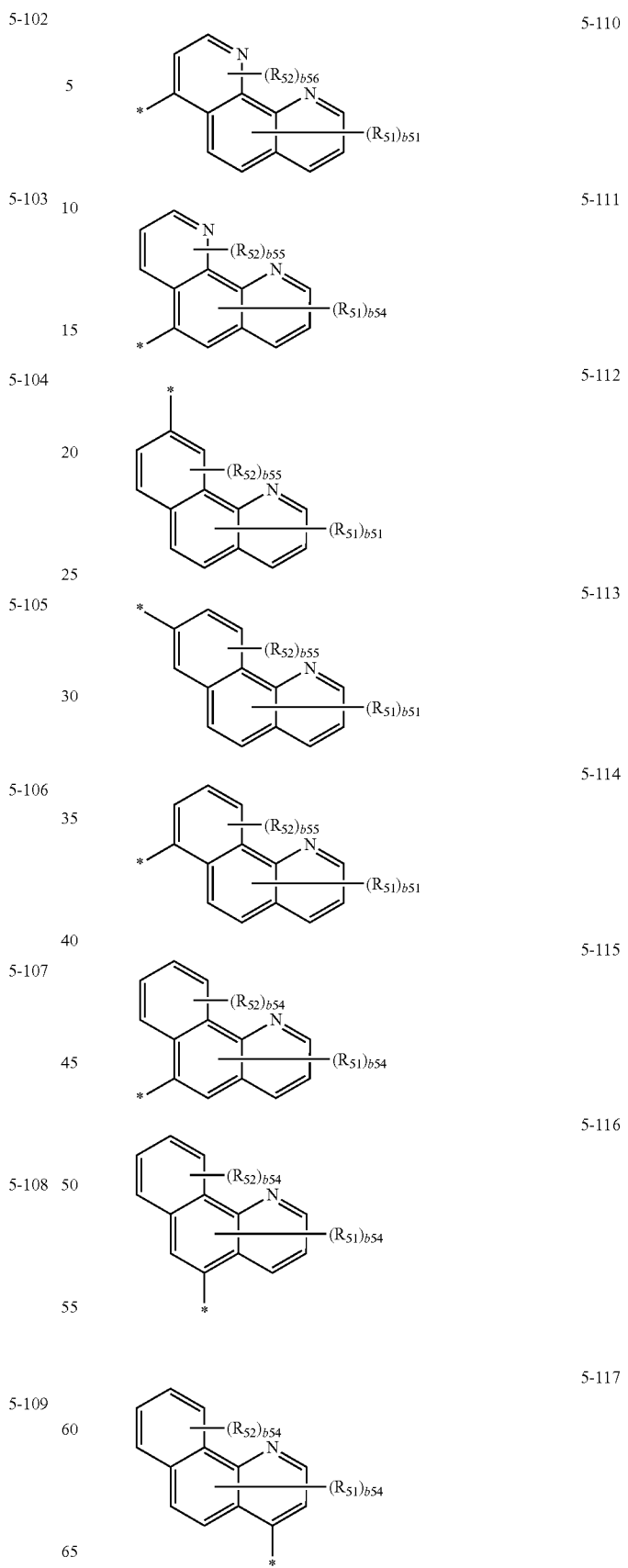

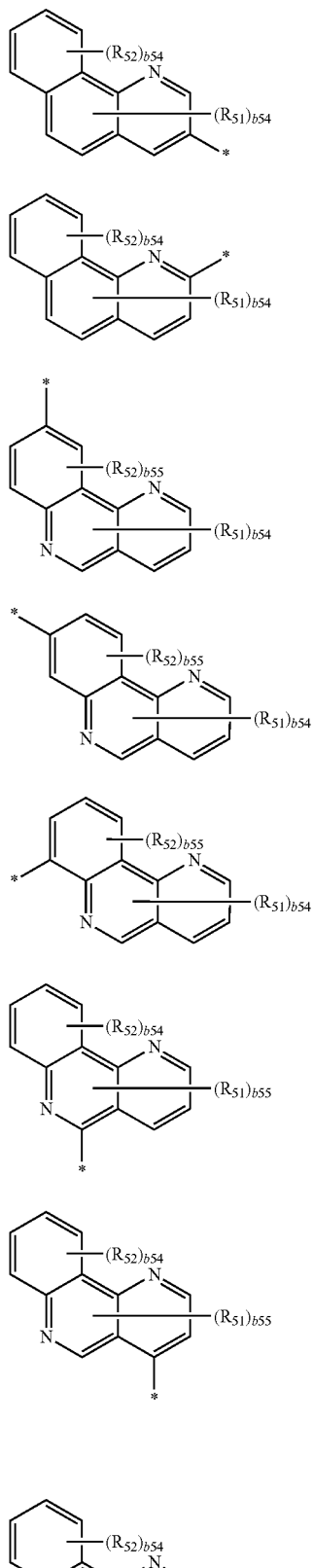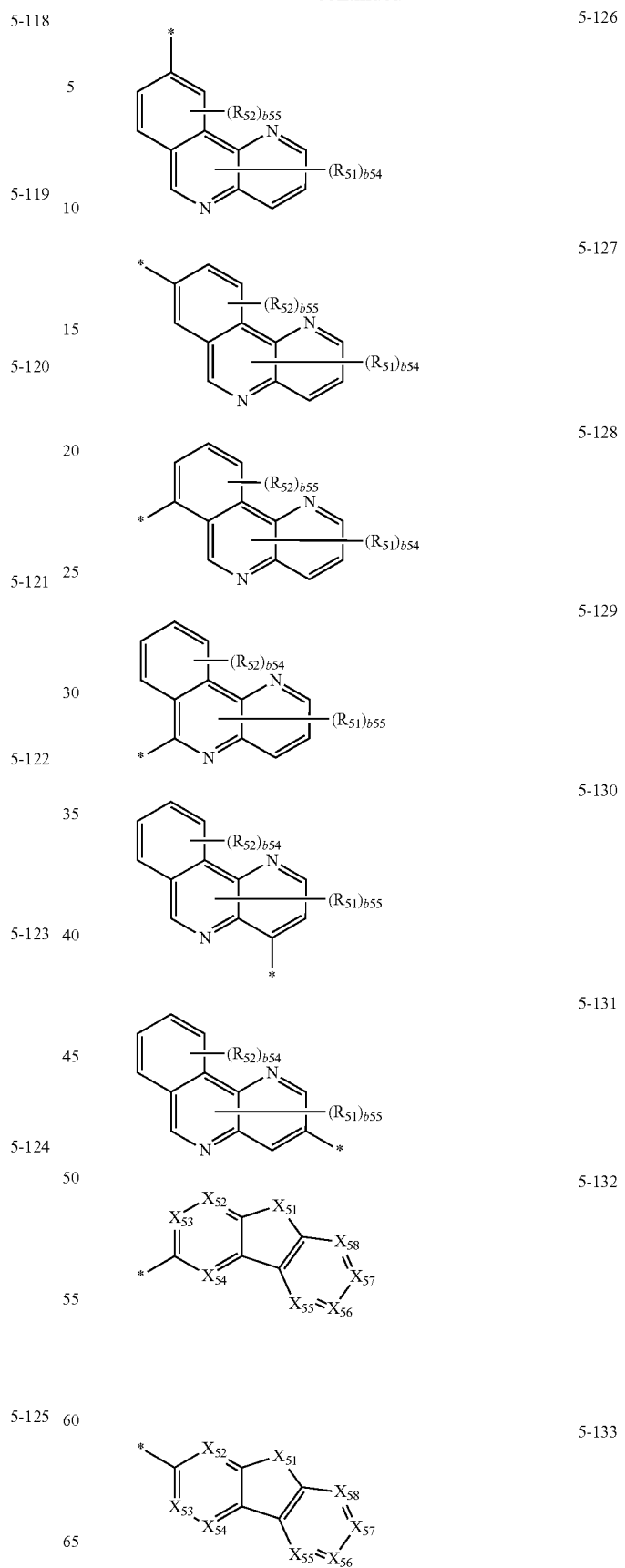

-continued 5-134
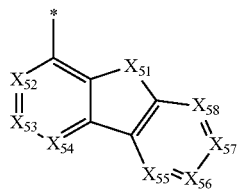

5-135
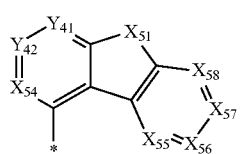

5-136
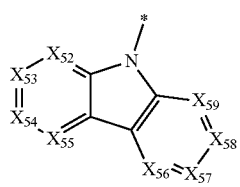

5-137
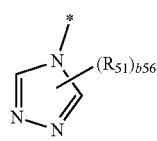

5-138
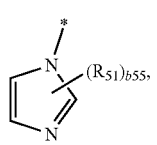

wherein, in Formulae 5-1 to 5-138, $X_{51}$ is selected from O, S, $N(R_{51})$, and $C(R_{51})(R_{60})$, $X_{52}$ is N or $C(R_{52})$, $X_{53}$ is N or $C(R_{53})$, $X_{54}$ is N or $C(R_{54})$, $X_{55}$ is N or $C(R_{55})$, $X_{56}$ is N or $C(R_{56})$, $X_{57}$ is N or $C(R_{57})$, $X_{58}$ is N or $C(R_{58})$, and $X_{59}$ is N or $C(R_{59})$, $R_{51}$ to $R_{60}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a thiophenyl group, a furanyl group, a silolyl group, a carbazolyl group, an indolyl group, an isoindolyl group, a benzofuranyl group, a benzothiophenyl group, a benzosilolyl group, a dibenzofuranyl group, a dibenzothiophenyl group, a benzocarbazolyl group, a dibenzocarbazolyl group, a dibenzosilolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O) ($Q_{31}$), —S(=O)$_2$($Q_{31}$), —P(=O)($Q_{31}$)($Q_{32}$), and —P(=S)($Q_{31}$)($Q_{32}$), $Q_{31}$ to $Q_{33}$ are each independently selected from a $C_1$-$C_{60}$ alkyl group, a phenyl group, a biphenyl group, and a terphenyl group, b51 is selected from 1, 2, 3, 4, and 5,
b52 is selected from 1, 2, 3, 4, 5, 6, and 7,
b53 is selected from 1, 2, 3, 4, 5, 6, 7, 8, and 9,
b54 is selected from 1, 2, 3, and 4,
b55 is selected from 1, 2, and 3,
b56 is selected from 1 and 2,
b57 is selected from 1, 2, 3, 4, 5, and 6, and
* indicates a binding site to a neighboring atom.

13. The diamine compound of claim 5, wherein:

$R_{11}$ to $R_{14}$ are each independently selected from a group represented by Formula 2 and groups represented by Formulae 6-1 to 6-257:

6-1
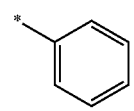

6-2
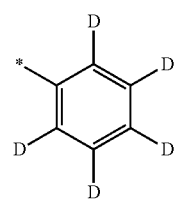

6-3
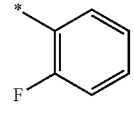

6-4
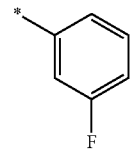

6-5
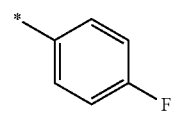

6-6
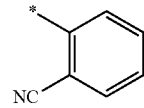

6-7
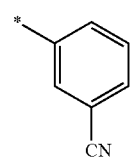

6-8
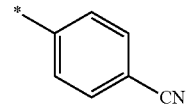

6-9
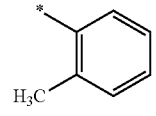

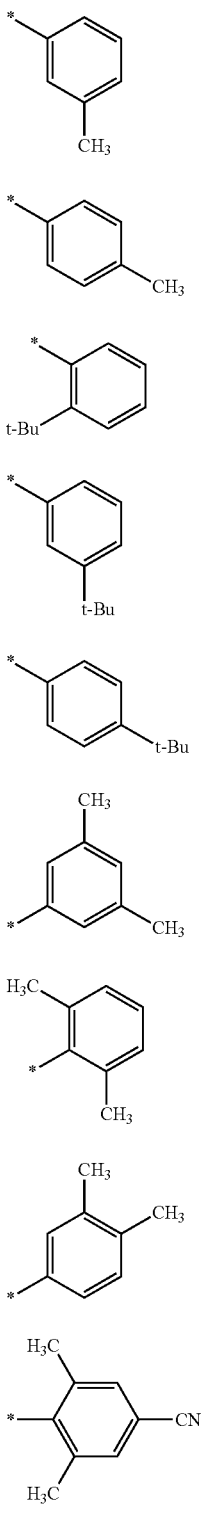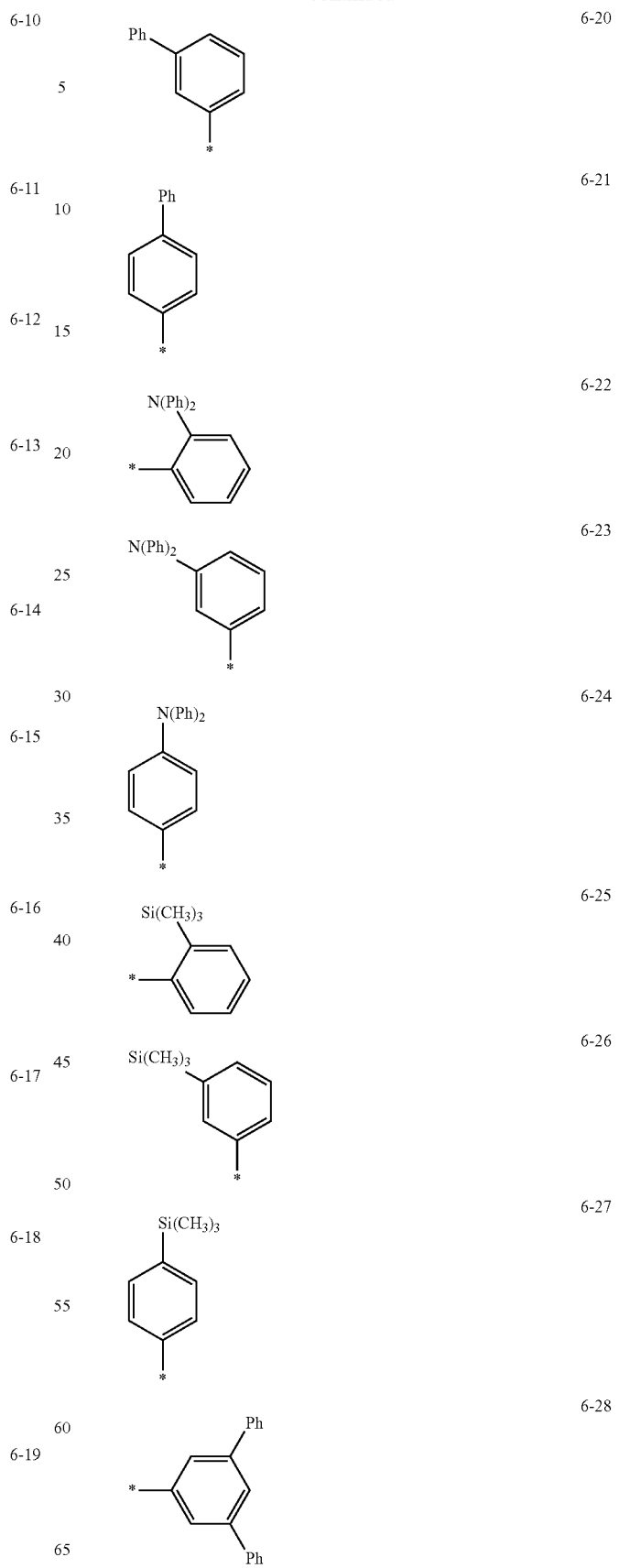

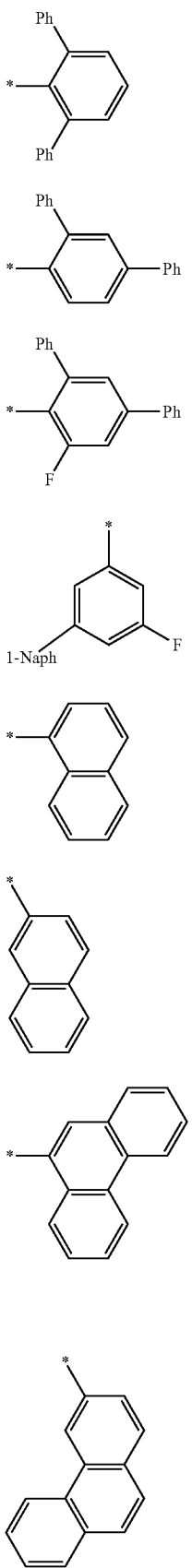
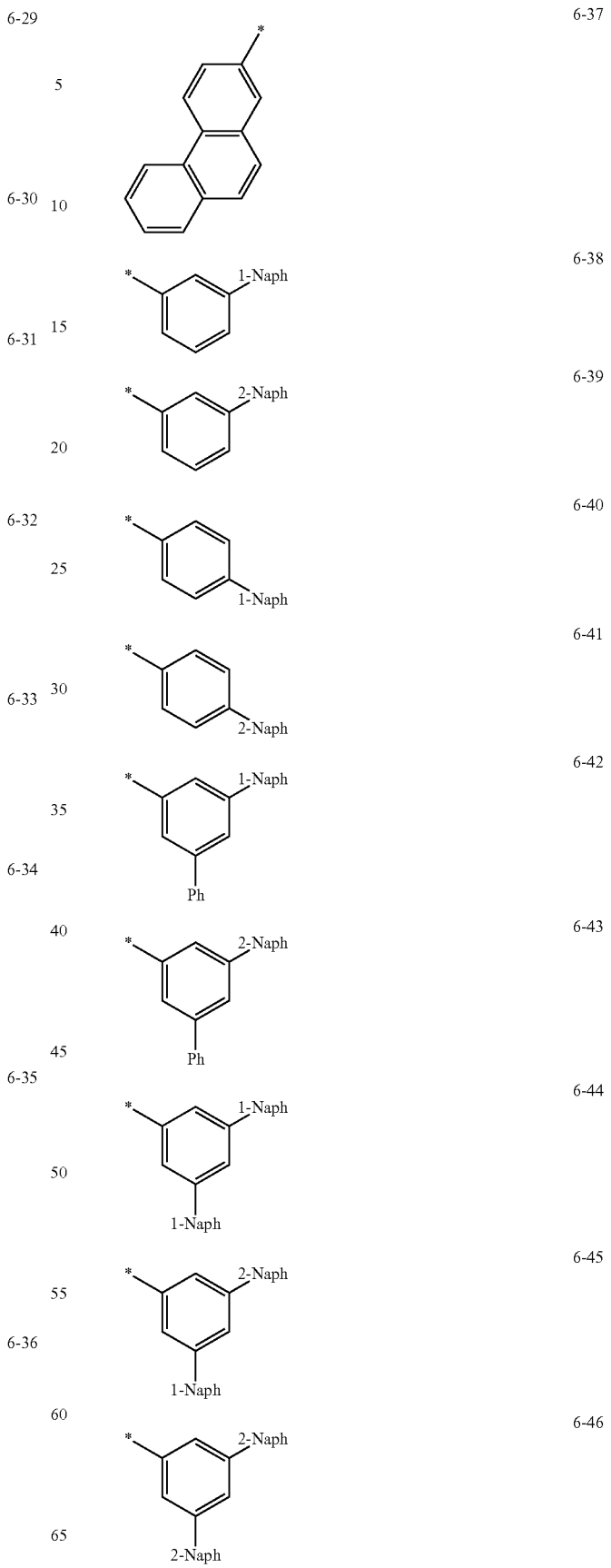

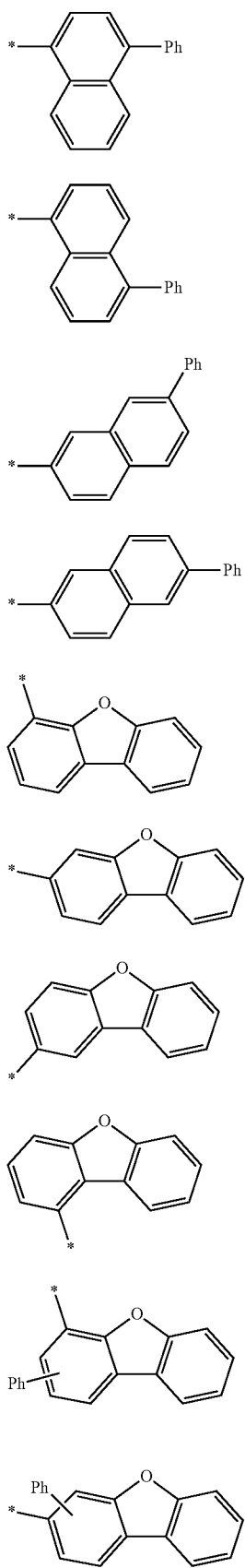
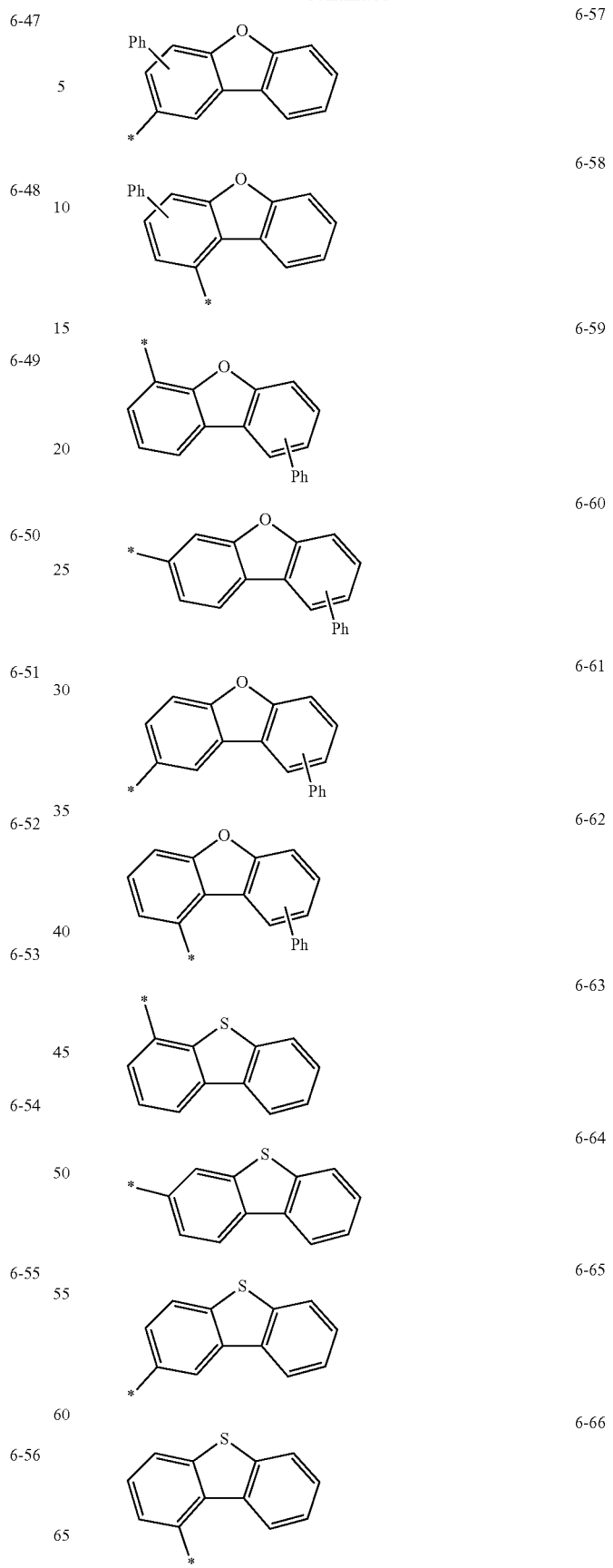

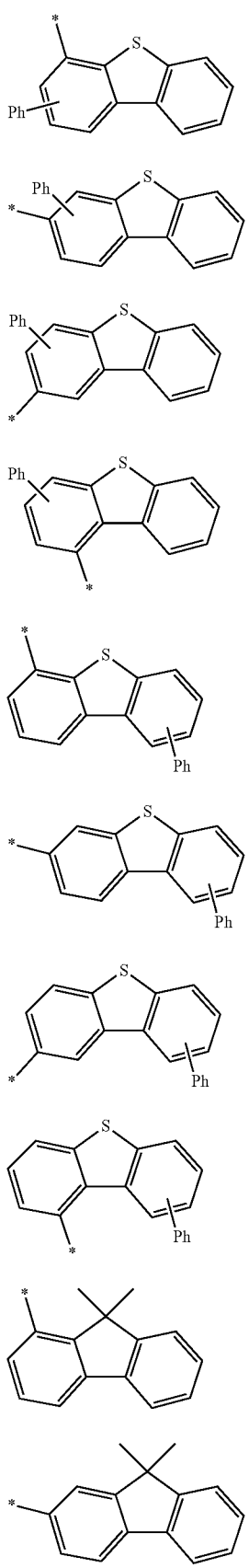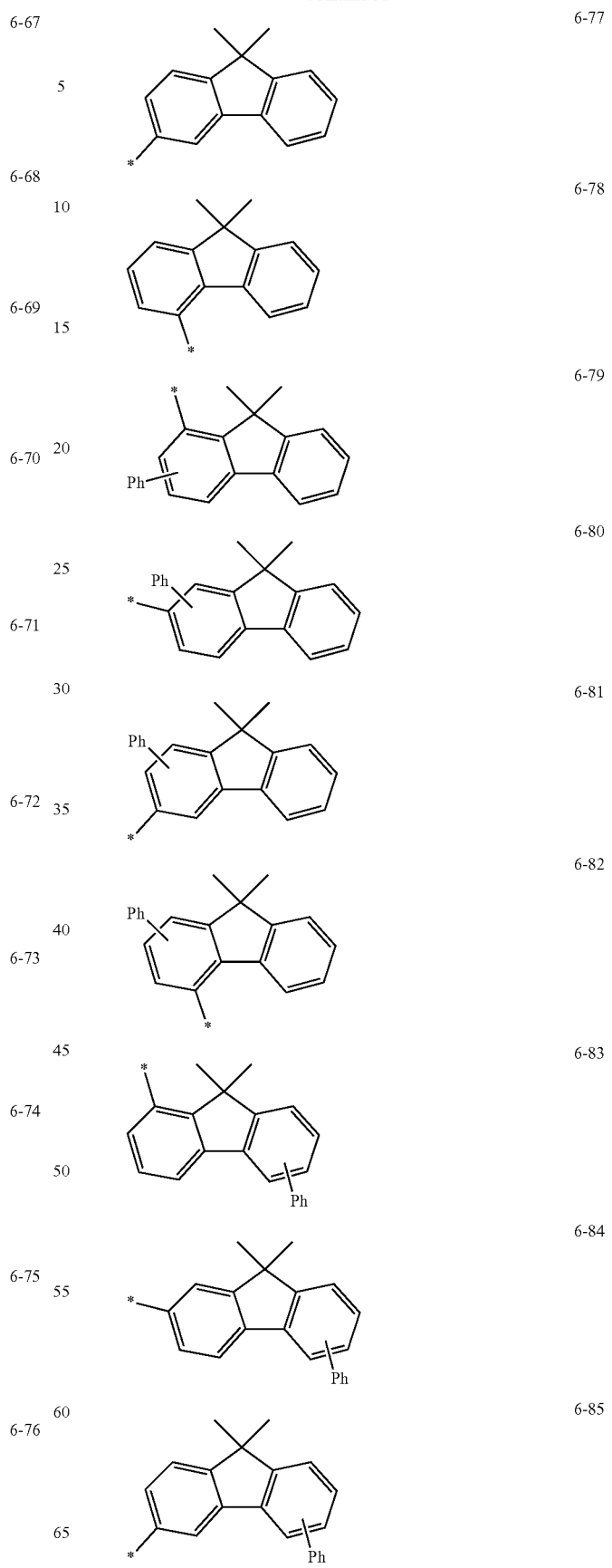

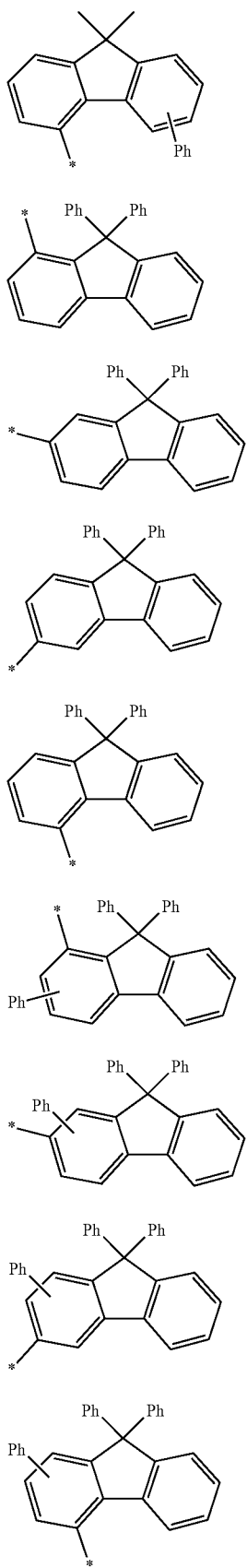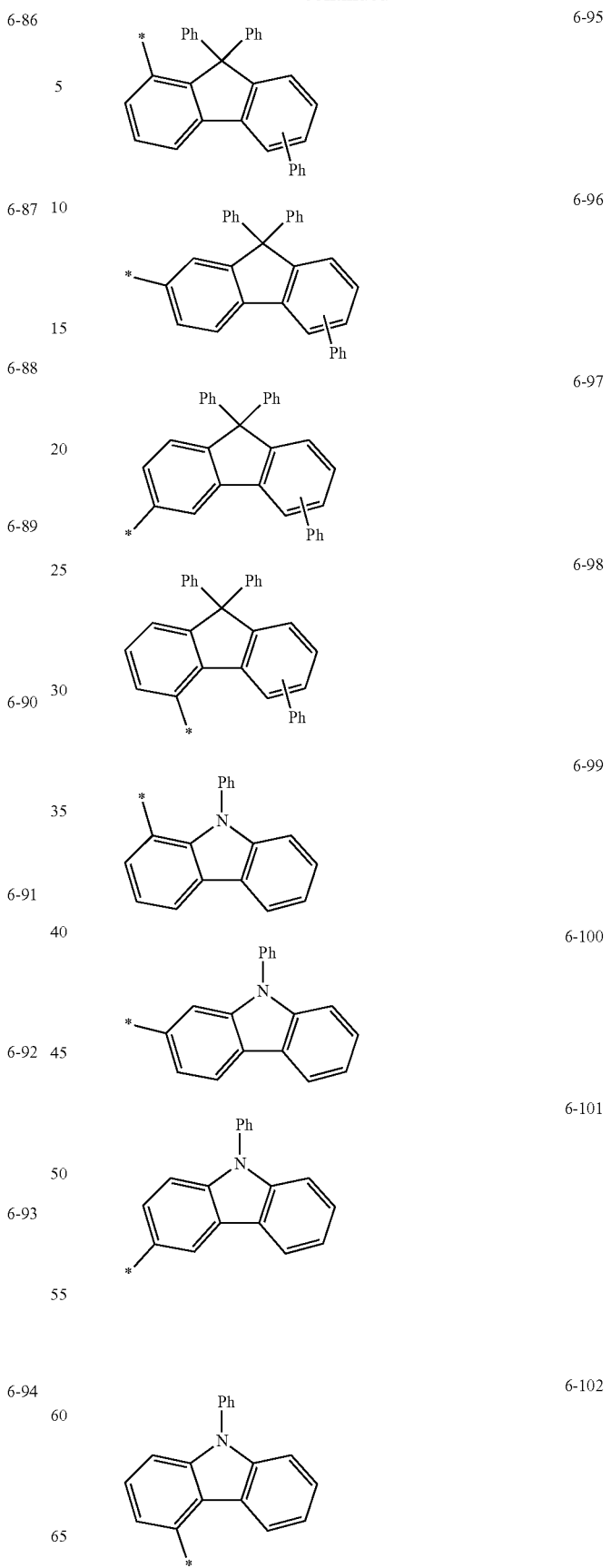

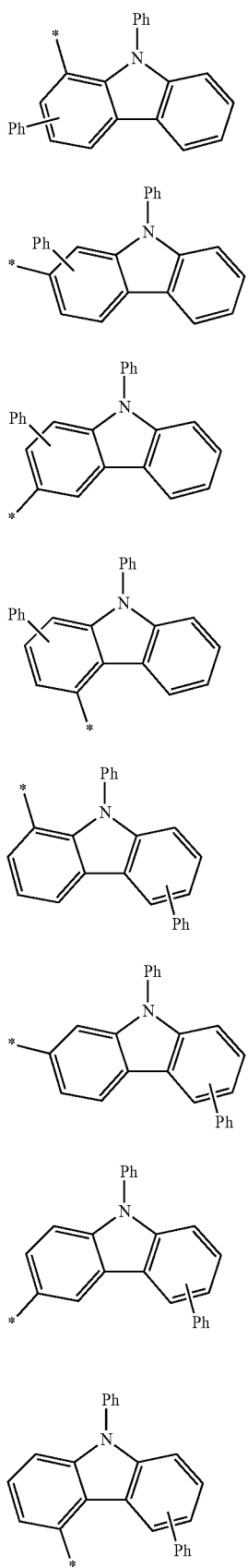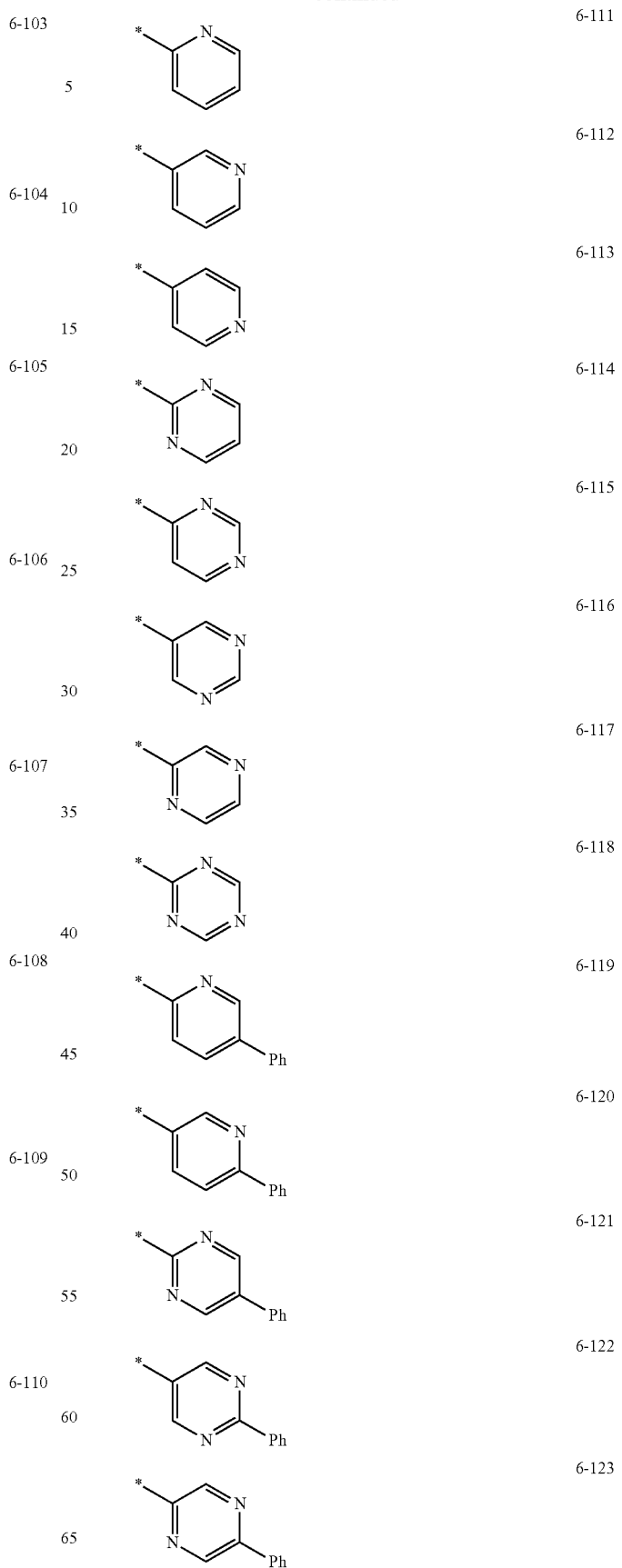

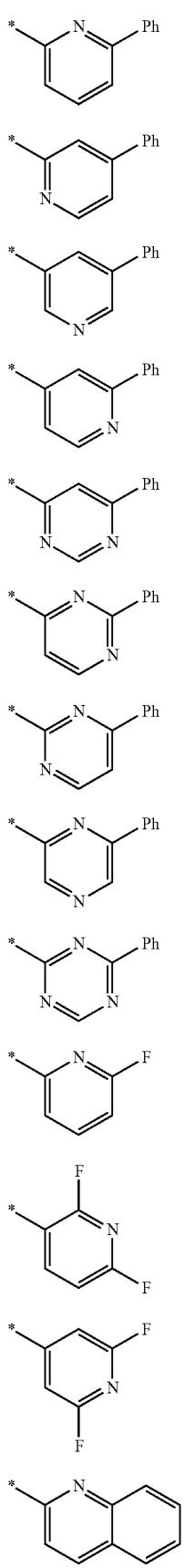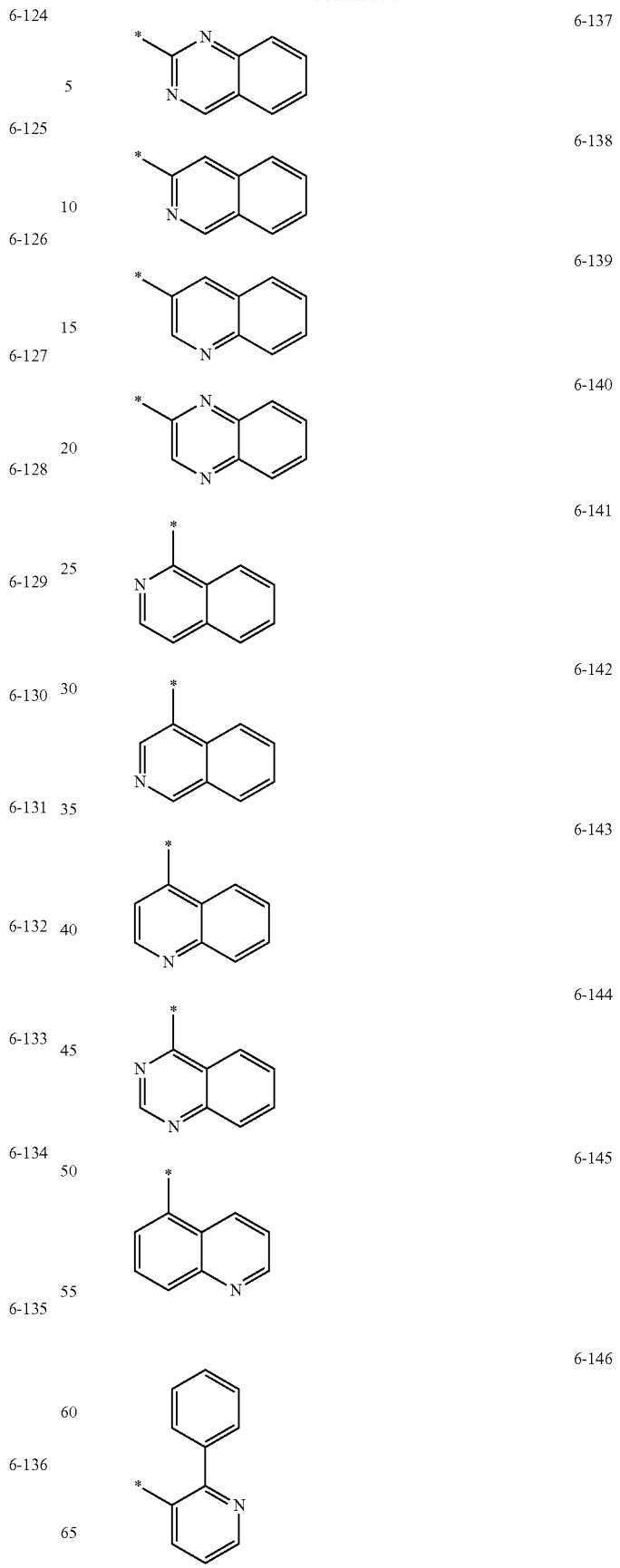

6-147
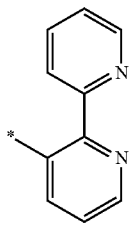
6-148
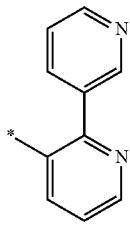
6-149
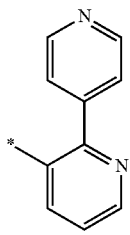
6-150
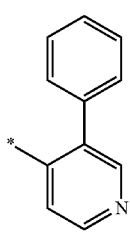
6-151
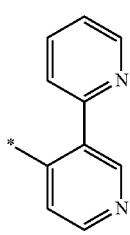
6-152
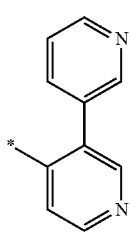
6-153
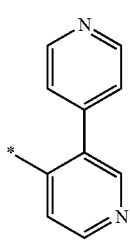
6-154
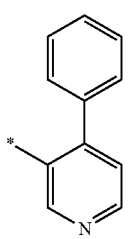
6-155
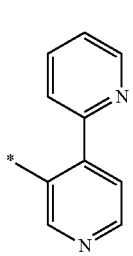
6-156
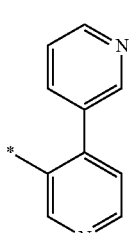
6-157
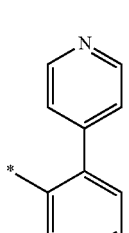
6-158
6-159
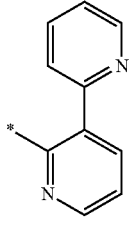

6-160 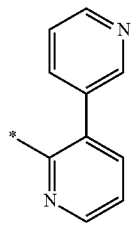
6-161 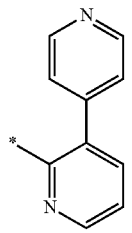
6-162 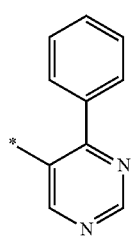
6-163 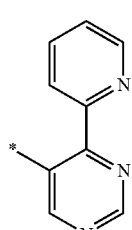
6-164 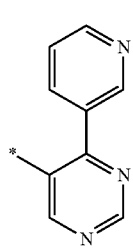
6-165 
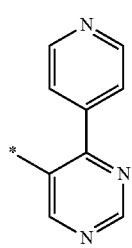
6-166 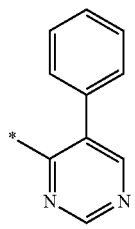
6-167 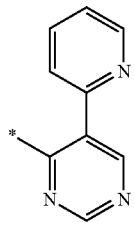
6-168 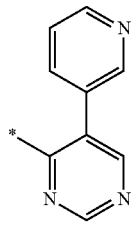
6-169 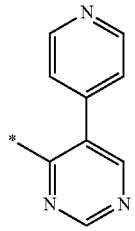
6-170 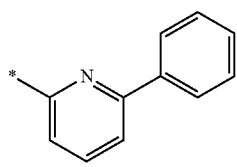
6-171 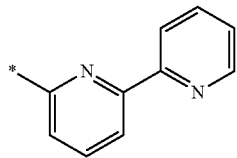
6-172 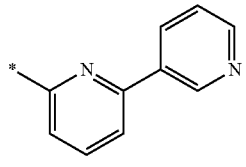
6-173 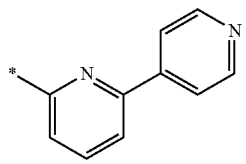

| 225 | 226 |
|---|---|
| -continued | -continued |
6-174 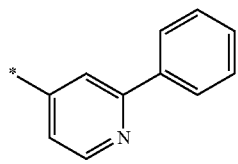
6-175 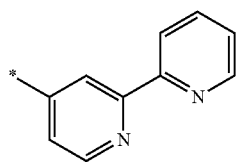
6-176 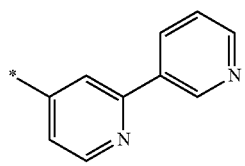
6-177 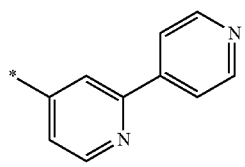
6-178 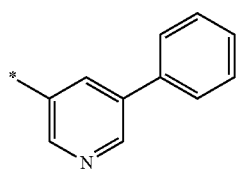
6-179 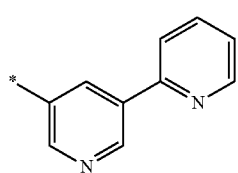
6-180 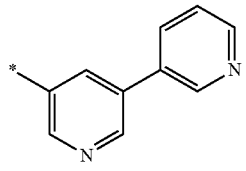
6-181 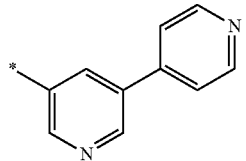
6-182 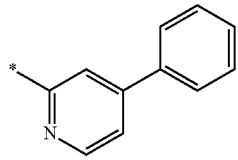
6-183 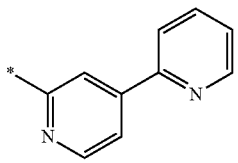
6-184 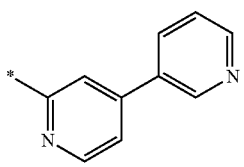
6-185 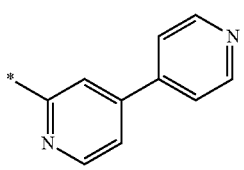
6-186 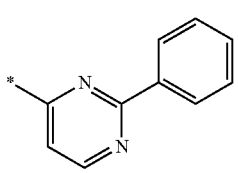
6-187 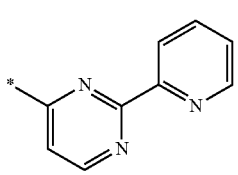
6-188 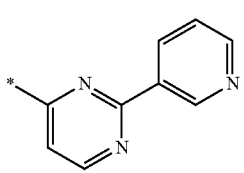
6-189 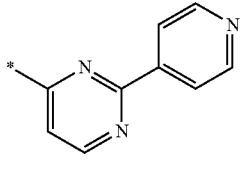
6-190 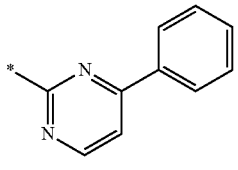
6-191 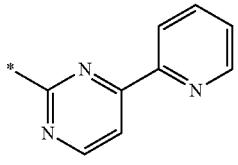

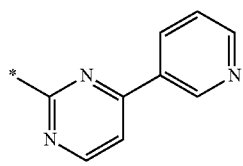
6-192
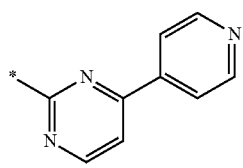
6-193
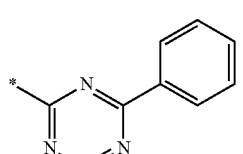
6-194
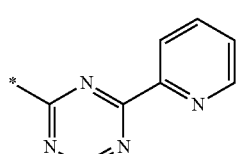
6-195
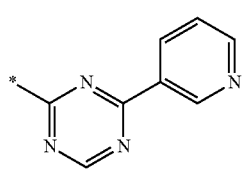
6-196
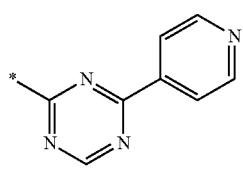
6-197
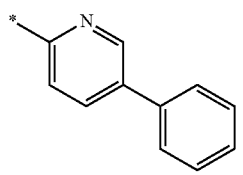
6-198
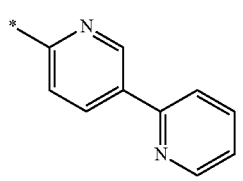
6-199
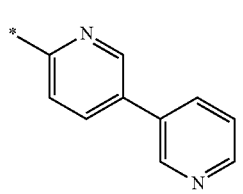
6-200
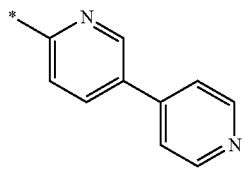
6-201
6-202
6-203
6-204
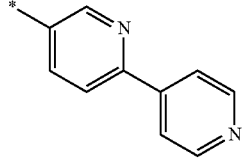
6-205
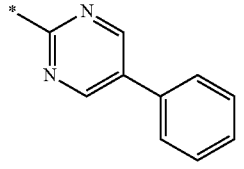
6-206
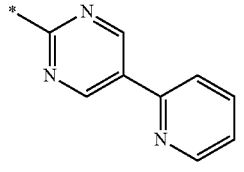
6-207
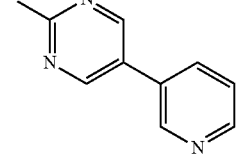
6-208
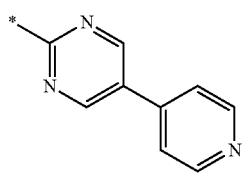
6-209

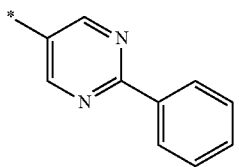
6-210
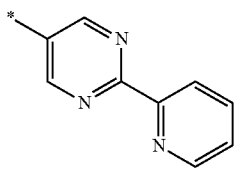
6-211
6-212
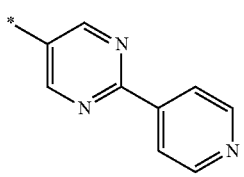
6-213
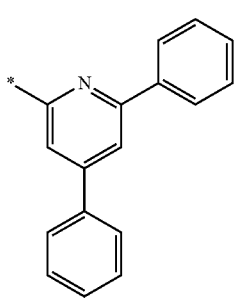
6-214
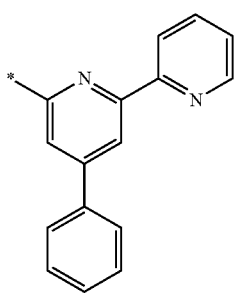
6-215
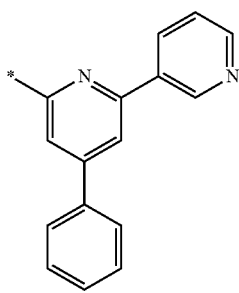
6-216
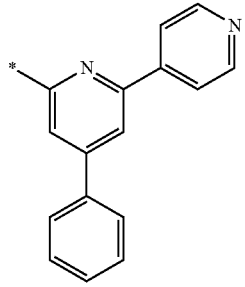
6-217
6-218
6-219
6-220
6-221

6-222 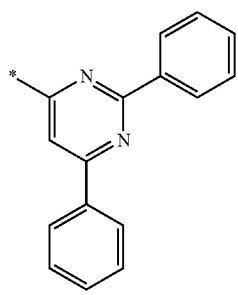
6-223 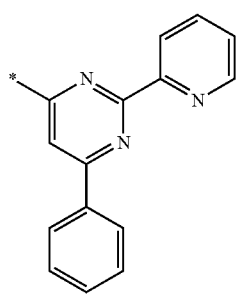
6-224 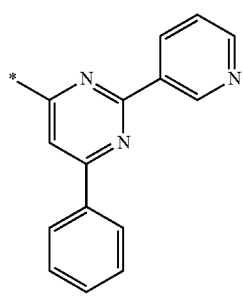
6-225 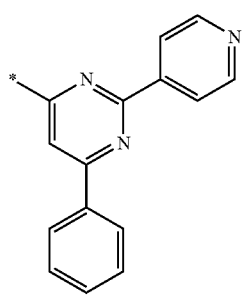
6-226 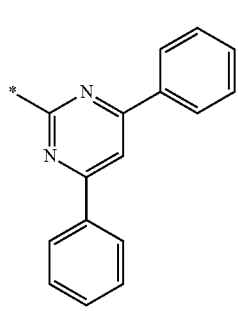
6-227 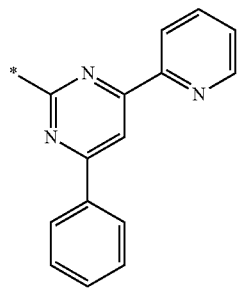
6-228 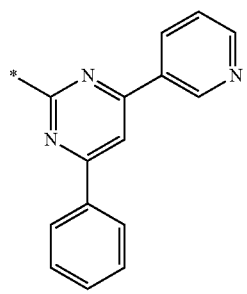
6-229 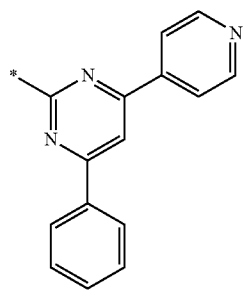
6-230 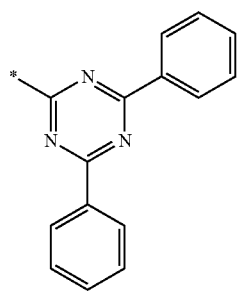
6-231 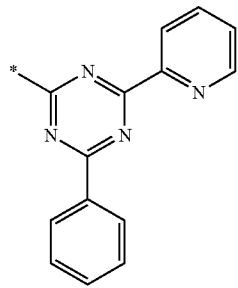

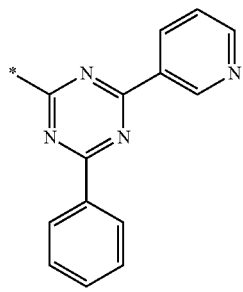
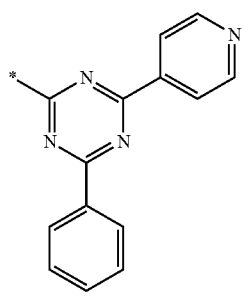
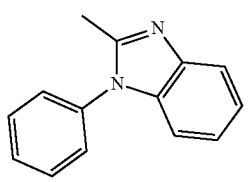
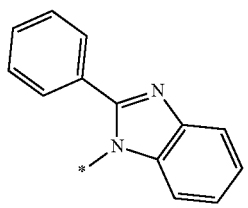
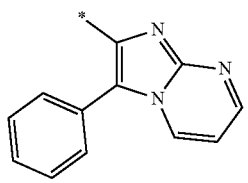
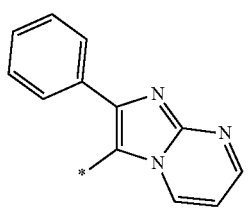
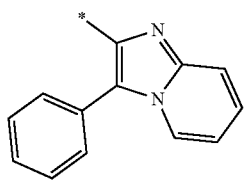
6-232
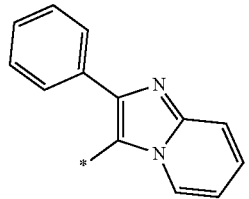
6-233
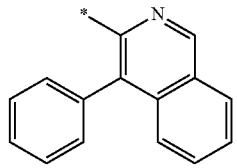
6-234
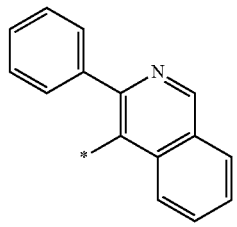
6-235
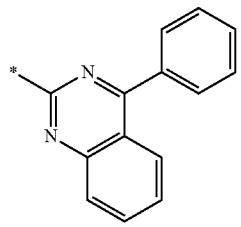
6-236
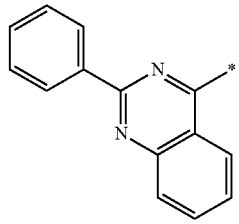
6-237
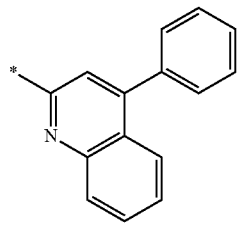
6-238
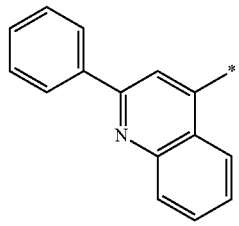
6-239
6-240
6-241
6-242
6-243
6-244
6-245

-continued 6-246 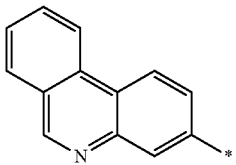

6-247 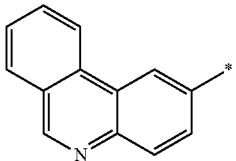

6-248 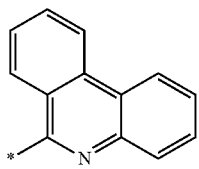

6-249 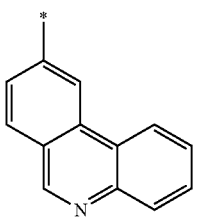

6-250 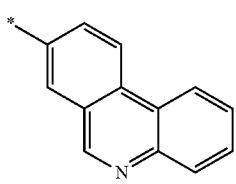

6-251 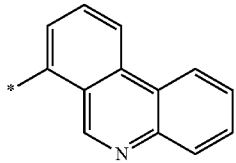

6-252 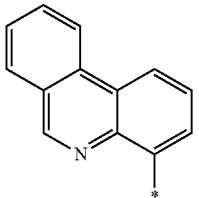

6-253 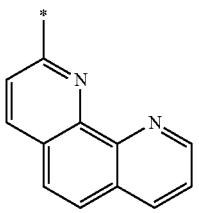

-continued 6-254 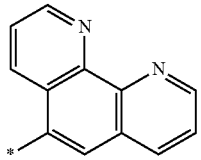

6-255 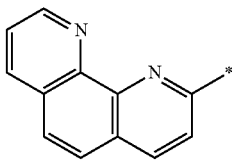

6-256 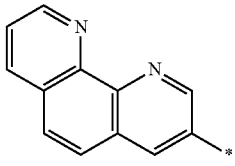

6-257 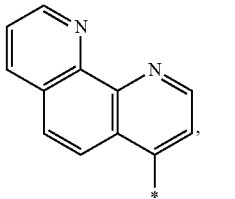

wherein, in Formulae 6-1 to 6-257,
t-Bu indicates a tert-butyl group,
Ph indicates a phenyl group,
1-Naph indicates a 1-naphthyl group,
2-Naph indicates a 2-naphthyl group, and
\* indicates a binding site to a neighboring atom.

14. The diamine compound of claim 5, wherein:
   $R_{15}$, $R_{16}$, and $R_{21}$ to $R_{23}$ are each independently selected from:
   hydrogen, deuterium, —F, —Cl, —Br, —I, a cyano group, a $C_1$-$C_{20}$ alkyl group, and a $C_1$-$C_{20}$ alkoxy group;
   a $C_1$-$C_{20}$ alkyl group and a $C_1$-$C_{20}$ alkoxy group, each substituted with at least one selected from deuterium, —F, —Cl, —Br, —I, a cyano group, a phenyl group, and a biphenyl group;
   a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group, each substituted with at least one selected from deuterium, —F, —Cl, —Br, —I, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, an indolocarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)($Q_{31}$), —S(=O)$_2$($Q_{31}$), —P(=O)($Q_{31}$)($Q_{32}$), and —P(=S)($Q_{31}$)($Q_{32}$); and —Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), and $Q_1$ to $Q_3$ and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

15. The diamine compound of claim 5, wherein:

$R_{15}$, $R_{16}$, $R_{22}$, and $R_{23}$ are each independently selected from:

hydrogen, deuterium, —F, —Cl, —Br, —I, a cyano group, a methyl group, an ethyl group, an n-propyl group, an isopropyl group, an n-butyl group, an isobutyl group, a sec-butyl group, and a tert-butyl group; and a methyl group, an ethyl group, an n-propyl group, an isopropyl group, an n-butyl group, an isobutyl group, a sec-butyl group, and a tert-butyl group, each substituted with at least one selected from deuterium, —F, —Cl, —Br, —I, and a cyano group.

16. The diamine compound of claim 5, wherein:

the diamine compound represented by Formula 1 is represented by one selected from Formulae 1-1 and 1-2:

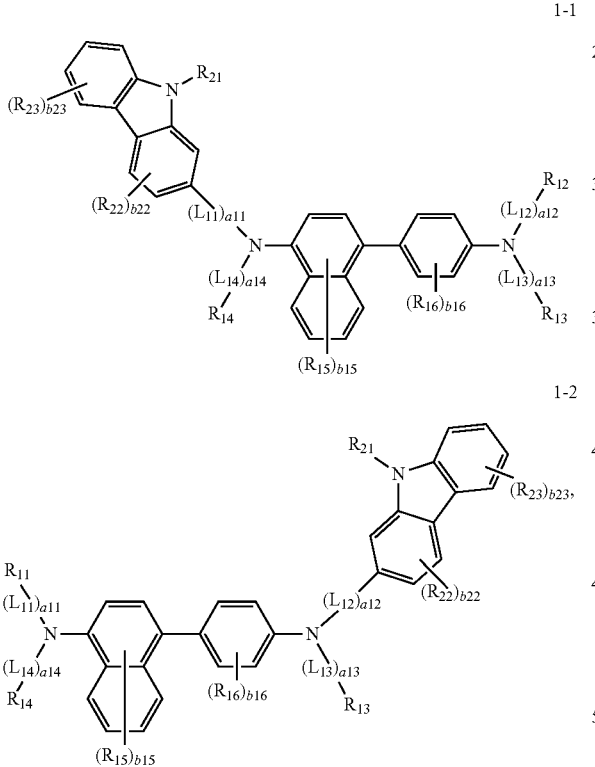

wherein, in Formulae 1-1 and 1-2, $L_{11}$ to $L_{14}$, a11 to a14, $R_{15}$, $R_{16}$, b15, and b16 are respectively the same as described in Formula 1, $R_{21}$ to $R_{23}$, b22, and b23 are respectively the same as described in Formula 2, and $R_{11}$ to $R_{14}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

17. The diamine compound of claim 5, wherein:

the diamine compound represented by Formula 1 is represented by one selected from Formulae 1-11 and 1-12:

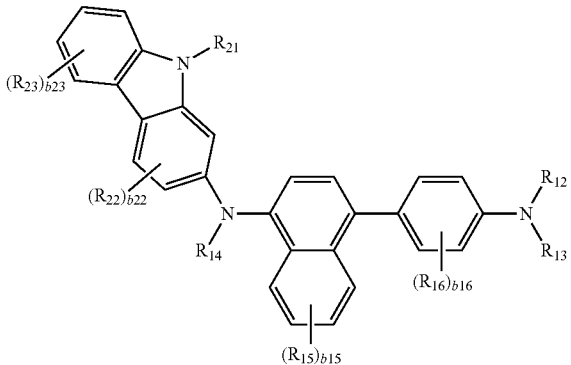

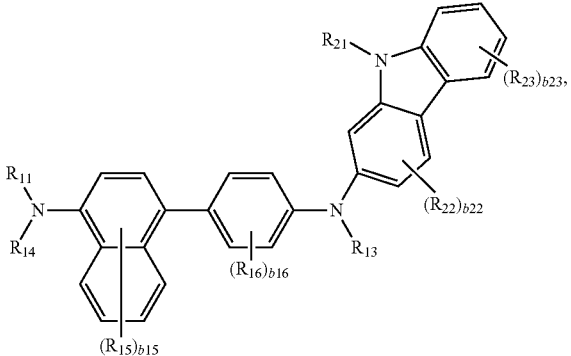

wherein, in Formulae 1-11 and 1-12, $R_{15}$, $R_{16}$, b15, and b16 are respectively the same as described in Formula 1, $R_{21}$ to $R_{23}$, b22, and b23 are respectively the same as described in Formula 2, $R_{11}$ to $R_{14}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

18. The diamine compound of claim 17, wherein:

$R_{15}$, $R_{16}$, $R_{22}$, and $R_{23}$ in Formulae 1-11 and 1-12 are each independently selected from:

hydrogen, deuterium, —F, —Cl, —Br, —I, a cyano group, a methyl group, an ethyl group, an n-propyl group, an isopropyl group, an n-butyl group, an isobutyl group, a sec-butyl group, and a tert-butyl group; and a methyl group, an ethyl group, an n-propyl group, an isopropyl group, an n-butyl group, an isobutyl group, a sec-butyl group, and a tert-butyl group, each substituted with at least one selected from deuterium, —F, —Cl, —Br, —I, and a cyano group.
19. The diamine compound of claim 5, wherein:
the diamine compound represented by Formula 1 is selected from Compounds 145 to 176:
145
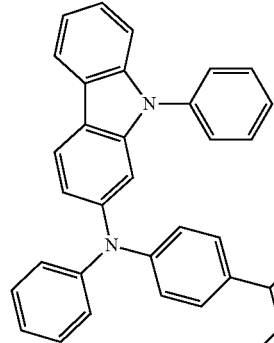
146
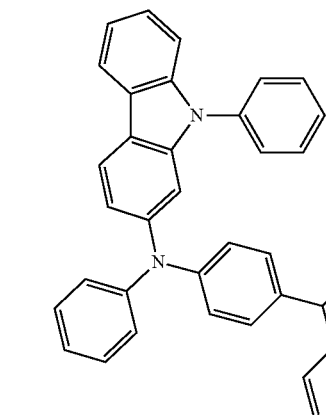
147
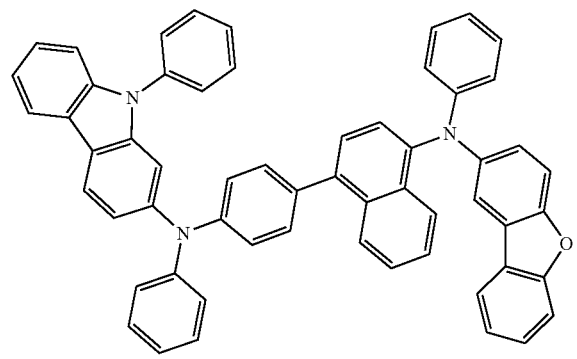
-continued
148
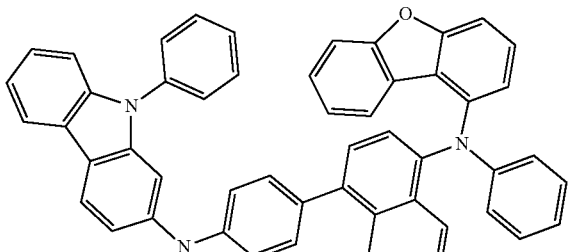
149
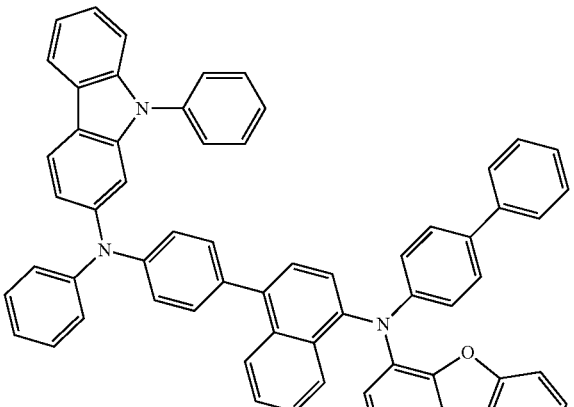
150
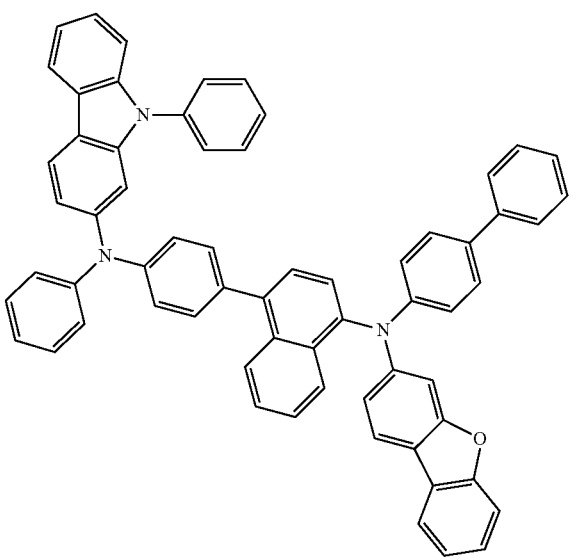

151
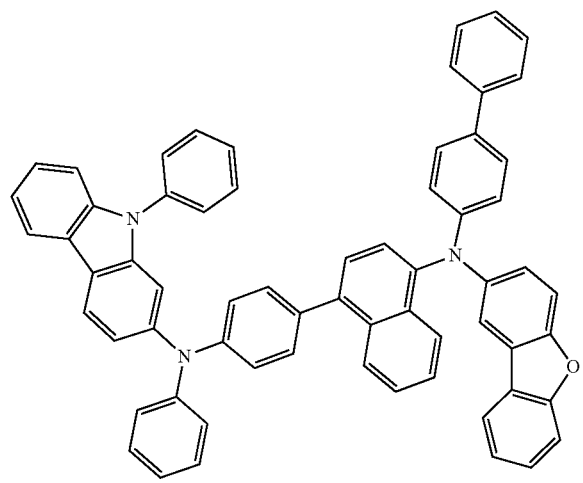
154
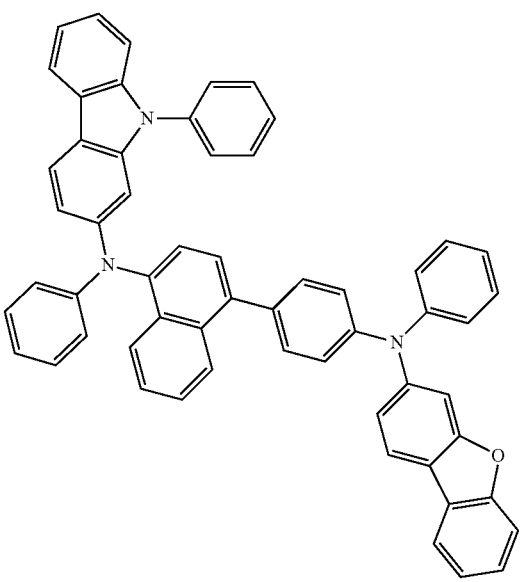
152
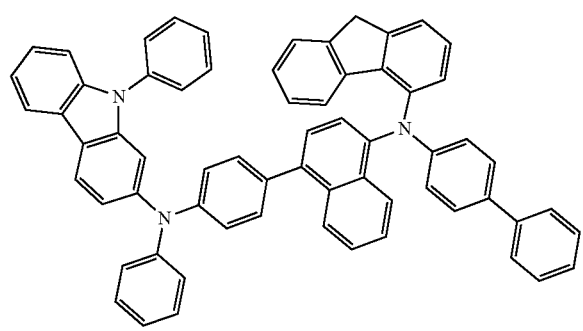
155
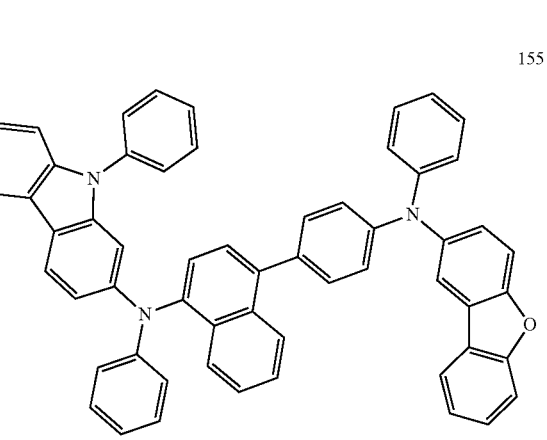
153
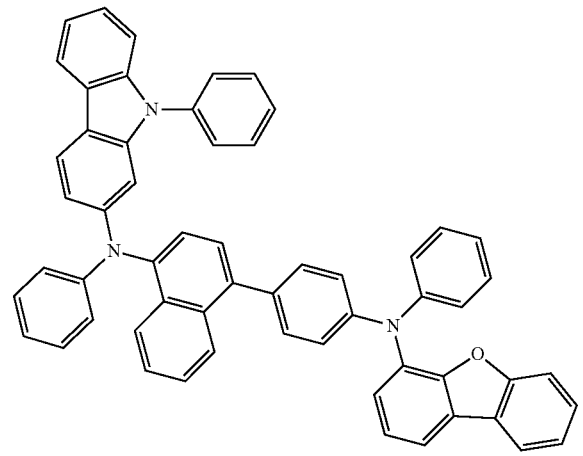
156
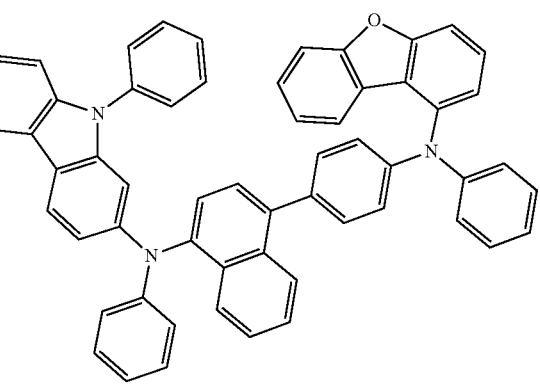

157
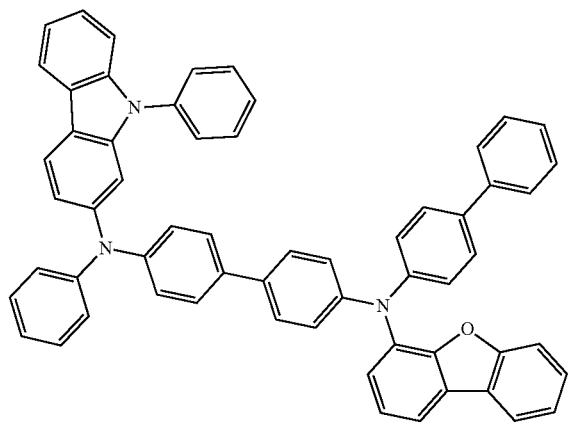
160
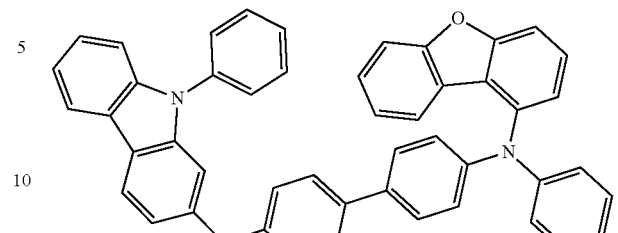
158
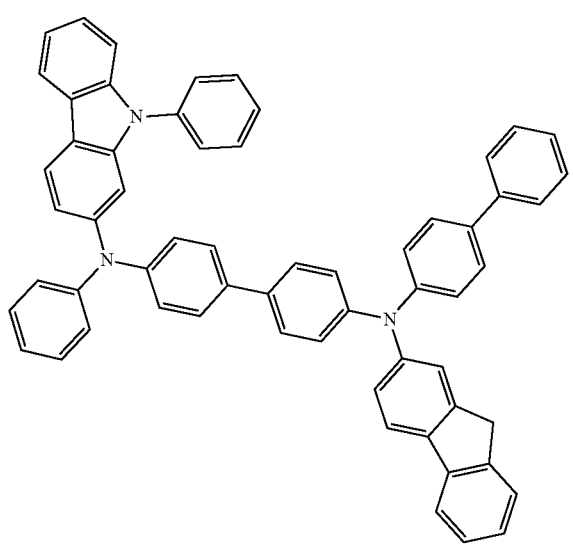
161
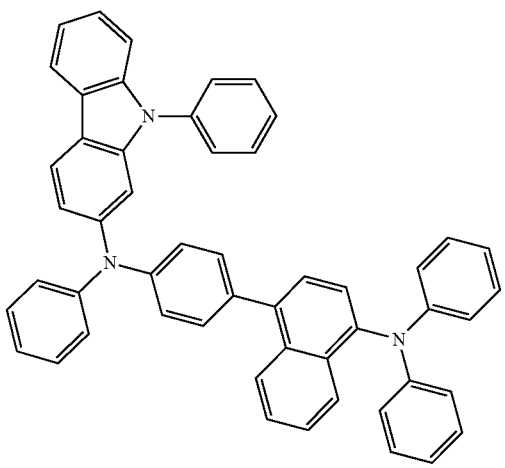
159
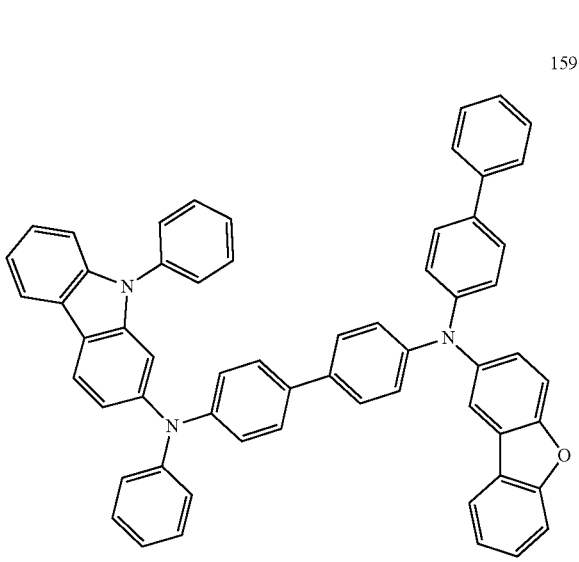
162
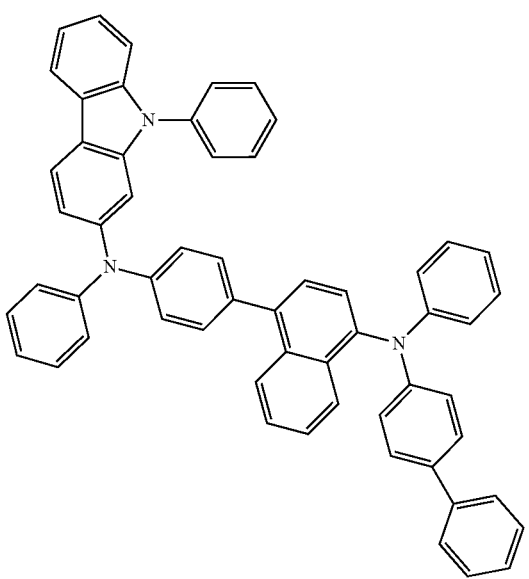

-continued
163
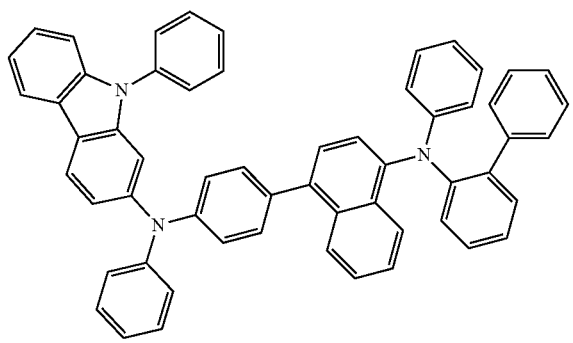
164
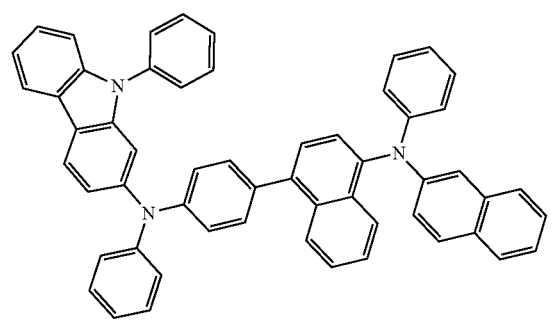
165
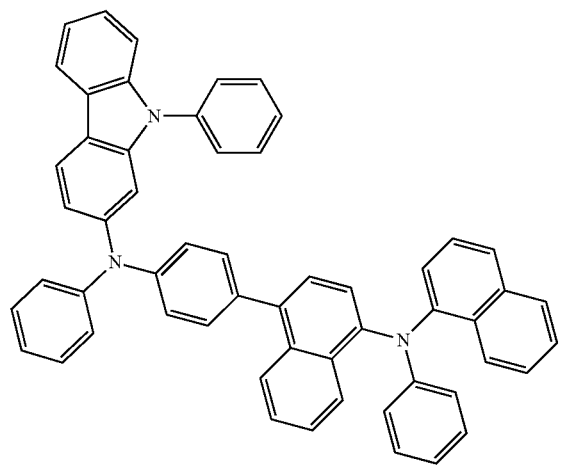
-continued
166
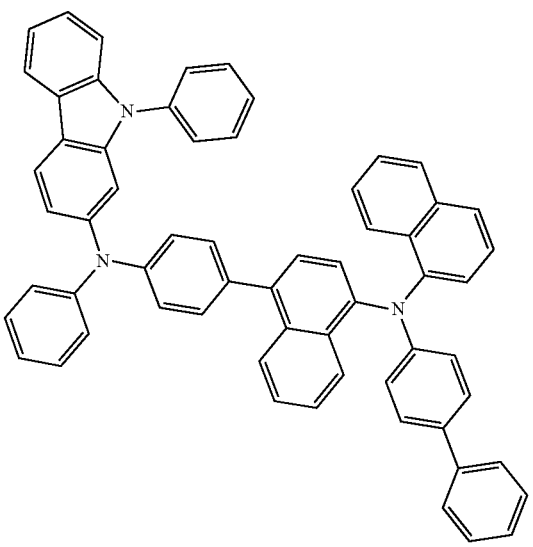
167
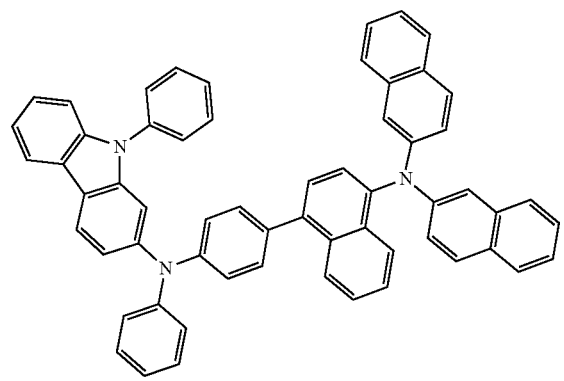
168

169
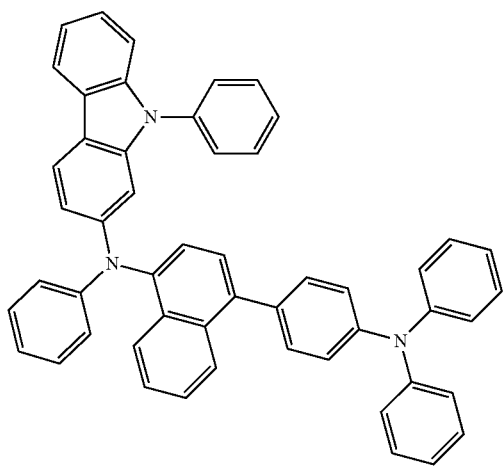
170
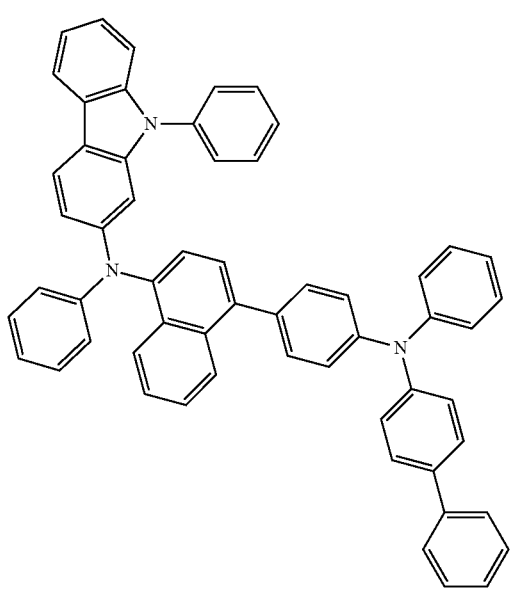
171
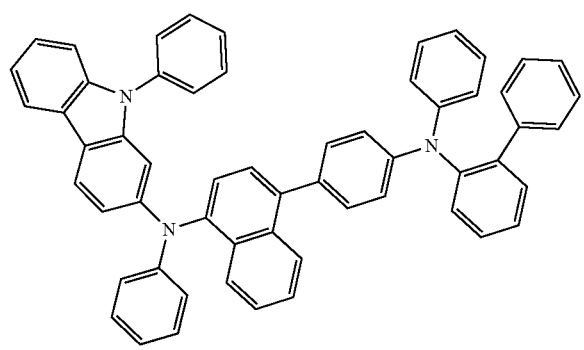
172
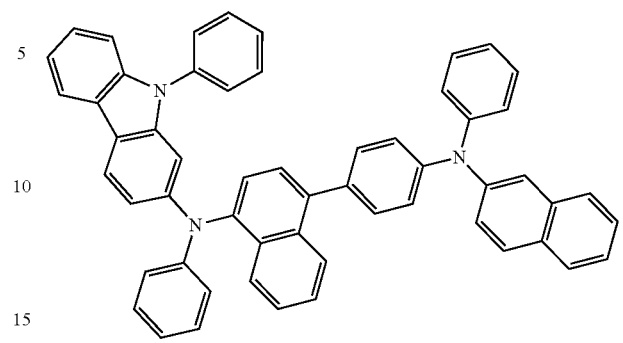
173
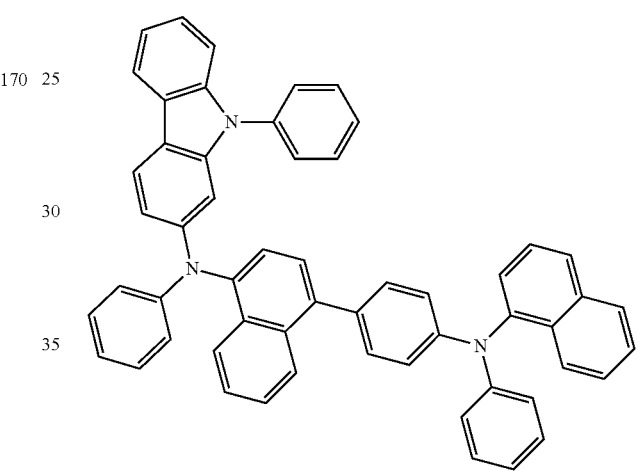
174
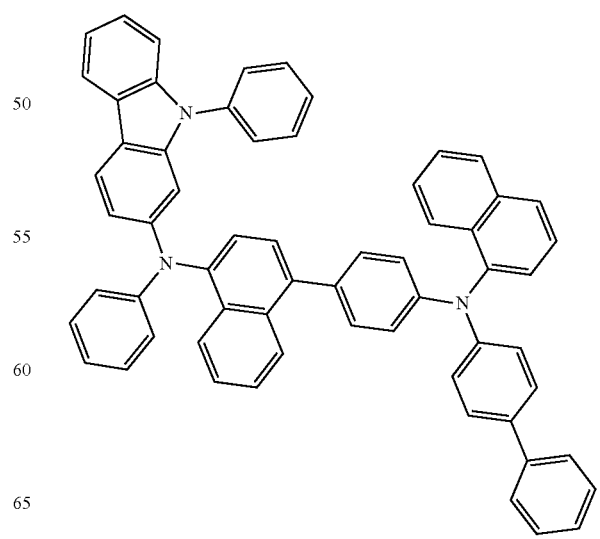

251
-continued
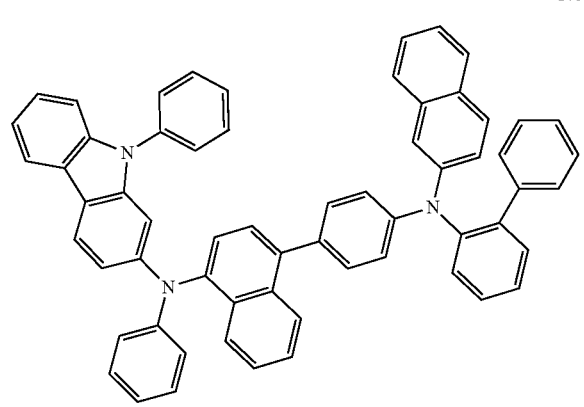
175
252
-continued
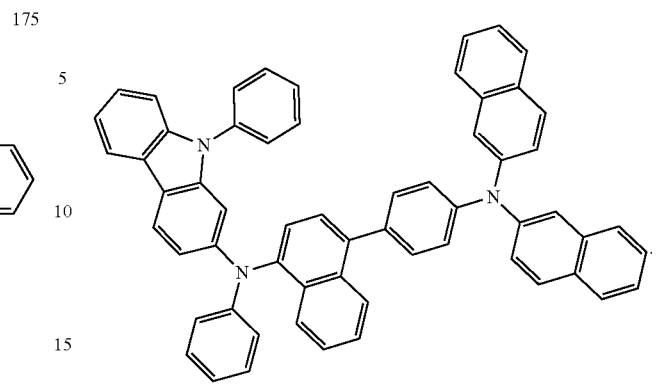
176
* * * * *

UNITED STATES PATENT AND TRADEMARK OFFICE
CERTIFICATE OF CORRECTION

PATENT NO. : 11,944,006 B2
APPLICATION NO. : 16/277289
DATED : March 26, 2024
INVENTOR(S) : Jongwoo Kim et al.

It is certified that error appears in the above-identified patent and that said Letters Patent is hereby corrected as shown below:

In the Claims

In Column 183, Line 10, in Claim 5, after "and" insert -- * --.

In Column 189, Line 21, in Claim 9, delete "$C_1$-$C_{60}$" and insert -- $C_1$-$C_{20}$ --.

In Column 189, Line 22, in Claim 9, delete "$C_1$-$C_{60}$" and insert -- $C_1$-$C_{20}$ --.

In Column 193, Lines 23-30, in Claim 12, in Formulae 5-14, delete

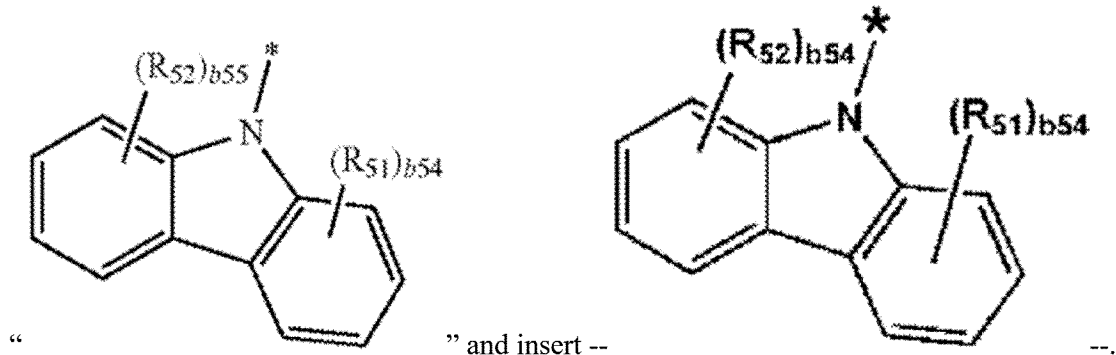

In Column 205, Line 59, in Claim 12, delete "—S(=O) ($Q_{31}$)," and insert -- —S(=O)($Q_{31}$), --.

Signed and Sealed this
Fourth Day of February, 2025

Coke Morgan Stewart
*Acting Director of the United States Patent and Trademark Office*

CERTIFICATE OF CORRECTION (continued)  Page 2 of 8
U.S. Pat. No. 11,944,006 B2

In Column 233, Lines 26-33, in Claim 13, in Formulae 6-234, delete

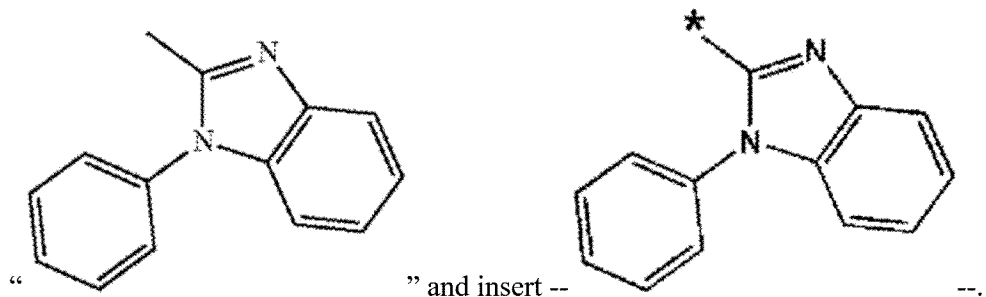

" " and insert -- -- .

In Column 240, Lines 9-24, in Claim 17, in Formulae 1-11, delete

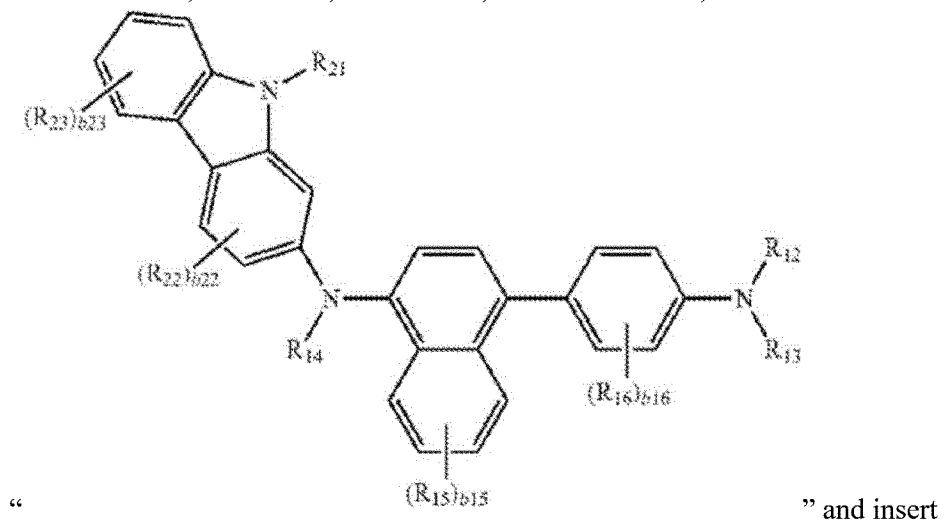

" " and insert

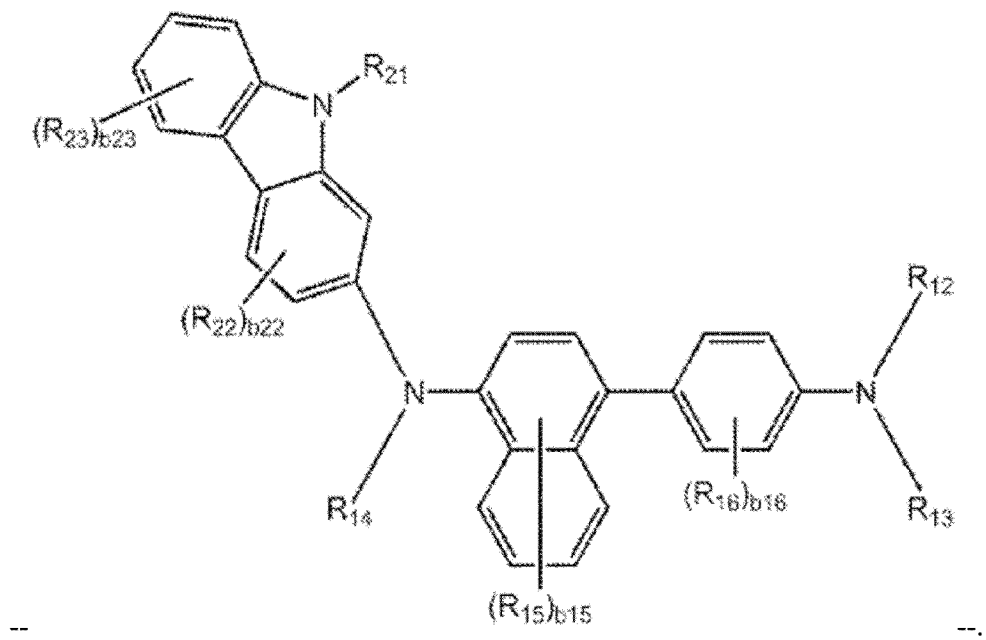

-- -- .

CERTIFICATE OF CORRECTION (continued)
U.S. Pat. No. 11,944,006 B2

In Column 243, Lines 29-41, in Claim 19, in Compound 152, delete

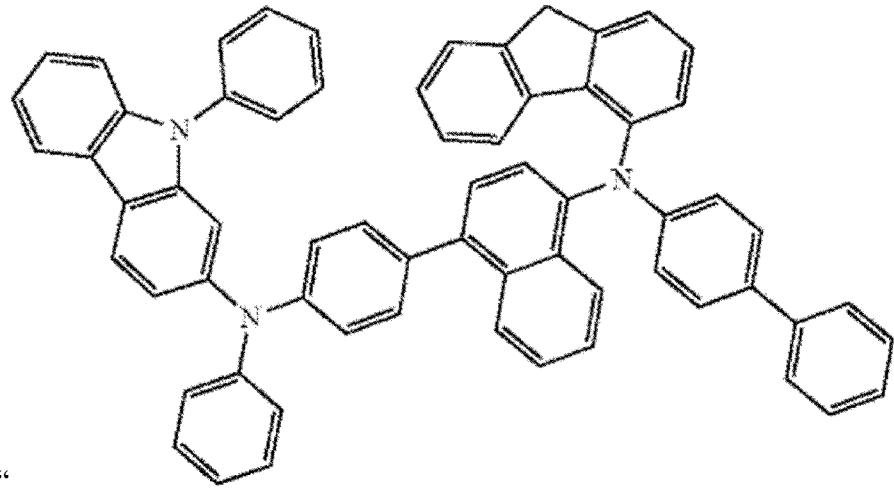

" and insert

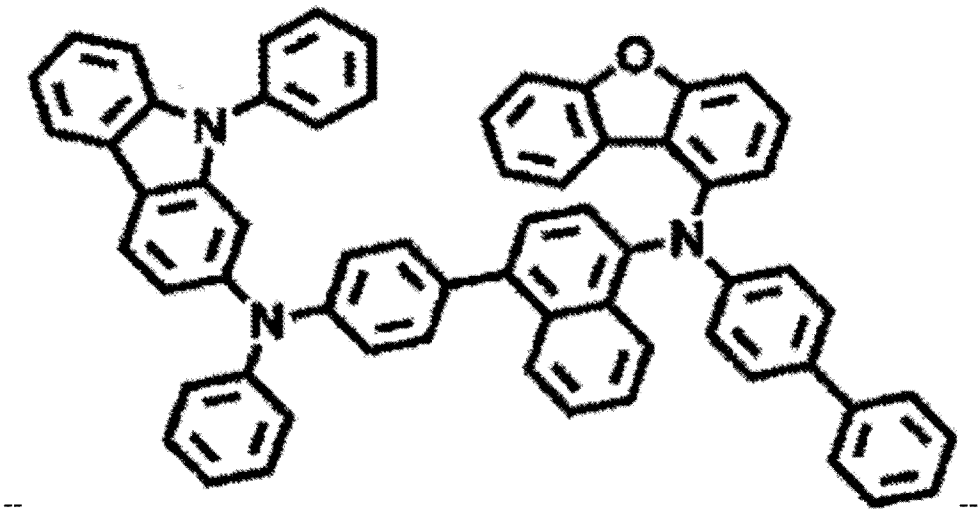

--.

In Column 244, Lines 51-66, in Claim 19, in Compound 156, delete

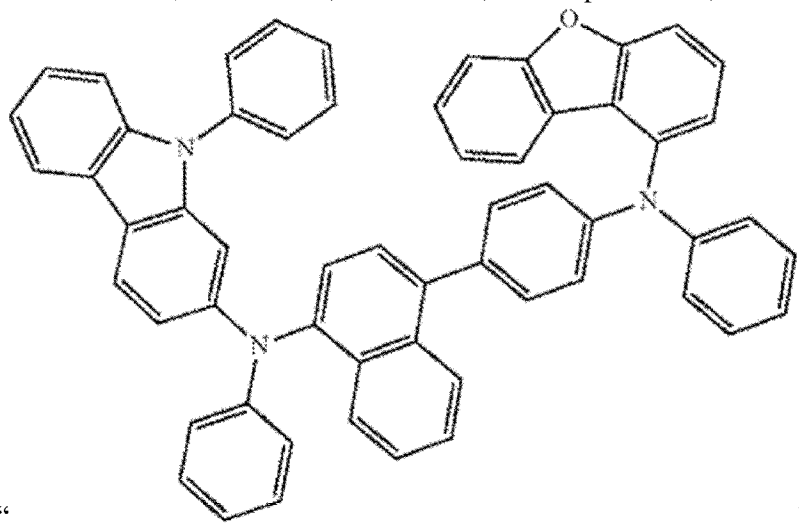

" and insert

CERTIFICATE OF CORRECTION (continued)
U.S. Pat. No. 11,944,006 B2

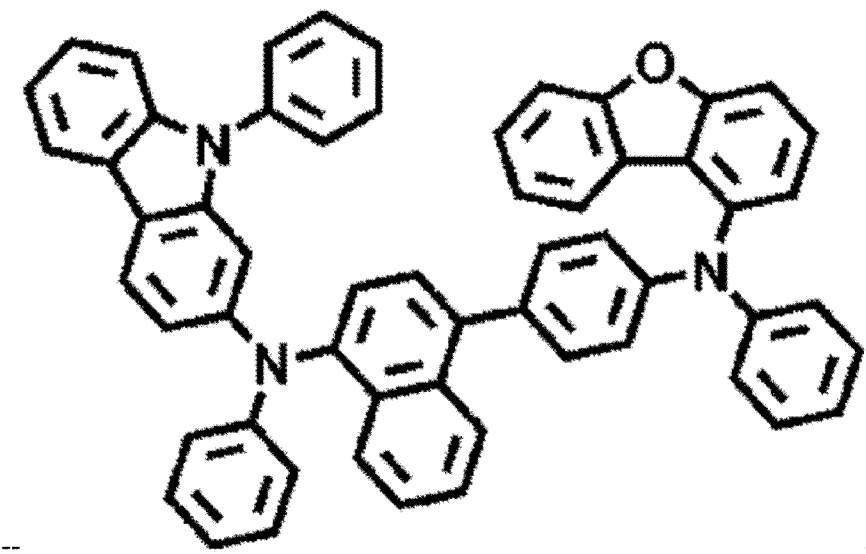

--.

In Column 245, Lines 21-41, in Claim 19, in Compound 158, delete

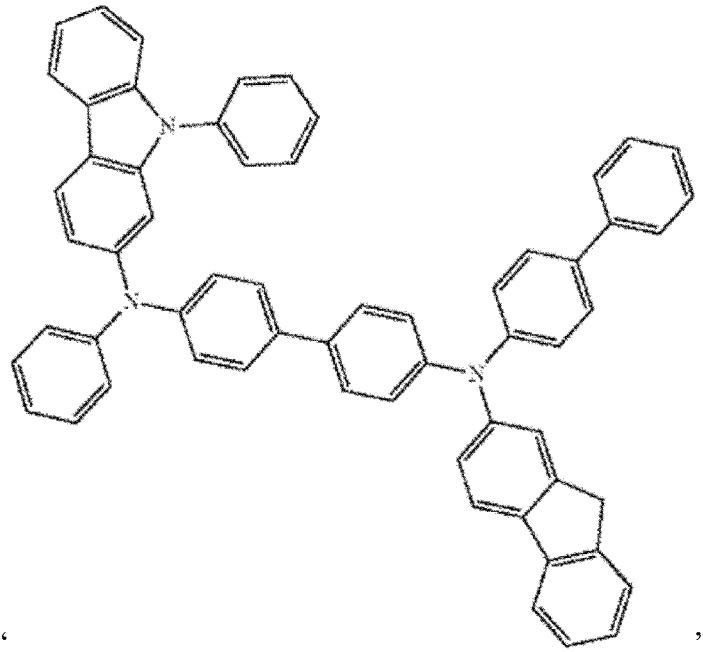

" and insert

CERTIFICATE OF CORRECTION (continued)
U.S. Pat. No. 11,944,006 B2

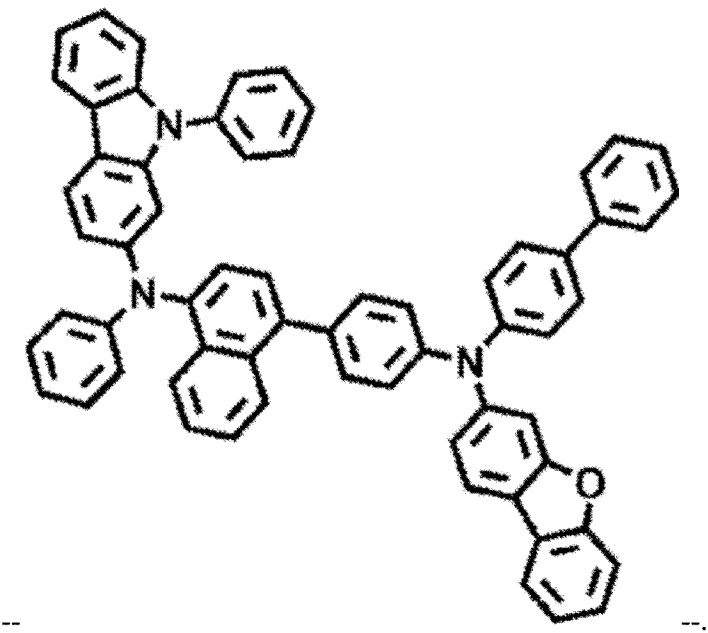

--                                   --.

In Column 246, Lines 2-17, in Claim 19, in Compound 160, delete

"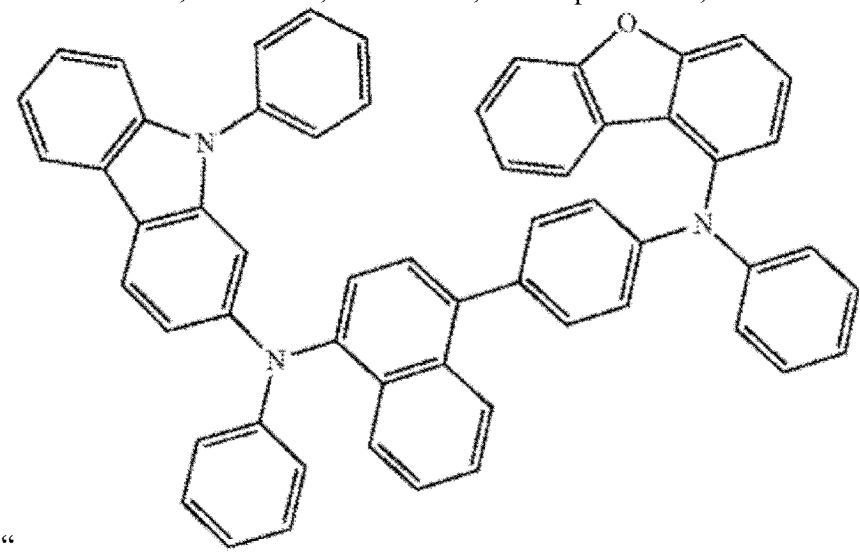"  and insert

CERTIFICATE OF CORRECTION (continued)
U.S. Pat. No. 11,944,006 B2

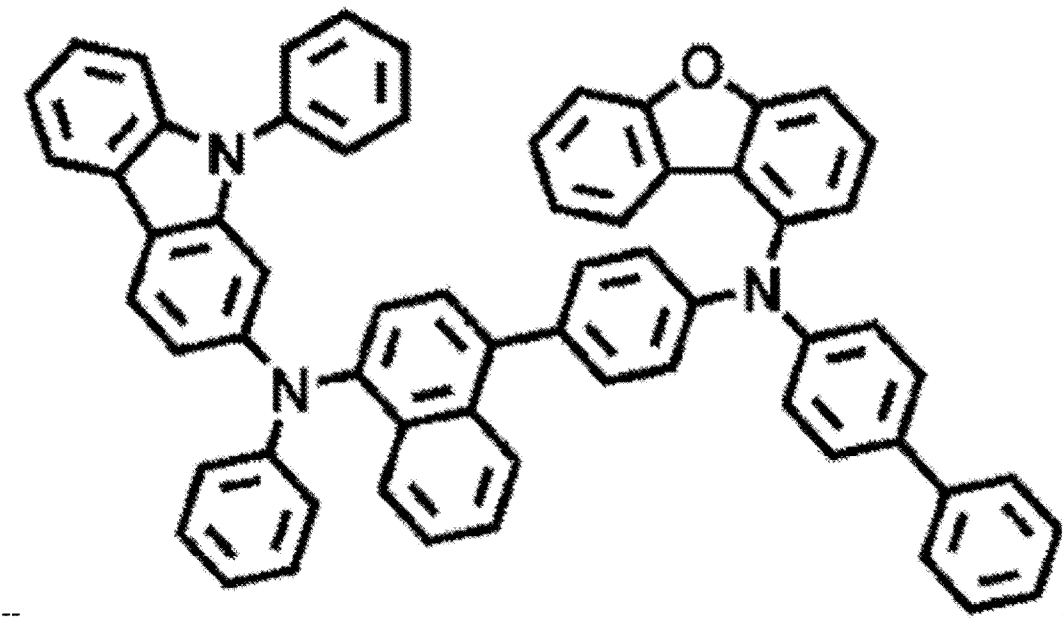

-- --.

In Column 247, Lines 2-16, in Claim 19, in Compound 163, delete

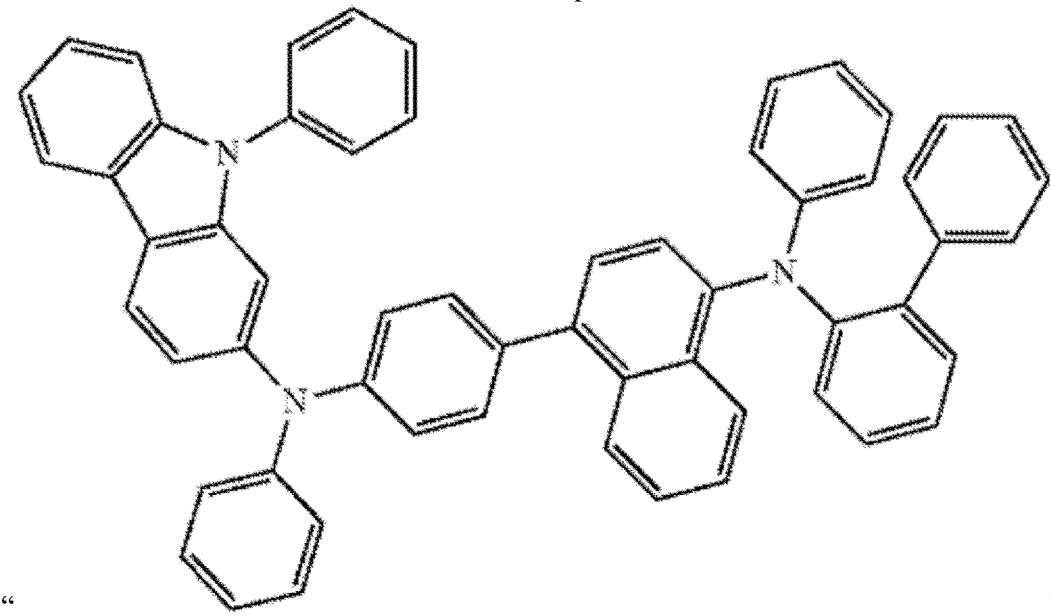

" " and insert

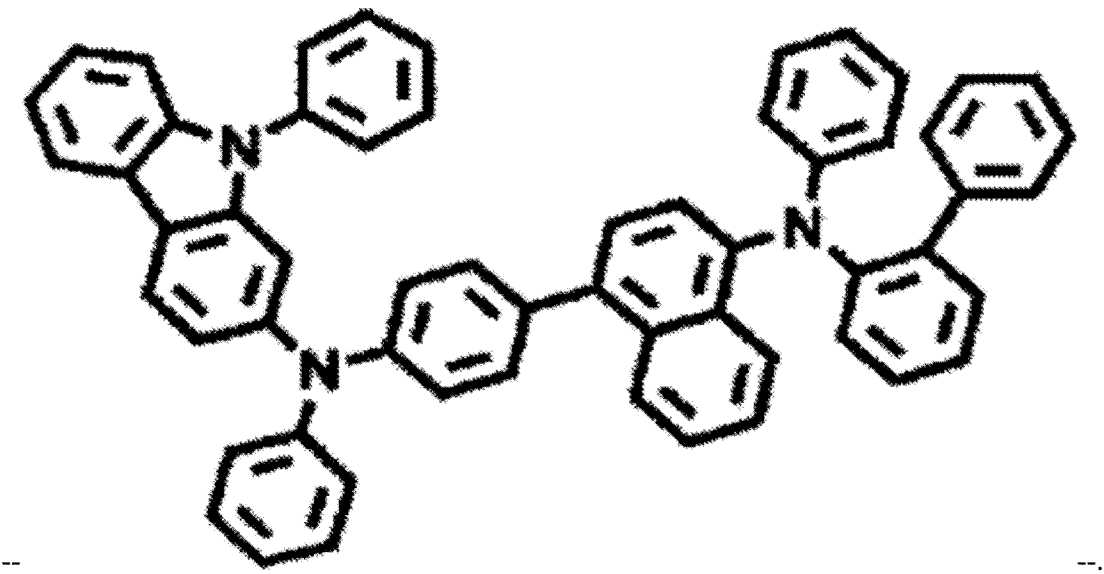
--.
In Column 247, Lines 47-66, in Claim 19, in Compound 165, delete "
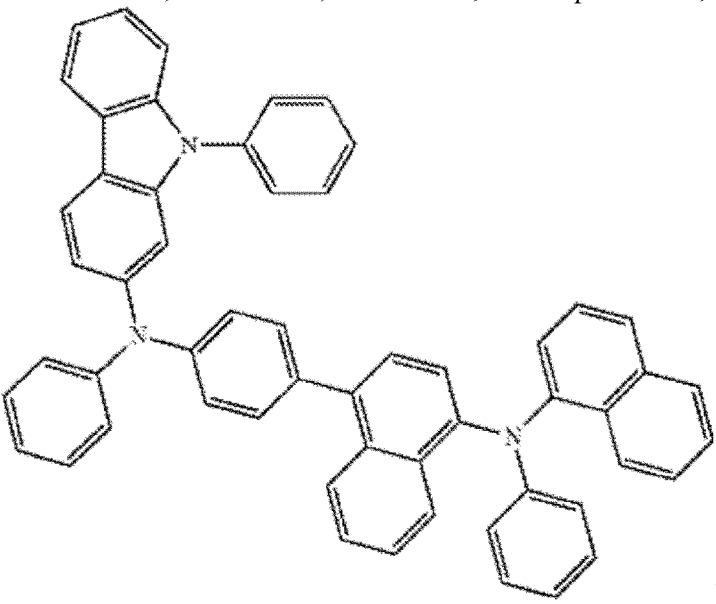
" and insert

CERTIFICATE OF CORRECTION (continued)